US011987601B2

(12) United States Patent
Lavoie et al.

(10) Patent No.: US 11,987,601 B2
(45) Date of Patent: *May 21, 2024

(54) NOROVIRUS FUSION PROTEINS AND VLPS COMPRISING NOROVIRUS FUSION PROTEINS

(71) Applicant: ARAMIS BIOTECHNOLOGIES INC., Quebec (CA)

(72) Inventors: Pierre-Olivier Lavoie, Quebec (CA); Marc-Andre D'Aoust, Quebec (CA)

(73) Assignee: ARAMIS BIOTECHNOLOGIES INC., Quebec (CA)

( * ) Notice: Subject to any disclaimer, the term of this patent is extended or adjusted under 35 U.S.C. 154(b) by 8 days.

This patent is subject to a terminal disclaimer.

(21) Appl. No.: 17/735,706

(22) Filed: May 3, 2022

(65) Prior Publication Data

US 2023/0024533 A1 Jan. 26, 2023

Related U.S. Application Data

(62) Division of application No. 16/496,244, filed as application No. PCT/CA2018/050352 on Mar. 23, 2018, now Pat. No. 11,608,361.

(60) Provisional application No. 62/475,660, filed on Mar. 23, 2017.

(51) Int. Cl.

| | |
|---|---|
| ***C07K 14/005*** | (2006.01) |
| ***A61K 39/12*** | (2006.01) |
| ***C07K 16/10*** | (2006.01) |
| ***C12N 7/00*** | (2006.01) |
| ***C12N 15/82*** | (2006.01) |
| *A61K 9/00* | (2006.01) |

(52) U.S. Cl.

CPC ............ *C07K 14/005* (2013.01); *A61K 39/12* (2013.01); *C07K 16/10* (2013.01); *C12N 7/00* (2013.01); *C12N 15/8257* (2013.01); *A61K 9/0019* (2013.01); *C07K 2319/00* (2013.01); *C12N 2770/16022* (2013.01); *C12N 2770/16023* (2013.01); *C12N 2770/16034* (2013.01)

(58) Field of Classification Search

None

See application file for complete search history.

(56) References Cited

U.S. PATENT DOCUMENTS

| | | | |
|---|---|---|---|
| 4,962,028 A | 10/1990 | Bedbrook et al. | |
| 7,527,801 B2 | 5/2009 | Coit et al. | |
| 8,119,145 B2 | 2/2012 | Coit et al. | |
| 8,124,104 B2 | 2/2012 | Coit et al. | |
| 8,142,793 B2 | 3/2012 | Coit et al. | |
| 8,980,275 B2 | 3/2015 | Steadman et al. | |
| 9,428,739 B2 | 8/2016 | Coit et al. | |
| 10,065,994 B2 | 9/2018 | Settembre et al. | |
| 11,608,361 B2 * | 3/2023 | Lavoie | C07K 16/10 |
| 2013/0171185 A1 | 7/2013 | Settembre | |
| 2019/0002890 A1 * | 1/2019 | Martini | C12N 9/2465 |
| 2020/0148725 A1 | 5/2020 | Lavoie | |
| 2023/0024533 A1 * | 1/2023 | Lavoie | C12N 7/00 |

FOREIGN PATENT DOCUMENTS

| | | |
|---|---|---|
| WO | 2007/081447 A2 | 7/2007 |
| WO | 2010/017542 A1 | 2/2010 |
| WO | 2012/006293 A1 | 1/2012 |
| WO | 2016/019890 A1 | 2/2016 |

OTHER PUBLICATIONS

Sainsbury et al. (Plant Physiology. 2008; 148: 122-1218).*

Bertolotti-Ciarlet et al., "The 3End of Norwalk Virus mRNA Contains Determinants That Regulate the Expression and Stability of the Viral Capsid Protein VP1: a Novel Function for the VP2 Protein", Journal of Virology, vol. 77, No. 21, Nov. 2003, pp. 11603-11615, 15 pages total.

Mason et al., "Expression of Norwalk virus capsid protein in transgenic tobacco and potato and its oral immunogenicity in mice", Proc. Natl. Acad. Sci. USA, vol. 93, pp. 5335-5340, May 1996, 6 pages total.

Tacket et al., "Human Immune Responses to a Novel Norwalk Virus Vaccine Delivered in Transgenic Potatoes", The Journal of Infectious Diseases, vol. 182, pp. 302-305, 2000, 4 pages total.

Huang et al., "A DNA Replicon System for Rapid High-Level Production of Virus-Like Particles in Plants", Biotechnology and Bioengineering, vol. 103, No. 4, pp. 706-714, Jul. 1, 2009, 9 pages total.

Huo et al., "Chimeric VLPs with GII.3 P2 domain in a backbone of GII.4 VP1 confers novel HBGA binding ability", Virus Research, vol. 224, pp. 1-5, 2016, 5 pages total.

"CaliciNet Data—Norovirus US OutbreakMap", Centers for Disease Control and Prevention, Retrieved from Internet on Nov. 11, 2019, https://www.cdc.gov/norovirus/reporting/calicinet/data.html, 3 pages total.

International Search Report dated Jun. 12, 2018 issued by the International Searching Authority in International Application No. PCT/CA2018/050352.

Mathew, Lolita et al. "Norovirus Narita 104 Virus-Like Particles expressed in Nicotiana benthamiana Induce Serum and Mucosal Immune Responses" BioMed Research International, Hindawi Publishing Corporation, vol. 2014, Published May 11, 2014, pp. 1-10.

(Continued)

*Primary Examiner* — Shanon A. Foley

(74) *Attorney, Agent, or Firm* — Sughrue Mion, PLLC

(57) ABSTRACT

Nucleic acids encoding norovirus VP1 fusion proteins and VLPs comprising the norovirus VP1 fusion proteins are provided. Methods for norovirus VP1 fusion protein and norovirus VLP production in plants are also described. The VP1 fusion protein comprises, a first sequence encoding an S domain derived from a first norovirus strain, and a second sequence encoding a P domain derived from a second norovirus strain.

20 Claims, 71 Drawing Sheets

Specification includes a Sequence Listing.

(56) References Cited

OTHER PUBLICATIONS

Saunders, Keith et al. "Exploiting plant virus-derived components to achieve in planta expression and for templates for synthetic biology applications" New Phytologist, 2013, vol. 200, Accepted Jan. 31, 2013, pp. 16-26.
Tan, Ming, et al. "The P Domain of Norovirus Capsid Protein forms Dimer and Binds to Histo-Blood Group Antigen Receptors" Journal of Virology, Jun. 2004, vol. 78, No. 12, pp. 6233-6242.
Smith et al., "The Dynamic Capsid Structures of the Noroviruses", Viruses vol. 11. No. 235, doi:10.3390/v11030235, 2019 (18 pages total).

* cited by examiner

FIGURE 2A

| Norovirus VP1 major capsid amino acid sequences | | |
|---|---|---|
| Access (Uniprot) | Access (NCBI) | Strain name |
| Q83884 | NP_056821 | Hu/GI.1/United States/Norwalk/1968 |
| D2DEL3 | ACU56258 | Hu/GI.2/Leuven/2003/BEL |
| H2DG70 | AEY77318 | Hu/GI.3/S29/2008/Lilla Edet/Sweden |
| K4LM89 | AFV08795 | Hu/GII.4/Sydney/NSW0514/2012/AU |
| M9T020 | AGI96397 | Hu/GII.6/Ohio/490/2012/USA |
| H9AWU4 | AFC89656 | Hu/GII.13/VA173/2010/USA |
| A0A077KVU6 | AID51513 | Hu/GII.17/Kawasaki323/2014/JP |

| Norovirus VP2 major capsid amino acid sequences | | |
|---|---|---|
| Access (Uniprot) | Access (NCBI) | Strain name |
| Q83885 | NP_056822 | Hu/GI.1/United States/Norwalk/1968 |
| D2DEL4 | ACU56259 | Hu/GI.2/Leuven/2003/BEL |
| H2DG71 | AEY77319 | Hu/GI.3/S29/2008/Lilla Edet/Sweden |
| K4LB50 | AFV08796 | Hu/GII.4/Sydney/NSW0514/2012/AU |
| W6APL0 | AHI59155 | Hu/GII.6/HS245/2010/USA |
| H9AWU5 | AFC89657 | Hu/GII.13/VA173/2010/USA |
| A0A077KP84 | BAP33935 | Hu/GII.17/Kawasaki323/2014/JP |

FIGURE 2B

| DNA accession numbers for VP1 and VP2 gene sequences | | |
|---|---|---|
| Genotype | Genome access no (NCBI) | Strain name |
| GI.1 | M87661 | Hu/GI.1/United States/Norwalk/1968 |
| GI.2 | FJ515294 | Hu/GI.2/Leuven/2003/BEL |
| GI.3 | JN603244 | Hu/GI.3/S29/2008/Lilla Edet/Sweden |
| GII.4 | JX459908 | Hu/GII.4/Sydney/NSW0514/2012/AU |
| GII.6 | KC464321 (VP1), KJ407072 (VP2) | Hu/GII.6/Ohio/490/2012/USA (VP1), Hu/GII.6/HS245/2010/USA (VP2) |
| GII.13 | JN899242 | Hu/GII.13/VA173/2010/USA |
| GII.17 | AB983218 | Hu/GII.17/Kawasaki323/2014/JP |

FIGURE 2C

| | Norovirus VP1 major capsid protein homology | | | | | | |
|---|---|---|---|---|---|---|---|
| | GI.1 | GI.2 | GI.3 | GII.4 | GII.6 | GII.13 | GII.17 |
| GI.1 | | 69.5% | 65.8% | 41.8% | 44.2% | 44.4% | 44.7% |
| GI.2 | | | 66.1% | 41.7% | 42.1% | 43.5% | 43.2% |
| GI.3 | | | | 43.3% | 44.9% | 43.5% | 45.4% |
| GII.4 | | | | | 60.8% | 62.3% | 65.6% |
| GII.6 | | | | | | 66.6% | 71.5% |
| GII.13 | | | | | | | 75.7% |

| | Norovirus VP2 minor capsid protein homology | | | | | | |
|---|---|---|---|---|---|---|---|
| | GI.1 | GI.2 | GI.3 | GII.4 | GII.6 | GII.13 | GII.17 |
| GI.1 | | 70.4% | 62.5% | 31.1% | 35.0% | 36.3% | 34.1% |
| GI.2 | | | 63.0% | 30.6% | 34.1% | 36.6% | 34.9% |
| GI.3 | | | | 30.5% | 34.2% | 38.3% | 31.7% |
| GII.4 | | | | | 52.4% | 53.9% | 57.3% |
| GII.6 | | | | | | 62.6% | 60.3% |
| GII.13 | | | | | | | 67.2% |

FIGURE 2D

| | VP1 protein homology (GII.4 strains) | | | | | |
|---|---|---|---|---|---|---|
| | US96 | FH02 | Hnt04 | 2006b | NO09 | Syd12 |
| US96 | | 95.4% | 94.1% | 93.1% | 93.3% | 92.4% |
| FH02 | | | 95.7% | 95.0% | 94.1% | 93.1% |
| Hnt04 | | | | 94.1% | 93.9% | 93.1% |
| 2006b | | | | | 95.2% | 94.8% |
| NO09 | | | | | | 97.4% |
| Syd12 | | | | | | |

| | VP1 (P domain only) protein homology (GII.4 strains) | | | | | |
|---|---|---|---|---|---|---|
| | US96 | FH02 | Hnt04 | 2006b | NO09 | Syd12 |
| US96 | | 93.7% | 92.2% | 89.7% | 90.3% | 88.7% |
| FH02 | | | 94.7% | 92.5% | 91.2% | 90.3% |
| Hnt04 | | | | 92.2% | 91.5% | 90.9% |
| 2006b | | | | | 93.4% | 92.8% |
| NO09 | | | | | | 96.9% |
| Syd12 | | | | | | |

| | VP1 (P2 sub-domain only) protein homology (GII.4 strains) | | | | | |
|---|---|---|---|---|---|---|
| | US96 | FH02 | Hnt04 | 2006b | NO09 | Syd12 |
| US96 | | 89.6% | 86.1% | 81.3% | 83.3% | 81.3% |
| FH02 | | | 91.0% | 84.0% | 83.3% | 82.6% |
| Hnt04 | | | | 86.1% | 84.0% | 84.0% |
| 2006b | | | | | 87.5% | 87.5% |
| NO09 | | | | | | 94.4% |
| Syd12 | | | | | | |

FIGURE 4A

| | S DOMAIN | P DOMAIN 230 | SEQ ID NO: |
|---|---|---|---|
| VP1_Norwalk_1968_GI_1_Q83884_Rf | LVPPTVE | QKTRPFTL | 88 |
| VP1_Leuven_2003_GI_2_D2DEL3 | LVPPTIE | QKTRAFTV | 89 |
| VP1_LillaEdet_2008_GI_3_H2DG70 | LVPPNVE | QKTKPFSV | 90 |
| VP1_Sydney_2012_GII_4_K4LM89 | LVPPTVE | SRTKPFSV | 91 |
| VP1_Ohio_2012_GII_6_M9T020 | VLPPTVE | SKTKPFSL | 92 |
| VP1_VA173_2010_GII_13_H9AWU4 | LVPPSVE | SKTKPFTL | 93 |
| VP1_Kawasaki_2014_GII_17_A0A077KVU6 | LVPPSVE | SKTKPFSL | 94 |
| CONSENSUS | LVPPtvE | sKTKpFsl | 95 |

FIGURE 4B

| | Norovirus VP1 major capsid protein homology | | | | | | | |
|---|---|---|---|---|---|---|---|---|
| | GI.1 | S(GI.1) +P(GI.2) | S(GI.1) +P(GI.3) | S(GI.1) +P(GII.4) | S(GI.1) +P(GII.6) | S(GI.1) +P(GII.12) | S(GI.1) +P(GII.13) | S(GI.1) +P(GII.17) |
| GI.1 | | 75.8% | 75.0% | 60.4% | 60.8% | 62.6% | 61.8% | 62.4% |
| S(GI.1) +P(GI.2) | | | 74.6% | 59.6% | 59.1% | 61.3% | 60.5% | 60.7% |
| S(GI.1) +P(GI.3) | | | | 60.2% | 61.2% | 60.9% | 60.2% | 62.2% |
| S(GI.1) +P(GII.4) | | | | | 70.2% | 75.0% | 73.0% | 76.1% |
| S(GI.1) +P(GII.6) | | | | | | 76.6% | 74.7% | 79.1% |
| S(GI.1) +P(GII.12) | | | | | | | 78.3% | 80.8% |
| S(GI.1) +P(GII.13) | | | | | | | | 79.0% |

FIGURE 4C

| | Norovirus VP1 major capsid protein homology | | | | | | | | |
|---|---|---|---|---|---|---|---|---|---|
| | GII.12 | S(GII.12) +P(GI.1) | S(GII.12) +P(GI.2) | S(GII.12) +P(GI.3) | S(GII.12) +P(GI.5) | S(GII.12) +P(GII.1) | S(GII.12) +P(GII.2) | S(GII.12) +P(GII.3) | S(GII.12) +P(GII.4) |
| GII.12 | | 62.2% | 61.0% | 60.7% | 60.1% | 86.9% | 80.3% | 77.1% | 74.6% |
| S(GII.12) +P(GI.1) | | | | | | | | | 60.0% |
| S(GII.12) +P(GI.2) | | | | | | | | | 59.3% |
| S(GII.12) +P(GI.3) | | | | | | | | | 59.6% |
| S(GII.12) +P(GI.5) | | | | | | | | | 60.1% |
| S(GII.12) +P(GII.1) | | | | | | | | | 73.5% |
| S(GII.12) +P(GII.2) | | | | | | | | | 70.7% |
| S(GII.12) +P(GII.3) | | | | | | | | | 73.2% |
| | | | | | | | | | |

| | S(GII.12) +P(GII.5) | S(GII.12) +P(GII.6) | S(GII.12) +P(GII.7) | S(GII.12) +P(GII.13 ) | S(GII.12) +P(GII.14 ) | S(GII.12) +P(GII.17 ) | S(GII.12) +P(GII.21 ) |
|---|---|---|---|---|---|---|---|
| GII.12 | 82.1% | 76.2% | 76.6% | 77.9% | 75.7% | 80.4% | 79.5% |
| S(GII.12) +P(GII.3) | 73.0% | 70.0% | 73.6% | 72.8% | 72.7% | 76.0% | 72.7% |

FIGURE 4D

| | Norovirus VP1 major capsid protein homology | | | | | | | | | |
|---|---|---|---|---|---|---|---|---|---|---|
| | GI.5 | S(GI.5) +P(GII.4) | GII.1 | S(GII.1) +P(GI.3) | S(GII.1) +P(GII.4) | S(GII.1) +P(GII.17) | GII.14 | S(GII.14) +P(GII.4) | GII.21 | S(GII.21) +P(GII.4) |
| GI.5 | | 60.6% | 45.7% | 60.1% | 44.6% | 45.9% | 46.0% | 44.0% | 45.9% | 44.9% |
| S(GI.5) +P(GII.4) | | | 57.4% | 44.3% | 83.7% | 60.1% | 56.0% | 83.2% | 57.0% | 84.1% |
| GII.1 | | | | 60.8% | 73.3% | 80.4% | 69.0% | 65.7% | 71.9% | 66.7% |
| S(GII.1) +P(GI.3) | | | | | 59.6% | 61.9% | 52.6% | 52.2% | 54.6% | 53.1% |
| S(GII.1) +P(GII.4) | | | | | | 76.0% | 64.9% | 92.4% | 65.9% | 93.3% |
| S(GII.1) +P(GII.17) | | | | | | | 68.5% | 68.4% | 71.3% | 69.4% |
| GII.14 | | | | | | | | 72.5% | 65.1% | 63.8% |
| S(GII.14) +P(GII.4) | | | | | | | | | 63.9% | 91.3% |
| GII.21 | | | | | | | | | | 72.5% |
| S(GII.21) +P(GII.4) | | | | | | | | | | |

S(GI.1) +P(GII.4)
S(GI.1/Norwalk/68/US)+
P(GII.4 Sydney/NSW0514/2012/AU)

Figure 7A

IF-NoV(US68)VP1(ORF2).c (SEQ ID NO: 72)

TCGTGCTTCGGCACCAGTACAATGATGATGGCGTCTAAGGACGCTACAT

Figure 7B

IF-NoV(US68)VP1(ORF2).r (SEQ ID NO: 73)

ACTAAAGAAAATAGGCCTTTATCGGCGCAGACCAAGCCTACCTCTTGCCGAGCTGGCAG

Figure 7C

Construct 1190 from left to right t-DNA borders (underlined). 2X35S/CPMV-160/NOS with Plastocyanine-P19-Plastocyanine silencing inhibitor expression cassette (SEQ ID NO: 74)

<u>TGGCAGGATATATTGTGGTGTAAACA</u>AATTGACGCTTAGACAACTTAATAACACATTGCGGACGTTTTTAATGTACTGAATTAACG
CCGAATCCCGGGCTGGTATATTTATATGTTGTCAAATAACTCAAAAACCATAAAAGTTTAAGTTAGCAAGTGTGTACATTTTTACTT
GAACAAAAATATTCACCTACTACTGTTATAAATCATTATTAAACATTAGAGTAAAGAAATATGGATGATAAGAACAAGAGTAGTGA
TATTTTGACAACAATTTTGTTGCAACATTTGAGAAAATTTTGTTGTTCTCTCTTTTCATTGGTCAAAAACAATAGAGAGAGAAAAAG
GAAGAGGGAGAATAAAAACATAATGTGAGTATGAGAGAGAAAGTTGTACAAAAGTTGTACCAAAATAGTTGTACAAATATCATT
GAGGAATTTGACAAAAGCTACACAAATAAGGGTTAATTGCTGTAAATAAATAAGGATGACGCATTAGAGAGATGTACCATTAGAG
AATTTTTGGCAAGTCATTAAAAAGAAAGAATAAATTATTTTTAAAATTAAAAGTTGAGTCATTTGATTAAACATGTGATTATTTAAT
GAATTGATGAAAGAGTTGGATTAAAGTTGTATTAGTAATTAGAATTTGGTGTCAAATTTAATTTGACATTTGATCTTTTCCTATATA
TTGCCCCATAGAGTCAGTTAACTCATTTTTATATTTCATAGATCAAATAAGAGAAATAACGGTATATTAATCCCTCCAAAAAAAAAA
AACGGTATATTTACTAAAAAATCTAAGCCACGTAGGAGGATAACAGGATCCCCGTAGGAGGATAACATCCAATCCAACCAATCAC
AACAATCCTGATGAGATAACCCACTTTAAGCCCACGCATCTGTGGCACATCTACATTATCTAAATCACACATTCTTCCACACATCTG
AGCCACACAAAAACCAATCCACATCTTTATCACCCATTCTATAAAAAATCACACTTTGTGAGTCTACACTTTGATTCCCTTCAAACAC
ATACAAAGAGAAGAGACTAATTAATTAATTAATCATCTTGAGAGAAAATGGAACGAGCTATACAAGGAAACGACGCTAGGGAAC
AAGCTAACAGTGAACGTTGGGATGGAGGATCAGGAGGTACCACTTCTCCCTTCAAACTTCCTGACGAAAGTCCGAGTTGGACTGA
GTGGCGGCTACATAACGATGAGACGAATTCGAATCAAGATAATCCCCTTGGTTTCAAGGAAAGCTGGGGTTTCGGGAAAGTTGTA
TTTAAGAGATATCTCAGATACGACAGGACGGAAGCTTCACTGCACAGAGTCCTTGGATCTTGGACGGGAGATTCGGTTAACTATG
CAGCATCTCGATTTTTCGGTTTCGACCAGATCGGATGTACCTATAGTATTCGGTTTCGAGGAGTTAGTATCACCGTTTCTGGAGGG
TCGCGAACTCTTCAGCATCTCTGTGAGATGGCAATTCGGTCTAAGCAAGAACTGCTACAGCTTGCCCCAATCGAAGTGGAAAGTA
ATGTATCAAGAGGATGCCCTGAAGGTACTCAAACCTTCGAAAAAGAAAGCGAGTAAGTTAAAATGCTTCTTCGTCTCCTATTTATA
ATATGGTTTGTTATTGTTAATTTTGTTCTTGTAGAAGAGCTTAATTAATCGTTGTTGTTATGAAATACTATTTGTATGAGATGAACTG
GTGTAATGTAATTCATTTACATAAGTGGAGTCAGAATCAGAATGTTTCCTCCATAACTAACTAGACATGAAGACCTGCCGCGTACA
ATTGTCTTATATTTGAACAACTAAAATTGAACATCTTTTGCCACAACTTTATAAGTGGTTAATATAGCTCAAATATATGGTCAAGTTC
AATAGATTAATAATGGAAATATCAGTTATCGAAATTCATTAACAATCAACTTAACGTTATTAACTACTAATTTTATATCATCCCCTTT
GATAAATGATAGTACACCAATTAGGAAGGAGCATGCTCGCCTAGGAGATTGTCGTTTCCCGCCTTCAGTTTGCAAGCTGCTCTAGC
CGTGTAGCCAATACGCAAACCGCCTCTCCCCGCGCGTTGGGAATTACTAGCGCGTGTCGACAAGCTTGCATGCCGGTCAACATGG
TGGAGCACGACACACTTGTCTACTCCAAAAATATCAAAGATACAGTCTCAGAAGACCAAAGGGCAATTGAGACTTTTCAACAAAG
GGTAATATCCGGAAACCTCCTCGGATTCCATTGCCCAGCTATCTGTCACTTTATTGTGAAGATAGTGGAAAAGGAAGGTGGCTCCT
ACAAATGCCATCATTGCGATAAAGGAAAGGCCATCGTTGAAGATGCCTCTGCCGACAGTGGTCCCAAAGATGGACCCCCACCCAC
GAGGAGCATCGTGGAAAAAGAAGACGTTCCAACCACGTCTTCAAAGCAAGTGGATTGATGTGATAACATGGTGGAGCACGACAC
ACTTGTCTACTCCAAAAATATCAAAGATACAGTCTCAGAAGACCAAAGGGCAATTGAGACTTTTCAACAAAGGGTAATATCCGGA
AACCTCCTCGGATTCCATTGCCCAGCTATCTGTCACTTTATTGTGAAGATAGTGGAAAAGGAAGGTGGCTCCTACAAATGCCATCA
TTGCGATAAAGGAAAGGCCATCGTTGAAGATGCCTCTGCCGACAGTGGTCCCAAAGATGGACCCCCACCCACGAGGAGCATCGT
GGAAAAAGAAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTTGATAAAAG

CGAACGTGGGGAAACCCGAACCAAACCTTCTTCTAAACTCTCTCTCATCTCTCTTAAAGCAAACTTCTCTCTTGTCTTTCTTGCGTGA
GCGATCTTCAACGTTGTCAGATCGTGCTTCGGCACCGCGGATGGCGAAAAACGTTGCGATTTTCGGCTTATTGTTTTCTCTTCTTGT
GTTGGTTCCTTCTCAGATCTTCGCCTGCAGGCTCCTCAGCCAAAACGACACCCCCATCTGTCTATCCACTGGCCCCTGGATCTGCTG
CCCAAACTAACTCCATGGTGACCCTGGGATGCCTGGTCAAGGGCTATTTCCCTGAGCCAGTGACAGTGACCTGGAACTCTGGATCC
CTGTCCAGCGGTGTGCACACCTTCCCAGCTGTCCTGCAGTCTGACCTCTACACTCTGAGCAGCTCAGTGACTGTCCCCTCCAGCACC
TGGCCCAGCGAGACCGTCACCTGCAACGTTGCCCACCCGGCCAGCAGCACCAAGGTGGACAAGAAAATTGTGCCCAGGGATTGT
GGTTGTAAGCCTTGCATATGTACAGTCCCAGAAGTATCATCTGTCTTCATCTTCCCCCCAAAGCCCAAGGATGTGCTCACCATTACT
CTGACTCCTAAGGTCACGTGTGTTGTGGTAGACATCAGCAAGGATGATCCCGAGGTCCAGTTCAGCTGGTTTGTAGATGATGTGG
AGGTGCACACAGCTCAGACGCAACCCCGGGAGGAGCAGTTCAACAGCACTTTCCGCTCAGTCAGTGAACTTCCCATCATGCACCA
GGACTGGCTCAATGGCAAGGAGCGATCGCTCACCATCACCATCACCATCACCATCACCATTAAAGGCCTATTTTCTTTAGTTTGAAT
TTACTGTTATTCGGTGTGCATTTCTATGTTTGGTGAGCGGTTTTCTGTGCTCAGAGTGTGTTTATTTTATGTAATTTAATTTCTTTGTG
AGCTCCTGTTTAGCAGGTCGTCCCTTCAGCAAGGACACAAAAAGATTTTAATTTTATTAAAAAAAAAAAAAAAAAAAAGACCGGGAA
TTCGATATCAAGCTTATCGACCTGCAGATCGTTCAAACATTTGGCAATAAAGTTTCTTAAGATTGAATCCTGTTGCCGGTCTTGCGA
TGATTATCATATAATTTCTGTTGAATTACGTTAAGCATGTAATAATTAACATGTAATGCATGACGTTATTTATGAGATGGGTTTTTAT
GATTAGAGTCCCGCAATTATACATTTAATACGCGATAGAAAACAAAATATAGCGCGCAAACTAGGATAAATTATCGCGCGCGGTG
TCATCTATGTTACTAGATCTCTAGAGTCTCAAGCTTGGCGCGCCCACGTGACTAGTGGCACTGGCCGTCGTTTTACAACGTCGTGA
CTGGGAAAACCCTGGCGTTACCCAACTTAATCGCCTTGCAGCACATCCCCCTTTCGCCAGCTGGCGTAATAGCGAAGAGGCCCGCA
CCGATCGCCCTTCCCAACAGTTGCGCAGCCTGAATGGCGAATGCTAGAGCAGCTTGAGCTTGGATCAGATTGTCGTTTCCCGCCTT
CAGTTTAAACTATCAGTGTTTGACAGGATATATTGGCGGGTAAACCTAAGAGAAAAGAGCGTTTA

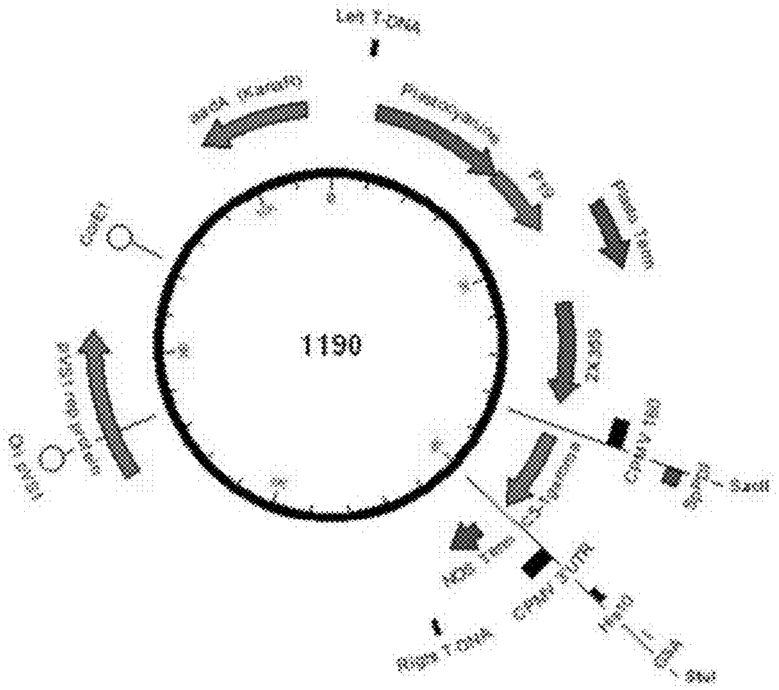

Figure 8A

Expression cassette number 2720 from 2X35S promoter to NOS terminator. Wild-type VP1 from Norovirus GI.1/Norwalk/1968/US strain is underlined. (SEQ ID NO: 75)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGATGATGGCGTCTAAG
GACGCTACATCAAGCGTGGATGGCGCTAGTGGCGCTGGTCAGTTGGTACCGGAGGTTAATGCTTCTGACCCTCTTGC
AATGGATCCTGTAGCAGGTTCTTCGACAGCAGTCGCGACTGCTGGACAAGTTAATCCTATTGATCCCTGGATAATTA
ATAATTTTGTGCAAGCCCCCCAAGGTGAATTTACTATTTCCCCAAATAATACCCCCGGTGATGTTTTGTTTGATTTGAG
TTTGGGTCCCCATCTTAATCCTTTCTTGCTCCATCTATCACAAATGTATAATGGTTGGGTTGGTAACATGAGAGTCAG
GATTATGCTAGCTGGTAATGCCTTTACTGCGGGGAAGATAATAGTTTCCTGCATACCCCCTGGTTTTGGTTCACATAA
TCTTACTATAGCACAAGCAACTCTCTTTCCACATGTGATTGCTGATGTTAGGACTCTAGACCCCATTGAGGTGCCTTT
GGAAGATGTTAGGAATGTTCTCTTTCATAATAATGATAGAAATCAACAAACCATGCGCCTTGTGTGCATGCTGTACA
CCCCCCTCCGCACTGGTGGTGGTACTGGTGATTCTTTTGTAGTTGCAGGGCGAGTTATGACTTGCCCCAGTCCTGATT
TTAATTTCTTGTTTTTAGTCCCTCCTACGGTGGAGCAGAAAACCAGGCCCTTCACACTCCCAAATCTGCCATTGAGTTC
TCTGTCTAACTCACGTGCCCCTCTCCCAATCAGTAGTATGGGCATTTCCCCAGACAATGTCCAGAGTGTGCAGTTCCA
AAATGGTCGGTGTACTCTGGATGGCCGCCTGGTTGGCACCACCCCAGTTTCATTGTCACATGTTGCCAAGATAAGAG
GGACCTCCAATGGCACTGTAATCAACCTTACTGAATTGGATGGCACACCCTTTCACCCTTTTGAGGGCCCTGCCCCCA
TTGGGTTTCCAGACCTCGGTGGTTGTGATTGGCATATCAATATGACACAGTTTGGCCATTCTAGCCAGACCCAGTAT
GATGTAGACACCACCCCTGACACTTTTGTCCCCCATCTTGGTTCAATTCAGGCAAATGGCATTGGCAGTGGTAATTAT
GTTGGTGTTCTTAGCTGGATTTCCCCCCCATCACACCCGTCTGGCTCCCAAGTTGACCTTTGGAAGATCCCCAATTAT
GGGTCAAGTATTACGGAGGCAACACATCTAGCCCCTTCTGTATACCCCCCTGGTTTCGGAGAGGTATTGGTCTTTTTC
ATGTCAAAAATGCCAGGTCCTGGTGCTTATAATTTGCCCTGTCTATTACCACAAGAGTACATTTCACATCTTGCTAGT
GAACAAGCCCCTACTGTAGGTGAGGCTGCCCTGCTCCACTATGTTGACCCTGATACCGGTCGGAATCTTGGGGAATT
CAAAGCATACCCTGATGGTTTCCTCACTTGTGTCCCCAATGGGGCTAGCTCGGGTCCACAACAGCTGCCGATCAATG
GGGTCTTTGTCTTTGTTTCATGGGTGTCCAGATTTTATCAATTAAAGCCTGTGGGAACTGCCAGCTCGGCAAGAGGT
AGGCTTGGTCTGCGCCGATAAAGGCCTATTTTCTTTAGTTTGAATTTACTGTTATTCGGTGTGCATTTCTATGTTTGGT
GAGCGGTTTTCTGTGCTCAGAGTGTGTTTATTTTATGTAATTTAATTTCTTTGTGAGCTCCTGTTTAGCAGGTCGTCCC
TTCAGCAAGGACACAAAAAGATTTTAATTTTATTAAAAAAAAAAAAAAAAAAAGACCGGGAATTCGATATCAAGCTTA
TCGACCTGCAGATCGTTCAAACATTTGGCAATAAAGTTTCTTAAGATTGAATCCTGTTGCCGGTCTTGCGATGATTAT
CATATAATTTCTGTTGAATTACGTTAAGCATGTAATAATTAACATGTAATGCATGACGTTATTTATGAGATGGGTTTTT

ATGATTAGAGTCCCGCAATTATACATTTAATACGCGATAGAAAACAAAATATAGCGCGCAAACTAGGATAAATTATC
GCGCGCGGTGTCATCTATGTTACTAGAT

Figure 9A

IF-NoV(US68)VP1(ORF2)(hCod).c (SEQ ID NO: 76)

TCGTGCTTCGGCACCAGTACAATGATGATGGCTAGTAAAGATGCGACCT

Figure 9B

IF-NoV(US68)VP1(ORF2)(hCod).r (SEQ ID NO: 77)

ACTAAAGAAAATAGGCCTTTATCTCCGCAGACCGAGGCGTCCGCGGGCAGAA

Figure 9C

Expression cassette number 2724 from 2X35S promoter to NOS terminator. Human codon-optimized VP1 from Norovirus GI.1/Norwalk/1968/US strain is underlined. (SEQ ID NO: 78)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGATGATGGCTAGTAAA
GATGCGACCTCCTCTGTGGATGGTGCGTCAGGGGCAGGACAACTCGTACCCGAGGTAAACGCCAGCGACCCACTTG
CCATGGACCCCGTTGCCGGAAGTTCCACAGCAGTGGCCACAGCCGGTCAAGTGAATCCAATTGATCCGTGGATTATC
AACAATTTCGTCCAGGCACCCCAGGGCGAGTTCACAATTTCACCAAACAATACACCGGGCGATGTGCTATTCGATCT
TTCCTTGGGTCCTCACCTTAACCCTTTTCTACTCCATCTCTCACAGATGTACAATGGTTGGGTAGGAAACATGAGAGT
CCGGATCATGCTGGCTGGCAATGCCTTTACCGCTGGCAAGATCATCGTCAGTTGTATTCCTCCCGGATTTGGATCTCA
TAATCTGACCATTGCTCAAGCGACTCTCTTTCCCCATGTCATCGCCGACGTTAGGACCCTGGACCCCATCGAGGTGCC
CCTGGAGGACGTCCGGAATGTTTTGTTCCACAACAACGACAGAAACCAGCAGACGATGAGACTTGTCTGTATGCTCT
ATACCCCACTGCGGACTGGAGGCGGGACTGGAGACTCCTTCGTTGTGGCAGGAAGAGTGATGACATGCCCCTCCCC
CGACTTCAACTTTCTTTTTCTGGTCCCACCAACCGTTGAGCAGAAGACGCGGCCCTTTACACTGCCCAATCTCCCGCTT
TCAAGTCTGAGTAATTCACGGGCCCCATTGCCGATCTCCTCAATGGGAATCTCCCCCGACAACGTCCAGTCTGTCCAA
TTCCAAAATGGGAGATGCACACTGGACGGTCGCCTGGTGGGAACAACTCCGGTGTCCCTCTCACATGTCGCCAAAAT
CCGCGGCACATCAAATGGTACCGTAATCAATCTGACAGAACTTGATGGCACGCCCTTCCATCCCTTTGAAGGACCAG
CCCCTATTGGATTTCCTGATCTGGGAGGTTGCGACTGGCACATAAACATGACACAGTTTGGCCACTCCAGCCAGACA
CAGTATGATGTCGATACAACCCCAGATACCTTCGTGCCACACCTGGGATCTATTCAAGCTAACGGTATTGGATCCGG
CAACTACGTGGGAGTCTTATCTTGGATCTCACCACCATCCCACCCCTCAGGATCCCAGGTTGACTTGTGGAAGATACC
GAATTATGGATCCTCGATCACTGAAGCCACGCACCTCGCACCTTCCGTCTACCCACCAGGTTTTGGAGAAGTCTTGGT

GTTTTTCATGAGCAAAATGCCCGGCCCTGGAGCCTACAATCTCCCTTGCCTACTCCCTCAAGAGTATATTAGTCACCT
CGCATCTGAGCAGGCCCCGACCGTTGGCGAGGCAGCCCTGCTGCATTATGTGGATCCGGACACCGGCAGGAACCTG
GGTGAGTTCAAAGCTTATCCTGACGGTTTTCTAACATGTGTACCAAATGGCGCTTCCAGCGGCCCTCAACAGCTCCCA
ATCAATGGCGTGTTCGTTTTTGTCAGCTGGGTAAGCCGCTTCTACCAGCTGAAGCCCGTGGGGACAGCTTCTTCTGC
CCGCGGACGCCTCGGTCTGCGGAGATAAAGGCCTATTTTCTTTAGTTTGAATTTACTGTTATTCGGTGTGCATTTCTA
TGTTTGGTGAGCGGTTTTCTGTGCTCAGAGTGTGTTTATTTTATGTAATTTAATTTCTTTGTGAGCTCCTGTTTAGCAG
GTCGTCCCTTCAGCAAGGACACAAAAAGATTTTAATTTTATTAAAAAAAAAAAAAAAAAAAGACCGGGAATTCGATAT
CAAGCTTATCGACCTGCAGATCGTTCAAACATTTGGCAATAAAGTTTCTTAAGATTGAATCCTGTTGCCGGTCTTGCG
ATGATTATCATATAATTTCTGTTGAATTACGTTAAGCATGTAATAATTAACATGTAATGCATGACGTTATTTATGAGAT
GGGTTTTTATGATTAGAGTCCCGCAATTATACATTTAATACGCGATAGAAAACAAAATATAGCGCGCAAACTAGGAT
AAATTATCGCGCGCGGTGTCATCTATGTTACTAGAT

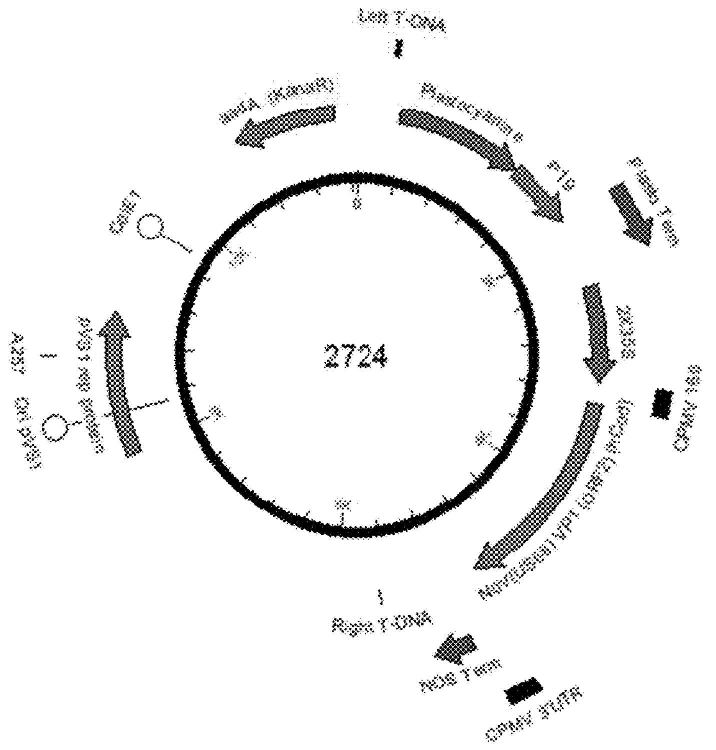

Figure 10A

IF-NoV(US68)VP2(ORF3)(hCod).c (SEQ ID NO: 79)

TCGTGCTTCGGCACCAGTACAATGGCTCAGGCCATTATTGGCGCCAT

Figure 10B

IF-NoV(US68)VP2(ORF3)(hCod).r (SEQ ID NO: 80)

ACTAAAGAAAATAGGCCTTCAGCGGCGGTTGTTAGCGAACAGAGGAAGTC

Figure 10C

Expression cassette number 2725 from 2X35S promoter to NOS terminator. Human codon-optimized VP2 from Norovirus GI.1/Norwalk/1968/US strain is underlined. (SEQ ID NO: 81)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGGCTCAGGCCATTATT
GGCGCCATCGCTGCAAGTACAGCCGGGAGTGCATTGGGGGCCGGAATACAGGTGGGCGGGGAAGCTGCATTGCA
GAGCCAGCGGTACCAGCAAAACCTGCAGTTACAGGAGAATAGCTTTAAACACGACAGGGAGATGATTGGATATCA
GGTGGAGGCCAGCAATCAGCTGCTCGCCAAAAACTTGGCTACTCGATACTCATTACTGCGCGCCGGGGGGTTGACT
AGCGCCGACGCCGCACGATCTGTCGCAGGCGCCCCCGTGACTCGGATCGTAGACTGGAACGGGGTACGAGTCTCG
GCTCCCGAGTCGTCTGCAACCACCCTGAGGTCGGGAGGGTTTATGTCCGTGCCCATCCCATTCGCTAGCAAACAGAA
ACAGGTCCAGAGCTCCGGAATCTCCAATCCCAATTACTCCCCTAGCTCTATCTCTCGTACCACTTCCTGGGTCGAGAG
TCAGAACAGCAGTAGATTTGGCAACCTGAGCCCCTACCATGCTGAAGCCCTGAACACTGTGTGGTTGACTCCACCTG
GTAGCACGGCCTCCTCAACCCTGAGTTCCGTGCCTCGCGGGTACTTCAATACCGACAGACTTCCTCTGTTCGCTAACA
ACCGCCGCTGAAGGCCTATTTTCTTTAGTTTGAATTTACTGTTATTCGGTGTGCATTTCTATGTTTGGTGAGCGGTTTT
CTGTGCTCAGAGTGTGTTTATTTTATGTAATTTAATTTCTTTGTGAGCTCCTGTTTAGCAGGTCGTCCCTTCAGCAAGG
ACACAAAAAGATTTTAATTTTATTAAAAAAAAAAAAAAAAAAGACCGGGAATTCGATATCAAGCTTATCGACCTGCA
GATCGTTCAAACATTTGGCAATAAAGTTTCTTAAGATTGAATCCTGTTGCCGGTCTTGCGATGATTATCATATAATTTC
TGTTGAATTACGTTAAGCATGTAATAATTAACATGTAATGCATGACGTTATTTATGAGATGGGTTTTTATGATTAGAG

TCCCGCAATTATACATTTAATACGCGATAGAAAACAAAATATAGCGCGCAAACTAGGATAAATTATCGCGCGCGGTG
TCATCTATGTTACTAGAT

Figure 11A

IF-GI2Leu03VP1.c (SEQ ID NO: 82)

TCGTGCTTCGGCACCAGTACAATGATGATGGCTTCAAAGGATGCTCCCCAAA

Figure 11B

IF-GI2Leu03VP1.r (SEQ ID NO: 83)

ACTAAAGAAAATAGGCCTTCAGATTCGGCGGACCCCTAGCCTGCCGCGTGCCGTAGA

Figure 11C

Expression cassette number 3300 from 2X35S promoter to NOS terminator. Human codon-optimized VP1 from Norovirus GI.2/Leuven/2003/Bel strain is underlined. (SEQ ID NO: 84)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGATGATGGCTTCAAAG
GATGCTCCCCAAAGCGCGGACGGAGCTAGCGGCGCCGGACAGTTGGTTCCGGAAGTCAACACTGCCGATCCACTGC
CCATGGAACCCGTAGCTGGTCCAACAACCGCTGTTGCCACCGCCGGCCAGGTTAACATGATCGATCCATGGATTGTT
AATAACTTTGTACAGAGCCCCCAGGGGGAGTTCACAATTTCTCCGAACAATACCCCTGGGGACATTCTGTTCGATCT
GCAACTGGGCCCACACTTGAATCCTTTCCTGAGCCATCTTTCACAGATGTACAACGGATGGGTTGGGAACATGCGTG
TTCGGATCCTCCTTGCTGGCAACGCCTTCAGTGCTGGCAAGATTATCGTGTGCTGCGTACCACCAGGGTTTACCTCGA
GTTCATTAACCATTGCTCAGGCCACCCTTTTCCCTCACGTGATCGCAGACGTGCGTACCTTAGAACCAATCGAAATGC
CCCTGGAAGATGTACGGAACGTGCTGTACCATACTAATGATAACCAGCCAACGATGAGATTAGTGTGCATGCTGTAC
ACCCCCCTGAGAACTGGAGGAGGTTCTGGAAATTCCGACAGTTTTGTGGTGGCTGGCAGGGTCCTGACCGCTCCCA
GTAGCGACTTCAGCTTTTTGTTCCTCGTTCCTCCTACAATCGAACAAAAAACAAGAGCATTCACAGTGCCCAACATTC
CACTGCAGACTTTAAGCAATTCCAGGTTTCCCAGCTTGATCCAGGGTATGATCCTTTCTCCCGACGCCTCCCAAGTTG
TGCAGTTCCAGAATGGGAGATGTCTTATCGACGGTCAGCTTCTGGGAACAACCCCTGCCACCTCCGGGCAACTCTTC
CGGGTGAGAGGCAAAATCAATCAGGGCGCCAGAACACTGAATCTGACAGAAGTGGACGGGAAACCCTTTATGGCG
TTCGATAGCCCCGCGCCCGTTGGATTCCCTGACTTCGGCAAGTGTGATTGGCACATGCGCATCAGTAAGACTCCCAA

CAACACTTCATCTGGAGACCCCATGAGGAGCGTGGATGTCCAGACCGACGTGCAGGGCTTCGTGCCGCACTTGGGA
TCTATCCAGTTCGATGAGGTGTTCAATCACCCTACTGGCGACTACATAGGCACAATTGAGTGGATAAGTCAACCATCT
ACACCTCCAGGGACCGACATAAACCTGTGGGAAATTCCTGATTACGGGTCATCCCTGAGTCAAGCTGCCAATCTTGC
ACCCCCTGTCTTTCCCCCCGGCTTTGGTGAGGCTCTTGTTTACTTCGTCTCTGCATTTCCTGGTCCTAACAACCGCTCC
GCCCCTAACGATGTTCCGTGTTTGTTACCCCAGGAATATGTGACTCATTTCGTTTCCGAACAGGCACCCACCATGGGG
GACGCTGCCCTGCTACACTATGTGGACCCCGACACCAATAGAAACCTCGGCGAGTTCAAACTCTACCCCGGGGGATA
CCTGACCTGTGTTCCAAATGGAGTGGGAGCAGGCCCACAACAGCTGCCCCTGAATGGGGTCTTCCTGTTCGTTTCTT
GGGTGTCACGCTTTTACCAGCTGAAGCCCGTTGGCACAGCTTCTACGGCACGCGGCAGGCTAGGGGTCCGCCGAAT
CTGAAGGCCTATTTTCTTTAGTTTGAATTTACTGTTATTCGGTGTGCATTTCTATGTTTGGTGAGCGGTTTTCTGTGCT
CAGAGTGTGTTTATTTTATGTAATTTAATTTCTTTGTGAGCTCCTGTTTAGCAGGTCGTCCCTTCAGCAAGGACACAAA
AAGATTTTAATTTTATTAAAAAAAAAAAAAAAAAAGACCGGGAATTCGATATCAAGCTTATCGACCTGCAGATCGTT
CAAACATTTGGCAATAAAGTTTCTTAAGATTGAATCCTGTTGCCGGTCTTGCGATGATTATCATATAATTTCTGTTGAA
TTACGTTAAGCATGTAATAATTAACATGTAATGCATGACGTTATTTATGAGATGGGTTTTTATGATTAGAGTCCCGCA
ATTATACATTTAATACGCGATAGAAAACAAAATATAGCGCGCAAACTAGGATAAATTATCGCGCGCGGTGTCATCTA
TGTTACTAGAT

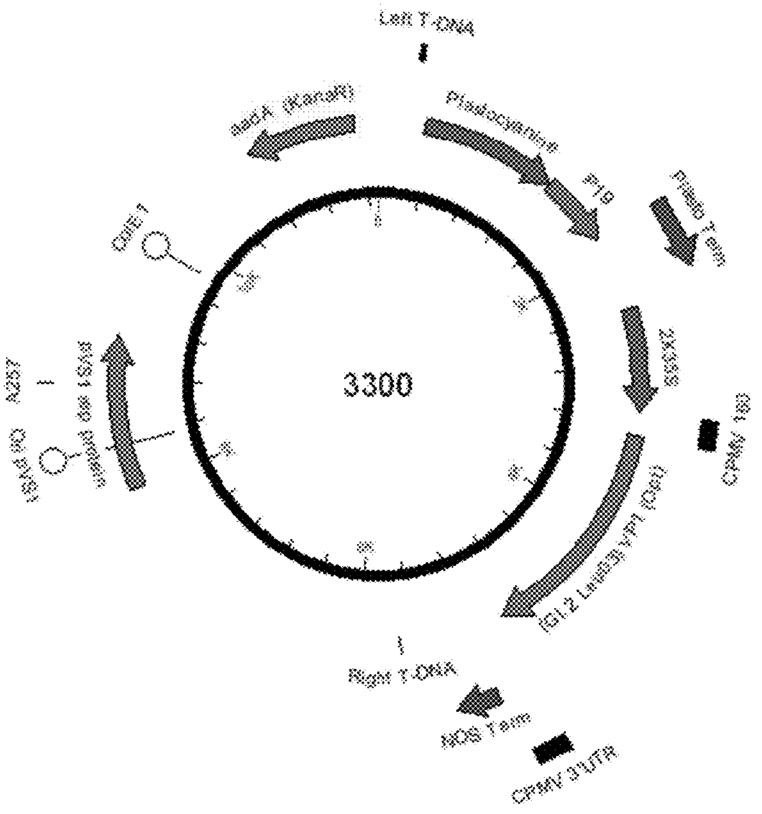

Figure 12A

GI2Leu+GI1VP1.r (SEQ ID NO: 85)

ATGCTCTTGTTTTTTGCTCAACGGTTGGTGGGACCAGAAAAAGAAAGTTGAAGTCG

Figure 12B

GI1VP1+GI2Leu.c (SEQ ID NO: 86)

TCCCACCAACCGTTGAGCAAAAAACAAGAGCATTCACAGTGCCCAACAT

Figure 12C

Expression cassette number 3360 from 2X35S promoter to NOS terminator. Human codon-optimized fusion VP1 S(GI.1)+P(GI.2) protein gene sequence is underlined. (SEQ ID NO: 87)

GTCAACATGGTGGAGCACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTATCTGTCACTTTATTGTGA
AGATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGTCT
TCAAAGCAAGTGGATTGATGTGATAACATGGTGGAGCACGACACACTTGTCTACTCCAAAAATATCAAAGATACAGT
CTCAGAAGACCAAAGGGCAATTGAGACTTTTCAACAAAGGGTAATATCCGGAAACCTCCTCGGATTCCATTGCCCAG
CTATCTGTCACTTTATTGTGAAGATAGTGGAAAAGGAAGGTGGCTCCTACAAATGCCATCATTGCGATAAAGGAAAG
GCCATCGTTGAAGATGCCTCTGCCGACAGTGGTCCCAAAGATGGACCCCCACCCACGAGGAGCATCGTGGAAAAAG
AAGACGTTCCAACCACGTCTTCAAAGCAAGTGGATTGATGTGATATCTCCACTGACGTAAGGGATGACGCACAATCC
CACTATCCTTCGCAAGACCCTTCCTCTATATAAGGAAGTTCATTTCATTTGGAGAGGTATTAAAATCTTAATAGGTTTT
GATAAAAGCGAACGTGGGGAAACCCGAACCAAACCTTCTTCTAAACTCTCTCTCATCTCTCTTAAAGCAAACTTCTCT
CTTGTCTTTCTTGCGTGAGCGATCTTCAACGTTGTCAGATCGTGCTTCGGCACCAGTACAATGATGATGGCTAGTAAA
GATGCGACCTCCTCTGTGGATGGTGCGTCAGGGGCAGGACAACTCGTACCCGAGGTAAACGCCAGCGACCCACTTG
CCATGGACCCCGTTGCCGGAAGTTCCACAGCAGTGGCCACAGCCGGTCAAGTGAATCCAATTGATCCGTGGATTATC
AACAATTTCGTCCAGGCACCCCAGGGCGAGTTCACAATTTCACCAAACAATACACCGGGCGATGTGCTATTCGATCT
TTCCTTGGGTCCTCACCTTAACCCTTTTCTACTCCATCTCTCACAGATGTACAATGGTTGGGTAGGAAACATGAGAGT
CCGGATCATGCTGGCTGGCAATGCCTTTACCGCTGGCAAGATCATCGTCAGTTGTATTCCTCCCGGATTTGGATCTCA
TAATCTGACCATTGCTCAAGCGACTCTCTTTCCCCATGTCATCGCCGACGTTAGGACCCTGGACCCCATCGAGGTGCC
CCTGGAGGACGTCCGGAATGTTTTGTTCCACAACAACGACAGAAACCAGCAGACGATGAGACTTGTCTGTATGCTCT
ATACCCCACTGCGGACTGGAGGCGGGACTGGAGACTCCTTCGTTGTGGCAGGAAGAGTGATGACATGCCCCTCCCC
CGACTTCAACTTTCTTTTTCTGGTCCCACCAACCGTTGAGCAAAAAACAAGAGCATTCACAGTGCCCAACATTCCACT
GCAGACTTTAAGCAATTCCAGGTTTCCCAGCTTGATCCAGGGTATGATCCTTTCTCCCGACGCCTCCCAAGTTGTGCA
GTTCCAGAATGGGAGATGTCTTATCGACGGTCAGCTTCTGGGAACAACCCCTGCCACCTCCGGGCAACTCTTCCGGG
TGAGAGGCAAAATCAATCAGGGCGCCAGAACACTGAATCTGACAGAAGTGGACGGGAAACCCTTTATGGCGTTCG
ATAGCCCCGCGCCCGTTGGATTCCCTGACTTCGGCAAGTGTGATTGGCACATGCGCATCAGTAAGACTCCCAACAAC
ACTTCATCTGGAGACCCCATGAGGAGCGTGGATGTCCAGACCGACGTGCAGGGCTTCGTGCCGCACTTGGGATCTA
TCCAGTTCGATGAGGTGTTCAATCACCCTACTGGCGACTACATAGGCACAATTGAGTGGATAAGTCAACCATCTACA

CCTCCAGGGACCGACATAAACCTGTGGGAAATTCCTGATTACGGGTCATCCCTGAGTCAAGCTGCCAATCTTGCACC
CCCTGTCTTTCCCCCCGGCTTTGGTGAGGCTCTTGTTTACTTCGTCTCTGCATTTCCTGGTCCTAACAACCGCTCCGCCC
CTAACGATGTTCCGTGTTTGTTACCCCAGGAATATGTGACTCATTTCGTTTCCGAACAGGCACCCACCATGGGGGAC
GCTGCCCTGCTACACTATGTGGACCCCGACACCAATAGAAACCTCGGCGAGTTCAAACTCTACCCCGGGGGATACCT
GACCTGTGTTCCAAATGGAGTGGGAGCAGGCCCACAACAGCTGCCCCTGAATGGGGTCTTCCTGTTCGTTTCTTGGG
TGTCACGCTTTTACCAGCTGAAGCCCGTTGGCACAGCTTCTACGGCACGCGGCAGGCTAGGGGTCCGCCGAATCTG
AAGGCCTATTTTCTTTAGTTTGAATTTACTGTTATTCGGTGTGCATTTCTATGTTTGGTGAGCGGTTTTCTGTGCTCAG
AGTGTGTTTATTTTATGTAATTTAATTTCTTTGTGAGCTCCTGTTTAGCAGGTCGTCCCTTCAGCAAGGACACAAAAA
GATTTTAATTTTATTAAAAAAAAAAAAAAAAAAAGACCGGGAATTCGATATCAAGCTTATCGACCTGCAGATCGTTCA
AACATTTGGCAATAAAGTTTCTTAAGATTGAATCCTGTTGCCGGTCTTGCGATGATTATCATATAATTTCTGTTGAATT
ACGTTAAGCATGTAATAATTAACATGTAATGCATGACGTTATTTATGAGATGGGTTTTTATGATTAGAGTCCCGCAAT
TATACATTTAATACGCGATAGAAAACAAAATATAGCGCGCAAACTAGGATAAATTATCGCGCGCGGTGTCATCTATG
TTACTAGAT

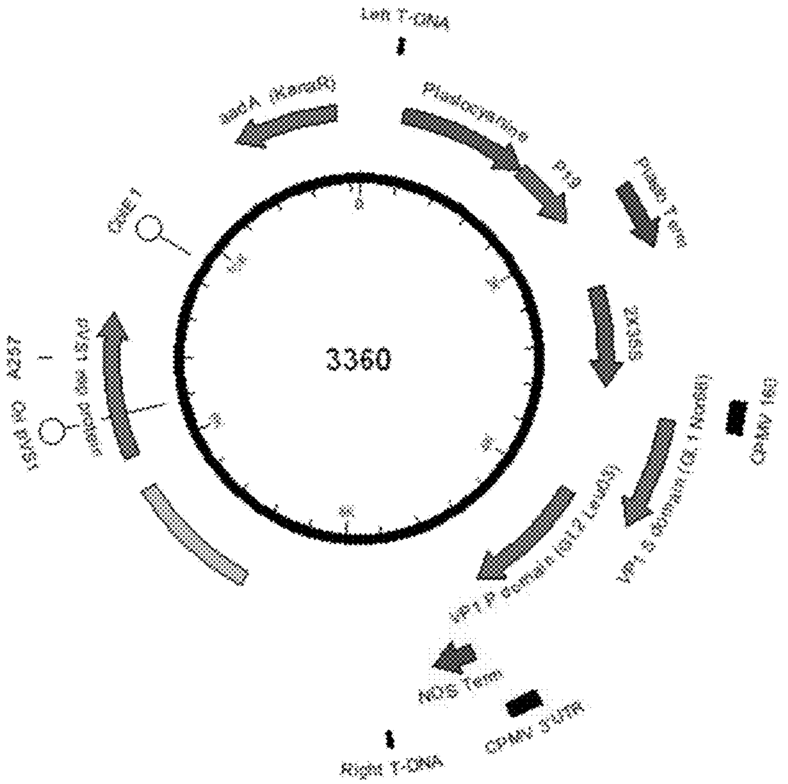

Figure 13A

Amino acid sequence of VP1 G1.1 (SEQ ID NO: 1)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVEQKTRPFTLPN
LPLSSLSNSRAPLPISSMGISPDNVQSVQFQNGRCTLDGRLVGTTPVSLSHVAKIRGTSNGTVINLTELDGTPFHPFEGPAPI
GFPDLGGCDWHINMTQFGHSSQTQYDVDTTPDTFVPHLGSIQANGIGSGNYVGVLSWISPPSHPSGSQVDLWKIPNYG
SSITEATHLAPSVYPPGFGEVLVFFMSKMPGPGAYNLPCLLPQEYISHLASEQAPTVGEAALLHYVDPDTGRNLGEFKAYP
DGFLTCVPNGASSGPQQLPINGVFVFVSWVSRFYQLKPVGTASSARGRLGLRR

Figure 13B

Nucleic acid sequence of wild-type VP1 G1.1 (SEQ ID NO: 13)

ATGATGATGGCGTCTAAGGACGCTACATCAAGCGTGGATGGCGCTAGTGGCGCTGGTCAGTTGGTACCGGAGGTTA
ATGCTTCTGACCCTCTTGCAATGGATCCTGTAGCAGGTTCTTCGACAGCAGTCGCGACTGCTGGACAAGTTAATCCTA
TTGATCCCTGGATAATTAATAATTTTGTGCAAGCCCCCCAAGGTGAATTTACTATTTCCCCAAATAATACCCCCGGTG
ATGTTTTGTTTGATTTGAGTTTGGGTCCCCATCTTAATCCTTTCTTGCTCCATCTATCACAAATGTATAATGGTTGGGTT
GGTAACATGAGAGTCAGGATTATGCTAGCTGGTAATGCCTTTACTGCGGGGAAGATAATAGTTTCCTGCATACCCCC
TGGTTTTGGTTCACATAATCTTACTATAGCACAAGCAACTCTCTTTCCACATGTGATTGCTGATGTTAGGACTCTAGAC
CCCATTGAGGTGCCTTTGGAAGATGTTAGGAATGTTCTCTTTCATAATAATGATAGAAATCAACAAACCATGCGCCTT
GTGTGCATGCTGTACACCCCCCTCCGCACTGGTGGTGGTACTGGTGATTCTTTTGTAGTTGCAGGGCGAGTTATGAC
TTGCCCCAGTCCTGATTTTAATTTCTTGTTTTTAGTCCCTCCTACGGTGGAGCAGAAAACCAGGCCCTTCACACTCCCA
AATCTGCCATTGAGTTCTCTGTCTAACTCACGTGCCCCTCTCCCAATCAGTAGTATGGGCATTTCCCCAGACAATGTCC
AGAGTGTGCAGTTCCAAAATGGTCGGTGTACTCTGGATGGCCGCCTGGTTGGCACCACCCCAGTTTCATTGTCACAT
GTTGCCAAGATAAGAGGGACCTCCAATGGCACTGTAATCAACCTTACTGAATTGGATGGCACACCCTTTCACCCTTTT
GAGGGCCCTGCCCCCATTGGGTTTCCAGACCTCGGTGGTTGTGATTGGCATATCAATATGACACAGTTTGGCCATTC
TAGCCAGACCCAGTATGATGTAGACACCACCCCTGACACTTTTGTCCCCCATCTTGGTTCAATTCAGGCAAATGGCAT
TGGCAGTGGTAATTATGTTGGTGTTCTTAGCTGGATTTCCCCCCCATCACACCCGTCTGGCTCCCAAGTTGACCTTTG
GAAGATCCCCAATTATGGGTCAAGTATTACGGAGGCAACACATCTAGCCCCTTCTGTATACCCCCCTGGTTTCGGAG
AGGTATTGGTCTTTTTCATGTCAAAAATGCCAGGTCCTGGTGCTTATAATTTGCCCTGTCTATTACCACAAGAGTACA
TTTCACATCTTGCTAGTGAACAAGCCCCTACTGTAGGTGAGGCTGCCCTGCTCCACTATGTTGACCCTGATACCGGTC
GGAATCTTGGGGAATTCAAAGCATACCCTGATGGTTTCCTCACTTGTGTCCCCAATGGGGCTAGCTCGGGTCCACAA
CAGCTGCCGATCAATGGGGTCTTTGTCTTTGTTTCATGGGTGTCCAGATTTTATCAATTAAAGCCTGTGGGAACTGCC
AGCTCGGCAAGAGGTAGGCTTGGTCTGCGCCGATAA

Figure 13C

Nucleic acid sequence of human codon-optimized VP1 G1.1 (SEQ ID NO: 18)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGCAGAAGACGCGGCCCTTTA
CACTGCCCAATCTCCCGCTTTCAAGTCTGAGTAATTCACGGGCCCCATTGCCGATCTCCTCAATGGGAATCTCCCCCG
ACAACGTCCAGTCTGTCCAATTCCAAAATGGGAGATGCACACTGGACGGTCGCCTGGTGGGAACAACTCCGGTGTC
CCTCTCACATGTCGCCAAAATCCGCGGCACATCAAATGGTACCGTAATCAATCTGACAGAACTTGATGGCACGCCCTT
CCATCCCTTTGAAGGACCAGCCCCTATTGGATTTCCTGATCTGGGAGGTTGCGACTGGCACATAAACATGACACAGT
TTGGCCACTCCAGCCAGACACAGTATGATGTCGATACAACCCCAGATACCTTCGTGCCACACCTGGGATCTATTCAA
GCTAACGGTATTGGATCCGGCAACTACGTGGGAGTCTTATCTTGGATCTCACCACCATCCCACCCCTCAGGATCCCAG
GTTGACTTGTGGAAGATACCGAATTATGGATCCTCGATCACTGAAGCCACGCACCTCGCACCTTCCGTCTACCCACCA
GGTTTTGGAGAAGTCTTGGTGTTTTTCATGAGCAAAATGCCCGGCCCTGGAGCCTACAATCTCCCTTGCCTACTCCCT
CAAGAGTATATTAGTCACCTCGCATCTGAGCAGGCCCCGACCGTTGGCGAGGCAGCCCTGCTGCATTATGTGGATCC
GGACACCGGCAGGAACCTGGGTGAGTTCAAAGCTTATCCTGACGGTTTTCTAACATGTGTACCAAATGGCGCTTCCA
GCGGCCCTCAACAGCTCCCAATCAATGGCGTGTTCGTTTTTGTCAGCTGGGTAAGCCGCTTCTACCAGCTGAAGCCC
GTGGGGACAGCTTCTTCTGCCCGCGGACGCCTCGGTCTGCGGAGATAA

Figure 14A

Amino acid sequence of VP1 G1.2_Leuven_2003_D2DEL3 (SEQ ID NO: 2)

MMMASKDAPQSADGASGAGQLVPEVNTADPLPMEPVAGPTTAVATAGQVNMIDPWIVNNFVQSPQGEFTISPNNT
PGDILFDLQLGPHLNPFLSHLSQMYNGWVGNMRVRILLAGNAFSAGKIIVCCVPPGFTSSSLTIAQATLFPHVIADVRTLEP
IEMPLEDVRNVLYHTNDNQPTMRLVCMLYTPLRTGGGSGNSDSFVVAGRVLTAPSSDFSFLFLVPPTIEQKTRAFTVPNIP
LQTLSNSRFPSLIQGMILSPDASQVVQFQNGRCLIDGQLLGTTPATSGQLFRVRGKINQGARTLNLTEVDGKPFMAFDSP
APVGFPDFGKCDWHMRISKTPNNTSSGDPMRSVDVQTDVQGFVPHLGSIQFDEVFNHPTGDYIGTIEWISQPSTPPGT
DINLWEIPDYGSSLSQAANLAPPVFPPGFGEALVYFVSAFPGPNNRSAPNDVPCLLPQEYVTHFVSEQAPTMGDAALLHY
VDPDTNRNLGEFKLYPGGYLTCVPNGVGAGPQQLPLNGVFLFVSWVSRFYQLKPVGTASTARGRLGVRRI

Figure 14B

Nucleic acid sequence of human codon-optimized VP1 G1.2_Leuven_2003_D2DEL3 (SEQ ID NO: 54)

ATGATGATGGCTTCAAAGGATGCTCCCCAAAGCGCGGACGGAGCTAGCGGCGCCGGACAGTTGGTTCCGGAAGTC
AACACTGCCGATCCACTGCCCATGGAACCCGTAGCTGGTCCAACAACCGCTGTTGCCACCGCCGGCCAGGTTAACAT
GATCGATCCATGGATTGTTAATAACTTTGTACAGAGCCCCCAGGGGGAGTTCACAATTTCTCCGAACAATACCCCTG
GGGACATTCTGTTCGATCTGCAACTGGGCCCACACTTGAATCCTTTCCTGAGCCATCTTTCACAGATGTACAACGGAT
GGGTTGGGAACATGCGTGTTCGGATCCTCCTTGCTGGCAACGCCTTCAGTGCTGGCAAGATTATCGTGTGCTGCGTA
CCACCAGGGTTTACCTCGAGTTCATTAACCATTGCTCAGGCCACCCTTTTCCCTCACGTGATCGCAGACGTGCGTACC
TTAGAACCAATCGAAATGCCCCTGGAAGATGTACGGAACGTGCTGTACCATACTAATGATAACCAGCCAACGATGA
GATTAGTGTGCATGCTGTACACCCCCCTGAGAACTGGAGGAGGTTCTGGAAATTCCGACAGTTTTGTGGTGGCTGG
CAGGGTCCTGACCGCTCCCAGTAGCGACTTCAGCTTTTTGTTCCTCGTTCCTCCTACAATCGAACAAAAAACAAGAGC
ATTCACAGTGCCCAACATTCCACTGCAGACTTTAAGCAATTCCAGGTTTCCCAGCTTGATCCAGGGTATGATCCTTTCT
CCCGACGCCTCCCAAGTTGTGCAGTTCCAGAATGGGAGATGTCTTATCGACGGTCAGCTTCTGGGAACAACCCCTGC
CACCTCCGGGCAACTCTTCCGGGTGAGAGGCAAAATCAATCAGGGCGCCAGAACACTGAATCTGACAGAAGTGGAC
GGGAAACCCTTTATGGCGTTCGATAGCCCCGCGCCCGTTGGATTCCCTGACTTCGGCAAGTGTGATTGGCACATGCG
CATCAGTAAGACTCCCAACAACACTTCATCTGGAGACCCCATGAGGAGCGTGGATGTCCAGACCGACGTGCAGGGC
TTCGTGCCGCACTTGGGATCTATCCAGTTCGATGAGGTGTTCAATCACCCTACTGGCGACTACATAGGCACAATTGA
GTGGATAAGTCAACCATCTACACCTCCAGGGACCGACATAAACCTGTGGGAAATTCCTGATTACGGGTCATCCCTGA
GTCAAGCTGCCAATCTTGCACCCCCTGTCTTTCCCCCCGGCTTTGGTGAGGCTCTTGTTTACTTCGTCTCTGCATTTCCT
GGTCCTAACAACCGCTCCGCCCCTAACGATGTTCCGTGTTTGTTACCCCAGGAATATGTGACTCATTTCGTTTCCGAA
CAGGCACCCACCATGGGGGACGCTGCCCTGCTACACTATGTGGACCCCGACACCAATAGAAACCTCGGCGAGTTCA
AACTCTACCCCGGGGGATACCTGACCTGTGTTCCAAATGGAGTGGGAGCAGGCCCACAACAGCTGCCCCTGAATGG
GGTCTTCCTGTTCGTTTCTTGGGTGTCACGCTTTTACCAGCTGAAGCCCGTTGGCACAGCTTCTACGGCACGCGGCAG
GCTAGGGGTCCGCCGAATCTGA

Figure 15A

Amino acid sequence of VP1 GI.3_LillaEdet_2008_H2DG70 (SEQ ID NO: 3)

MMMASKDAPTNMDGTSGAGQLVPEVSTAEPISMEPVAGAATAAATAGQVNMIDPWIMSNYVQAPQGEFTISPNNT
PGDILFDLQLGPHLNPFLSHLAQMYNGWVGNMKVRVLLAGNAFTAGKIIISCVPPGFAAQNVSIAQATMFPHVIADVRV
LEPIEVPLEDVRNVLFHNNDSTPTMRLICMLYTPLRASGSSSGTDPFVIAGRVLTCPSPDFNFLFLVPPNVEQKTKPFSVPNL
PLNVLSNSRVPSLIKSMMVSQDHGQMVQFQNGRVTLDGQLQGTTPTSASQLCKIRGTVYHATGGQGLNLTEIDGTPYH
AFESPAPIGFPDLGECDWHINASPANAFTDGSIIHRIDVAQDSTFAPHLGTIHYTNADYNANVGLICSLEWLSPPSGGAPK
VNPWAIPRYGSTLTEAAQLAPPIYPPGFGEAIVFFMSDFPIANGSDGLSVPCTIPQEFVTHFVNEQAPTRGEAALLHYVDP
DTHRNLGEFKLYPEGFMTCVPNSSGSGPQTLPINGVFTFISWVSRFYQLKPVGTTGPVRRLGIRRS

Figure 15B

Nucleic acid sequence of human codon-optimized VP1 GI.3_LillaEdet_2008_H2DG70 (SEQ ID NO: 55)

ATGATGATGGCTTCCAAGGATGCTCCCACAAACATGGATGGAACAAGCGGCGCGGGGCAACTTGTGCCGGAGGTG
TCCACGGCGGAACCCATTTCCATGGAACCTGTGGCCGGCGCAGCCACTGCTGCCGCCACCGCAGGACAGGTAAACA
TGATCGACCCCTGGATCATGTCAAATTACGTTCAGGCTCCACAGGGGGAGTTTACCATAAGCCCAAACAACACCCCG
GGTGACATCTTGTTTGACCTGCAGCTAGGACCACACTTGAATCCGTTTCTGAGTCACTTGGCTCAGATGTATAATGGA
TGGGTTGGAAACATGAAGGTGCGCGTGCTCCTGGCGGGCAATGCATTCACAGCCGGGAAGATTATTATCTCTTGCG
TGCCACCTGGATTTGCAGCCCAGAACGTGTCTATCGCACAGGCAACCATGTTTCCGCATGTCATCGCAGATGTGCGC
GTGCTAGAGCCCATCGAGGTGCCCCTTGAGGACGTGCGCAACGTCCTATTCCATAACAATGATAGCACCCCCACCAT
GCGCTTGATATGTATGTTATATACTCCCCTCCGCGCCAGTGGGTCCAGCTCCGGGACCGATCCTTTTGTGATTGCTGG
GCGGGTGTTGACTTGTCCTAGCCCTGACTTCAACTTCCTTTTTCTGGTGCCTCCAAATGTAGAACAGAAAACAAAGCC
ATTCAGCGTGCCAAACCTGCCCCTTAACGTGCTGTCGAATTCCCGAGTGCCTTCCCTTATTAAGTCCATGATGGTATC
TCAGGATCACGGTCAAATGGTGCAGTTTCAGAACGGCCGAGTGACGTTAGACGGGCAGCTGCAGGGCACAACCCC
AACCAGTGCCAGTCAGCTGTGTAAGATCAGAGGCACCGTCTACCACGCAACTGGCGGACAGGGGCTGAATCTTACT
GAGATCGATGGTACCCCCTACCATGCATTCGAGTCACCTGCACCTATTGGATTTCCCGATCTTGGGGAGTGTGATTG
GCATATCAATGCTTCACCTGCCAACGCTTTCACAGACGGGTCTATTATTCATCGCATTGACGTAGCACAGGATAGCAC
ATTTGCCCCGCACCTGGGTACCATCCACTATACGAACGCAGATTACAACGCAAACGTGGGTCTTATCTGTAGCCTAG
AGTGGCTATCTCCGCCAAGCGGTGGGGCCCCTAAAGTTAACCCATGGGCTATTCCTCGGTACGGGTCTACGCTGACT
GAGGCCGCTCAGCTGGCACCCCCCATATATCCACCAGGATTCGGGGAAGCCATTGTTTTCTTTATGTCCGATTTTCCG
ATAGCCAACGGTTCAGATGGCCTTAGTGTCCCTTGCACGATTCCACAGGAATTTGTGACACACTTCGTAAACGAGCA
GGCTCCTACTCGGGGCGAGGCTGCCTTGTTGCATTACGTAGACCCCGATACCCATAGAAACCTGGGCGAATTCAAAC
TCTACCCTGAAGGTTTCATGACCTGCGTACCTAACTCCTCCGGCAGTGGCCCTCAAACCTTGCCGATCAACGGCGTGT
TCACGTTTATCAGCTGGGTTTCACGGTTTTACCAACTCAAGCCCGTCGGAACAACTGGGCCAGTTCGGAGGCTCGGG
ATCAGACGGAGCTAG

Figure 16A

Amino acid sequence of VP1 GI.5_Siklos_HUN5407_2013_HUN_AHW99832 (SEQ ID NO: 44)

MMMASKDAPSSADGANGAGQLVPEVNNAEPLPLDPVAGASTALATAGQVNMIDPWIFNNFVQAPQGEFTISPNNTP
GDILFDLQLGPHLNPFLAHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVEQKTRPFSVPNIPL
QLLSNSRVPNLIQSMVLSPDQAQNVQFQNGRCTTDGQLLGTTPVSVSQILKFRGKVSAGSKVINLTELDGSPFLAFEAPAP
TGFPDLGTSDWHVEMSLNSNSQSSGNPILLRDIHPNSSEFVPHLGSVCVTAAIEVAGDYTGTIQWTSQPSNVTPVPDVNF
WTIPHYGSNLAEASQLAPVVYPPGFGEAIVYFMSPIPGPNTAHKPNLVPCLLPQEFVTHFVSEQAPSMGEAALVHYVDPD
TNRNLGEFKLYPEGFITCVPNGTGPQQLPLNGVFVFASWVSRFYQLKPVGTASSARGRLGVRR

Figure 16B

Amino acid sequence of GII.1_Ascension208_2010_USA_AFA55174 native VP1 (SEQ ID NO: 45)

MKMASNDAAPSNDGAAGLVPEVNNETMALEPVAGASIAAPLTGQNNVIDPWIRMNFVQAPNGEFTVSPRNSPGEVLL
NLELGPELNPFLAHLSRMYNGYAGGVEVQVLLAGNAFTAGKLVFAAIPPHFPLENLSPGQITMFPHVIIDVRTLEPVLLPLP
DVRNNFFHYNQQPEPRMRLVAMLYTPLRSNGSGDDVFTVSCRVLTRPSPDFDFNYLVPPTVESKTKPFTLPILTIGELSNS
RFPVPIDELYTSPNEGVVVQPQNGRSTLDGELLGTTQLVPSNICALRGRINAQVPDDHHQWNLQVTNANGTSFDPTEDV
PAPLGTPDFLANIYGVTSQRNPDNTCRAHDGVLATWSPKFTPKLGSVVLGTWEESDLDLNQPTRFTPVGLYDTGHFDQ
WVLPNYSGRLTLNMNLAPSVAPLFPGEQILFFRSHIPLKGGTSNGAIDCLLPQEWIQHFYQESAPSPTDVALIRYTNPDTG
RVLFEAKLHRQGFITVANSGSRPIVVPPNGYFRFDSWVNQFYSLAPMGTGNGRRRVQ

Figure 16C

Amino acid sequence of VP1 GII.2_CGMH47_2011_TW_AGT39206 (SEQ ID NO: 66)

MKMASNDAAPSTDGAAGLVPESNNEVMALEPVAGAALAAPVTGQTNIIDPWIRANFVQAPNGEFTVSPRNSPGEVLL
NLELGPELNPYLAHLARMYNGYAGGMEVQVMLAGNAFTAGKLVFAAVPPHFPVENLSPQQITMFPHVIIDVRTLEPVLL
PLPDVRNNFFHYNQKDDPKMRIVAMLYTPLRSNGSGDDVFTVSCRVLTRPSPDFDFTYLVPPTVESKTKPFTLPILTLGELS
NSRFPVSIDQMYTSPNEVISVQCQNGRCTLDGELQGTTQLQVSGICAFKGEVTAHLHDNDHLYNVTITNLNGSPFDPSED
IPAPLGVPDFQGRVFGVISQRDKHNTPGHNEPANRAHDAVVPTYTAQYTPKLGQIQIGTWQTDDLTVNQPVKFTPVGL
NDTDHFNQWVVPRYAGALNLNTNLAPSVAPVFPGERLLFFRSYIPLKGGYGTPAIDCLLPQEWVQHFYQEAAPSMSEVA
LVRYINPDTGRALFEAKLHRAGFMTVSSNTSAPVV

VPANGYFRFDSWVNQFYSLAPMGTGNGRRRIQ

Figure 16D

Amino acid sequence of VP1 GII.3_Jingzhou_2013402_CHN_AGX01095 (SEQ ID NO: 67)

MKMASNDAAPSNDGAAGLVPEISSEAMALEPVAGAAIAAPLTGQQNIIDPWIMNNFVQAPGGEFTVSPRNSPGEVLLN
LELGPEINPYLAHLARMYNGYAGGFEVQVVLAGNAFTAGKIIFAAIPPNFPIDNLSAAQITMCPHVIVDVRQLEPVNLPMP
DVRNNFFHYNQGSDSRLRLIAMLYTPLRANNSGDDVFTVSCRVLTRPSPDFSFNFLVPPTVESKTKPFSLPILTISEMSNSRF
PVPIDSLHTSPTENIVVQCQNGRVTLDGELMGTTQLLPSQICAFRGTLTRSTSRASDQADTATPRLFNYYWHIQLDNLNG
TPYDPAEDIPAPLGTPDFRGKVFGVASQRNPDATTRAHEAKIDTTSGRFTPKLGSLEISTESGDFDQNQPTRFTPVGIGVD
HEPDFQQWALPDYAGQFTHNMNLAPAVAPNFPGEQLLFFRSQLPSSGGRSNGILDCLVPQEWVQHFYQESAPSQTQV
ALVRYVNPDTGRVLFEAKLHKLRFMTIAKSGDSPITVPPNGYFRFESWVNPFYTLAPMGTGNGRRRIQ

Figure 16E

Amino acid sequence of VP1 GII.5_Alberta_2013_CA_ALT54485 (SEQ ID NO: 68)

MKMASNDATPSNDGAAGLVPESNNEAMALEPVVGASLAAPVTGQTNIIDPWIRTNFVQAPNGEFTVSPRNSPGEILVN
LELGPELNPYLAHLARMYNGYAGGMEVQVLLAGNAFTAGKIIFAAVPPYFPVENLSPSQITMFPHVIIDVRTLEPVLLPMP
DVRSTLFHFNQKDEPKMRLVAMLYTPLRSNGSGDDVFTVSCRILTRPSPEFDFTYLVPPTVESKTKPFTLPVLTLGELSNSRF
PLSIDEMVTSPNESIVVQPQNGRVTLDGELLGTTQLQACNICSIRGKVTGQVPNEQHMWNLEITNLNGTQFDPTDDVPA
PLGVPDFAGEVFGVLSQRNRGESNPANRAHDAVVATYSDKYTPKLGLVQIGTWNTNDVENQPTKFTPIGLNEVANGHR
FEQWTLPRYSGALTLNMNLAPAVAPLFPGERLLFFRSYVPLKGGFGNPAIDCLVPQEWVQHFYQESAPSLGDVALVRYV
NPDTGRVLFEAKLHKGGFLTVSSTSTGPVVVPANGYFRFDSWVNQFYSLAPMGTGNGRRRFQ

Figure 16F

Amino acid sequence of VP1 GII.7_Musa_2010_AII73774 (SEQ ID NO: 69)

MKMASNDAAPSNDGAAGLVPEINNEVMPLEPVAGASLATPVVGQQNIIDPWIRNNFVQAPAGEFTVSPRNSPGEILLD
LELGPELNPYLAHLARMYNGHAGGMEVQIVLAGNAFTAGKIIFAAIPPGFPYENLSPSQITMCPHVIIDVRQLEPVLLPMP
DIRNNFFHYNQGNDPKLRLIAMLYTPLRANNSGDDVFTVSCRVLTKPSPDFEFTFLVPPTVESKTKQFTLPILKISEMTNSRF
PVPVEMMYTARNENQVVQPQNGRVTLDGELLGTTPLLAVNICKFKGEVIAKNGDVRSYRMDMEITNTDGTPIDPTEDT
PGPIGSPDFQGILFGVASQRNKNEQNPATRAHEANINTGGDQYAPKLAQVKFFSESQDFEVHQPTVFTPVGVAGDTSHP
FRQWVLPRYGGHLTNNTHLAPAVAPLFPGEQILFFRSQIPSSGGHELGYMDCLVPQEWVQHFYQEAATAQSEVALIRFIN
PDTGRVLFEAKLHKQGFITVAHTGDNPIVMPPNGYFRFEAWVNQFYSLAPVGTGNGRRRIQ

Figure 16G

Amino acid sequence of VP1 consensus sequence from genotypes GI.1, GI.2, GI.3, GII.4, GII.6, GII.13 and GII.17 (SEQ ID NO: 70)

```
GI.1 SEQ ID NO:1      MMMASKDATSSVDGASGAGQLVPEVNASDPLAMDPVAGSSTAVATAGQVNPIDPWIINNF
GI.2 SEQ ID NO:2      MMMASKDAPQSADGASGAGQLVPEVNTADPLPMEPVAGPTTAVATAGQVNMIDPWIVNNF
GI.3 SEQ ID NO:3      MMMASKDAPTNMDGTSGAGQLVPEVSTAEPISMEPVAGAATAAATAGQVNMIDPWIMSNY
GII.4 SEQ ID NO:4     MKMASSDANPSDGS----AANLVPEVNN-EVMALEPVVGAAIAAPVAGQQNVIDPWIRNNF
GII.6 SEQ ID NO:5     MKMASNDAAPSNDG---AANLVPEANN-EVMALEPVVGASIAAPVVGQQNIIDPWIRENF
GII.13 SEQ ID NO:6    MKMASNDAAPSNDG---AASLVPEAIN-ETMPLEPVAGASIAAPVAGQTNIIDPWIRTNF
GII.17 SEQ ID NO:7    MKMASNDAAPSNDG---AAGLVPEGNN-ETLPLEPVAGAAIAAPVTGQNNIIDPWIRTNF
VP1 Con SEQ ID NO:70  MkMASXDAXpsXdGaSgAsXLVPEvnXneXXXlePVaGaXiAapvaGQXNXIDPWIrXNf

GI.1 SEQ ID NO:1      VQAPQGEFTISPNNTPGDVLFDLSLGPHLNPFLLHLSQMYNGWVGNMRVRIMLAGNAFTA
GI.2 SEQ ID NO:2      VQSPQGEFTISPNNTPGDILFDLQLGPHLNPFLSHLSQMYNGWVGNMRVRILLAGNAFSA
GI.3 SEQ ID NO:3      VQAPQGEFTISPNNTPGDILFDLQLGPHLNPFLSHLAQMYNGWVGNMKVRVLLAGNAFTA
GII.4 SEQ ID NO:4     VQAPGGEFTVSPRNAPGEILWSAPLGPDLNPYLSHLARMYNGYAGGFEVQVILAGNAFTA
GII.6 SEQ ID NO:5     VQAPQGEFTVSPRNSPGEMLLNLELGPELNPYLSHLSRMYNGYAGGMQVQVVLAGNAFTA
GII.13 SEQ ID NO:6    VQAPNGEFTVSPRNSPGEILLNLELGPDLNPYLAHLSRMYNGYAGGVEVQVLLAGNAFTA
GII.17 SEQ ID NO:7    VQAPNGEFTVSPRNSPGEILLNLELGPDLNPYLAHLSRMYNGYAGGVEVQVLLAGNAFTA
VP1 Con SEQ ID NO:70  VQaPqGEFTvSPrNXPGeiLXXlXLGPXLNPyLsHLsrMYNGyaGgmXVqvlLAGNAFtA

GI.1 SEQ ID NO:1      GKIIVSCIPPGFGSHNLTIAQATLFPHVIADVRTLDPIEVPLEDVRNVLFHNNDRNQQTM
GI.2 SEQ ID NO:2      GKIIVCCVPPGFTSSSLTIAQATLFPHVIADVRTLEPIEMPLEDVRNVLYHTND-NQPTM
GI.3 SEQ ID NO:3      GKIIISCVPPGFAAQNVSIAQATMFPHVIADVRVLEPIEVPLEDVRNVLFHNND-STPTM
GII.4 SEQ ID NO:4     GKVIFAAVPPNFPTEGLSPSQVTMFPHIVVDVRQLEPVLIPLPDVRNNFYHYNQSNDPTI
GII.6 SEQ ID NO:5     GKIIFAAVPPHFPVENINAAQITMCPHVIVDVRQLEPVLLPLPDIRNRFFHYNQENTSRM
GII.13 SEQ ID NO:6    GKILFAAIPPNFPVDMISPAQITMLPHLIVDVRTLEPIMIPLPDVRNVFYHFNNQPQPRM
GII.17 SEQ ID NO:7    GKILFAAVPPNFPVEFLSPAQITMLPHLIVDVRTLEPIMIPLPDVRNIFFHYNNQPNSRM
```

```
VP1 Con SEQ ID NO:70  GKiifaavPFXFpXXXlsXaQXTmfPHvivDVRtLePiXXPLpDvRNvffHXNKXnXptm

GI.1 SEQ ID NO:1      RLVCMLYTPLRTGGGTG--DSFVVAGRVMTCPSPDFNFLFLVPPTVEQKTRPFTLPNLPL
GI.2 SEQ ID NO:2      RLVCMLYTPLRTGGGSGNSDSFVVAGRVLTAPSSDFSFLFLVPPTIEQKTRAFTVPNIPL
GI.3 SEQ ID NO:3      RLICMLYTPLRASGSSSGTDPFVIAGRVLTCPSPDFNFLFLVPPNVEQKTKPFSVPNLPL
GII.4 SEQ ID NO:4     KLIAMLYTPLRANNA--GDDVFTVSCRVLTRPSPDFDFIFLVPPTVESKTKPFSVPVLTV
GII.6 SEQ ID NO:5     RLVAMLYTPLRAN-S--GEDVFTVSCRVLTRPAPDFEFTFLVPPTVESKTKPFSLPILTL
GII.13 SEQ ID NO:6    RLVAMLYTPLRSNGS--GDDVFTVSCRVLTRPTPDFEFIYLVPPSVESKTKPFTLPILTI
GII.17 SEQ ID NO:7    RLVAMLYTPLRSNGS--GDDVFTVSCRVLTRPTPDFEFTYLVPPSVESKTKPFSLPILTL
VP1 Con SEQ ID NO:70  rLvaMLYTPLRXogsXXXXDvFtvscRVlTrPspDFXFXfLVPPtvEskTkpFslPXltl

GI.1 SEQ ID NO:1      SSLSNSRAPLPISSMGISPDNVQSVQFQNGRCTLDGRLVGTTPVSLSHVAKIRGTSN---
GI.2 SEQ ID NO:2      QTLSNSRFPSLIQGMILSPDASQVVQFQNGRCLIDGQLLGTTPATSGQLFRVRGKIN--Q
GI.3 SEQ ID NO:3      NVLSNSRVPSLIKSMMVSQDHGQMVQFQNGRVTLDGQLQGTTPTSASQLCKIRGTVYHAT
GII.4 SEQ ID NO:4     EEMTNSRFPIPLEKLFTGPSSAFVVQPQNGRCTTDGVLLGTTQLSPVNICTFRGDVTHIT
GII.6 SEQ ID NO:5     GELSNSRFPAPIDMLYTDPNEGIVVQPQNGRCTLDGTLQGTTQLVPTQICAFRGTLIGQT
GII.13 SEQ ID NO:6    SELTNSRFPISIEQLYTAPNENNVVQCQNGRCTLDGELQGTTQLLSSAVCSYRGRTVANS
GII.17 SEQ ID NO:7    SELTNSRFPVPIDSLFTAQNNVLQVQCQNGRCTLDGELQGTTQLLPSGICAFRGRVTAET
VP1 Con SEQ ID NO:70  KelsNSRfPXpiXXlKtXpXXXXvVQXQNGRctlDGXLqGTTqlXXsXXcXXRGXXXXKt

GI.1 SEQ ID NO:1      -GT-------------------VINLTELDGTPFHPF-EGPAPIGFPDLGGCDWHINMTQFGHS
GI.2 SEQ ID NO:2      GAR-----------------TLNLTEVDGKPFMAF-DSPAPVGFPDFGKCDWHMRISKTPNN
GI.3 SEQ ID NO:3      GGQ-----------------GLNLTEIDGTPYHAF-ESPAPIGFPDLGECDWHINASFANAF
GII.4 SEQ ID NO:4     GSR---------------NYTMNLASQNWNDYDPTEEIPAPLGTPDFVGKIQGVLTQTTR--
GII.6 SEQ ID NO:5     SRSPDSTDSAPRRRDHPLHVQLKNLDGTQYDPTDEVPAVLGAIDFKGTVFGVASQRDVSG
GII.13 SEQ ID NO:6    GDN-------------WDQNVLQLTYPSGASYDPTDEVPAPLGTQDFSGILYGVLTQDNVRE
GII.17 SEQ ID NO:7    D-R-------------RDKWHMQLQNLNGTTYDPTDDVPAPLGTPDFKGVVFGVASQRNVGN
VP1 Con SEQ ID NO:70  gRSFDSTDSAPRdXXXXXXXnLtXXdgtXydptdXXPAplGXpDfXgXXXgvXXqXXXXX

GI.1 SEQ ID NO:1      S----------QTQYDVDTTPDTFVPHLGSIQANGI-----GSG-------NYVGVLSWISPPSHPSGS
GI.2 SEQ ID NO:2      TS-SGDPMRSVDVQTDVQGFVPHLGSIQFDEVFNHPTG----DYIGTIEWISQPSTPPGT
GI.3 SEQ ID NO:3      -T-DGSIIHRIDVA-QDSTFAPHLGTIHYTNADYNANV----GLICSLEWLSPPSGG-AP
GII.4 SEQ ID NO:4     -TDGSTRGHKATVYTGSADFAPKLGRVQFSTDTDRDFEANQNTKFTPVGVIQDGGTTHRN
```

Figure 16G
Continued

```
GII.6 SEQ ID NO:5      QQVGATRAHEVHINTTDPRYTPKLGSILMYSE-SDDFVTGQPVRFTPIGMGDN-------
GII.13 SEQ ID NO:6     NTSEAKNAKGVYISTTSGKFTPKIGSIGLHSI-TEDVRFNQQSRFTPVGVAQNENT-----
GII.17 SEQ ID NO:7     DAPGSTRAHEAVISTYSPQFVPKLGSVNFRSN-DNDFQ-LQPTKFTPVGINDDGDH-----
VP1 Con SEQ ID NO:70   XXXgXXXXhXXXXXtXsXXXXpkXGsXXXXXXXXXdfXXXXXXXftpXgXXXXXXXpXXX

GI.1 SEQ ID NO:1       QVDLWKIPNYGSSITEATHLAPSVYPPGFGEVLVFFMSKMPGPGA-----YNLPCLLPQE
GI.2 SEQ ID NO:2       DISLWEIPDYGSSLSQAANLAPPVFPPGFGEALVYFVSAFPGPNNRS-APNDVPCLLPQE
GI.3 SEQ ID NO:3       KVNPWAIPKYGSTLTEAAQLAPPIYPPGFGEAIVFFMSDFPIANG-S-DGLSVPCTIPQE
GII.4 SEQ ID NO:4      EPQQWVLPSYSGRNTHNVHLAPAVAPTFPGEQLLFFRSTMPGCSGYP--NMDLDCLLPQE
GII.6 SEQ ID NO:5      DWHQWELPDYPGHLTLNMNLAPAVAPAFPGERILFFRSIVPSAGGYG--SGQIDCLIPQE
GII.13 SEQ ID NO:6     PFQQWVLPHYAGALALNTNLAPAVAPTFPGEQLLFFRSRVPCVQGLQGQDAFIDCLLPQE
GII.17 SEQ ID NO:7     PFRQWELPDYSGLLTLNMNLAPPVAPNFPGEQLLFFRSFVPCSGGYN--QGIVDCLIPQE
VP1 Con SEQ ID NO:70   XXXqWXlPXYXgXltXnXnLAPXvaPXfpGEXllfFrSXXPXXXgyXXQXXXXdCllPQE

GI.1 SEQ ID NO:1       YISHLASEQAPTVGEAALLHYVDPDTGRNLGEFKAYPDGFLTCVPNGASSGPQQLPINGV
GI.2 SEQ ID NO:2       YVTHFVSEQAPTMGDAALLHYVDPDTNRNLGEFKLYPGGYLTCVPNGVGAGPQQLPLNGV
GI.3 SEQ ID NO:3       FVTHFVNEQAPTRGEAALLHYVDPDTHRNLGEFKLYPEGFMTCVPNSSGSGPQTLPINGV
GII.4 SEQ ID NO:4      WVQYFYQEAAPAQSDVALLRFVNPDTGRVLFECKLHKSGYVTVAH---TGQHDLVIPPNGY
GII.6 SEQ ID NO:5      WVQHFYQEAAPSQSAVALIRYVNPDTGRNIFEAKLHREGFITVAN--SGNNPIVVPPNGY
GII.13 SEQ ID NO:6     WVNHFYQEAAPSQADVALIRYVNPDTGRTLFEAKLHRSGFITVSH--TGAYPLVVPPNGH
GII.17 SEQ ID NO:7     WIQHFYQESAPSQSDVALIRYVNPDTGRTLFEAKLHRSGYITVAH--SGDYPLVVPANGY
VP1 Con SEQ ID NO:70   wvXhfyqEXAPXqXdvALlryVnPDTgRnlfEXKlhXXGfXTvXXXgXgXXpXvXPXNGX

GI.1 SEQ ID NO:1       FVFVSWVSRFYQLKPVGTASSARGRLGLRR-
GI.2 SEQ ID NO:2       FLFVSWVSRFYQLKPVGTASTARGRLGVRRI
GI.3 SEQ ID NO:3       FTFISWVSRFYQLKPVGTTGPVR-RLGIRRS
GII.4 SEQ ID NO:4      FRFDSWVNQFYTLAPMGNGTGRRRAV------
GII.6 SEQ ID NO:5      FRFEAWVNQFYTLTPMGTGQGRRRDQ-----
GII.13 SEQ ID NO:6     FRFDSWVNQFYSLAPMGTGNGRRRVQ-----
GII.17 SEQ ID NO:7     FRFDSWVNQFYSLAPMGTGNGRRRAQ------
VP1 Con SEQ ID NO:70   FrFXsWVnqFYXLXPmGtgXgrRrXXGXRXX
```

Amino acid sequence of VP1 GII.4_Sydney_2012_K4LM89 (SEQ ID NO: 4)

MKMASSDANPSDGSAANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIVVDVRQLEPVLI
PLPDVRNNFYHYNQSNDPTIKLIAMLYTPLRANNAGDDVFTVSCRVLTRPSPDFDFIFLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV

Figure 17B

Nucleic acid sequence of human codon-optimized VP1 GII.4_Sydney_2012_K4LM89 (SEQ ID NO: 56)

ATGAAAATGGCCTCGAGTGACGCTAACCCTAGTGACGGCAGCGCCGCCAATCTTGTGCCTGAGGTTAATAATGAGG
TGATGGCCCTGGAGCCTGTGGTGGGCGCAGCCATAGCAGCGCCCGTGGCCGGTCAGCAGAATGTGATTGACCCGT
GGATACGCAACAATTTTGTCCAAGCCCCTGGTGGGGAGTTCACCGTTAGCCCGAGAAATGCGCCAGGAGAAATCCT
GTGGTCGGCCCCATTGGGACCCGATCTGAACCCCTATTTGTCACATCTCGCTCGGATGTACAACGGGTATGCCGGCG
GATTTGAAGTGCAGGTGATTCTGGCTGGGAACGCGTTCACTGCTGGCAAAGTGATCTTTGCAGCGGTGCCTCCCAAC
TTCCCCACTGAAGGACTGTCTCCAAGCCAGGTCACAATGTTTCCACACATCGTGGTGGACGTACGGCAGCTAGAGCC
TGTCCTGATTCCCCTCCCTGATGTACGCAATAATTTCTACCACTACAATCAATCCAATGATCCGACCATTAAACTCATC
GCGATGTTGTACACCCCTCTGCGCGCTAACAATGCTGGAGACGACGTATTCACCGTGTCATGCAGAGTGCTCACCAG
ACCTTCACCAGACTTTGACTTTATCTTCTTAGTGCCCCCCACTGTTGAGAGCCGAACCAAGCCCTTTAGTGTCCCCGTA
CTCACAGTCGAGGAGATGACAAATAGCCGCTTTCCAATCCCCCTTGAGAAACTGTTCACAGGACCTTCCTCGGCATTC
GTGGTTCAGCCACAGAACGGACGCTGCACAACTGACGGCGTGCTGCTCGGAACCACCCAGCTTAGCCCTGTTAATAT
CTGTACGTTTAGAGGCGACGTAACTCACATAACTGGCTCACGGAACTATACCATGAATCTGGCATCACAGAATTGGA
ATGACTACGACCCAACCGAAGAGATTCCCGCACCTCTTGGAACCCCCGACTTTGTGGGAAAAATACAGGGCGTCCTG
ACACAAACCACCAGAACCGATGGCTCCACACGGGGACACAAGGCAACCGTCTACACTGGCTCTGCCGATTTTGCCCC
GAAACTGGGTAGAGTGCAGTTTGAGACCGACACTGACCGGGACTTTGAAGCCAATCAGAATACTAAGTTCACACCT
GTAGGAGTGATTCAGGACGGGGGCACCACTCACCGGAACGAGCCGCAACAATGGGTCCTGCCCTCTTATAGCGGG
AGGAATACTCATAATGTGCATTTGGCTCCTGCAGTGGCTCCCACGTTTCCCGGGGAACAACTGCTCTTTTTTCGTTCA
ACCATGCCTGGATGCTCCGGATATCCCAATATGGATCTCGATTGCCTGCTCCCACAGGAATGGGTGCAGTATTTTTAT
CAAGAGGCCGCACCAGCCCAATCCGACGTCGCACTTCTGCGGTTCGTGAATCCAGACACAGGCCGCGTGTTGTTTGA
GTGCAAATTGCACAAATCAGGATACGTTACAGTGGCTCATACTGGACAGCATGACCTGGTGATCCCACCCAACGGAT
ATTTTAGGTTCGACTCCTGGGTGAATCAGTTTTATACATTAGCCCCCATGGGGAATGGGACTGGCAGACGCAGGGCT
GTCTGA

Figure 18A

Amino acid sequence of VP1 GII.6_Ohio_2012_M9T020 (SEQ ID NO: 5)

MKMASNDAAPSNDGAANLVPEANNEVMALEPVVGASIAAPVVGQQNIIDPWIRENFVQAPQGEFTVSPRNSPGEMLL
NLELGPELNPYLSHLSRMYNGYAGGMQVQVVLAGNAFTAGKIIFAAVPPHFPVENINAAQITMCPHVIVDVRQLEPVLLP
LPDIRNRFFHYNQENTSRMRLVAMLYTPLRANSGEDVFTVSCRVLTRPAPDFEFTFLVPPTVESKTKPFSLPILTLGELSNSR
FPAPIDMLYTDPNEGIVVQPQNGRCTLDGTLQGTTQLVPTQICAFRGTLIGQTSRSPDSTDSAPRRRDHPLHVQLKNLDG
TQYDPTDEVPAVLGAIDFKGTVFGVASQRDVSGQQVGATRAHEVHINTTDPRYTPKLGSILMYSESDDFVTGQPVRFTPI
GMGDNDWHQWELPDYPGHLTLNMNLAPAVAPAFPGERILFFRSIVPSAGGYGSGQIDCLIPQEWVQHFYQEAAPSQS
AVALIRYVNPDTGRNIFEAKLHREGFITVANSGNNPIVVPPNGYFRFEAWVNQFYTLTPMGTGQGRRRDQ

Figure 18B

Nucleic acid sequence of human codon-optimized VP1 GII.6_Ohio_2012_M9T020 (SEQ ID NO: 60)

ATGAAGATGGCAAGCAACGACGCAGCTCCCTCCAATGATGGTGCCGCCAACCTGGTCCCCGAAGCTAATAATGAGG
TGATGGCGTTAGAGCCGGTGGTTGGCGCATCTATTGCAGCGCCTGTGGTCGGACAGCAGAACATCATTGATCCCTG
GATTCGCGAGAACTTCGTACAAGCTCCACAGGGGGAGTTCACAGTCTCCCCCCGGAACTCCCCGGGCGAGATGCTG
CTCAATCTGGAACTCGGCCCTGAACTAAACCCTTATCTGTCACACCTTTCACGGATGTACAATGGCTACGCAGGAGG
AATGCAAGTTCAGGTGGTCCTGGCCGGCAATGCTTTCACCGCGGGCAAAATCATCTTTGCGGCCGTTCCTCCACACT
TCCCTGTCGAAAATATCAACGCCGCCCAGATTACTATGTGCCCCCACGTGATTGTGGATGTGCGACAGTTAGAGCCA
GTTCTGCTGCCCCTGCCCGACATCAGAAACCGGTTCTTCCATTACAATCAAGAGAATACTTCACGGATGAGACTTGTT
GCGATGCTGTACACCCCTCTTCGTGCAAATTCCGGCGAAGACGTGTTCACTGTGTCTTGTCGAGTACTTACCCGACCC
GCCCCCGATTTCGAATTCACCTTCCTGGTTCCCCCTACTGTGGAGAGCAAGACAAAACCCTTCAGCCTCCCAATCTTA
ACACTCGGGGAGCTGTCTAATTCACGCTTCCCCGCACCTATTGATATGCTGTATACTGACCCCAACGAGGGGATAGT
GGTGCAGCCCCAAAATGGACGGTGTACTCTCGACGGCACGCTCCAGGGCACAACCCAACTGGTGCCAACCCAGATT
TGTGCATTCAGGGGCACTTTGATTGGGCAGACATCGAGATCTCCAGATTCTACTGATTCCGCGCCAAGGAGGAGGG
ACCACCCACTCCACGTTCAGTTAAAAAACCTGGACGGAACCCAGTACGACCCTACAGACGAGGTCCCCGCTGTCCTC
GGAGCCATCGACTTTAAAGGAACTGTATTTGGAGTGGCATCCCAAAGGGATGTCTCGGGGCAGCAGGTGGGAGCT
ACGAGAGCACATGAAGTCCACATTAACACCACAGACCCAAGATATACCCCAAAACTAGGGTCAATTTTAATGTATTC
GGAATCAGACGATTTTGTTACAGGTCAGCCCGTGCGGTTTACCCCGATCGGAATGGGGGACAACGATTGGCACCAG
TGGGAATTGCCCGATTACCCTGGACACCTCACCTTGAATATGAATCTGGCCCCAGCCGTCGCGCCCGCCTTCCCCGGT
GAGCGGATCCTCTTTTTTAGAAGCATAGTGCCCTCCGCAGGTGGGTATGGATCAGGGCAGATTGATTGCCTGATCCC
CCAAGAATGGGTACAGCATTTCTACCAGGAAGCAGCCCCTAGCCAGTCCGCAGTAGCACTGATCAGATATGTTAATC
CTGATACGGGAAGGAACATCTTCGAAGCAAAACTGCACCGTGAGGGCTTCATTACCGTCGCCAACAGTGGTAATAA
CCCTATTGTGGTGCCTCCTAATGGATACTTCAGGTTTGAGGCATGGGTGAATCAGTTTTATACTCTGACTCCCATGGG
GACAGGCCAGGGGCGACGCCGGGATCAGTGA

Figure 19A

Amino acid sequence of VP1 GII.13_VA173_2010_H9AWU4 (SEQ ID NO: 6)

MKMASNDAAPSNDGAASLVPEAINETMPLEPVAGASIAAPVAGQTNIIDPWIRTNFVQAPNGEFTVSPRNS
PGEILLNLELGPDLNPYLAHLSRMYNGYAGGVEVQVLLAGNAFTAGKILFAAIPPNFPVDMISPAQITMLPHLI
VDVRTLEPIMIPLPDVRNVFYHFNNQPQPRMRLVAMLYTPLRSNGSGDDVFTVSCRVLTRPTPDFEFIYLVPP
SVESKTKPFTLPILTISELTNSRFPISIEQLYTAPNENNVVQCQNGRCTLDGELQGTTQLLSSAVCSYRGRTVANS
GDNWDQNVLQLTYPSGASYDPTDEVPAPLGTQDFSGILYGVLTQDNVRENTGEAKNAKGVYISTTSGKFTPK
IGSIGLHSITEDVRPNQQSRFTPVGVAQNENTPFQQWVLPHYAGALALNTNLAPAVAPTFPGEQLLFFRSRVP
CVQGLQGQDAFIDCLLPQEWVNHFYQEAAPSQADVALIRYVNPDTGRTLFEAKLHRSGFITVSHTGAYPLVV
PPNGHFRFDSWVNQFYSLAPMGTGNGRRRVQ

Figure 19B

Nucleic acid sequence of human codon-optimized VP1 GII.13_VA173_2010_H9AWU4 (SEQ ID NO: 61)

ATGAAAATGGCTTCTAATGATGCCGCGCCCAGCAATGATGGTGCCGCCAGCCTTGTGCCCGAAGCAATTAACGAGA
CAATGCCCTTGGAGCCAGTCGCCGGGGCTTCTATTGCGGCCCCAGTTGCTGGACAGACGAATATCATCGATCCTTGG
ATACGGACTAATTTTGTTCAAGCTCCTAACGGAGAGTTCACTGTCTCCCCCCGTAATAGTCCTGGCGAGATCCTGTTG
AACCTCGAGTTGGGGCCAGATCTCAATCCTTACCTGGCTCATCTGTCGAGAATGTACAACGGGTACGCGGGGGGGG
TTGAGGTGCAGGTCTTACTGGCAGGTAACGCATTCACAGCAGGCAAGATTCTGTTTGCGGCCATCCCTCCTAATTTTC
CAGTGGATATGATATCTCCAGCACAGATTACAATGCTGCCCCATTTGATAGTGGATGTGCGGACACTTGAACCTATC
ATGATCCCTTTGCCCGATGTCCGAAATGTGTTTTATCATTTCAACAACCAGCCGCAGCCAAGAATGCGTCTCGTCGCG
ATGCTGTACACCCCGTTGCGGTCCAACGGCTCTGGCGATGATGTTTTCACAGTGTCGTGTCGAGTGTTAACCCGCCCT
ACCCCAGATTTTGAGTTTATATATCTAGTTCCCCCTTCTGTGGAAAGCAAGACTAAACCCTTTACTCTTCCCATTCTGA
CTATATCCGAGCTTACCAACTCCCGGTTCCCCATCTCAATCGAGCAACTGTACACTGCACCCAACGAGAACAACGTAG
TCCAGTGCCAGAACGGGAGATGTACCCTGGACGGGGAGCTCCAAGGGACCACGCAACTGTTAAGTTCAGCCGTTTG
CAGTTACAGAGGCAGGACTGTGGCGAACTCTGGTGATAACTGGGATCAAAATGTGTTGCAGCTGACTTACCCATCC
GGCGCAAGCTACGATCCAACAGATGAGGTGCCAGCGCCCCTTGGCACACAGGATTTCTCAGGAATTCTATACGGGG
TGCTTACTCAGGATAATGTGCGAGAAAATACTGGCGAGGCCAAGAATGCTAAAGGAGTGTATATAAGCACGACAAG
CGGTAAGTTTACCCCCAAAATTGGCAGTATTGGGCTCCACAGCATTACTGAGGACGTCCGCCCAAACCAGCAGTCTC
GTTTCACTCCCGTGGGGGTGGCACAGAACGAGAACACACCTTTCCAGCAGTGGGTCTTGCCCCATTATGCAGGTGCT
TTGGCGCTCAATACAAATCTGGCACCCGCCGTAGCGCCGACATTTCCTGGGGAGCAATTGCTGTTCTTTAGAAGCCG
CGTCCCGTGTGTTCAGGGCTTGCAGGGCCAGGACGCGTTCATTGATTGCCTCTTGCCCCAGGAATGGGTCAACCACT
TTTATCAGGAGGCAGCGCCCTCTCAAGCAGATGTGGCCCTGATAAGATATGTGAATCCCGACACAGGACGGACTTT
GTTTGAGGCAAAACTCCACCGGTCAGGATTCATTACTGTGAGTCACACAGGAGCCTATCCCCTTGTGGTTCCACCTAA
TGGCCACTTCAGGTTCGACTCTTGGGTCAATCAGTTTTATTCGCTGGCACCAATGGGTACCGGGAATGGTCGCCGTC
GGGTGCAATGA

Figure 20A

Amino acid sequence of VP1 GII.17_Kawa_2014_A0A077KVU6 (SEQ ID NO: 7)

MKMASNDAAPSNDGAAGLVPEGNNETLPLEPVAGAAIAAPVTGQNNIIDPWIRTNFVQAPNGEFTVSPRNS
PGEILLNLELGPDLNPYLAHLSRMYNGYAGGVEVQVLLAGNAFTAGKILFAAVPPNFPVEFLSPAQITMLPHLI
VDVRTLEPIMIPLPDVRNTFFHYNNQPNSRMRLVAMLYTPLRSNGSGDDVFTVSCRVLTRPTPDFEFTYLVPP
SVESKTKPFSLPILTLSELTNSRFPVPIDSLFTAQNNVLQVQCQNGRCTLDGELQGTTQLLPSGICAFRGRVTAE
TDHRDKWHMQLQNLNGTTYDPTDDVPAPLGTPDFKGVVFGVASQRNVGNDAPGSTRAHEAVISTYSPQFV
PKLGSVNFRSNDNDFQLQPTKFTPVGINDDGDHPFRQWELPDYSGLLTLNMNLAPPVAPNFPGEQLLFFRSF
VPCSGGYNQGIVDCLIPQEWIQHFYQESAPSQSDVALIRYVNPDTGRTLFEAKLHRSGYITVAHSGDYPLVVPA
NGYFRFDSWVNQFYSLAPMGTGNGRRRAQ

Figure 20B

Nucleic acid sequence of human codon-optimized VP1 GII.17_Kawa_2014_A0A077KVU6 (SEQ ID NO: 62)

ATGAAAATGGCATCTAACGACGCAGCCCCCTCAAACGATGGCGCTGCTGGACTCGTGCCGGAGGGGAATAATGAG
ACACTTCCACTAGAGCCGGTTGCAGGCGCCGCTATAGCTGCCCCAGTGACAGGGCAGAATAATATTATAGACCCTTG
GATTCGGACAAACTTCGTGCAGGCACCCAACGGCGAGTTTACAGTATCCCCCCGGAACTCCCCAGGTGAGATACTCC
TGAATCTTGAGCTCGGCCCTGACCTCAATCCATATCTGGCTCATCTGAGCCGCATGTACAATGGTTACGCTGGGGGG
GTCGAAGTGCAGGTCCTCCTGGCCGGAAACGCCTTTACCGCTGGCAAAATTCTGTTTGCCGCCGTTCCACCAAACTTT
CCAGTCGAATTCCTCTCTCCCGCGCAAATAACCATGCTGCCACATTTGATCGTTGACGTGCGGACCCTGGAGCCAATA
ATGATTCCCCTGCCGGATGTGCGTAACACCTTTTTCCATTATAACAATCAGCCAAACTCTCGGATGAGACTTGTTGCT
ATGCTGTACACCCCCCTGCGGAGCAACGGCAGTGGCGATGATGTGTTTACCGTGAGTTGCAGAGTCCTGACGCGCC
CAACCCCGGACTTCGAGTTCACCTACCTGGTGCCCCCTTCTGTGGAATCTAAGACCAAACCGTTTTCACTGCCAATCT
TAACTCTCTCCGAACTGACTAACAGCCGGTTTCCAGTACCCATAGATTCTCTTTTTACCGCTCAAAACAACGTACTCCA
AGTCCAGTGCCAGAACGGCCGCTGTACGCTTGATGGTGAGTTGCAGGGGACAACACAGCTACTCCCCAGTGGCATC
TGTGCATTCCGGGGCCGCGTGACCGCTGAGACAGACCATCGTGACAAATGGCACATGCAACTCCAAAACTTAAACG
GGACCACCTACGACCCAACCGACGACGTCCCTGCTCCGCTAGGGACTCCTGACTTTAAGGGGGTGGTGTTCGGAGT
GGCCTCTCAGCGGAATGTTGGGAATGACGCCCCCGGCTCTACCCGAGCTCACGAGGCCGTTATCTCAACATATAGCC
CCCAATTTGTGCCCAAGCTCGGATCCGTTAATTTTCGTAGTAACGACAACGACTTCCAACTGCAACCAACGAAGTTTA
CGCCAGTGGGGATTAATGATGATGGAGACCATCCTTTCCGCCAATGGGAACTACCAGATTATTCTGGGCTGCTCACC
CTCAATATGAACCTCGCCCCACCCGTGGCCCCTAATTTCCCCGGTGAGCAGCTGCTGTTTTTTCGGAGCTTTGTGCCA
TGCAGTGGCGGATATAATCAAGGCATCGTAGACTGCTTGATTCCCCAAGAGTGGATACAACATTTTTACCAGGAAAG
TGCGCCCTCCCAGTCCGATGTGGCCCTGATACGGTACGTTAACCCCGATACCGGAAGAACATTATTCGAAGCGAAAT
TGCACAGATCAGGGTACATTACCGTTGCACATTCCGGCGATTATCCCCTGGTGGTTCCCGCCAACGGTTACTTTAGGT
TCGATAGTTGGGTCAACCAGTTCTATTCACTAGCCCCAATGGGCACCGGTAACGGCAGACGCCGGGCTCAGTAG

Figure 21A

Amino acid sequence of VP1 US96: GII.4/Dresden174/1997/DE_AY741811 (SEQ ID NO: 8)

MKMASNDANPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKVIFAAVPPNFPTEGLSPSQVTMFPHIIVDVRQLEPVLIP
LPDVRNNFYHYNQSNDSTIKLIAMLYTPLKANNAGDDVFTVSCRVLTRPSPDFDFIFLVPPTVESRTKPFTVPILTVEEMSN
SRFPIPLEKLYTGPSSAFVVQPQNGRCTTDGVLLGTTQLSAVNICTFRGDVTHIAGSHDYTMNLASQNWNNYDPTEEIPA
PLGTPDFVGKIQGMLTQTTREDGSTRAHKATVSTGSVHFTPKLGSVQYTTDTNNDFQTGQNTKFTPVGVIQDGNNHQN
EPQQWVLPNYSGRTGHNVHLAPAVAPTFPGEQLLFFRSTMPGCSGYPNMNLDCLLPQEWVQHFYQEAAPAQSDVALL
RFVNPDTGRVLFECKLHKSGYVTVAHTGPHDLVIPPNGYFRFDSWVNQFYTLAPMGNGAGRRRAL

Figure 21B

Amino acid sequence of VP1 FH02: GII.4/FarmingtonHills/2002/US_AY502023 (SEQ ID NO: 9)

MKMASNDANPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEGLSPSQVTMFPHIIVDVRQLEPVLIP
LPDVRNNFYHYNQLNDPTIKLIAMLYTPLRANNAGEDVFTVSCRVLTRPSPDFDFIFLVPPTVESRTKPFTVPILTVEEMTN
SRFPIPLEKLFTGPSGAFVVQPQNGRCTTDGVLLGTTQLSPVNICTFRGDVTHIAGTHNYTMNLASQNWNNYDPTEEIPA
PLGTPDFVGRIQGMLTQTTRGDGSTRGHKATVSTGDVHFTPKLGSIQFNTDTNNDFETGQNTKFTPVGVVQDGNGTH
QNEPQQWVLPSYSGRTGHNVHLAPAVAPTFPGEQLLFFRSTMPGCSGYPNMNLDCLLPQEWVQHFYQEAAPAQSDV
ALLRFVNPDTGRVLFECKLHKSGYVTVAHTGQHDLVIPPNGYFRFDSWVNQFYTLAPMGNGTGRRRAL

Figure 21C

Amino acid sequence of VP1 Hnt04:GII.4/Hunter-NSW504D/2004/AU_DQ078814 (SEQ ID NO: 10)

MKMASNDATPSDGSTANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEVLSPSQVTMFPHIIVDVRQLEPVLIP
LPDVRNNLYHYNQSNDPTIRLIAMLYTPLRANNAGDDVFTVSCRVLTRPSPDFDFIFLVPPTVESRTKPFSVPILTVEEMTN
SRFPIPLEKLFTGPSSAFVVQPQNGRCTTDGVLLGTTQLSPVNICTFRGDVTHIAGTQNYTMNLASQNWNNYDPTEEIPA
PLGTPDFVGRIQGVLTQTTRRDGSTRGHKATVSTGSVHFTPKLGSVQFSTDTSNDFETGQNTRFTPVGVVQDGSTTHQN
EPQQWVLPDYSGRDSHNVHLAPAVAPTFPGEQLLFFRSTMPGCSGYPNMNLDCLLPQEWVQHFYQESAPAQSDVALL
RFVNPDTGRVLFECKLHKSGYVTVAHTGQHDLVIPPNGYFRFDSWVNQFYTLAPMGNGAGRRRAL

Figure 21D

Amino acid sequence of VP1 2006b: GII.4/Shellharbour-NSW696T/2006/AU_EF684915 (SEQ ID NO: 11)

MKMASNDANPSDGSAANLVPEVNNEVMALEPVVGAAIAAPVAGQQNVIDPWIRNNFVQAPGGEFTVSPRNAPGEIL
WSAPLGPDLNPYLSHLARMYNGYAGGFEVQVILAGNAFTAGKIIFAAVPPNFPTEGLSPSQVTMFPHIIVDVRQLEPVLIP
LPDVRNNFYHYNQSNDSTIKLIAMLYTPLRANNAGEDVFTVSCRVLTRPSPDFDFIFLVPPTVESRTKPFTVPILTVEEMTNS
RFPIPLEKLFTGPSGAFVVQPQNGRCTTDGVLLGTTQLSPVNICTFRGDVTHIAGSRNYTMNLASLKWNKYDPTEEIPAPL
GTPDFVGKIQGVLTQTTKGDGSTRGHKATIYTGSAPFTPKLGSVQFSTDTENDFETHQNTKFTPVGVTQDGSTTHRNEPQ
QWVLPSYSGRNVHNVHLAPAVAPTFPGEQLLFFRSTMPGCSGYPNMDLDCLLPQEWVQHFYQEAAPAQSDVALLRFV
NPDTGRVLFECKLHKSGYVTVAHTGQHDLVIPPNGYFRFDSWVNQFYTLAPMGNGTGRRRAL

Figure 21E

Amino acid sequence of VP1 NO09: GII.4/Orange-NSW001P/2008/AU_GQ845367 (SEQ ID NO: 12)

MKMASSDANPSDGSTANLVPEVNNEVMALEPVVGAAIAAPVAGQQNVIDPWIRNNFVQAPGGEFTVSPRNAPGEIL
WSAPLGPDMNPYLSHLARMYNGYAGGFEVQVILAGNAFTAGKIIFAAVPPNFPTEGLSPSQVTMFPHIIVDVRQLEPVLI
PLPDVRNNFYHYNQSNDPTIKLIAMLYTPLRANNAGDDVFTVSCRVLTRPSPDFDFIFLVPPTVESRTKPFSVPILTVEEMT
NSRFPIPLEKLFTGPSSAFVVQPQNGRCTTDGVLLGTTQLSPVNICTFRGDVTHIAGSRNYTMNLASQNWNSYDPTEEIPA
PLGTPDFVGKIQGVLTQTTRTDGSTRGHKATVYTGSADFSPKLGRVQFATDTDNDFDANQNTKFTPVGVIQDGNTAHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAL

Figure 22A

Amino acid sequence of VP1 GII.12_HS206_2010_USA_AEI29586 (SEQ ID NO: 28)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPVPIDELYTSPNESLVVQPQNGRCALDGELQGTTQLLPTAICSFRGRINQKVSGENHVWNMQVTNIDGTPFDPTEDV
PAPLGTPDFSGKLFGVLSQRDHDNACRSHDAVIATNSAKFTPKLGAIQIGTWEQDDVHINQPTKFTPVGLFESEGFNQW
TLPNYSGALTLNMGLAPPVAPTFPGEQILFFRSHIPLKGGVADPVIDCLLPQEWIQHLYQESAPSQTDVALIRFTNPDTGRV
LFEAKLHRSGYITVANTGSRPIVVPANGYFRFDSWVNQFYSLAPMGTGNGRRRVQ

Figure 22B

Amino acid sequence of GII.14_Saga_2008_JPN_ADE28701 native VP1 (SEQ ID NO: 46)

MKMASNDATPSDDGAAGLVPEINNEVMALEPVAGASIAAPVVGQQNIIDPWIRNNFVQAPAGEFTVSPRNSPGELLLD
LELGPELNPYLAHLARMYNGHAGGMEVQIVLAGNAFTAGKILFAAIPPSFPYENLSPAQLTMCPHVIVDVRQLEPVLLPM
PDIRNVFYHYNQNNSPKLRLVAMLYTPLRANNSGDDVFTVSCRVLTRPSPDFQFTFLVPPTVESKTKNFTLPVLRVSEMTN
SRFPVVLDQMYTSRNENIIVQPQNGRCTTDGELLGTTILQSVSICNFKGTMQAKLNEEPRYQLQLTNLDGSPIDPTDDMP
APLGTPDFQAMLYGVASQRSSIDNATRAHDAQIDTAGDTFAPKIGQVRFKSSSNDFDLHDPTKFTPIGVNVDDQHPFRQ
WSLPNYGGHLALNNHLAPAVTPLFPGEQILFFRSYIPSAGGHTDGAMDCLLPQEWVEHFYQEAAPSQSDIALVRFINPDT
GRVLFEAKLHKQGFLTIAASGDHPIVMPTNGYFRFEAWVNPFYTLAPVGTGSGRRRIQ

Figure 22C

Amino acid sequence of VP1 GII.21_Sali_2011_USA_AFC89665 (SEQ ID NO: 47)

MKMASNDAAPSNDGATGLVPEINTETLPLEPVAGAAIAAPVTGQNNIIDPWIRNNFVQAPNGEFTVSPRNSPGEILMNL
ELGPDLNPYLAHLSRMYNGYAGGVEVQVLLAGNAFTAGKILFAAVPPNFPVDMLSPAQITMLPHLIVDVRTLEPIMIPLP
DVRNVFYHFNNQPAPRMRLVAMLYTPLRSNGSGDDVFTVSCRVLTRPTPDFEFTYLVPPSVESKTKPFTLPILTIGELTNSR
FPAPIDQLYTSPNAQVVVQPQNGRCTLDGELQGTTQLLTTAICSYRGMTSNPTSDYWDDHLLHLVHPNGATYDPTEDVP
APFGTQDFRGILYGMLTQNPRTSGDEAANSHGIYISSTSEKFTPKLGTIGLHQVQGDIASNQQSKFTPVGIAVNGNTPFRQ
WELPNYSGALTLNTNLAPAVGPNFPGEQILFFRSNVPSVQGGQPIEIDCLIPQEWVSHFYQESAPSQSDVALVRYVNPDT
GRTIFEAKLHRQGFITIAATGSNPVVVPPNGYFRFDSWVNQFYALAPMGTGNGRRRVQ

Figure 23A

Amino acid sequence of native VP2 G1.1 (SEQ ID NO: 14)

MAQAIIGAIAASTAGSALGAGIQVGGEAALQSQRYQQNLQLQENSFKHDREMIGYQVEASNQLLAKNLATRYSLLRAGG
LTSADAARSVAGAPVTRIVDWNGVRVSAPESSATTLRSGGFMSVPIPFASKQKQVQSSGISNPNYSPSSISRTTSWVESQ
NSSRFGNLSPYHAEALNTVWLTPPGSTASSTLSSVPRGYFNTDRLPLFANNRR

Figure 23B

Nucleic acid sequence of wild-type VP2 G1.1 (SEQ ID NO: 15)

ATGGCCCAAGCCATAATTGGTGCAATTGCTGCTTCCACAGCAGGTAGTGCTCTGGGAGCGGGCATACAGGTTGGTG
GCGAAGCGGCCCTCCAAAGCCAAAGGTATCAACAAAATTTGCAACTGCAAGAAAATTCTTTTAAACATGACAGGGA
AATGATTGGGTATCAGGTTGAAGCTTCAAATCAATTATTGGCTAAAAATTTGGCAACTAGATATTCACTCCTCCGTGC
TGGGGGTTTGACCAGTGCTGATGCAGCAAGATCTGTGGCAGGAGCTCCAGTCACCCGCATTGTAGATTGGAATGGC
GTGAGAGTGTCTGCTCCCGAGTCCTCTGCTACCACATTGAGATCCGGTGGCTTCATGTCAGTTCCCATACCATTTGCC
TCTAAGCAAAAACAGGTTCAATCATCTGGTATTAGTAATCCAAATTATTCCCCTTCATCCATTTCTCGAACCACTAGTT
GGGTCGAGTCACAAAACTCATCGAGATTTGGAAATCTTTCTCCATACCACGCGGAGGCTCTCAATACAGTGTGGTTG
ACTCCACCCGGTTCAACAGCCTCTTCTACACTGTCTTCTGTGCCACGTGGTTATTTCAATACAGACAGGTTGCCATTAT
TCGCAAATAATAGGCGATGA

Figure 23C

Nucleic acid sequence of human codon-optimized VP2 G1.1 (SEQ ID NO: 19)

ATGGCTCAGGCCATTATTGGCGCCATCGCTGCAAGTACAGCCGGGAGTGCATTGGGGGCCGGAATACAGGTGGGC
GGGGAAGCTGCATTGCAGAGCCAGCGGTACCAGCAAAACCTGCAGTTACAGGAGAATAGCTTTAAACACGACAGG
GAGATGATTGGATATCAGGTGGAGGCCAGCAATCAGCTGCTCGCCAAAAACTTGGCTACTCGATACTCATTACTGCG
CGCCGGGGGGTTGACTAGCGCCGACGCCGCACGATCTGTCGCAGGCGCCCCCGTGACTCGGATCGTAGACTGGAA
CGGGGTACGAGTCTCGGCTCCCGAGTCGTCTGCAACCACCCTGAGGTCGGGAGGGTTTATGTCCGTGCCCATCCCAT
TCGCTAGCAAACAGAAACAGGTCCAGAGCTCCGGAATCTCCAATCCCAATTACTCCCCTAGCTCTATCTCTCGTACCA
CTTCCTGGGTCGAGAGTCAGAACAGCAGTAGATTTGGCAACCTGAGCCCCTACCATGCTGAAGCCCTGAACACTGTG
TGGTTGACTCCACCTGGTAGCACGGCCTCCTCAACCCTGAGTTCCGTGCCTCGCGGGTACTTCAATACCGACAGACTT
CCTCTGTTCGCTAACAACCGCCGCTGA

FIGURE 23D

Nucleic acid sequence of human codon-optimized VP2 GII.4/ Sydney/NSW0514/2012/AU (SEQ ID NO:120)

ATGGCTGGGGCCTTTTTTGCAGGTTTGGCTAGTGACGTCCTCGGGTCGGGCCTCGGAAGTCTGATCAATGCAGGAG
CTGGAGCGATTAATCAAAAAGTCGAGTTCGAGAATAACCGGAAACTTCAACAGGCAAGTTTCCAATTCTCAAGCAAT
TTGCAGCAGGCCTCATTCCAACACGACAAGGAAATGCTCCAGGCCCAGATTGAGGCCACCAAGAAACTGCAACAAG
AGATGATGAAGGTCAAACAGGCCATGCTGCTGGAGGGCGGCTTTTTCGAGACCGATGCTGCGCGCGGAGCCATCA
ACGCCCCAATGACAAAGGCACTCGACTGGAGTGGCACACGGTATTGGGCACCCGATGCCAGAACGACTACCTATAA
TGCCGGAAGGTTCTCCACACCTCAACCTTCTGGTGCCCTCCCAGGGCGCGCAAATCTGAGGGACGCTGTGCCCGCTA
GGGGCTCCTCATCAAAGTCTTCCAATAGCTCCACTGCAACCTCGGTTTACTCAAACCAGACCACTTCAACAAGATTAG
GATCAACCGCCGTGTCGGGAACATCTGTCTCCTCTTTTCCTTCTACAGCACGAACCAGGTCTTGGGTCGAGGACCAG
AGCAGAAACCTGTCTCCGTCCATGCGCGGTGCTCACAACATTTCCTTCGTGACCCCTCCTTCTTCCCGATCCTCCAGCC
AAGGGACAGTGTCCACAGTGCCCAAAGAAGTGCTCGACTCTTGGACAGGTGCGTTCAATACCAGACGCCAGCCTCT
CTTTGCTCATATACGCAAAAGGGGTGAGTCACGAGCA

Figure 23E

Amino acid sequence of VP2 GII.4/Sydney/NSW0514/2012/AU (SEQ ID NO:121)

MAGAFFAGLASDVLGSGLGSLINAGAGAINQKVEFENNRKLQQASFQFSSNLQQASFQHDKEMLQAQIEATKKLQQEM
MKVKQAMLLEGGFFETDAARGAINAPMTKALDWSGTRYWAPDARTTTYNAGRFSTPQPSGALPGRANLRDAVPARGS
SSKSSNSSTATSVYSNQTTSTRLGSTAVSGTSVSSFPSTARTRSWVEDQSRNLSPSMRGAHNISFVTPPSSRSSSQGTVSTV
PKEVLDSWTGAFNTRRQPLFAHIRKRGESRA

Figure 24A

Nucleic acid sequence of wild-type VP1/VP2 G1.1 (SEQ ID NO: 16)

ATGATGATGGCGTCTAAGGACGCTACATCAAGCGTGGATGGCGCTAGTGGCGCTGGTCAGTTGGTACCGGAGGTTA
ATGCTTCTGACCCTCTTGCAATGGATCCTGTAGCAGGTTCTTCGACAGCAGTCGCGACTGCTGGACAAGTTAATCCTA
TTGATCCCTGGATAATTAATAATTTTGTGCAAGCCCCCCAAGGTGAATTTACTATTTCCCCAAATAATACCCCCGGTG
ATGTTTTGTTTGATTTGAGTTTGGGTCCCCATCTTAATCCTTTCTTGCTCCATCTATCACAAATGTATAATGGTTGGGTT
GGTAACATGAGAGTCAGGATTATGCTAGCTGGTAATGCCTTTACTGCGGGGAAGATAATAGTTTCCTGCATACCCCC
TGGTTTTGGTTCACATAATCTTACTATAGCACAAGCAACTCTCTTTCCACATGTGATTGCTGATGTTAGGACTCTAGAC
CCCATTGAGGTGCCTTTGGAAGATGTTAGGAATGTTCTCTTTCATAATAATGATAGAAATCAACAAACCATGCGCCTT
GTGTGCATGCTGTACACCCCCCTCCGCACTGGTGGTGGTACTGGTGATTCTTTTGTAGTTGCAGGGCGAGTTATGAC
TTGCCCCAGTCCTGATTTTAATTTCTTGTTTTTAGTCCCTCCTACGGTGGAGCAGAAAACCAGGCCCTTCACACTCCCA
AATCTGCCATTGAGTTCTCTGTCTAACTCACGTGCCCCTCTCCCAATCAGTAGTATGGGCATTTCCCCAGACAATGTCC
AGAGTGTGCAGTTCCAAAATGGTCGGTGTACTCTGGATGGCCGCCTGGTTGGCACCACCCCAGTTTCATTGTCACAT
GTTGCCAAGATAAGAGGGACCTCCAATGGCACTGTAATCAACCTTACTGAATTGGATGGCACACCCTTTCACCCTTTT
GAGGGCCCTGCCCCCATTGGGTTTCCAGACCTCGGTGGTTGTGATTGGCATATCAATATGACACAGTTTGGCCATTC
TAGCCAGACCCAGTATGATGTAGACACCACCCCTGACACTTTTGTCCCCCATCTTGGTTCAATTCAGGCAAATGGCAT
TGGCAGTGGTAATTATGTTGGTGTTCTTAGCTGGATTTCCCCCCCATCACACCCGTCTGGCTCCCAAGTTGACCTTTG
GAAGATCCCCAATTATGGGTCAAGTATTACGGAGGCAACACATCTAGCCCCTTCTGTATACCCCCCTGGTTTCGGAG
AGGTATTGGTCTTTTTCATGTCAAAAATGCCAGGTCCTGGTGCTTATAATTTGCCCTGTCTATTACCACAAGAGTACA
TTTCACATCTTGCTAGTGAACAAGCCCCTACTGTAGGTGAGGCTGCCCTGCTCCACTATGTTGACCCTGATACCGGTC
GGAATCTTGGGGAATTCAAAGCATACCCTGATGGTTTCCTCACTTGTGTCCCCAATGGGGCTAGCTCGGGTCCACAA
CAGCTGCCGATCAATGGGGTCTTTGTCTTTGTTTCATGGGTGTCCAGATTTTATCAATTAAAGCCTGTGGGAACTGCC
AGCTCGGCAAGAGGTAGGCTTGGTCTGCGCCGATAATGGCCCAAGCCATAATTGGTGCAATTGCTGCTTCCACAGC
AGGTAGTGCTCTGGGAGCGGGCATACAGGTTGGTGGCGAAGCGGCCCTCCAAAGCCAAAGGTATCAACAAAATTT
GCAACTGCAAGAAAATTCTTTTAAACATGACAGGGAAATGATTGGGTATCAGGTTGAAGCTTCAAATCAATTATTGG
CTAAAAATTTGGCAACTAGATATTCACTCCTCCGTGCTGGGGGTTTGACCAGTGCTGATGCAGCAAGATCTGTGGCA
GGAGCTCCAGTCACCCGCATTGTAGATTGGAATGGCGTGAGAGTGTCTGCTCCCGAGTCCTCTGCTACCACATTGAG
ATCCGGTGGCTTCATGTCAGTTCCCATACCATTTGCCTCTAAGCAAAAACAGGTTCAATCATCTGGTATTAGTAATCC
AAATTATTCCCCTTCATCCATTTCTCGAACCACTAGTTGGGTCGAGTCACAAAACTCATCGAGATTTGGAAATCTTTCT
CCATACCACGCGGAGGCTCTCAATACAGTGTGGTTGACTCCACCCGGTTCAACAGCCTCTTCTACACTGTCTTCTGTG
CCACGTGGTTATTTCAATACAGACAGGTTGCCATTATTCGCAAATAATAGGCGATGA

Figure 24B

Nucleic acid sequence of wild-type VP1/VP2/3'UTR G1.1 (SEQ ID NO: 17)

ATGATGATGGCGTCTAAGGACGCTACATCAAGCGTGGATGGCGCTAGTGGCGCTGGTCAGTTGGTACCGGAGGTTA
ATGCTTCTGACCCTCTTGCAATGGATCCTGTAGCAGGTTCTTCGACAGCAGTCGCGACTGCTGGACAAGTTAATCCTA
TTGATCCCTGGATAATTAATAATTTTGTGCAAGCCCCCCAAGGTGAATTTACTATTTCCCCAAATAATACCCCCGGTG
ATGTTTTGTTTGATTTGAGTTTGGGTCCCCATCTTAATCCTTTCTTGCTCCATCTATCACAAATGTATAATGGTTGGGTT
GGTAACATGAGAGTCAGGATTATGCTAGCTGGTAATGCCTTTACTGCGGGGAAGATAATAGTTTCCTGCATACCCCC
TGGTTTTGGTTCACATAATCTTACTATAGCACAAGCAACTCTCTTTCCACATGTGATTGCTGATGTTAGGACTCTAGAC
CCCATTGAGGTGCCTTTGGAAGATGTTAGGAATGTTCTCTTTCATAATAATGATAGAAATCAACAAACCATGCGCCTT
GTGTGCATGCTGTACACCCCCCTCCGCACTGGTGGTGGTACTGGTGATTCTTTTGTAGTTGCAGGGCGAGTTATGAC
TTGCCCCAGTCCTGATTTTAATTTCTTGTTTTTAGTCCCTCCTACGGTGGAGCAGAAAACCAGGCCCTTCACACTCCCA
AATCTGCCATTGAGTTCTCTGTCTAACTCACGTGCCCCTCTCCCAATCAGTAGTATGGGCATTTCCCCAGACAATGTCC
AGAGTGTGCAGTTCCAAAATGGTCGGTGTACTCTGGATGGCCGCCTGGTTGGCACCACCCCAGTTTCATTGTCACAT
GTTGCCAAGATAAGAGGGACCTCCAATGGCACTGTAATCAACCTTACTGAATTGGATGGCACACCCTTTCACCCTTTT
GAGGGCCCTGCCCCCATTGGGTTTCCAGACCTCGGTGGTTGTGATTGGCATATCAATATGACACAGTTTGGCCATTC
TAGCCAGACCCAGTATGATGTAGACACCACCCCTGACACTTTTGTCCCCCATCTTGGTTCAATTCAGGCAAATGGCAT
TGGCAGTGGTAATTATGTTGGTGTTCTTAGCTGGATTTCCCCCCCATCACACCCGTCTGGCTCCCAAGTTGACCTTTG
GAAGATCCCCAATTATGGGTCAAGTATTACGGAGGCAACACATCTAGCCCCTTCTGTATACCCCCCTGGTTTCGGAG
AGGTATTGGTCTTTTTCATGTCAAAAATGCCAGGTCCTGGTGCTTATAATTTGCCCTGTCTATTACCACAAGAGTACA
TTTCACATCTTGCTAGTGAACAAGCCCCTACTGTAGGTGAGGCTGCCCTGCTCCACTATGTTGACCCTGATACCGGTC
GGAATCTTGGGGAATTCAAAGCATACCCTGATGGTTTCCTCACTTGTGTCCCCAATGGGGCTAGCTCGGGTCCACAA
CAGCTGCCGATCAATGGGGTCTTTGTCTTTGTTTCATGGGTGTCCAGATTTTATCAATTAAAGCCTGTGGGAACTGCC
AGCTCGGCAAGAGGTAGGCTTGGTCTGCGCCGATAATGGCCCAAGCCATAATTGGTGCAATTGCTGCTTCCACAGC
AGGTAGTGCTCTGGGAGCGGGCATACAGGTTGGTGGCGAAGCGGCCCTCCAAAGCCAAAGGTATCAACAAAATTT
GCAACTGCAAGAAAATTCTTTTAAACATGACAGGGAAATGATTGGGTATCAGGTTGAAGCTTCAAATCAATTATTGG
CTAAAAATTTGGCAACTAGATATTCACTCCTCCGTGCTGGGGGTTTGACCAGTGCTGATGCAGCAAGATCTGTGGCA
GGAGCTCCAGTCACCCGCATTGTAGATTGGAATGGCGTGAGAGTGTCTGCTCCCGAGTCCTCTGCTACCACATTGAG
ATCCGGTGGCTTCATGTCAGTTCCCATACCATTTGCCTCTAAGCAAAAACAGGTTCAATCATCTGGTATTAGTAATCC
AAATTATTCCCCTTCATCCATTTCTCGAACCACTAGTTGGGTCGAGTCACAAAACTCATCGAGATTTGGAAATCTTTCT
CCATACCACGCGGAGGCTCTCAATACAGTGTGGTTGACTCCACCCGGTTCAACAGCCTCTTCTACACTGTCTTCTGTG
CCACGTGGTTATTTCAATACAGACAGGTTGCCATTATTCGCAAATAATAGGCGATGATGTTGTAATATGAAATGTGG
GCATCATATTCATTTAATTAGGTTTAATTAGGTTTAATTTGATGTT

Figure 24C

Nucleic acid sequence of human codon-optimized VP1/VP2 G1.1 (SEQ ID NO: 20)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGCAGAAGACGCGGCCCTTTA
CACTGCCCAATCTCCCGCTTTCAAGTCTGAGTAATTCACGGGCCCCATTGCCGATCTCCTCAATGGGAATCTCCCCCG
ACAACGTCCAGTCTGTCCAATTCCAAAATGGGAGATGCACACTGGACGGTCGCCTGGTGGGAACAACTCCGGTGTC
CCTCTCACATGTCGCCAAAATCCGCGGCACATCAAATGGTACCGTAATCAATCTGACAGAACTTGATGGCACGCCCTT
CCATCCCTTTGAAGGACCAGCCCCTATTGGATTTCCTGATCTGGGAGGTTGCGACTGGCACATAAACATGACACAGT
TTGGCCACTCCAGCCAGACACAGTATGATGTCGATACAACCCCAGATACCTTCGTGCCACACCTGGGATCTATTCAA
GCTAACGGTATTGGATCCGGCAACTACGTGGGAGTCTTATCTTGGATCTCACCACCATCCCACCCCTCAGGATCCCAG
GTTGACTTGTGGAAGATACCGAATTATGGATCCTCGATCACTGAAGCCACGCACCTCGCACCTTCCGTCTACCCACCA
GGTTTTGGAGAAGTCTTGGTGTTTTTCATGAGCAAAATGCCCGGCCCTGGAGCCTACAATCTCCCTTGCCTACTCCCT
CAAGAGTATATTAGTCACCTCGCATCTGAGCAGGCCCCGACCGTTGGCGAGGCAGCCCTGCTGCATTATGTGGATCC
GGACACCGGCAGGAACCTGGGTGAGTTCAAAGCTTATCCTGACGGTTTTCTAACATGTGTACCAAATGGCGCTTCCA
GCGGCCCTCAACAGCTCCCAATCAATGGCGTGTTCGTTTTTGTCAGCTGGGTAAGCCGCTTCTACCAGCTGAAGCCC
GTGGGGACAGCTTCTTCTGCCCGCGGACGCCTCGGTCTGCGGAGATAATGGCTCAGGCCATTATTGGCGCCATCGCT
GCAAGTACAGCCGGGAGTGCATTGGGGGCCGGAATACAGGTGGGCGGGGAAGCTGCATTGCAGAGCCAGCGGTA
CCAGCAAAACCTGCAGTTACAGGAGAATAGCTTTAAACACGACAGGGAGATGATTGGATATCAGGTGGAGGCCAG
CAATCAGCTGCTCGCCAAAAACTTGGCTACTCGATACTCATTACTGCGCGCCGGGGGGTTGACTAGCGCCGACGCCG
CACGATCTGTCGCAGGCGCCCCCGTGACTCGGATCGTAGACTGGAACGGGGTACGAGTCTCGGCTCCCGAGTCGTC
TGCAACCACCCTGAGGTCGGGAGGGTTTATGTCCGTGCCCATCCCATTCGCTAGCAAACAGAAACAGGTCCAGAGCT
CCGGAATCTCCAATCCCAATTACTCCCCTAGCTCTATCTCTCGTACCACTTCCTGGGTCGAGAGTCAGAACAGCAGTA
GATTTGGCAACCTGAGCCCCTACCATGCTGAAGCCCTGAACACTGTGTGGTTGACTCCACCTGGTAGCACGGCCTCC
TCAACCCTGAGTTCCGTGCCTCGCGGGTACTTCAATACCGACAGACTTCCTCTGTTCGCTAACAACCGCCGCTGA

Figure 24D

Nucleic acid sequence of human codon-optimized VP1/VP2/3'UTR G1.1 (SEQ ID NO: 21)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGCAGAAGACGCGGCCCTTTA
CACTGCCCAATCTCCCGCTTTCAAGTCTGAGTAATTCACGGGCCCCATTGCCGATCTCCTCAATGGGAATCTCCCCCG
ACAACGTCCAGTCTGTCCAATTCCAAAATGGGAGATGCACACTGGACGGTCGCCTGGTGGGAACAACTCCGGTGTC
CCTCTCACATGTCGCCAAAATCCGCGGCACATCAAATGGTACCGTAATCAATCTGACAGAACTTGATGGCACGCCCTT
CCATCCCTTTGAAGGACCAGCCCCTATTGGATTTCCTGATCTGGGAGGTTGCGACTGGCACATAAACATGACACAGT
TTGGCCACTCCAGCCAGACACAGTATGATGTCGATACAACCCCAGATACCTTCGTGCCACACCTGGGATCTATTCAA
GCTAACGGTATTGGATCCGGCAACTACGTGGGAGTCTTATCTTGGATCTCACCACCATCCCACCCCTCAGGATCCCAG
GTTGACTTGTGGAAGATACCGAATTATGGATCCTCGATCACTGAAGCCACGCACCTCGCACCTTCCGTCTACCCACCA
GGTTTTGGAGAAGTCTTGGTGTTTTTCATGAGCAAAATGCCCGGCCCTGGAGCCTACAATCTCCCTTGCCTACTCCCT
CAAGAGTATATTAGTCACCTCGCATCTGAGCAGGCCCCGACCGTTGGCGAGGCAGCCCTGCTGCATTATGTGGATCC
GGACACCGGCAGGAACCTGGGTGAGTTCAAAGCTTATCCTGACGGTTTTCTAACATGTGTACCAAATGGCGCTTCCA
GCGGCCCTCAACAGCTCCCAATCAATGGCGTGTTCGTTTTTGTCAGCTGGGTAAGCCGCTTCTACCAGCTGAAGCCC
GTGGGGACAGCTTCTTCTGCCCGCGGACGCCTCGGTCTGCGGAGATAATGGCTCAGGCCATTATTGGCGCCATCGCT
GCAAGTACAGCCGGGAGTGCATTGGGGGCCGGAATACAGGTGGGCGGGGAAGCTGCATTGCAGAGCCAGCGGTA
CCAGCAAAACCTGCAGTTACAGGAGAATAGCTTTAAACACGACAGGGAGATGATTGGATATCAGGTGGAGGCCAG
CAATCAGCTGCTCGCCAAAAACTTGGCTACTCGATACTCATTACTGCGCGCCGGGGGGTTGACTAGCGCCGACGCCG
CACGATCTGTCGCAGGCGCCCCCGTGACTCGGATCGTAGACTGGAACGGGGTACGAGTCTCGGCTCCCGAGTCGTC
TGCAACCACCCTGAGGTCGGGAGGGTTTATGTCCGTGCCCATCCCATTCGCTAGCAAACAGAAACAGGTCCAGAGCT
CCGGAATCTCCAATCCCAATTACTCCCCTAGCTCTATCTCTCGTACCACTTCCTGGGTCGAGAGTCAGAACAGCAGTA
GATTTGGCAACCTGAGCCCCTACCATGCTGAAGCCCTGAACACTGTGTGGTTGACTCCACCTGGTAGCACGGCCTCC
TCAACCCTGAGTTCCGTGCCTCGCGGGTACTTCAATACCGACAGACTTCCTCTGTTCGCTAACAACCGCCGCTGATGT
TGTAATATGAAATGTGGGCATCATATTCATTTAATTAGGTTTAATTAGGTTTAATTTGATGTT

Figure 25A

Amino acid sequence of S(GI.1)+P(GI.2) fusion VP1 (SEQ ID NO: 22)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVEQKTRAFTVP
NIPLQTLSNSRFPSLIQGMILSPDASQVVQFQNGRCLIDGQLLGTTPATSGQLFRVRGKINQGARTLNLTEVDGKPFMAF
DSPAPVGFPDFGKCDWHMRISKTPNNTSSGDPMRSVDVQTDVQGFVPHLGSIQFDEVFNHPTGDYIGTIEWISQPSTPP
GTDINLWEIPDYGSSLSQAANLAPPVFPPGFGEALVYFVSAFPGPNNRSAPNDVPCLLPQEYVTHFVSEQAPTMGDAALL
HYVDPDTNRNLGEFKLYPGGYLTCVPNGVGAGPQQLPLNGVFLFVSWVSRFYQLKPVGTASTARGRLGVRRI*

Figure 25B

Nucleic acid sequence of human codon optimized S(GI.1)+P(GI.2) fusion VP1 (SEQ ID NO: 57)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGCAAAAAACAAGAGCATTCA
CAGTGCCCAACATTCCACTGCAGACTTTAAGCAATTCCAGGTTTCCCAGCTTGATCCAGGGTATGATCCTTTCTCCCG
ACGCCTCCCAAGTTGTGCAGTTCCAGAATGGGAGATGTCTTATCGACGGTCAGCTTCTGGGAACAACCCCTGCCACC
TCCGGGCAACTCTTCCGGGTGAGAGGCAAAATCAATCAGGGCGCCAGAACACTGAATCTGACAGAAGTGGACGGG
AAACCCTTTATGGCGTTCGATAGCCCCGCGCCCGTTGGATTCCCTGACTTCGGCAAGTGTGATTGGCACATGCGCAT
CAGTAAGACTCCCAACAACACTTCATCTGGAGACCCCATGAGGAGCGTGGATGTCCAGACCGACGTGCAGGGCTTC
GTGCCGCACTTGGGATCTATCCAGTTCGATGAGGTGTTCAATCACCCTACTGGCGACTACATAGGCACAATTGAGTG
GATAAGTCAACCATCTACACCTCCAGGGACCGACATAAACCTGTGGGAAATTCCTGATTACGGGTCATCCCTGAGTC
AAGCTGCCAATCTTGCACCCCCTGTCTTTCCCCCCGGCTTTGGTGAGGCTCTTGTTTACTTCGTCTCTGCATTTCCTGG
TCCTAACAACCGCTCCGCCCCTAACGATGTTCCGTGTTTGTTACCCCAGGAATATGTGACTCATTTCGTTTCCGAACA
GGCACCCACCATGGGGGACGCTGCCCTGCTACACTATGTGGACCCCGACACCAATAGAAACCTCGGCGAGTTCAAA
CTCTACCCCGGGGGATACCTGACCTGTGTTCCAAATGGAGTGGGAGCAGGCCCACAACAGCTGCCCCTGAATGGGG
TCTTCCTGTTCGTTTCTTGGGTGTCACGCTTTTACCAGCTGAAGCCCGTTGGCACAGCTTCTACGGCACGCGGCAGGC
TAGGGGTCCGCCGAATCTGA

Figure 26A

Amino acid sequence of S(GI.1)+P(GI.3) fusion VP1 (SEQ ID NO: 23)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVEQKTKPFSVPN
LPLNVLSNSRVPSLIKSMMVSQDHGQMVQFQNGRVTLDGQLQGTTPTSASQLCKIRGTVYHATGGQGLNLTEIDGTPY
HAFESPAPIGFPDLGECDWHINASPANAFTDGSIIHRIDVAQDSTFAPHLGTIHYTNADYNANVGLICSLEWLSPPSGGAP
KVNPWAIPRYGSTLTEAAQLAPPIYPPGFGEAIVFFMSDFPIANGSDGLSVPCTIPQEFVTHFVNEQAPTRGEAALLHYVD
PDTHRNLGEFKLYPEGFMTCVPNSSGSGPQTLPINGVFTFISWVSRFYQLKPVGTTGPVRRLGIRRS*

Figure 26B

Nucleic acid sequence of human codon optimized S(GI.1)+P(GI.3) fusion VP1 (SEQ ID NO: 58)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGCAGAAAACAAAGCCATTCA
GCGTGCCAAACCTGCCCCTTAACGTGCTGTCGAATTCCCGAGTGCCTTCCCTTATTAAGTCCATGATGGTATCTCAGG
ATCACGGTCAAATGGTGCAGTTTCAGAACGGCCGAGTGACGTTAGACGGGCAGCTGCAGGGCACAACCCCAACCA
GTGCCAGTCAGCTGTGTAAGATCAGAGGCACCGTCTACCACGCAACTGGCGGACAGGGGCTGAATCTTACTGAGAT
CGATGGTACCCCCTACCATGCATTCGAGTCACCTGCACCTATTGGATTTCCCGATCTTGGGGAGTGTGATTGGCATAT
CAATGCTTCACCTGCCAACGCTTTCACAGACGGGTCTATTATTCATCGCATTGACGTAGCACAGGATAGCACATTTGC
CCCGCACCTGGGTACCATCCACTATACGAACGCAGATTACAACGCAAACGTGGGTCTTATCTGTAGCCTAGAGTGGC
TATCTCCGCCAAGCGGTGGGGCCCCTAAAGTTAACCCATGGGCTATTCCTCGGTACGGGTCTACGCTGACTGAGGCC
GCTCAGCTGGCACCCCCCATATATCCACCAGGATTCGGGGAAGCCATTGTTTTCTTTATGTCCGATTTTCCGATAGCC
AACGGTTCAGATGGCCTTAGTGTCCCTTGCACGATTCCACAGGAATTTGTGACACACTTCGTAAACGAGCAGGCTCC
TACTCGGGGCGAGGCTGCCTTGTTGCATTACGTAGACCCCGATACCCATAGAAACCTGGGCGAATTCAAACTCTACC
CTGAAGGTTTCATGACCTGCGTACCTAACTCCTCCGGCAGTGGCCCTCAAACCTTGCCGATCAACGGCGTGTTCACGT
TTATCAGCTGGGTTTCACGGTTTTACCAACTCAAGCCCGTCGGAACAACTGGGCCAGTTCGGAGGCTCGGGATCAGA
CGGAGCTAG

Figure 27A

Amino acid sequence of S(GI.1)+P(GII.4) fusion VP1 (SEQ ID NO: 24)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVESRTKPFSVPV
LTVEEMTNSRFPIPLEKLFTGPSSAFVVQPQNGRCTTDGVLLGTTQLSPVNICTFRGDVTHITGSRNYTMNLASQNWNDY
DPTEEIPAPLGTPDFVGKIQGVLTQTTRTDGSTRGHKATVYTGSADFAPKLGRVQFETDTDRDFEANQNTKFTPVGVIQD
GGTTHRNEPQQWVLPSYSGRNTHNVHLAPAVAPTFPGEQLLFFRSTMPGCSGYPNMDLDCLLPQEWVQYFYQEAAPA
QSDVALLRFVNPDTGRVLFECKLHKSGYVTVAHTGQHDLVIPPNGYFRFDSWVNQFYTLAPMGNGTGRRRAV*

Figure 27B

Nucleic acid sequence of human codon optimized S(GI.1)+P(GII.4) fusion VP1 (SEQ ID NO: 59)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGAGCCGAACCAAGCCCTTTAG
TGTCCCCGTACTCACAGTCGAGGAGATGACAAATAGCCGCTTTCCAATCCCCCTTGAGAAACTGTTCACAGGACCTTC
CTCGGCATTCGTGGTTCAGCCACAGAACGGACGCTGCACAACTGACGGCGTGCTGCTCGGAACCACCCAGCTTAGC
CCTGTTAATATCTGTACGTTTAGAGGCGACGTAACTCACATAACTGGCTCACGGAACTATACCATGAATCTGGCATCA
CAGAATTGGAATGACTACGACCCAACCGAAGAGATTCCCGCACCTCTTGGAACCCCCGACTTTGTGGGAAAAATACA
GGGCGTCCTGACACAAACCACCAGAACCGATGGCTCCACACGGGGACACAAGGCAACCGTCTACACTGGCTCTGCC
GATTTTGCCCCGAAACTGGGTAGAGTGCAGTTTGAGACCGACACTGACCGGGACTTTGAAGCCAATCAGAATACTA
AGTTCACACCTGTAGGAGTGATTCAGGACGGGGGCACCACTCACCGGAACGAGCCGCAACAATGGGTCCTGCCCTC
TTATAGCGGGAGGAATACTCATAATGTGCATTTGGCTCCTGCAGTGGCTCCCACGTTTCCCGGGGAACAACTGCTCT
TTTTTCGTTCAACCATGCCTGGATGCTCCGGATATCCCAATATGGATCTCGATTGCCTGCTCCCACAGGAATGGGTGC
AGTATTTTTATCAAGAGGCCGCACCAGCCCAATCCGACGTCGCACTTCTGCGGTTCGTGAATCCAGACACAGGCCGC
GTGTTGTTTGAGTGCAAATTGCACAAATCAGGATACGTTACAGTGGCTCATACTGGACAGCATGACCTGGTGATCCC
ACCCAACGGATATTTTAGGTTCGACTCCTGGGTGAATCAGTTTTATACATTAGCCCCCATGGGGAATGGGACTGGCA
GACGCAGGGCTGTCTGA

Figure 28A

Amino acid sequence of S(GI.1)+P(GII.6) fusion VP1 (SEQ ID NO: 25)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVESKTKPFSLPIL
TLGELSNSRFPAPIDMLYTDPNEGIVVQPQNGRCTLDGTLQGTTQLVPTQICAFRGTLIGQTSRSPDSTDSAPRRRDHPLH
VQLKNLDGTQYDPTDEVPAVLGAIDFKGTVFGVASQRDVSGQQVGATRAHEVHINTTDPRYTPKLGSILMYSESDDFVT
GQPVRFTPIGMGDNDWHQWELPDYPGHLTLNMNLAPAVAPAFPGERILFFRSIVPSAGGYGSGQIDCLIPQEWVQHFY
QEAAPSQSAVALIRYVNPDTGRNIFEAKLHREGFITVANSGNNPIVVPPNGYFRFEAWVNQFYTLTPMGTGQGRRRDQ*

Figure 28B

Nucleic acid sequence of human codon optimized S(GI.1)+P(GII.6) fusion VP1 (SEQ ID NO: 63)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGAGCAAGACAAAACCCTTCA
GCCTCCCAATCTTAACACTCGGGGAGCTGTCTAATTCACGCTTCCCCGCACCTATTGATATGCTGTATACTGACCCCA
ACGAGGGGATAGTGGTGCAGCCCCAAAATGGACGGTGTACTCTCGACGGCACGCTCCAGGGCACAACCCAACTGG
TGCCAACCCAGATTTGTGCATTCAGGGGCACTTTGATTGGGCAGACATCGAGATCTCCAGATTCTACTGATTCCGCG
CCAAGGAGGAGGGACCACCCACTCCACGTTCAGTTAAAAAACCTGGACGGAACCCAGTACGACCCTACAGACGAGG
TCCCCGCTGTCCTCGGAGCCATCGACTTTAAAGGAACTGTATTTGGAGTGGCATCCCAAAGGGATGTCTCGGGGCA
GCAGGTGGGAGCTACGAGAGCACATGAAGTCCACATTAACACCACAGACCCAAGATATACCCCAAAACTAGGGTCA
ATTTTAATGTATTCGGAATCAGACGATTTTGTTACAGGTCAGCCCGTGCGGTTTACCCCGATCGGAATGGGGGACAA
CGATTGGCACCAGTGGGAATTGCCCGATTACCCTGGACACCTCACCTTGAATATGAATCTGGCCCCAGCCGTCGCGC
CCGCCTTCCCCGGTGAGCGGATCCTCTTTTTTAGAAGCATAGTGCCCTCCGCAGGTGGGTATGGATCAGGGCAGATT
GATTGCCTGATCCCCCAAGAATGGGTACAGCATTTCTACCAGGAAGCAGCCCCTAGCCAGTCCGCAGTAGCACTGAT
CAGATATGTTAATCCTGATACGGGAAGGAACATCTTCGAAGCAAAACTGCACCGTGAGGGCTTCATTACCGTCGCCA
ACAGTGGTAATAACCCTATTGTGGTGCCTCCTAATGGATACTTCAGGTTTGAGGCATGGGTGAATCAGTTTTATACTC
TGACTCCCATGGGGACAGGCCAGGGGCGACGCCGGGATCAGTGA

Figure 29A

Amino acid sequence of S(GI.1)+P(GII.13) fusion VP1 (SEQ ID NO: 26)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVESKTKPFTLPIL
TISELTNSRFPISIEQLYTAPNENNVVQCQNGRCTLDGELQGTTQLLSSAVCSYRGRTVANSGDNWDQNVLQLTYPSGAS
YDPTDEVPAPLGTQDFSGILYGVLTQDNVRENTGEAKNAKGVYISTTSGKFTPKIGSIGLHSITEDVRPNQQSRFTPVGVA
QNENTPFQQWVLPHYAGALALNTNLAPAVAPTFPGEQLLFFRSRVPCVQGLQGQDAFIDCLLPQEWVNHFYQEAAPSQ
ADVALIRYVNPDTGRTLFEAKLHRSGFITVSHTGAYPLVVPPNGHFRFDSWVNQFYSLAPMGTGNGRRRVQ*

Figure 29B

Nucleic acid sequence of human codon optimized S(GI.1)+P(GII.13) fusion VP1 (SEQ ID NO: 64)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGAGCAAGACTAAACCCTTTAC
TCTTCCCATTCTGACTATATCCGAGCTTACCAACTCCCGGTTCCCCATCTCAATCGAGCAACTGTACACTGCACCCAAC
GAGAACAACGTAGTCCAGTGCCAGAACGGGAGATGTACCCTGGACGGGGAGCTCCAAGGGACCACGCAACTGTTA
AGTTCAGCCGTTTGCAGTTACAGAGGCAGGACTGTGGCGAACTCTGGTGATAACTGGGATCAAAATGTGTTGCAGC
TGACTTACCCATCCGGCGCAAGCTACGATCCAACAGATGAGGTGCCAGCGCCCCTTGGCACACAGGATTTCTCAGGA
ATTCTATACGGGGTGCTTACTCAGGATAATGTGCGAGAAAATACTGGCGAGGCCAAGAATGCTAAAGGAGTGTATA
TAAGCACGACAAGCGGTAAGTTTACCCCCAAAATTGGCAGTATTGGGCTCCACAGCATTACTGAGGACGTCCGCCCA
AACCAGCAGTCTCGTTTCACTCCCGTGGGGGTGGCACAGAACGAGAACACACCTTTCCAGCAGTGGGTCTTGCCCCA
TTATGCAGGTGCTTTGGCGCTCAATACAAATCTGGCACCCGCCGTAGCGCCGACATTTCCTGGGGAGCAATTGCTGT
TCTTTAGAAGCCGCGTCCCGTGTGTTCAGGGCTTGCAGGGCCAGGACGCGTTCATTGATTGCCTCTTGCCCCAGGAA
TGGGTCAACCACTTTTATCAGGAGGCAGCGCCCTCTCAAGCAGATGTGGCCCTGATAAGATATGTGAATCCCGACAC
AGGACGGACTTTGTTTGAGGCAAAACTCCACCGGTCAGGATTCATTACTGTGAGTCACACAGGAGCCTATCCCCTTG
TGGTTCCACCTAATGGCCACTTCAGGTTCGACTCTTGGGTCAATCAGTTTTATTCGCTGGCACCAATGGGTACCGGGA
ATGGTCGCCGTCGGGTGCAATGA

Figure 30A

Amino acid sequence of S(GI.1)+P(GII.17) fusion VP1 (SEQ ID NO: 27)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVEQKTRPFTLPN
LPLSSLSNSRAPLPISSMGISPDNVQSVQFQNGRCTLDGRLVGTTQLLPSGICAFRGRVTAETDHRDKWHMQLQNLNGT
TYDPTDDVPAPLGTPDFKGVVFGVASQRNVGNDAPGSTRAHEAVISTYSPQFVPKLGSVNFRSNDNDFQLQPTKFTPVG
INDDGDHPFRQWELPDYSGLLTLNMNLAPSVYPPGFGEVLVFFMSKMPGPGAYNLPCLLPQEYISHLASEQAPTVGEAA
LLHYVDPDTGRNLGEFKAYPDGFLTCVPNGASSGPQQLPINGVFVFVS

Figure 30B

Nucleic acid sequence of human codon optimized S(GI.1)+P(GII.17) fusion VP1 (SEQ ID NO: 65)

ATGATGATGGCTAGTAAAGATGCGACCTCCTCTGTGGATGGTGCGTCAGGGGCAGGACAACTCGTACCCGAGGTAA
ACGCCAGCGACCCACTTGCCATGGACCCCGTTGCCGGAAGTTCCACAGCAGTGGCCACAGCCGGTCAAGTGAATCC
AATTGATCCGTGGATTATCAACAATTTCGTCCAGGCACCCCAGGGCGAGTTCACAATTTCACCAAACAATACACCGG
GCGATGTGCTATTCGATCTTTCCTTGGGTCCTCACCTTAACCCTTTTCTACTCCATCTCTCACAGATGTACAATGGTTG
GGTAGGAAACATGAGAGTCCGGATCATGCTGGCTGGCAATGCCTTTACCGCTGGCAAGATCATCGTCAGTTGTATTC
CTCCCGGATTTGGATCTCATAATCTGACCATTGCTCAAGCGACTCTCTTTCCCCATGTCATCGCCGACGTTAGGACCCT
GGACCCCATCGAGGTGCCCCTGGAGGACGTCCGGAATGTTTTGTTCCACAACAACGACAGAAACCAGCAGACGATG
AGACTTGTCTGTATGCTCTATACCCCACTGCGGACTGGAGGCGGGACTGGAGACTCCTTCGTTGTGGCAGGAAGAG
TGATGACATGCCCCTCCCCCGACTTCAACTTTCTTTTTCTGGTCCCACCAACCGTTGAGTCTAAGACCAAACCGTTTTC
ACTGCCAATCTTAACTCTCTCCGAACTGACTAACAGCCGGTTTCCAGTACCCATAGATTCTCTTTTTACCGCTCAAAAC
AACGTACTCCAAGTCCAGTGCCAGAACGGCCGCTGTACGCTTGATGGTGAGTTGCAGGGGACAACACAGCTACTCC
CCAGTGGCATCTGTGCATTCCGGGGCCGCGTGACCGCTGAGACAGACCATCGTGACAAATGGCACATGCAACTCCA
AAACTTAAACGGGACCACCTACGACCCAACCGACGACGTCCCTGCTCCGCTAGGGACTCCTGACTTTAAGGGGGTG
GTGTTCGGAGTGGCCTCTCAGCGGAATGTTGGGAATGACGCCCCCGGCTCTACCCGAGCTCACGAGGCCGTTATCTC
AACATATAGCCCCCAATTTGTGCCCAAGCTCGGATCCGTTAATTTTCGTAGTAACGACAACGACTTCCAACTGCAACC
AACGAAGTTTACGCCAGTGGGGATTAATGATGATGGAGACCATCCTTTCCGCCAATGGGAACTACCAGATTATTCTG
GGCTGCTCACCCTCAATATGAACCTCGCCCCACCCGTGGCCCCTAATTTCCCCGGTGAGCAGCTGCTGTTTTTTCGGA
GCTTTGTGCCATGCAGTGGCGGATATAATCAAGGCATCGTAGACTGCTTGATTCCCCAAGAGTGGATACAACATTTT
TACCAGGAAAGTGCGCCCTCCCAGTCCGATGTGGCCCTGATACGGTACGTTAACCCCGATACCGGAAGAACATTATT
CGAAGCGAAATTGCACAGATCAGGGTACATTACCGTTGCACATTCCGGCGATTATCCCCTGGTGGTTCCCGCCAACG
GTTACTTTAGGTTCGATAGTTGGGTCAACCAGTTCTATTCACTAGCCCCAATGGGCACCGGTAACGGCAGACGCCGG
GCTCAGTAG

Figure 31A

Amino acid sequence of S(GI.1)+P(GII.12) fusion VP1 (SEQ ID NO: 71)

MMMASKDATSSVDGASGAGQLVPEVNASDPLAMDPVAGSSTAVATAGQVNPIDPWIINNFVQAPQGEFTISPNNTP
GDVLFDLSLGPHLNPFLLHLSQMYNGWVGNMRVRIMLAGNAFTAGKIIVSCIPPGFGSHNLTIAQATLFPHVIADVRTLD
PIEVPLEDVRNVLFHNNDRNQQTMRLVCMLYTPLRTGGGTGDSFVVAGRVMTCPSPDFNFLFLVPPTVESKTKPFTLPIL
TIGELTNSRFPVPIDELYTSPNESLVVQPQNGRCALDGELQGTTQLLPTAICSFRGRINQKVSGENHVWNMQVTNIDGTP
FDPTEDVPAPLGTPDFSGKLFGVLSQRDHDNACRSHDAVIATNSAKFTPKLGAIQIGTWEQDDVHINQPTKFTPVGLFES
EGFNQWTLPNYSGALTLNMGLAPPVAPTFPGEQILFFRSHIPLKGGVADPVIDCLLPQEWIQHLYQESAPSQTDVALIRFT
NPDTGRVLFEAKLHRSGYITVANTGSRPIVVPANGYFRFDSWVNQFYSLAPMGTGNGRRRVQ*

Figure 31B

Amino acid sequence of S(GI.5)+P(GII.4) fusion VP1 (SEQ ID NO: 48)

MMMASKDAPSSADGANGAGQLVPEVNNAEPLPLDPVAGASTALATAGQVNMIDPWIFNNFVQAPQGEFTISPNNTP
GDILFDLQLGPHLNPFLAHLSQMYNGWVGNMRVRVILAGNAFTAGKVIICCVPPGFQSRTLSIAQATLFPHIIADVRTLEPI
EIPLEDVRNTLYHTNDNQPTMRLLCMLYTPLRTGGGSGGTDAFVVAGRVLTCPSSDFNFLFLVPPTVESRTKPFSVPVLTV
EEMTNSRFPIPLEKLFTGPSSAFVVQPQNGRCTTDGVLLGTTQLSPVNICTFRGDVTHITGSRNYTMNLASQNWNDYDP
TEEIPAPLGTPDFVGKIQGVLTQTTRTDGSTRGHKATVYTGSADFAPKLGRVQFETDTDRDFEANQNTKFTPVGVIQDGG
TTHRNEPQQWVLPSYSGRNTHNVHLAPAVAPTFPGEQLLFFRSTMPGCSGYPNMDLDCLLPQEWVQYFYQEAAPAQS
DVALLRFVNPDTGRVLFECKLHKSGYVTVAHTGQHDLVIPPNGYFRFDSWVNQFYTLAPMGNGTGRRRAV*

Figure 32A

Amino acid sequence of S(GII.1)+P(GI.3) fusion VP1 (SEQ ID NO: 49)

MKMASNDAAPSNDGAAGLVPEVNNETMALEPVAGASIAAPLTGQNNVIDPWIRMNFVQAPNGEFTVSPRNSPGEVLL
NLELGPELNPFLAHLSRMYNGYAGGVEVQVLLAGNAFTAGKLVFAAIPPHFPLENLSPGQITMFPHVIIDVRTLEPVLLPLP
DVRNNFFHYNQQPEPRMRLVAMLYTPLRSNGSGDDVFTVSCRVLTRPSPDFDFNYLVPPTVEQKTKPFSVPNLPLNVLS
NSRVPSLIKSMMVSQDHGQMVQFQNGRVTLDGQLQGTTPTSASQLCKIRGTVYHATGGQGLNLTEIDGTPYHAFESPA
PIGFPDLGECDWHINASPANAFTDGSIIHRIDVAQDSTFAPHLGTIHYTNADYNANVGLICSLEWLSPPSGGAPKVNPWAI
PRYGSTLTEAAQLAPPIYPPGFGEAIVFFMSDFPIANGSDGLSVPCTIPQEFVTHFVNEQAPTRGEAALLHYVDPDTHRNL
GEFKLYPEGFMTCVPNSSGSGPQTLPINGVFTFISWVSRFYQLKPVGTTGPVRRLGIRRS*

Figure 32B

Amino acid sequence of S(GII.1)+P(GII.4) fusion VP1 (SEQ ID NO: 50)

MKMASNDAAPSNDGAAGLVPEVNNETMALEPVAGASIAAPLTGQNNVIDPWIRMNFVQAPNGEFTVSPRNSPGEVLL
NLELGPELNPFLAHLSRMYNGYAGGVEVQVLLAGNAFTAGKLVFAAIPPHFPLENLSPGQITMFPHVIIDVRTLEPVLLPLP
DVRNNFFHYNQQPEPRMRLVAMLYTPLRSNGSGDDVFTVSCRVLTRPSPDFDFNYLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV*

Figure 32C

Amino acid sequence of S(GII.1)+P(GII.17) fusion VP1 (SEQ ID NO: 51)

MKMASNDAAPSNDGAAGLVPEVNNETMALEPVAGASIAAPLTGQNNVIDPWIRMNFVQAPNGEFTVSPRNSPGEVLL
NLELGPELNPFLAHLSRMYNGYAGGVEVQVLLAGNAFTAGKLVFAAIPPHFPLENLSPGQITMFPHVIIDVRTLEPVLLPLP
DVRNNFFHYNQQPEPRMRLVAMLYTPLRSNGSGDDVFTVSCRVLTRPSPDFDFNYLVPPTVESKTKPFSLPILTLSELTNS
RFPVPIDSLFTAQNNVLQVQCQNGRCTLDGELQGTTQLLPSGICAFRGRVTAETDHRDKWHMQLQNLNGTTYDPTDDV
PAPLGTPDFKGVVFGVASQRNVGNDAPGSTRAHEAVISTYSPQFVPKLGSVNFRSNDNDFQLQPTKFTPVGINDDGDHP
FRQWELPDYSGLLTLNMNLAPPVAPNFPGEQLLFFRSFVPCSGGYNQGIVDCLIPQEWIQHFYQESAPSQSDVALIRYVN
PDTGRTLFEAKLHRSGYITVAHSGDYPLVVPANGYFRFDSWVNQFYSLAPMGTGNGRRRAQ*

Figure 33A

Amino acid sequence of S(GII.12)+P(GI.1) fusion VP1 (SEQ ID NO: 29)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVEQKTRPFTLPNLPLSSLSN
SRAPLPISSMGISPDNVQSVQFQNGRCTLDGRLVGTTPVSLSHVAKIRGTSNGTVINLTELDGTPFHPFEGPAPIGFPDLG
GCDWHINMTQFGHSSQTQYDVDTTPDTFVPHLGSIQANGIGSGNYVGVLSWISPPSHPSGSQVDLWKIPNYGSSITEAT
HLAPSVYPPGFGEVLVFFMSKMPGPGAYNLPCLLPQEYISHLASEQAPTVGEAALLHYVDPDTGRNLGEFKAYPDGFLTC
VPNGASSGPQQLPINGVFVFVSWVSRFYQLKPVGTASSARGRLGLRR*

Figure 33B

Amino acid sequence of S(GII.12)+P(GI.2)fusion VP1 (SEQ ID NO: 30)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVEQKTRAFTVPNIPLQTLS
NSRFPSLIQGMILSPDASQVVQFQNGRCLIDGQLLGTTPATSGQLFRVRGKINQGARTLNLTEVDGKPFMAFDSPAPVGF
PDFGKCDWHMRISKTPNNTSSGDPMRSVDVQTDVQGFVPHLGSIQFDEVFNHPTGDYIGTIEWISQPSTPPGTDINLW
EIPDYGSSLSQAANLAPPVFPPGFGEALVYFVSAFPGPNNRSAPNDVPCLLPQEYVTHFVSEQAPTMGDAALLHYVDPDT
NRNLGEFKLYPGGYLTCVPNGVGAGPQQLPLNGVFLFVSWVSRFYQLKPVGTASTARGRLGVRRI*

Figure 33C

Amino acid sequence of S(GII.12)+P(GI.3) fusion VP1 (SEQ ID NO: 31)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVEQKTKPFSVPNLPLNVLS
NSRVPSLIKSMMVSQDHGQMVQFQNGRVTLDGQLQGTTPTSASQLCKIRGTVYHATGGQGLNLTEIDGTPYHAFESPA
PIGFPDLGECDWHINASPANAFTDGSIIHRIDVAQDSTFAPHLGTIHYTNADYNANVGLICSLEWLSPPSGGAPKVNPWAI
PRYGSTLTEAAQLAPPIYPPGFGEAIVFFMSDFPIANGSDGLSVPCTIPQEFVTHFVNEQAPTRGEAALLHYVDPDTHRNL
GEFKLYPEGFMTCVPNSSGSGPQTLPINGVFTFISWVSRFYQLKPVGTTGPVRRLGIRRS*

Figure 33D

Amino acid sequence of S(GII.12)+P(GI.5) fusion VP1 (SEQ ID NO: 32)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVEQKTRPFSVPNIPLQLLSN
SRVPNLIQSMVLSPDQAQNVQFQNGRCTTDGQLLGTTPVSVSQILKFRGKVSAGSKVINLTELDGSPFLAFEAPAPTGFP
DLGTSDWHVEMSLNSNSQSSGNPILLRDIHPNSSEFVPHLGSVCVTAAIEVAGDYTGTIQWTSQPSNVTPVPDVNFWTIP
HYGSNLAEASQLAPVVYPPGFGEAIVYFMSPIPGPNTAHKPNLVPCLLPQEFVTHFVSEQAPSMGEAALVHYVDPDTNR
NLGEFKLYPEGFITCVPNGTGPQQLPLNGVFVFASWVSRFYQLKPVGTASSARGRLGVRR*

Figure 33E

Amino acid sequence of S(GII.12)+P(GII.1) fusion VP1 (SEQ ID NO: 33)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELSNS
RFPVPIDELYTSPNEGVVVQPQNGRSTLDGELLGTTQLVPSNICALRGRINAQVPDDHHQWNLQVTNANGTSFDPTEDV
PAPLGTPDFLANIYGVTSQRNPDNTCRAHDGVLATWSPKFTPKLGSVVLGTWEESDLDLNQPTRFTPVGLYDTGHFDQ
WVLPNYSGRLTLNMNLAPSVAPLFPGEQILFFRSHIPLKGGTSNGAIDCLLPQEWIQHFYQESAPSPTDVALIRYTNPDTG
RVLFEAKLHRQGFITVANSGSRPIVVPPNGYFRFDSWVNQFYSLAPMGTGNGRRRVQ*

Figure 33F

Amino acid sequence of S(GII.12)+P(GII.2) fusion VP1 (SEQ ID NO: 34)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTLGELSNS
RFPVSIDQMYTSPNEVISVQCQNGRCTLDGELQGTTQLQVSGICAFKGEVTAHLHDNDHLYNVTITNLNGSPFDPSEDIP
APLGVPDFQGRVFGVISQRDKHNTPGHNEPANRAHDAVVPTYTAQYTPKLGQIQIGTWQTDDLTVNQPVKFTPVGLND
TDHFNQWVVPRYAGALNLNTNLAPSVAPVFPGERLLFFRSYIPLKGGYGTPAIDCLLPQEWVQHFYQEAAPSMSEVALV
RYINPDTGRALFEAKLHRAGFMTVSSNTSAPVVVPANGYFRFDSWVNQFYSLAPMGTGNGRRRIQ*

Figure 33G

Amino acid sequence of S(GII.12)+P(GII.3) fusion VP1 (SEQ ID NO: 35)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFSLPILTISEMSNS
RFPVPIDSLHTSPTENIVVQCQNGRVTLDGELMGTTQLLPSQICAFRGTLTRSTSRASDQADTATPRLFNYYWHIQLDNLN
GTPYDPAEDIPAPLGTPDFRGKVFGVASQRNPDATTRAHEAKIDTTSGRFTPKLGSLEISTESGDFDQNQPTRFTPVGIGV
DHEPDFQQWALPDYAGQFTHNMNLAPAVAPNFPGEQLLFFRSQLPSSGGRSNGILDCLVPQEWVQHFYQESAPSQTQ
VALVRYVNPDTGRVLFEAKLHKLRFMTIAKSGDSPITVPPNGYFRFESWVNPFYTLAPMGTGNGRRRIQ*

Figure 33H

Amino acid sequence of S(GII.12)+P(GII.4) fusion VP1 (SEQ ID NO: 36)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESRTKPFSVPVLTVEEMT
NSRFPIPLEKLFTGPSSAFVVQPQNGRCTTDGVLLGTTQLSPVNICTFRGDVTHITGSRNYTMNLASQNWNDYDPTEEIP
APLGTPDFVGKIQGVLTQTTRTDGSTRGHKATVYTGSADFAPKLGRVQFETDTDRDFEANQNTKFTPVGVIQDGGTTHR
NEPQQWVLPSYSGRNTHNVHLAPAVAPTFPGEQLLFFRSTMPGCSGYPNMDLDCLLPQEWVQYFYQEAAPAQSDVAL
LRFVNPDTGRVLFECKLHKSGYVTVAHTGQHDLVIPPNGYFRFDSWVNQFYTLAPMGNGTGRRRAV*

Figure 33I

Amino acid sequence of S(GII.12)+P(GII.5) fusion VP1 (SEQ ID NO: 37)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPVLTLGELSN
SRFPLSIDEMVTSPNESIVVQPQNGRVTLDGELLGTTQLQACNICSIRGKVTGQVPNEQHMWNLEITNLNGTQFDPTDD
VPAPLGVPDFAGEVFGVLSQRNRGESNPANRAHDAVVATYSDKYTPKLGLVQIGTWNTNDVENQPTKFTPIGLNEVAN
GHRFEQWTLPRYSGALTLNMNLAPAVAPLFPGERLLFFRSYVPLKGGFGNPAIDCLVPQEWVQHFYQESAPSLGDVALV
RYVNPDTGRVLFEAKLHKGGFLTVSSTSTGPVVVPANGYFRFDSWVNQFYSLAPMGTGNGRRRFQ*

Figure 33J

Amino acid sequence of S(GII.12)+P(GII.6) fusion VP1 (SEQ ID NO: 38)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFSLPILTLGELSNS
RFPAPIDMLYTDPNEGIVVQPQNGRCTLDGTLQGTTQLVPTQICAFRGTLIGQTSRSPDSTDSAPRRRDHPLHVQLKNLD
GTQYDPTDEVPAVLGAIDFKGTVFGVASQRDVSGQQVGATRAHEVHINTTDPRYTPKLGSILMYSESDDFVTGQPVRFT
PIGMGDNDWHQWELPDYPGHLTLNMNLAPAVAPAFPGERILFFRSIVPSAGGYGSGQIDCLIPQEWVQHFYQEAAPSQ
SAVALIRYVNPDTGRNIFEAKLHREGFITVANSGNNPIVVPPNGYFRFEAWVNQFYTLTPMGTGQGRRRDQ*

Figure 33K

Amino acid sequence of S(GII.12)+P(GII.7) fusion VP1 (SEQ ID NO: 39)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKQFTLPILKISEMTN
SRFPVPVEMMYTARNENQVVQPQNGRVTLDGELLGTTPLLAVNICKFKGEVIAKNGDVRSYRMDMEITNTDGTPIDPTE
DTPGPIGSPDFQGILFGVASQRNKNEQNPATRAHEANINTGGDQYAPKLAQVKFFSESQDFEVHQPTVFTPVGVAGDTS
HPFRQWVLPRYGGHLTNNTHLAPAVAPLFPGEQILFFRSQIPSSGGHELGYMDCLVPQEWVQHFYQEAATAQSEVALIR
FINPDTGRVLFEAKLHKQGFITVAHTGDNPIVMPPNGYFRFEAWVNQFYSLAPVGTGNGRRRIQ*

Figure 33L

Amino acid sequence of S(GII.12)+P(GII.13) fusion VP1 (SEQ ID NO: 40)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTISELTNS
RFPISIEQLYTAPNENNVVQCQNGRCTLDGELQGTTQLLSSAVCSYRGRTVANSGDNWDQNVLQLTYPSGASYDPTDEV
PAPLGTQDFSGILYGVLTQDNVRENTGEAKNAKGVYISTTSGKFTPKIGSIGLHSITEDVRPNQQSRFTPVGVAQNENTPF
QQWVLPHYAGALALNTNLAPAVAPTFPGEQLLFFRSRVPCVQGLQGQDAFIDCLLPQEWVNHFYQEAAPSQADVALIR
YVNPDTGRTLFEAKLHRSGFITVSHTGAYPLVVPPNGHFRFDSWVNQFYSLAPMGTGNGRRRVQ*

Figure 33M

Amino acid sequence of S(GII.12)+P(GII.14) fusion VP1 (SEQ ID NO: 41)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKNFTLPVLRVSEMT
NSRFPVVLDQMYTSRNENIIVQPQNGRCTTDGELLGTTILQSVSICNFKGTMQAKLNEEPRYQLQLTNLDGSPIDPTDDM
PAPLGTPDFQAMLYGVASQRSSIDNATRAHDAQIDTAGDTFAPKIGQVRFKSSSNDFDLHDPTKFTPIGVNVDDQHPFR
QWSLPNYGGHLALNNHLAPAVTPLFPGEQILFFRSYIPSAGGHTDGAMDCLLPQEWVEHFYQEAAPSQSDIALVRFINPD
TGRVLFEAKLHKQGFLTIAASGDHPIVMPTNGYFRFEAWVNPFYTLAPVGTGSGRRRIQ*

Figure 33N

Amino acid sequence of S(GII.12)+P(GII.17) fusion VP1 (SEQ ID NO: 42)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFSLPILTLSELTNS
RFPVPIDSLFTAQNNVLQVQCQNGRCTLDGELQGTTQLLPSGICAFRGRVTAETDHRDKWHMQLQNLNGTTYDPTDDV
PAPLGTPDFKGVVFGVASQRNVGNDAPGSTRAHEAVISTYSPQFVPKLGSVNFRSNDNDFQLQPTKFTPVGINDDGDHP
FRQWELPDYSGLLTLNMNLAPPVAPNFPGEQLLFFRSFVPCSGGYNQGIVDCLIPQEWIQHFYQESAPSQSDVALIRYVN
PDTGRTLFEAKLHRSGYITVAHSGDYPLVVPANGYFRFDSWVNQFYSLAPMGTGNGRRRAQ*

Figure 33O

Amino acid sequence of S(GII.12)+P(GII.21) fusion VP1 (SEQ ID NO: 43)

MKMASNDAAPSNDGAAGLVPEVNNETMALEPVAGASIAAPLTGQNNVIDPWIRLNFVQAPNGEFTVSPRNSPGEVLL
NLELGPELNPYLAHLSRMYNGYAGGVEVQVLLAGNAFTAGKLVFAAVPPHFPLENISPGQITMFPHVIIDVRTLEPVLLPLP
DVRNNFFHYNQQNEPRMRLVAMLYTPLRSNGSGDDVFTVSCRVLTRPSPDFDFNYLVPPTVESKTKPFTLPILTIGELTNS
RFPAPIDQLYTSPNADVVVQPQNGRCTLDGELQGTTQLLTTAICSYRGMTSNPTSDYWDDHLLHLVHPNGATYDPTEDV
PAPFGTQDFRGILYGMLTQNPRTSGDEAANSHGIYISSTSEKFTPKLGTIGLHQVQGDIASNQQSKFTPVGIAVNGNTPFR
QWELPNYSGALTLNTNLAPAVGPNFPGEQILFFRSNVPSVQGGQPIEIDCLIPQEWVSHFYQESAPSQSDVALVRYVNPD
TGRTIFEAKLHRQGFITIAATGSNPVVVPPNGYFRFDSWVNQFYALAPMGTGNGRRRVQ*

Figure 34A

Amino acid sequence of S(GII.14)+P(GII.4) fusion VP1 (SEQ ID NO: 52)

MKMASNDATPSDDGAAGLVPEINNEVMALEPVAGASIAAPVVGQQNIIDPWIRNNFVQAPAGEFTVSPRNSPGELLLD
LELGPELNPYLAHLARMYNGHAGGMEVQIVLAGNAFTAGKILFAAIPPSFPYENLSPAQLTMCPHVIVDVRQLEPVLLPM
PDIRNVFYHYNQNNSPKLRLVAMLYTPLRANNSGDDVFTVSCRVLTRPSPDFQFTFLVPPTVESRTKPFSVPVLTVEEMTN
SRFPIPLEKLFTGPSSAFVVQPQNGRCTTDGVLLGTTQLSPVNICTFRGDVTHITGSRNYTMNLASQNWNDYDPTEEIPAP
LGTPDFVGKIQGVLTQTTRTDGSTRGHKATVYTGSADFAPKLGRVQFETDTDRDFEANQNTKFTPVGVIQDGGTTHRNE
PQQWVLPSYSGRNTHNVHLAPAVAPTFPGEQLLFFRSTMPGCSGYPNMDLDCLLPQEWVQYFYQEAAPAQSDVALLR
FVNPDTGRVLFECKLHKSGYVTVAHTGQHDLVIPPNGYFRFDSWVNQFYTLAPMGNGTGRRRAV*

Figure 34B

Amino acid sequence of S(GII.21)+P(GII.4) fusion VP1 (SEQ ID NO: 53)

MKMASNDAAPSNDGATGLVPEINTETLPLEPVAGAAIAAPVTGQNNIIDPWIRNNFVQAPNGEFTVSPRNSPGEILMNL
ELGPDLNPYLAHLSRMYNGYAGGVEVQVLLAGNAFTAGKILFAAVPPNFPVDMLSPAQITMLPHLIVDVRTLEPIMIPLP
DVRNVFYHFNNQPAPRMRLVAMLYTPLRSNGSGDDVFTVSCRVLTRPTPDFEFTYLVPPSVESRTKPFSVPVLTVEEMTN
SRFPIPLEKLFTGPSSAFVVQPQNGRCTTDGVLLGTTQLSPVNICTFRGDVTHITGSRNYTMNLASQNWNDYDPTEEIPAP
LGTPDFVGKIQGVLTQTTRTDGSTRGHKATVYTGSADFAPKLGRVQFETDTDRDFEANQNTKFTPVGVIQDGGTTHRNE
PQQWVLPSYSGRNTHNVHLAPAVAPTFPGEQLLFFRSTMPGCSGYPNMDLDCLLPQEWVQYFYQEAAPAQSDVALLR
FVNPDTGRVLFECKLHKSGYVTVAHTGQHDLVIPPNGYFRFDSWVNQFYTLAPMGNGTGRRRAV*

Figure 35

| Sequence identifier | Primer name | Nucleic acid sequence (5' to 3') |
|---|---|---|
| SEQ ID NO: 111 | IF-GI3Lil08VP1.c | TCGTGCTTCGGCACCAGTACAATGATGATGGCTTCCAAGGATGCTCCCA |
| SEQ ID NO: 98 | IF-GI3Lil08VP1.r | ACTAAAGAAAATAGGCCTCTAGCTCCGTCTGATCCCGAGCCTCCGAACT |
| SEQ ID NO: 112 | IF-GII4Syd12VP1.c | TCGTGCTTCGGCACCAGTACAATGAAAATGGCCTCGAGTGACGCTAACC |
| SEQ ID NO: 101 | IF-GII4Syd12VP1.r | ACTAAAGAAAATAGGCCTTCAGACAGCCCTGCGTCTGCCAGTCCCATT |
| SEQ ID NO: 113 | IF-GII6Ohi12VP1.c | TCGTGCTTCGGCACCAGTACAATGAAGATGGCAAGCAACGACGCAGCTC |
| SEQ ID NO: 104 | IF-GII6Ohi12VP1.r | ACTAAAGAAAATAGGCCTTCACTGATCCCGGCGTCGCCCCTGGCCTGTCCCCAT |
| SEQ ID NO: 114 | IF-GII13VA10VP1.c | TCGTGCTTCGGCACCAGTACAATGAAAATGGCTTCTAATGATGCCGCGCCCAGCAATGA |
| SEQ ID NO: 107 | IF-GII13VA10VP1.r | ACTAAAGAAAATAGGCCTTCATTGCACCCGACGGCGACCATTCCCGGTACCCA |
| SEQ ID NO: 115 | IF-GII17Kaw14VP1.c | TCGTGCTTCGGCACCAGTACAATGAAAATGGCATCTAACGACGCAGCCCCCTC |
| SEQ ID NO: 110 | IF-GII17Kaw14VP1.r | ACTAAAGAAAATAGGCCTCTACTGAGCCCGGCGTCTGCCGTTACCGGTGCCCATTG |
| SEQ ID NO: 96 | GI3Lil+GI1VP1.r | GAATGGCTTTGTTTTCTGCTCAACGGTTGGTGGGACCAGAAAAAGAAAGTTGAAGT |
| SEQ ID NO: 97 | GI1VP1+GI3Lil.c | TCCCACCAACCGTTGAGCAGAAAACAAAGCCATTCAGCGTGCCAAACC |
| SEQ ID NO: 99 | GII4Syd+GI1VP1.r | AAGGGCTTGGTTCGGCTCTCAACGGTTGGTGGGACCAGAAAAAGAAAGT |
| SEQ ID NO: 100 | GI1VP1+GII4Syd.c | TCCCACCAACCGTTGAGAGCCGAACCAAGCCCTTTAGTGTCCCCGTACT |

| | | |
|---|---|---|
| SEQ ID NO: 102 | GII6Ohi+GI1VP1.r | AAGGGTTTTGTCTTGCTCTCAACGGTTGGTGGGACCAGAAAAAGAAAGT |
| SEQ ID NO: 103 | GI1VP1+GII6Ohi.c | TCCCACCAACCGTTGAGAGCAAGACAAAACCCTTCAGCCTCCCAATCTTA |
| SEQ ID NO: 105 | GII13Va+GI1VP1.r | AAGGGTTTAGTCTTGCTCTCAACGGTTGGTGGGACCAGAAAAAGAAAGT |
| SEQ ID NO: 106 | GI1VP1+GII13Va.c | TCCCACCAACCGTTGAGAGCAAGACTAAACCCTTTACTCTTCCCATTCTG |
| SEQ ID NO: 108 | GII17Kaw+GI1VP1.r | AACGGTTTGGTCTTAGACTCAACGGTTGGTGGGACCAGAAAAAGAAAGTTGAAGT |
| SEQ ID NO: 109 | GI1VP1+GII17Kaw.c | TCCCACCAACCGTTGAGTCTAAGACCAAACCGTTTTCACTGCCAATCT |
| SEQ ID NO: 117 | IF-GII4Syd12VP2.c | TCGTGCTTCGGCACCAGTACAATGGCTGGGGCCTTTTTTGCAGGTTTGGCTAGT |
| SEQ ID NO: 119 | IF-GII4Syd12VP2.r | ACTAAAGAAAATAGGCCTTCATGCTCGTGACTCACCCCTTTTGCGTATATGAGC |
| SEQ ID NO:116 | IF-NoV(US68)VP2(ORF3).c | TCGTGCTTCGGCACCAGTACAATGGCCCAAGCCATAATTGGTGCAATT |
| SEQ ID NO:122 | IF-NoV(US68)VP2(ORF3).r | ACTAAAGAAAATAGGCCTTCATCGCCTATTATTTGCGAATAATGGCAACCTGT |
| SEQ ID NO:118 | IF-NoV(US68)VP1/VP2(ORF3)NoV3'UTR.r | ACTAAAGAAAATAGGCCTAACATCAAATTAAACCTAATTAAACCTAAT |

Figure 35
Continued

NOROVIRUS FUSION PROTEINS AND VLPS COMPRISING NOROVIRUS FUSION PROTEINS

CROSS REFERENCE TO RELATED APPLICATIONS

This application is a divisional of U.S. application Ser. No. 16/496,244 filed Sep. 20, 2019, which is a National Stage of International Application No. PCT/CA2018/050352 filed Mar. 23, 2018, claiming priority based on U.S. Provisional Patent Application No. 62/475,660, filed Mar. 23, 2017.

FIELD OF INVENTION

The present invention relates to norovirus fusion proteins, VLPs comprising norovirus fusion proteins, and methods of producing the same.

BACKGROUND OF THE INVENTION

The global disease burden attributed to norovirus infection is high, being associated with an estimated 20% of all worldwide diarrheal cases and causing over 200,000 deaths annually. Noroviruses are the primary cause of foodborne disease outbreaks in North America and are the causative agent for the majority of healthcare-associated outbreaks amongst the elderly. Norovirus strains are also recognized as being the leading cause of pediatric gastrointestinal illness worldwide.

Noroviruses comprise one of a number of genera of the family Caliciviridae. The human norovirus genome is a single-stranded, positive-sense RNA molecule encoding three open reading frames (ORFs) and capped on its 5' end by a VPg protein. ORF1 encodes six non-structural viral proteins, including VPg, an RNA-dependent RNA polymerase, and a viral protease. ORF2 encodes the major structural capsid protein (VP1). ORF3 encodes a minor capsid protein (VP2).

VP1 is comprised of 2 domains: a shell (S) domain, and a protruding (P) domain. The P domain is further comprised of a P1 sub-domain and a P2 sub-domain. The P2 subdomain is referred to as the hypervariable domain and is thought to play an important role in receptor binding and immune reactivity.

VP1 proteins form dimers via P domain-mediated protein interactions. Dimerization increases the stability of the virion capsid and results in formation of the protrusions extending from the base core of the norovirus particle formed by S domains. When expressed, norovirus VP1 proteins can automatically assemble to form 2 virion structures: a 180-mer capsid structure with T=3 icosahedral symmetry having a 38-40 nm diameter; and a 60-mer capsid structure with T=1 icosahedral symmetry having a 23 nm diameter.

VP2, the minor structural protein, has a molecular weight (MW) of approximately 21-24 kDa. Studies suggest that VP2 is highly basic and located inside the capsid. The function of VP2 has not yet been fully understood but it is generally believed to play a role in capsid stability by protecting the virions from disassembly and degradation (Bertolotti-Ciarlet A., Crawford S. E., Hutson A. M., Estes M. K. 2003, J. Virol. 77:11603-11615). VP2 may also have a function during RNA genome packaging. The amount of VP2 minor structural protein in virions is relatively low with 1.5 to 8 copies incorporated into the mature virion. Bertolotti-Ciarlet et. al. (2003) report that in insect and mammalian cells, VLPs composed of VP1/VP2 are more resistant to protease cleavage than those with only VP1, and that expression of VP2 in cis, results in an increase in VP1 protein production. In addition, the presence of the 3'UTR downstream of the ORF2 gene increases the steady-state levels of NV ORF2 mRNA. The greatest increase in VP1 expression was observed when ORF2+ORF3+3'UTR, residing on the same construct and under regulation of one promoter, was expressed. Expression of VP2 in trans did not result in any increase in VP1 expression, indicating that the subgenomic organization of ORF2-ORF2-3'UTR was required for the observed increase in VP1 production.

Noroviruses are classified according to their phylogenetic clustering of the VP1 amino acid sequence. Seven genogroups have been classified to date (GI through GVII) with only genogroups GI, GII, and GIV known to infect humans. Of the 32 specific genotypes currently associated with human infections, GII.4 noroviruses have been responsible for the majority of recent norovirus outbreaks. New strains of GII.4 emerge every two to three years, evolving by a process driven by mutations in epitope determining regions of the hypervariable P2 domain of VP1. This process allows the norovirus to escape humoral immune responses acquired by previous exposure to earlier strains.

While faced with the difficulty of rapidly evolving and genetically diverse norovirus strains, the development of effective norovirus vaccines has been exacerbated by additional challenges. For instance, until recently, human norovirus could not be grown in cell culture and even now, robust cell culture systems for both VLPs and live attenuated noroviruses are lacking.

An additional challenge in vaccine development is that immunity to norovirus infection is strain and genotype specific with minimal cross-immunity conferred against other genogroups. Furthermore, immunity to a norovirus strain is not life-long and is estimated to persist from anywhere between six months and nine years.

Various approaches have been undertaken to develop a suitable vaccine against norovirus infection including the production of recombinant norovirus proteins in plants and recombinant generation of fusion/chimeric VP1 proteins.

Mason et al. (*Proc Natl Acad Sci U.S.A.,* 1996, 93(11):5335-40) teach the use of genetically engineered tobacco plants and potato tubers to express GI.1 norovirus VLPs from native VP1 protein. The plant produced norovirus VLPs are morphologically and physically similar to the 38 nm Norwalk VLPs produced in insect cells. Oral administration of purified tobacco-produced Norwalk VLPs from native capsid protein, or potato tubers expressing GI.1 capsid protein induced a humoral immune response in mice and humans (Tacket et al., *J. Infect. Dis.,* 2000, 182(1):302-5).

Huang et al. (*Biotechnol. Bioeng.,* 2009, 103(4):706-14) describe a geminivirus-derived DNA replicon vector for production of GI.1 norovirus VLP in plants. Co-delivery of bean yellow dwarf virus-derived vector and Rep/RepA-supplying vector in *Nicotiana benthamiana* resulted in rapid and robust protein production.

Coit et al. (WO 2007/081447; U.S. Pat. Nos. 7,527,801; 8,119,145; 8,124,104; 8,142,793; 9,428,739) teach polynucleotides encoding capsid proteins and other immunogenic proteins from norovirus. The production of norovirus-derived multiple epitope fusion antigens comprising a norovirus NTPase-polymerase fusion protein is also described. The fusion protein may comprise a linker sequence. Methods to produce norovirus fusion proteins comprising VP1 are also disclosed.

Steadman et al. (U.S. Pat. No. 8,980,275) describe a chimeric protein comprising a Calicivirus capsid protein and at least one heterologous antigen, and the formation of VLPs when the chimeric protein is expressed in a host cell. A chimeric protein comprising a heterologous antigen, or fragment thereof, inserted into a P2 domain of the Calicivirus protein is also disclosed.

Lin et al. (WO 2016/019890) teach a fusion protein in which an antigen is fused, with or without a linker sequence, on both its N-terminal and C-terminal ends, to viral structural proteins, or fragments thereof, and wherein fusion improves the folding and antigenicity of the antigen. The viral structural protein may be any protein that contributes to the structure of the capsid or protein core of the virus, and the norovirus S domain or P domain are mentioned as examples.

Settembre et al. (U.S. Ser. No. 14/946,324) disclose immunogenic compositions comprising chimeric norovirus VP1 proteins capable of forming VLPs produced in insect cells, mammalian cells, avian cells, bacterial cells, yeast cells, or Tetrahymena cells. The chimeric VP1 proteins have all, or a portion, of a VP1 P domain from one strain of norovirus replaced with all, or a portion, of a P domain from a non-homologous norovirus strain.

Noroviruses are known to bind specific histo-blood group antigens (HBGA). Huo et al. (*Virus Res.,* 2016, 224:1-5) teach the production of chimeric VP1 capsid proteins where the P2 domain of a GII.4 Sydney 2012-like variant norovirus is exchanged for the P2 domain of a GII.3 strain norovirus. Results from in vitro HBGA-binding blockade assays indicate that although GII.3 norovirus VLPs do not bind to any synthetic or salivary HBGAs tested, the chimeric VLPs are capable of binding synthetic blood type A (trimer) and Le(x) HBGAs and blood type A, B and O salivary HBGAs. Furthermore, Huo et al. demonstrate that this binding can be competitively inhibited by anti-GII.3 serum but not anti-GI.2 or anti GII.4 serum.

SUMMARY OF THE INVENTION

The present invention relates to norovirus fusion proteins, virus like particles (VLPs) comprising norovirus fusion proteins, and methods of producing the same.

It is an object of the invention to produce norovirus fusion proteins, VLPs comprising norovirus fusion proteins, and to producing VLPs comprising norovirus fusion proteins in plants.

As described herein there is provided a nucleic acid encoding a norovirus VP1 fusion protein comprising, a first sequence encoding an S domain derived from a first norovirus strain, and a second sequence encoding a P domain derived from a second norovirus strain, the first and second sequence are selected from norovirus genogroups GI, GII, and GIV.

Also provided is the nucleic acid encoding the norovirus VP1 fusion protein as described above, wherein the first and second norovirus strains are independently selected from norovirus genotypes GI.1, GI.2, GI.3, GI.4, GI.5, GII.1, GII.2, GII.3, GII.4, GII.5, GII.6, GII.7, GII.12, GII.13, GII.14, GII.17 and GII.21 is also provided.

For example, which is not to be considered limiting, the first norovirus strain and the second norovirus strain may be independently selected from norovirus subtypes:

GI.1/US/1968,
GI.2/Leuven/2003/Bel,
GI.3/S29/2008/Lilla Edet/Sweden,
GI.5/AlbertaEI390/2013/CA,
GII.1/Ascension208/2010/USA,
GII.12/HS206/2010/USA,
GII.13/VA173/2010/USA,
GII.14/8610/Saga/2008/JPN,
GII.17/Kawazaki/2014/A0A077KVU6, and
GII.21/Salisbury150/2011/USA.

The nucleic acid as described above may also comprise a fifth sequence encoding a CPMV enhancer, the CPMV enhancer operatively linked with the first, second, third, and fourth sequences. The nucleic acid as described above may also be optimized for human codon usage, increased GC content, or a combination thereof.

A norovirus VP1 fusion protein encoded by the nucleic acid as described above is also described herein. Furthermore, a virus like particle (VLP) comprising the norovirus VP1 fusion protein encoded by the nucleic acid is also disclosed.

Methods to produce an antibody or antibody fragment using the norovirus fusion VP1 fusion protein or the VLP encoded by the nucleic acid, or the VLP comprising the norovirus VP1 fusion protein and norovirus VP2 protein encoded by the nucleic acid complex, are described herein. An antibody, an antibody fragment, or a combination thereof, produced using these methods is also provided.

The present disclosure also describes a method of producing a norovirus VP1 fusion protein in a plant host cell, for example the plant, the portion of a plant, or the plant cell. The method comprises introducing the nucleic acid, or nucleic acid complex, as described above into the plant host cell, and incubating the plant host cell under conditions that permit expression of the norovirus VP1 fusion protein. The method may further comprises a step of harvesting the plant host cell, for example the plant, the portion of a plant, or the plant cell, and purifying the norovirus VP1 fusion protein.

As described herein, there is a method of producing a VLP comprising a norovirus VP1 fusion protein in a plant, portion of the plant, or a plant cell. The method comprises introducing the nucleic acid as described herein into the plant, portion of the plant, or the plant cell, and incubating the plant, portion of the plant, or the plant cell under conditions that permit expression of the nucleic acid and the formation of the VLP. The method of producing the VLP may further comprise a step of harvesting the plant, portion of the plant, or the plant cell, producing a plant extract, and purifying the VLP, wherein the VLP has a diameter of about 15 nm to 50 nm, for example, about 23 nm (for T=1 icosahedral symmetry) or about 38 to about 40 nm (for T=3 icosahedral symmetry). Furthermore, in the step of introducing, a second nucleic acid sequence encoding a norovirus VP2 protein may be introduced in the plant, portion of the plant, or the plant cell, and in the step of incubating, the conditions permit co-expression and co-production, of both the VP1 fusion protein and the VP2 protein in the plant, the portion of a plant, or the plant cell A plant, portion of a plant, or a plant cell comprising the VLP produced by the method described above is also provided herein. A plant extract comprising the VLP produced by this method is also described.

Also provided is a composition for inducing an immune response. The composition comprises, an effective dose of the norovirus VP1 fusion protein encoded by the nucleic acid as described herein; and a pharmaceutically acceptable carrier, adjuvant, vehicle or excipient. Alternatively, the composition may comprise, an effective dose of the VLP produced by the method described herein, and a pharmaceutically acceptable carrier, adjuvant, vehicle or excipient.

A method of producing an antibody or an antibody fragment is also described. The method comprises, administering the norovirus fusion VP1 fusion protein as described above to a subject in need thereof, or a host animal, thereby producing the antibody or the antibody fragment.

Additionally there is provided a vaccine for inducing an immune response in a subject in need thereof, the vaccine comprising an effective dose of the norovirus VP1 fusion protein encoded by the nucleic acid described herein. Alternatively, the vaccine may comprise an effective dose of VLP produced by the method described herein.

The present disclosure also provides a method of inducing immunity to a norovirus infection in a subject comprising administering the norovirus VP1 fusion protein encoded by the nucleic acid described herein. The norovirus VP1 fusion protein may be administered orally, intranasally, intramuscularly, intraperitoneally, intravenously, or subcutaneously. Also provided is a method of inducing immunity to a norovirus infection in a subject comprising of administering the VLP produced by the method described herein. The VLP may be administered orally, intranasally, intramuscularly, intraperitoneally, intravenously, or subcutaneously.

Also described herein is a nucleic acid complex comprising, a VP1 sequence encoding a norovirus VP1 fusion protein, and a VP2 sequence encoding a norovirus VP2 protein, the VP1 sequence comprising a first and a second nucleic acid sequence, the first nucleic acid sequence encoding an S domain derived from a first norovirus strain, the second nucleic acid sequence encoding a P domain derived from a second norovirus strain, the VP2 sequence comprising a third nucleic acid sequence derived from the first norovirus strain and encoding the norovirus VP2 protein, wherein the VP1 sequence is operatively linked to a first regulatory region, and the VP2 sequence is operatively linked to a second regulatory region, and the VP1 sequence and the VP2 sequence are located on one nucleic acid segment, or the VP1 sequence and the VP2 sequence are located on separate nucleic acid segments. The first regulatory region, the second regulatory region, or the first and second regulatory region of the nucleic acid complex may comprise a CPMV enhancer element that is operatively linked with a promoter active in the plant. For example, the first and the second regulatory region may comprise the CPMV enhancer element, and the first and the second regulatory region may comprise the same promoter. Furthermore, the first and the second regulatory region may comprise a CPMV enhancer element, and the CPMV enhancer sequence of the first and the second regulatory region may be the same CPMV enhancer sequence. The first, the second, the third nucleic acid sequence, or all of the first, second and third nucleic acid sequence, may be optimized for human codon usage, increased GC content, or a combination thereof.

Also provided herein is a VLP comprising the norovirus VP1 fusion protein and the norovirus VP2 protein encoded by the nucleic acid complex as defined above. The VLP may have a diameter of about 15 nm to 50 nm, for example, from about 23 nm or about 38 nm.

A method of producing a virus like particle (VLP) in a plant, portion of a plant, or a plant cell is also described. The method comprises introducing the nucleic acid complex as defined above into the plant, the portion of a plant, or the plant cell, and incubating the plant, the portion of a plant, or the plant cell under conditions that permit the production of the VLP comprising the norovirus VP1 fusion protein and the norovirus VP2 protein. The method may further comprises a step of harvesting the plant, the portion of a plant, or the plant cell. Furthermore, the method may comprises a step of extracting, purifying, or both extracting and purifying, the VLP comprising the norovirus VP1 fusion protein and the norovirus VP2 protein, from the plant, the portion of a plant, or the plant cell.

Also included herein is a plant, portion of the plant, or the plant cell comprising the nucleic acid complex as described above. Furthermore, a plant extract comprising the VLP comprising the norovirus VP1 fusion protein and the norovirus VP2 protein, produced by the method described above is provided Also described herein is the VLP comprising the norovirus VP1 fusion protein and the norovirus VP2 protein produced by the method described above. The VLP may have a diameter of about 15 nm to 50 nm, for example about 23 nm or about 38 nm. Furthermore, a plant, portion of the plant, or the plant cell comprising the VLP comprising the VP1 fusion protein and the norovirus VP2 protein as described above is also provided.

A composition for inducing an immune response comprising, an effective dose of the VLP comprising the norovirus VP1 fusion protein and the norovirus VP2 protein described above, and a pharmaceutically acceptable carrier, adjuvant, vehicle or excipient is also presented herein. Also provided, is a method for inducing immunity to a norovirus infection in a subject, comprising, administering the composition as just described to the subject. Furthermore, the composition may be administered to the subject orally, intranasally, intramuscularly, intraperitoneally, intravenously, or subcutaneously.

Also described is a method for inducing immunity to a norovirus infection in a subject, the method comprising administering the VLP comprising, an effective dose of the VLP comprising the norovirus VP1 fusion protein and the norovirus VP2 protein as described above, to the subject. The VLP may be administered to the subject orally, intranasally, intramuscularly, intraperitoneally, intravenously, or subcutaneously.

A vaccine is also described herein. The vaccine comprising an effective dose of the VLP of the present disclosure for inducing an immune response. Also presented is a method for inducing immunity to a norovirus infection in a subject, comprising administering the vaccine as just described to the subject. The vaccine may be administered to the subject orally, intranasally, intramuscularly, intraperitoneally, intravenously, or subcutaneously.

The present disclosure also describes a method of producing an antibody or an antibody fragment comprising, administering the VLP comprising the norovirus VP1 fusion protein and the norovirus VP2 protein, described above, to a subject in need thereof, or a host animal, thereby producing the antibody or the antibody fragment, is also provided. For example, the antibody or antibody fragment may recognizes an epitope of the P domain.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 2A shows Uniprot and NCBI references for several norovirus VP1 (upper panel) and VP2 (lower panel) proteins. FIG. 2B shows NCBI references for several norovirus VP1 and VP2 nucleic acid sequences. FIG. 2C shows the amino acid sequence identity between norovirus VP1 (upper panel) and VP2 (lower panel) proteins. G1.1 (SEQ ID NO:1), G1.2 (SEQ ID NO:2), GI.3 (SEQ ID NO:3), GII.4 (SEQ ID NO:4), GII.6 (SEQ ID NO:5), GII.13 (SEQ ID NO:6), GII.17 (SEQ ID NO:7). FIG. 2D shows the amino acid sequence identity between several strains of norovirus GII.4 VP1 proteins (upper panel), the amino acid sequence identity between several strains of norovirus GII.4 VP1 P domain (middle panel), and the amino acid sequence identity between several strains of norovirus GII.4 P2 domain (lower panel). US96: GII.4/Dresden174/1997/DE (GII.4 variant: US 1995/96; SEQ ID NO:8); FH02: GII.4/FarmingtonHills/2002/US (SEQ ID NO:9); Hnt04:GII.4/Hunter-NSW504D/2004/AU (SEQ ID NO:10); 2006b: GII.4/Shellharbour-NSW696T/2006/AU (SEQ ID NO:11); NO09: GII.4/Orange-NSW001P/2008/AU (GII.4 variant New Orleans 2009; SEQ ID NO:12); Syd12: Hu/GII.4/Sydney/NSW0514/2012/AU (SEQ ID NO:4).

FIG. 4A shows the alignment of several amino acid sequences of norovirus S domain-P domain boundary for GI.1 (VP1 Norwalk 1968 GI.1 Q83884 Rf; SEQ ID NO:88), GI.2 (VP1 Leuven 2003 Gi.1 D2DEL3; SEQ ID NO:89), GI.3 (VP1 LillaEdet 2008 Gi.3 H2DG70; SEQ ID NO:90), GII.4 (VP1 Sydney 2012 GII.3 K4LM89; SEQ ID NO:91), GII.6 (VP1 Ohio 2012 GII.6 M9T020; SEQ ID NO:92), GII.13 (VP1 VA173 2010 GII.13 H9AWU4; SEQ ID NO:93), GII.17 (VP1 awasaki 2014 GII.17 A0A077KVU6; SEQ ID NO:94), and the consensus sequence (SEQ ID NO:95). FIG. 4B shows amino acid sequence identity between a GI.1 native norovirus VP1 protein (SEQ ID NO:1) and several VP1 fusion proteins as described herein (S(GI.1)+P(GI.2), SEQ ID NO:22; S(GI.1)+P(GI.3), SEQ ID NO:23; S(GI.1)+P(GII.4), SEQ ID NO:24; S(GI.1)+P (GII.6), SEQ ID NO:25; S(GI.1)+P(GII.12), SEQ ID NO:71; S(GI.1)+P(GII.13), SEQ ID NO:26; and S(GI.1)+P (GII.17), SEQ ID NO:27). FIG. 4C shows amino acid sequence identity between a GII.12 norovirus native VP1 protein (SEQ ID NO:28) and several VP1 fusion proteins demonstrating that GII-S domain may be used for VP1 fusions as described herein (S(GII.12)+P(GI.1), SEQ ID NO: 29; S(GII.12)+P(GI.2), SEQ ID NO: 30; S(GII.12)+P (GI.3), SEQ ID NO: 31; S(GII.12)+P(GI.5), SEQ ID NO: 32; S(GII.12)+P(GII.1), SEQ ID NO: 33; S(GII.12)+P (GII.2), SEQ ID NO: 34; S(GII.12)+P(GII.3), SEQ ID NO: 35; S(GII.12)+P(GII.4), SEQ ID NO: 36; S(GII.12)+P (GII.5), SEQ ID NO: 37; S(GII.12)+P(GII.6), SEQ ID NO: 38; S(GII.12)+P(GII.7), SEQ ID NO: 39; S(GII.12)+P (GII.13), SEQ ID NO: 40; S(GII.12)+P(GII.14), SEQ ID NO: 41; S(GII.12)+P(GII.17), SEQ ID NO: 42; S(GII.12)+ P(GII.21), SEQ ID NO: 43). FIG. 4D shows amino acid sequence identity between a GI.5 native VP1 protein (SEQ ID NO: 44), a GII.1 norovirus native VP1 protein (SEQ ID NO: 45), a GII.14 norovirus native VP1 protein (SEQ ID NO: 46), a GII.21 norovirus native VP1 protein (SEQ ID NO: 47) and several VP1 fusion proteins as described herein (S(GI.5)+P(GII.4), SEQ ID NO: 48; S(GII.1)+P(GI.3), SEQ ID NO: 49; S(GII.1)+P(GII.4), SEQ ID NO: 50; S(GII.1)+ P(GII.17), SEQ ID NO: 51; S(GII.14)+P(GII.4), SEQ ID NO: 52; S(GII.21)+P(GII.4), SEQ ID NO: 53). S: shell domain; P: P domain.

FIG. 15B); GI.5 Siklos/HUN5407/2013/HUN (SEQ ID NO:44: FIG. 16A); GII.1 Ascension208/2010/USA SEQ ID NO:45; FIG. 16B); GII.7 Musashimurayama/2010/JP (SEQ I NO:69; FIG. 16F). FIG. 17B) native VP1 co-expressed with GII.4/Sydney/NSW0514/2012/AU native VP2 (construct #3305; SEQ ID NO:120; FIG. 23D); Panel B (left hand side)—human codon optimized VP1 S(GI.1)+P(GII.4) fusion protein (construct 3362; SEQ ID NO:59; FIG. 27B); Panel B (right hand side)—human codon optimized VP1 S(GI.1)+P (GII.4) fusion protein (construct 3362; SEQ ID NO:59; FIG. 27B) co-expressed with human codon optimized GI.1/Norwalk native VP2 (construct #2725; SEQ ID NO:19; FIG. 23C); Panel C (left hand side)—human codon optimized VP1 S (GI.1)+P (GII.4) fusion protein (construct 3362; SEQ ID NO:59; FIG. 27B) co-expressed with human codon optimized GI.1/Norwalk native VP2 (construct #2725; SEQ ID NO:19; FIG. 23C); Panel C (right hand side)—human codon optimized VP1 S(GI.1)+P(GII.4) fusion protein (construct 3362; SEQ ID NO:59; FIG. 27B) co-expressed with human codon optimized GII.4/Sydney native VP2 (construct #3305; SEQ ID NO:120; FIG. 23D).

FIG. 7A shows the nucleotide sequence of primer IF-NoV(US68)VP1(ORF2).c (SEQ ID NO: 72); FIG. 7B shows the nucleotide sequence of primer IF-NoV(US68)VP1(ORF2).r (SEQ ID NO: 73); FIG. 7C shows the nucleotide sequence of construct 1190 from left to right t-DNA borders (underlined). 2X35S/CPMV-160/NOS with Plastocyanine-P19-Plastocyanine silencing inhibitor expression cassette (SEQ ID NO: 74); FIG. 7D shows a schematic representation of construct 1190.

FIG. 9A shows the nucleotide sequence of primer IF-NoV(US68)VP1(ORF2)(hCod).c (SEQ ID NO: 76); FIG. 9B shows the nucleotide sequence of primer IF-NoV(US68)VP1(ORF2)(hCod).r (SEQ ID NO: 77); FIG. 9C shows the nucleotide sequence of construct 2724 from 2X35S promoter to NOS terminator. Human codon-optimized VP1 from Norovirus GI.1/Norwalk/1968/US strain is underlined. (SEQ ID NO: 78); FIG. 9D shows a schematic representation of construct 2724.

FIG. 10A shows the nucleotide sequence of primer IF-NoV(US68)VP2(ORF3)(hCod).c (SEQ ID NO: 79); FIG. 10B shows the nucleotide sequence of primer IF-NoV(US68)VP2(ORF3)(hCod).r (SEQ ID NO: 80)

FIG. 11A shows the nucleotide sequence of primer IF-GI2Leu03VP1.c (SEQ ID NO: 82); FIG. 11B shows the nucleotide sequence of primer IF-GI2Leu03VP1.r (SEQ ID NO: 83); FIG. 11C shows the nucleotide sequence of construct 3300 from 2X35S promoter to NOS terminator. Human codon-optimized VP1 from Norovirus GI.2/Leuven/

2003/Bel strain is underlined. (SEQ ID NO: 84); FIG. 11D shows a schematic representation of construct 3300.

FIG. 12A shows the nucleotide sequence of primer GI2Leu+GI1VP1.r (SEQ ID NO: 85); FIG. 12B shows the nucleotide sequence of primer GI1VP1+GI2Leu.c (SEQ ID NO: 86); FIG. 12C shows the nucleotide sequence of construct 3360 from 2X35S promoter to NOS terminator. Human codon-optimized fusion VP1 S(GI.1)+P(GI.2) protein gene sequence is underlined. (SEQ ID NO: 87); FIG. 12D shows a schematic representation of construct 3360.

FIG. 13A shows the amino acid sequence of VP1 GI.1 United States Norwalk 1968 (SEQ ID NO:1); FIG. 13B shows the nucleic acid sequence of wild type VP1 GI.1 United States Norwalk 1968 (SEQ ID NO:13); FIG. 13C shows the nucleic acid sequence of human codon optimized VP1 GI.1 United States Norwalk 1968 (SEQ ID NO:18).

FIG. 14A shows the amino acid sequence of VP1 G1.2 Leuven 2003 D2DEL3 (SEQ ID NO:2); FIG. 14B shows the nucleic acid sequence of human codon optimized VP1 G1.2 Leuven 2003 D2DEL3 (SEQ ID NO:54).

FIG. 15A shows the amino acid sequence of VP1 GI.3 LillaEdet 2008 H2DG70 (SEQ ID NO:3); FIG. 15B shows the nucleic acid sequence of human codon optimized GI.3 LillaEdet 2008 H2DG70 (SEQ ID NO:55).

FIG. 16A shows the amino acid sequence of VP1 GI.5 Siklos HUN5407 2013 HUN AHW99832 (SEQ ID NO:44); FIG. 16B shows the amino acids sequence of VP1 GII.1 Ascension208 2010 USA AFA55174 (SEQ ID NO: 45); FIG. 16C shows the amino acid sequence of VP1 GII.2 CGMH47 2011 TW AGT39206 (SEQ ID NO: 66); FIG. 16D shows the amino acid sequence of VP1 GII.3 Jingzhou 2013402 CHN AGX01095 (SEQ ID NO: 67); FIG. 16E shows the amino acid sequence of VP1 GII.5 Alberta 2013 CA ALT54485 (SEQ ID NO: 68); FIG. 16F shows the amino acid sequence of VP1 GII.7 Musa 2010 A1173774 (SEQ ID NO: 69); FIG. 16G shows the amino acid sequence of VP1 consensus sequence from genotypes GI.1, GI.2, GI.3, GII.4, GII.6, GII.13 and GII.17 (SEQ ID NO: 70) the S-P domain boundary sequence is underlined, and the boundary indicated with a "||".

FIG. 17A shows the amino acid sequence of VP1 GII.4 Sydney 2012 K4LM89 (SEQ ID NO:4); FIG. 17B shows the nucleic acid sequence of human codon optimized VP1 GII.4 Sydney 2012 K4LM89 (SEQ ID NO:56).

FIG. 18A shows the amino acid sequence of VP1 GII.6 Ohio 2012 M9T020 (SEQ ID NO: 5); FIG. 18B shows the nucleic acid sequence of human codon optimized VP1 GII.6 Ohio 2012 M9T020 (SEQ ID NO: 60).

FIG. 19A shows the amino acid sequence of VP1 GII.13 VA173 2010 H9AWU4 (SEQ ID NO: 6); FIG. 19B shows the nucleic acid sequence of human codon optimized VP1 GII.13 VA173 2010 H9AWU4 (SEQ ID NO: 61).

FIG. 20A shows the amino acid sequence of VP1 GII.17 Kawa 2014 A0A077KVU6 (SEQ ID NO: 7); FIG. 20B shows the nucleic acid sequence of human codon optimized VP1 GII.17 Kawa 2014 A0A077KVU6 (SEQ ID NO: 62).

FIG. 21A shows the amino acid sequence of VP1 US96: GII.4/Dresden174/1997/DE AY741811 (SEQ ID NO: 8); FIG. 21B shows the Amino acid sequence of VP1 FH02: GII.4/FarmingtonHills/2002/US AY502023

(SEQ ID NO: 9); FIG. 21C shows the amino acid sequence of VP1 Hnt04:GII.4/Hunter-NSW504D/2004/AU DQ078814 (SEQ ID NO: 10); FIG. 21D shows the amino acid sequence of VP1 2006b: GII.4/Shellharbour-NSW696T/2006/AU EF684915 (SEQ ID NO: 11); FIG. 21E shows the amino acid sequence of VP1 NO09: GII.4/Orange-NSW001P/2008/AU GQ845367 (SEQ ID NO: 12);

FIG. 22A shows the amino acid sequence of VP1 GII.12 HS206 2010 USA AEI29586 (SEQ ID NO: 28); FIG. 22B shows the amino acid sequence of VP1GII.14 Saga 2008 JPN ADE28701 (SEQ ID NO: 46); FIG. 22C shows the amino acid sequence of VP1 GII.21 Sali 2011 USA AFC89665 (SEQ ID NO: 47).

FIG. 23A shows the amino acid sequence of native VP2 G1.1 (SEQ ID NO: 14); FIG. 23B shows the nucleic acid sequence of wild-type VP2 G1.1 (SEQ ID NO: 15); FIG. 23C shows the nucleic acid sequence of human codon-optimized VP2 G1.1 (SEQ ID NO: 19). FIG. 23D shows the nucleic acid sequence of human codon-optimized VP2 GII.4/Sydney/NSW0514/2012/AU (SEQ ID NO:120). FIG. 23E shows the amino acid sequence of VP2 GII.4/Sydney/NSW0514/2012/AU (SEQ ID NO:121).

FIG. 24A shows the nucleic acid sequence of wild-type VP1/VP2 G1.1 (SEQ ID NO: 16); FIG. 24B shows the nucleic acid sequence of wild-type VP1/VP2/3'UTR G1.1 (SEQ ID NO: 17); FIG. 24C shows the nucleic acid sequence of human codon-optimized VP1/VP2 G1.1 (SEQ ID NO: 20); FIG. 24D shows the nucleic acid sequence of human codon-optimized VP1/VP2/3'UTR G1.1 (SEQ ID NO: 21).

FIG. 25A shows the amino acid sequence of S(GI.1)+P (GI.2) fusion VP1 (SEQ ID NO: 22); FIG. 25B shows the nucleic acid sequence of human codon optimized S(GI.1)+P(GI.2) fusion VP1 (SEQ ID NO: 57).

FIG. 26A shows the amino acid sequence of S(GI.1)+P (GI.3) fusion VP1 (SEQ ID NO: 23); FIG. 26B shows the nucleic acid sequence of human codon optimized S(GI.1)+P(GI.3) fusion VP1 (SEQ ID NO: 58).

FIG. 27A shows the amino acid sequence of S(GI.1)+P (GII.4) fusion VP1 (SEQ ID NO: 24); FIG. 27B shows the nucleic acid sequence of human codon optimized S(GI.1)+P(GII.4) fusion VP1 (SEQ ID NO: 59).

FIG. 28A shows the amino acid sequence of S(GI.1)+P (GII.6) fusion VP1 (SEQ ID NO: 25); FIG. 28B shows the nucleic acid sequence of human codon optimized S(GI.1)+P(GII.6) fusion VP1 (SEQ ID NO: 63).

FIG. 29A shows the amino acid sequence of S(GI.1)+P (GII.13) fusion VP1 (SEQ ID NO: 26); FIG. 29B shows the nucleic acid sequence of human codon optimized S(GI.1)+P(GII.13) fusion VP1 (SEQ ID NO: 64).

FIG. 30A shows the amino acid sequence of S(GI.1)+P (GII.17) fusion VP1 (SEQ ID NO: 27); FIG. 30B shows the nucleic acid sequence of human codon optimized S(GI.1)+P(GII.17) fusion VP1 (SEQ ID NO: 65).

FIG. 31A shows the amino acid sequence of S(GI.1)+P (GII.12) fusion VP1 (SEQ ID NO: 71); FIG. 31B shows the amino acid sequence of S(GI.5)+P(GII.4) fusion VP1 (SEQ ID NO: 48).

FIG. 32A shows the amino acid sequence of S(GII.1)+P (GI.3) fusion VP1 (SEQ ID NO: 49); FIG. 32B shows the amino acid sequence of S(GII.1)+P(GII.4) fusion VP1 (SEQ ID NO: 50); FIG. 32C shows the amino acid sequence of S(GII.1)+P(GII.17) fusion VP1 (SEQ ID NO: 51).

FIG. 33A shows the amino acid sequence of S(GII.12)+P(GI.1) fusion VP1 (SEQ ID NO: 29); FIG. 33B shows the amino acid sequence of S(GII.12)+P(GI.2)fusion VP1 (SEQ ID NO: 30); FIG. 33C shows the amino acid sequence of S(GII.12)+P(GI.3) fusion VP1 (SEQ ID NO: 31); FIG. 33D shows the amino acid sequence of S(GII.12)+P(GI.5) fusion VP1 (SEQ ID NO: 32); FIG. 33E shows the amino acid sequence of S(GII.12)+P(GII.1) fusion VP1 (SEQ ID NO: 33); FIG. 33F shows the amino acid sequence of S(GII.12)+P(GII.2) fusion VP1 (SEQ ID NO: 34); FIG. 33G shows the amino acid sequence of S(GII.12)+P(GII.3) fusion VP1

(SEQ ID NO: 35); FIG. 33H shows the amino acid sequence of S(GII.12)+P(GII.4) fusion VP1 (SEQ ID NO: 36); FIG. 33I shows the amino acid sequence of S(GII.12)+P(GII.5) fusion VP1 (SEQ ID NO: 37); FIG. 33J shows the amino acid sequence of S(GII.12)+P(GII.6) fusion VP1 (SEQ ID NO: 38); FIG. 33K shows the amino acid sequence of S(GII.12)+P(GII.7) fusion VP1 (SEQ ID NO: 39); FIG. 33L shows the amino acid sequence of S(GII.12)+P(GII.13) fusion VP1 (SEQ ID NO: 40); FIG. 33M shows the amino acid sequence of S(GII.12)+P(GII.14) fusion VP1 (SEQ ID NO: 41); FIG. 33N shows the amino acid sequence of S(GII.12)+P(GII.17) fusion VP1 (SEQ ID NO: 42); FIG. 33O shows the amino acid sequence of S(GII.12)+P(GII.21) fusion VP1 (SEQ ID NO: 43).

FIG. 34A shows the amino acid sequence of S(GII.14)+P(GII.4) fusion VP1 (SEQ ID NO: 52); FIG. 34B shows the amino acid sequence of S(GII.21)+P(GII.4) fusion VP1 (SEQ ID NO: 53).

FIG. 35 shows a summary of primer sequences.

DETAILED DESCRIPTION

Figure 1A:
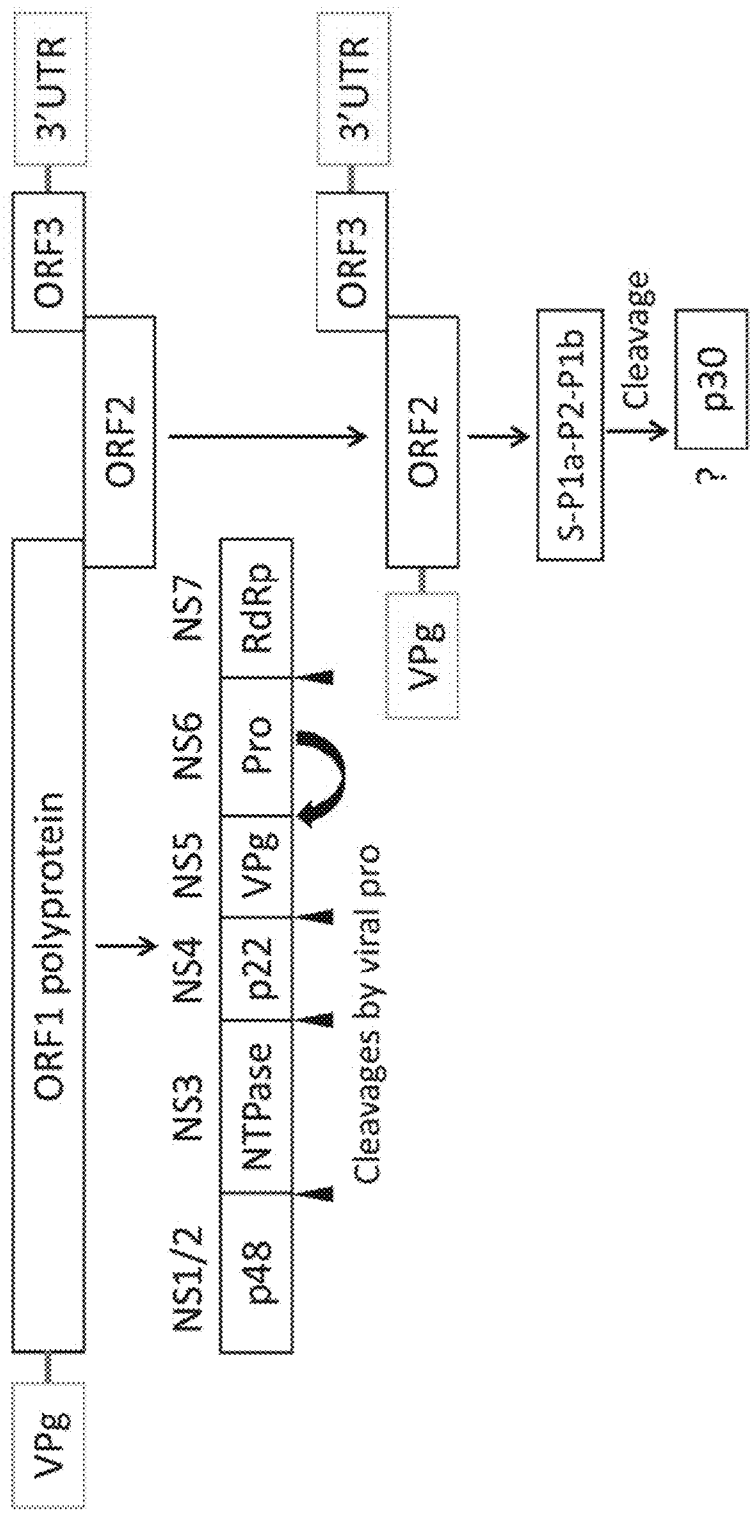
FIG. 1A shows a schematic representation of the linear structure of the norovirus genome and the polyprotein and proteins translated therefrom.

The following description is of a preferred embodiment.

As used herein, the terms "comprising," "having," "including" and "containing," and grammatical variations thereof, are inclusive or open-ended and do not exclude additional, un-recited elements and/or method steps. The term "consisting essentially of" when used herein in connection with a use or method, denotes that additional elements and/or method steps may be present, but that these additions do not materially affect the manner in which the recited method or use functions. The term "consisting of" when used herein in connection with a use or method, excludes the presence of additional elements and/or method steps. A use or method described herein as comprising certain elements and/or steps may also, in certain embodiments, consist essentially of those elements and/or steps, and in other embodiments consist of those elements and/or steps, whether or not these embodiments are specifically referred to. In addition, the use of the singular includes the plural, and "or" means "and/or" unless otherwise stated. The term "plurality" as used herein means more than one, for example, two or more, three or more, four or more, and the like. Unless otherwise defined herein, all technical and scientific terms used herein have the same meaning as commonly understood by one of ordinary skill in the art. As used herein, the term "about" refers to an approximately +/−10% variation from a given value. It is to be understood that such a variation is always included in any given value provided herein, whether or not it is specifically referred to. The use of the word "a" or "an" when used herein in conjunction with the term "comprising" may mean "one," but it is also consistent with the meaning of "one or more," "at least one" and "one or more than one."

The term "plant", "portion of a plant", "plant portion", "plant matter", "plant biomass", "plant material", plant extract", or "plant leaves", as used herein, may comprise an entire plant, tissue, cells, or any fraction thereof, intracellular plant components, extracellular plant components, liquid or solid extracts of plants, or a combination thereof, that are capable of providing the transcriptional, translational, and post-translational machinery for expression of one or more than one nucleic acids described herein, and/or from which an expressed protein or VLP may be extracted and purified. Plants may include, but are not limited to, agricultural crops including for example canola, *Brassica* spp., maize, *Nicotiana* spp., (tobacco) for example, *Nicotiana benthamiana, Nicotiana rustica, Nicotiana, tabacum, Nicotiana alata, Arabidopsis thaliana*, alfalfa, potato, sweet potato (*Ipomoea batatus*), *ginseng*, pea, oat, rice, soybean, wheat, barley, sunflower, cotton, corn, rye (*Secale cereale*), sorghum (*Sorghum bicolor, Sorghum vulgare*), safflower (Carthamus tinctorius).

The term "plant portion", as used herein, refers to any part of the plant including but not limited to leaves, stem, root, flowers, fruits, a plant cell obtained from leaves, stem, root, flowers, fruits, a plant extract obtained from leaves, stem, root, flowers, fruits, or a combination thereof. The term "plant extract", as used herein, refers to a plant-derived product that is obtained following treating a plant, a portion of a plant, a plant cell, or a combination thereof, physically (for example by freezing followed by extraction in a suitable buffer), mechanically (for example by grinding or homogenizing the plant or portion of the plant followed by extraction in a suitable buffer), enzymatically (for example using cell wall degrading enzymes), chemically (for example using one or more chelators or buffers), or a combination thereof. A plant extract may be further processed to remove undesired plant components for example cell wall debris. A plant extract may be obtained to assist in the recovery of one or more components from the plant, portion of the plant or plant cell, for example a protein (including protein complexes, protein surprastructures and/or VLPs), a nucleic acid, a lipid, a carbohydrate, or a combination thereof from the plant, portion of the plant, or plant cell. If the plant extract comprises proteins, then it may be referred to as a protein extract. A protein extract may be a crude plant extract, a partially purified plant or protein extract, or a purified product, that comprises one or more proteins, protein complexes, protein suprastructures, and/or VLPs, from the plant tissue. If desired a protein extract, or a plant extract, may be partially purified using techniques known to one of skill in the art, for example, the extract may be subjected to salt or pH precipitation, centrifugation, gradient density centrifugation, filtration, chromatography, for example, size exclusion chromatography, ion exchange chromatography, affinity chromatography, or a combination thereof. A protein extract may also be purified, using techniques that are known to one of skill in the art.

The term nucleic acid segment as used herein refers to a sequence of nucleic acids that encodes a protein of interest. In addition to the sequence of nucleic acids, the nucleic acid segment comprise a regulatory region and a terminator that are operatively linked to the sequence of nucleic acids. The regulatory region may for example comprise a promoter, and optionally, an enhancer element operatively linked to the promoter.

The term "nucleic acid complex" as used herein refers to a combination of two or more than two nucleic acid segments. The two or more than two nucleic acid segments may be present in a single nucleic acid, so that the nucleic acid complex comprises two, or more than two nucleic acid segments, with each nucleic acid segment under the control of a regulatory region and a terminator. Alternatively, the nucleic acid complex may comprise two or more separate nucleic acids, each of the nucleic acids comprising one or more than one nucleic acid segment, where each nucleic acid segment is under the control of a regulatory region and a terminator. For example a nucleic acid complex may comprise one nucleic acid that comprises two nucleic acid segments, a nucleic acid complex may comprise two nucleic acids, each nucleic acid comprising one nucleic acid segment, or a nucleic acid complex may comprise two or more than two nucleic acids, with each nucleic acid comprising one or more than one nucleic acid segment.

The term "vector" or "expression vector", as used herein, refers to a recombinant nucleic acid for transferring exogenous nucleic acid sequences into host cells (e.g. plant cells) and directing expression of the exogenous nucleic acid sequences in the host cells. "Expression cassette" refers to a nucleotide sequence comprising a nucleic acid of interest under the control of, and operably (or operatively) linked to, an appropriate promoter or other regulatory elements for transcription of the nucleic acid of interest in a host cell. As one of skill in the art would appreciate, the expression cassette may comprise a termination (terminator) sequence that is any sequence that is active the plant host. For example the termination sequence may be derived from the RNA-2 genome segment of a bipartite RNA virus, e.g. a comovirus, the termination sequence may be a NOS terminator, or terminator sequence may be obtained from the 3'UTR of the alfalfa plastocyanin gene.

The constructs of the present disclosure may further comprise a 3' untranslated region (UTR). A 3' untranslated region contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase gene (ssRUBISCO; U.S. Pat. No. 4,962,028; which is incorporated herein by reference), the promoter used in regulating plastocyanin expression.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a nucleotide sequence of interest, this may result in expression of the nucleotide sequence of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element may comprise a basal promoter element, responsible for the initiation of transcription, as well as other regulatory elements that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358). Examples, of potential inducible promoters include, but not limited to, tetracycline-inducible promoter (Gatz, C., 1997, Ann. Rev. Plant Physiol. Plant Mol. Biol. 48, 89-108), steroid inducible promoter (Aoyama, T. and Chua, N. H., 1997, Plant J. 2, 397-404) and ethanol-inducible promoter (Salter, M. G., et al, 1998, Plant Journal 16, 127-132; Caddick, M. X., et al, 1998, Nature Biotech. 16, 177-180) cytokinin inducible IB6 and CKI1 genes (Brandstatter, I. and Kieber, J. J., 1998, Plant Cell 10, 1009-1019; Kakimoto, T., 1996, Science 274, 982-985) and the auxin inducible element, DR5 (Ulmasov, T., et al., 1997, Plant Cell 9, 1963-1971).

A constitutive regulatory region directs the expression of a gene throughout the various parts of a plant and continuously throughout plant development. Examples of known constitutive regulatory elements include promoters associated with the CaMV 35S transcript. (p35S; Odell et al., 1985, Nature, 313: 810-812; which is incorporated herein by reference), the rice actin 1 (Zhang et al, 1991, *Plant Cell,* 3: 1155-1165), actin 2 (An et al., 1996, *Plant J.,* 10: 107-121), or tms 2 (U.S. Pat. No. 5,428,147), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), the tobacco translational initiation factor 4A gene (Mandel et al, 1995 Plant Mol. Biol. 29: 995-1004). the Cassava Vein Mosaic Virus promoter, pCAS, (Verdaguer et al., 1996); the promoter of the small subunit of ribulose biphosphate carboxylase, pRbcS: (Outchkourov et al., 2003), the pUbi (for monocots and dicots).

The term "constitutive" as used herein does not necessarily indicate that a nucleotide sequence under control of the constitutive regulatory region is expressed at the same level in all cell types, but that the sequence is expressed in a wide range of cell types even though variation in abundance is often observed.

The expression constructs as described above may be present in a vector. The vector may comprise border sequences which permit the transfer and integration of the expression cassette into the genome of the organism or host. The construct may be a plant binary vector, for example a binary transformation vector based on pPZP (Hajdukiewicz, et al. 1994). Other example constructs include pBin19 (see Frisch, D. A., L. W. Harris-Haller, et al. 1995, *Plant Molecular Biology* 27: 405-409).

The term "native", "native protein" or "native domain", as used herein, refers to a protein or domain having a primary amino acid sequence identical to wildtype. Native proteins or domains may be encoded by nucleotide sequences having 100% sequence similarity to the wildtype sequence. A native amino acid sequence may also be encoded by a human codon (hCod) optimized nucleotide sequence or a nucleotide sequence comprising an increased GC content when compared to the wild type nucleotide sequence provided that the amino acid sequence encoded by the hCod-nucleotide sequence exhibits 100% sequence identity with the native amino acid sequence.

By a nucleotide sequence that is "human codon optimized" or a "hCod" nucleotide sequence, it is meant the selection of appropriate DNA nucleotides for the synthesis of an oligonucleotide sequence or fragment thereof that approaches the codon usage generally found within an oligonucleotide sequence of a human nucleotide sequence. By "increased GC content" it is meant the selection of appropriate DNA nucleotides for the synthesis of an oligonucleotide sequence or fragment thereof in order to approach codon usage that, when compared to the corresponding native oligonucleotide sequence, comprises an increase of GC content, for example, from about 1 to about 30%, or any amount therebetween, over the length of the coding portion of the oligonucleotide sequence. For example, from about 1, 2, 4, 6, 8, 10, 12, 14, 16, 18, 20, 22, 24, 26, 28, 30%, or any amount therebetween, over the length of the coding portion of the oligonucleotide sequence. As described below, a human codon optimized nucleotide sequence, or a nucleotide sequence comprising an increased GC contact (when compared to the wild type nucleotide sequence) exhibits increased expression within a plant, portion of a plant, or a plant cell, when compared to expression of the non-human optimized (or lower GC content) nucleotide sequence.

Norovirus VP1 fusion proteins and methods of producing norovirus VP1 fusion proteins in plants are described herein. The norovirus VP1 fusion protein, comprises an S domain derived from a first norovirus strain fused to a P domain, or a portion of the P domain, derived from a second norovirus strain. It has been observed that expression of the VP1 fusion protein increases the yield of the P domain, or a portion of the P domain, derived from the second norovirus strain in plants, when compared to the yield of the P domain, or a portion of the P domain, of the second norovirus strain, when expressed in the same plant and under the same conditions, as a native VP1 protein comprising both an S domain and the P domain (or comprising the P domain that comprises a portion of the P domain), from the same second norovirus strain.

For example, the norovirus VP1 fusion protein, and methods of producing the norovirus VP1 fusion protein, may include a VP1 fusion protein comprising an S domain derived from a first norovirus strain fused to the P1 and P2 subdomains derived from a second norovirus strain:

$$S_{1st\ strain}\text{-}P1a_{2nd\ strain}\text{-}P2_{2nd\ strain}\text{-}P1b_{2nd\ strain},$$

also referred to as: "$S_1$-$P1a_2$-$P2_2$-$P1b_2$", or "$S_1$-$P_2$". The VP1 fusion protein, $S_1$-$P_2$, was observed to maintain or increase the yield of the P1 and P2 subdomains (P domain) derived from the second norovirus strain, as compared to the yield of the P subdomain of the second strain, when expressed in the same plant and under the same conditions as a native VP1 protein comprising both an S domain and the P domain, that comprises the P1 and P2 subdomains, from the same second norovirus strain. The sequence encoding the VP1 fusion protein may be optimized for human codon usage, for having an increased GC content, or a combination thereof.

Also provided herein are methods of increasing production of VLPs comprising norovirus VP1 fusion proteins in plants, wherein a nucleic acid encoding a norovirus VP1 fusion protein as described herein, for example $S_{1st\ strain}$-$P1a_{2nd\ strain}$-$P2_{2nd\ strain}$-$P1b_{2nd\ strain}$ ($S_1$-$P1a_2$-$P2_2$-$P1b_2$; $S_1$-$P_2$) is introduced into the plant or a portion of the plant. One or more than one type of norovirus fusion protein may be expressed in a plant or portion of the plant in order to produce a VLP comprising one or more than one type of norovirus fusion protein.

The methods of producing a VLP comprising a VP1 fusion protein may also comprise a step of co-expressing a nucleic acid sequence encoding a VP2 protein in the plant or portion of the plant.

The term "single construct" or "single constructs", as used herein, refers to nucleic acid vectors comprising a single nucleic acid sequence. The term "dual construct" or "dual constructs", as used herein, refers to a nucleic acid vector comprising two nucleic acid sequences.

By co-expression it is meant the introduction and expression of two or more nucleotide sequences, each of the two or more nucleotide sequences encoding a protein of interest, or a fragment of a protein of interest within a plant, portion of a plant or a plant cell. The two or more nucleotide sequences may be introduced into the plant, portion of the plant or the plant cell within one vector, so that each of the two or more nucleotide sequences is under the control of a separate regulatory region (e.g. comprising a dual construct). Alternatively, the two or more nucleotide sequences may be introduced into the plant, portion of the plant or the plant cell within separate vectors (e.g. comprising single constructs), and each vector comprising appropriate regulatory regions for the expression of the corresponding nucleic acid. For example, two nucleotide sequences, each on a separate vector and introduced into separate *A. tumefaciens* hosts, may be co-expressed by mixing suspensions of each *A. tumefaciens* host in a desired volume (for example, an equal volume, or the ratios of each *A. tumefaciens* host may be altered) before vacuum infiltration. In this manner, co-infiltration of multiple *Agrobacterium* suspensions permits co-expression of multiple transgenes.

The nucleic acid comprising encoding a norovirus VP1 fusion protein as described herein, for example, $S_1$-$P_2$ may further comprise sequences that enhance expression of the norovirus VP1 fusion protein in the plant, or in a portion of the plant. Sequences that enhance expression may include, a CPMV enhancer element in operative association with the nucleic acid encoding the norovirus VP1 fusion protein.

The sequence encoding the VP1 fusion protein may also be optimized for human codon usage, for having an increased GC content, or a combination thereof.

Furthermore, a nucleic acid encoding VP2 may be co-expressed along with the sequence encoding the VP1 fusion protein. The co-expression of a nucleic acid encoding VP2 may lead to increased stability, an increased yield, or both an increase in stability and yield, of VLPs that comprise the one or more than one type of VP1 fusion protein.

The term “CPMV enhancer element”, as used herein, refers to a nucleotide sequence encoding the 5'UTR regulating the Cowpea Mosaic Virus (CPMV) RNA2 polypeptide or a modified CPMV sequence as is known in the art. For example, a CPMV enhancer element or a CPMV expression enhancer, includes a nucleotide sequence as described in WO2015/14367; WO2015/103704; WO2007/135480; WO2009/087391; Sainsbury F., and Lomonossoff G. P., (2008, Plant Physiol. 148: pp. 1212-1218), each of which is incorporated herein by reference. A CPMV enhancer sequence can enhance expression of a downstream heterologous open reading frame (ORF) to which they are attached. The CPMV expression enhancer may include CPMV HT, CPMVX, CPMVX+, CPMV-HT+, CPMV HT+ [WT115], or CPMV HT+[511] (WO2015/14367; WO2015/103704 which are incorporated herein by reference). The CPMV expression enhancer may be used within a plant expression system comprising a regulatory region that is operatively linked with the CPMV expression enhancer sequence and a nucleotide sequence of interest. The term “5'UTR” or “5' untranslated region” or “5' leader sequence” refers to regions of an mRNA that are not translated. The 5'UTR typically begins at the transcription start site and ends just before the translation initiation site or start codon of the coding region. The 5" UTR may modulate the stability and/or translation of an mRNA transcript.

By “operatively linked” it is meant that the particular sequences interact either directly or indirectly to carry out an intended function, such as mediation or modulation of expression of a nucleic acid sequence. The interaction of operatively linked sequences may, for example, be mediated by proteins that interact with the operatively linked sequences.

When one or more than one type of the norovirus VP1 fusion protein is expressed in the plant, portion of the plant or the plant cell, the one or more than one type of VP1 fusion proteins auto-assemble into VLPs. The plant or portion of the plant may be harvested under suitable extraction and purification conditions to maintain the integrity of the VLP, and the VLP comprising the one or more than one type of VP1 fusion protein may be purified. The one or more than one VP1 fusion protein may also be co-expressed with nucleotide sequence encoding VP2, so that the VLP may comprise both VP1 fusion protein and VP2 protein. The present disclosure also provides for the production of one or more than one type of VP1 fusion protein as described herein within a plant, portion of a plant, or plant cell, and the extraction and purification of the one or more than one type of VP1 fusion protein from the plant, the portion of the plant, or the plant cell to produce plant matter, a plant extract, or a protein extract, comprising the VP1 fusion protein.

Plant matter, a plant extract, or a protein extract comprising the norovirus VP1 fusion protein, for example $S_1$-$P_2$, or VLPs comprising the norovirus a VP1 fusion protein as described herein, for example $S_1$-$P_2$ is also provided. The plant matter, plant extract, or protein extract may be used to induce immunity to norovirus infection in a subject. Alternatively, the VP1 fusion protein, or the VLP comprising the VP1 fusion protein (and optionally VP2), may be purified or partially purified, and the purified or partially purified preparation may be used in inducing immunity to norovirus infection in a subject.

The present disclosure also provides a composition comprising an effective dose of one or more than one type of norovirus VP1 fusion protein, for example, $S_1$-$P_2$, a combination thereof, or VLPs comprising one or more than one type of norovirus VP1 fusion protein, and optionally VP2, for example $S_1$-$P_2$, for inducing an immune response, and a pharmaceutically acceptable carrier, adjuvant, vehicle, or excipient.

Also provided herein are methods of inducing immunity to a norovirus infection in a subject comprising of administering one or more than one type of norovirus VP1 fusion protein or VLPs comprising one or more than one types of norovirus VP1 fusion proteins to a subject orally, intranasally, intramuscularly, intraperitoneally, intravenously, or subcutaneously.

The term “norovirus”, as used herein, refers to anon-enveloped viral strain of the genus norovirus of the family Caliciviridae that is characterized as having a single-stranded, positive-sense RNA. The norovirus genome is 7,654 nucleotides in length. The ORF1 encodes a nonstructural polyprotein that is cleaved by viral 3C-like protease into 6 proteins, including an RNA-dependent RNA polymerase. ORF2 and ORF3 encode a major (VP1) and a minor (VP2) capsid proteins, respectively (see FIG. 1A).

Norovirus strains as disclosed herein include, any known norovirus strain, but also modifications to known norovirus strains that are known to develop on a regular basis over time (See for example Parra G. I. et. al. PLoS Pathog 13(1): e1006136. doi:10.1371/journal. ppat.1006136). For example norovirus strains may include, but are not limited to GI.1/Norwalk/1968/US (GI.1; SEQ ID NO:1; FIG. 13A), GI.2/Leuven/2003/Bel (GI.2; SEQ ID NO:2; FIG. 14A), GI.3/S29/2008/Lilla Edet/Sweden (GI.3; SEQ ID NO:3; FIG. 15A), GI.5/Siklos/Hun5407/2013/HUN (GI.5; SEQ ID NO:44; FIG. 16A), GII.1/Ascension208/2010/USA (GII.1; SEQ ID NO:45; FIG. 16B), GII.2/CGMH47/2011/TW (GII.2; SEQ ID NO:66; FIG. 16C), GII.3/Jingzhou/2013402/CHN (GII.3; SEQ ID NO:67; FIG. 16D), GII.4/Sydney/NSW0514/2012/AU (GII.4; SEQ ID NO:4; FIG. 17A), GII.5/AlbertaEI390/2013/CA (GII.5; SEQ ID NO:68; FIG. 16E), GII.7/Musahimurayama/2010/JP (GII.7; SEQ ID NO:69; FIG. 16F), GII.12/HS206/2010/USA (GII.12; SEQ ID NO:28; FIG. 22A), GII.13/VA173/2010/USA (GII.13; SEQ ID NO: 6; FIG. 19A), GII.14/8610/Saga/2008/JP (GII.14; SEQ ID NO: 46; FIG. 46B), GII.17/Kawasaki323/2014/JP (GII.17; SEQ ID NO: 7; FIG. 20A), and GII.21/Salisbury150/2011/USA (GII.21; SEQ ID NO:47; FIG. 22C). Norovirus strains also include strains having from about 30-100%, or any amount therebetween, amino acid sequence identity to the VP1 protein, the VP2 protein, or both the VP1 and the VP2 proteins, with any of the above norovirus strains of the strains listed in FIGS. 2A and 2B, provided that the VP1 protein induces immunity to norovirus in a subject, when the VP1 protein is administered to the subject. For example, norovirus strains also include strains having 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100%, or any amount therebetween, amino acid sequence identity (sequence similarity; percent identity; percent similarity) to the VP1 protein, the VP2 protein, or both the VP1 and the VP2 proteins, with any of the above norovirus strains of the strains listed in FIGS. 2A and 2B, provided that the VP1 protein induces immunity to norovirus in a subject, when the VP1 protein is administered to the subject. An amino acid sequence identity comparison between the VP1 and the VP2 proteins of several norovirus strains, which are not to be considered limiting, is shown in FIG. 2C (VP1, upper panel; VP2, lower panel).

The terms "percent similarity", "sequence similarity", "percent identity", or "sequence identity", when referring to a particular sequence, are used for example as set forth in the University of Wisconsin GCG software program, or by manual alignment and visual inspection (see, e.g., Current Protocols in Molecular Biology, Ausubel et al., eds. 1995 supplement). Methods of alignment of sequences for comparison are well-known in the art. Optimal alignment of sequences for comparison can be conducted, using for example the algorithm of Smith & Waterman, (1981, Adv. Appl. Math. 2:482), by the alignment algorithm of Needleman & Wunsch, (1970, J. Mol. Biol. 48:443), by the search for similarity method of Pearson & Lipman, (1988, Proc. Natl. Acad. Sci. USA 85:2444), by computerized implementations of these algorithms (for example: GAP, BESTFIT, FASTA, and TFASTA in the Wisconsin Genetics Software Package, Genetics Computer Group (GCG), 575 Science Dr., Madison, Wis.).

An example of an algorithm suitable for determining percent sequence identity and sequence similarity are the BLAST and BLAST 2.0 algorithms, which are described in Altschul et al., (1977, Nuc. Acids Res. 25:3389-3402) and Altschul et al., (1990, J. Mol. Biol. 215:403-410), respectively. BLAST and BLAST 2.0 are used, with the parameters described herein, to determine percent sequence identity for the nucleic acids and proteins of the invention. For example the BLASTN program (for nucleotide sequences) may use as defaults a wordlength (W) of 11, an expectation (E) of 10, M=5, N=−4 and a comparison of both strands. For amino acid sequences, the BLASTP program may use as defaults a word length of 3, and expectation (E) of 10, and the BLOSUM62 scoring matrix (see Henikoff & Henikoff, 1989, Proc. Natl. Acad. Sci. USA 89:10915) alignments (B) of 50, expectation (E) of 10, M=5, N=−4, and a comparison of both strands. Software for performing BLAST analyses is publicly available through the National Center for Biotechnology Information (see URL: ncbi.nlm.nih.gov/).

Figure 1B:
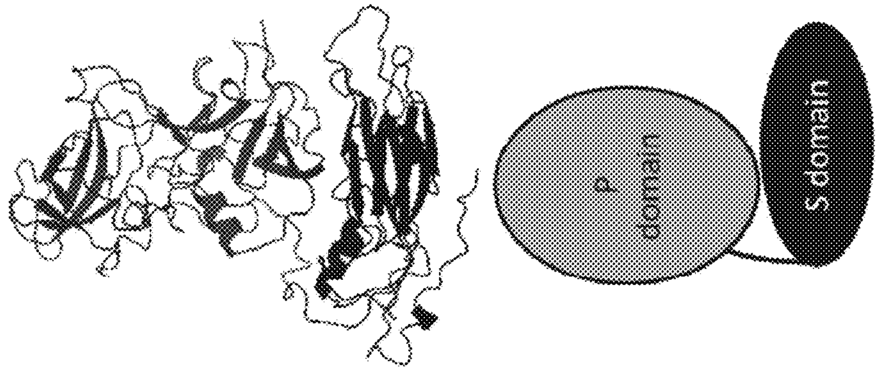
FIG. 1B shows a ribbon diagram representation of the 3-dimensional structure of the norovirus VP1 protein comprising a shell (S) domain, a P1 subdomain (P1), and a P2 subdomain (P2).

The term "VP1", as used herein, refers to the norovirus major capsid protein or polypeptide comprising an amino acid sequence similar to the protein or polypeptide encoded by ORF2 of one or more strains of norovirus as described herein. The major capsid protein folds into two principal domains, a shell (S) domain and a protruding (P) domain, which contains two subdomains, P1 and P2 (see FIG. 1B). The VP1 protein forms a dimer (FIG. 1C) when incorporated into a virion particle, or a VLP. The nucleotide sequence encoding the VP1 protein is comprised, in series, of: a first sequence, encoding the S domain; a second sequence, encoding a first portion of the P1 domain; a third sequence, encoding the P2 domain; and a fourth sequence, encoding a second portion of the P1 domain. When translated, the resulting polypeptide folds into the VP1 protein as depicted in FIG. 1B, comprising of a globular S domain (bottom of ribbon structure), a P1 subdomain (middle of ribbon structure), and a P2 subdomain (top of ribbon structure).

Figure 1C:
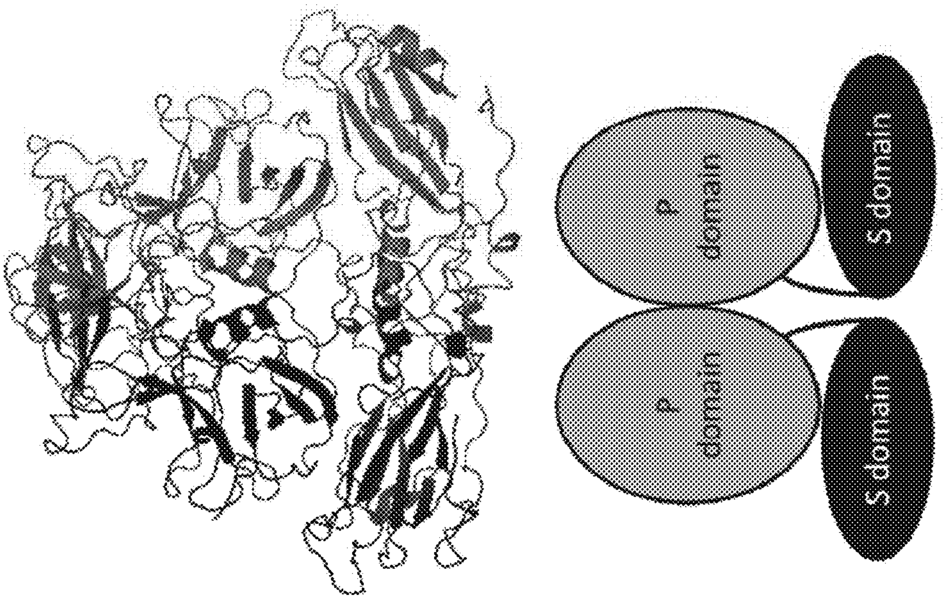
FIG. 1C shows a ribbon diagram representation of the 3-dimensional structure of a norovirus VP1 protein dimer comprising of two S domains (S), two P1 subdomains (P1), and two P2 subdomains (P2).

As shown in FIG. 1C, the VP1 protein dimerizes via P-domain interactions. These interactions stabilize the spontaneous assembly of norovirus capsid molecules.

Norovirus VP1 Protein Production in Plants

The VP1 protein as disclosed herein includes any VP1 protein comprising an amino acid sequence having from about 40 to about 100%, from about 50 to about 100%, from about 60 to about 100%, from about 70 to about 100%, from about 80 to about 100%, from about 85 to about 100% from about 90 to about 100%, or from about 95 to about 100% or any amount therebetween, sequence identity (which may be also termed sequence similarity) with a VP1 amino acid sequenced from a norovirus GI.1 (SEQ ID NO:1; FIG. 13A), GI.2 (SEQ ID NO:2; FIG. 14A), GI.3 (SEQ ID NO: 3; FIG. 15A), GII.4 (SEQ ID NO: 4; FIG. 17A), GII.6 (SEQ ID NO:5; FIG. 18A), GII.13 (SEQ ID NO: 6; FIG. 19A), GII.17(SEQ ID NO:7; FIG. 20A), provided that the VP1 protein induces immunity to norovirus in a subject, when the VP1 protein is administered to the subject. For example, the VP1 protein may comprise an amino acid sequence exhibiting from about 40, 42, 44, 46, 48, 50, 52, 54, 56, 58, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween sequence identity with a VP1 amino acid sequence from a norovirus GI.1 (SEQ ID NO:1), GI.2 (SEQ ID NO:2), GI.3 (SEQ ID NO:3), GII.4 (SEQ ID NO:4), GII.6 (SEQ ID NO:5), GII.13 (SEQ ID NO: 7; GII.17 (SEQ ID NO:7; see FIG. 2C, upper panel), provided that the VP1 protein induces immunity to norovirus in a subject, when the VP1 protein is administered to the subject.

It is well known in the art that the sequence of the P domain of the norovirus VP1 protein is hypervariable and readily mutates. For example as shown in FIG. 2D, the amino acid identity of six known GII.4 strains is compared. In this example, the full length amino acid sequence of the GII.4 VP1 protein exhibits from 93.1% to 97.4% sequence identity (upper panel FIG. 2D). However, the P domain of these same six GII.4 strains exhibits an amino acid sequence identity from 88.7% to 96.9%, and the P2 subdomain of these same six GII.4 strains exhibits an amino acid sequence identity from 81.3% to 94.4%. The P domain of VP1 proteins obtained from other norovirus strains exhibits a similar range of amino acid sequence identity. An example of the consensus amino acid sequence for VP1 is shown in FIG. 16G (SEQ ID NO:70).

The present disclosure therefore includes nucleic acid sequences that exhibit from about 60% to about 100%, or any amount therebetween, sequence identity with any of the nucleic acid sequences encoding VP1, including the S, P or both the S and P domains, between the strains identified above, and as listed in FIGS. 2A and 2B. For example, nucleic acid sequences may exhibit from about 60, 62, 64, 66, 68, 70, 72, 74, 76, 78, 80, 82, 84, 86, 88, 90, 92, 94, 96, 98, 100%, or any amount therebetween, sequence identity with any of the nucleic acid sequences encoding a norovirus VP1, including the S domain, P domain or both the S and P domains, from GI.1 (SEQ ID NO:1), GI.2 (SEQ ID NO:2), GI.3 (SEQ ID NO:3), GII.4 (SEQ ID NO:4), GII.6 (SEQ ID NO:5), GII.13 (SEQ ID NO:6), GII.17 (SEQ ID NO:7), provided that the VP1 protein induces immunity to norovirus in a subject, when the VP1 protein is administered to the subject.

Similarly, the present invention includes amino acid sequences that exhibit from about 40% to about 100% or any amount therebetween, sequence similarity with any of the VP1 sequences, including the S, P or both the S and P domains, from GI.1 (SEQ ID NO: 1), GI.2 (SEQ ID NO:2), GI.3 (SEQ ID NO:3), GII.4 (SEQ ID NO:4), GII.6 (SEQ ID NO:5), GII.13 (SEQ ID NO:6), GII.17 (SEQ ID NO:7). For example, from about 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100% or any amount therebetween, sequence similarity with any of the VP1 amino acid sequences, including the S domain, the P domain, or both the S and P domains. For example, as shown in FIG. 2C (upper panel), amino acid sequences of VP1 sequences between several norovirus strains, including but not limited to, GI.1, GI.2, GI.3, GII.4, GII.6, GII.13), exhibit a sequence identity from about 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100% or any amount therebetween, provided that the VP1 protein induces immunity to norovirus in a subject, when the VP1 protein is administered to the subject.

FIG. 2C (lower panel) also shows that these same norovirus strains (from GI.1 (SEQ ID NO:1), GI.2 (SEQ ID NO:2), GI.3 (SEQ ID NO:3), GII.4 (SEQ ID NO:4), GII.6 (SEQ ID NO:5), GII.13 (SEQ ID NO:6), GII.17 (SEQ ID NO:7), exhibit from about 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100% or any amount therebetween, amino acid sequence similarity of the VP2 protein.

FIG. 16G shows the consensus amino acid sequence (SEQ ID NO:70) of GI.1 (SEQ ID NO:1), GI.2 (SEQ ID NO:2), GI.3 (SEQ ID NO:3), GII.4 (SEQ ID NO:4), GII.6 (SEQ ID NO:5), GII.13 (SEQ ID NO:6), GII.17 (SEQ ID NO:7). Any of these VP1 proteins, or the VP1 consensus amino acid sequence may be used to prepare the VP1 fusion proteins described herein.

By "VP1 fusion protein" or "chimeric VP1 protein" it is meant, a protein comprising an S domain derived from a first norovirus strain fused to the P1 and P2 subdomains derived from a second norovirus strain:

$$S_{1st\ strain}\text{-}P1a_{2nd\ strain}\text{-}P2_{2nd\ strain}\text{-}P1b_{2nd\ strain}(S_1\text{-}P1a_2\text{-}P2_2\text{-}P1b_2;S_1\text{-}P_2).$$

The boundary between the S domain and the P domain of the norovirus VP1 amino acid sequence is well conserved (see FIG. 4A) and comprise of the following consensus sequence:

```
                              (SEQ ID NO: 88)
    . . . LVPPtvE||sKTkpFs . . .,
```

where "||" indicates the boundary between the S and P domains.

Examples of VP1 fusion protein of the form: $S_1$-P1$a_2$-$P2_2$-P1$b_2$ include, but are not limited to:

S(GI.1 Nor/68)+P (GI.2/Leuven/03) (SEQ ID NO:22, FIG. 25A; S(GI.1)+P(GI.2)): comprising an S domain from GI.1 Nor/68 (SEQ ID NO: 1) and a P domain from GI.2/Leuven/03 (SEQ ID NO:2), or a sequence that exhibits from about 59-100% or any amount therebetween (see FIG. 4B), sequence similarity with the amino acid sequence of the GI.1 VP1 protein, or the $S_1$-P1$a_2$-$P2_2$-P1$b_2$ fusion amino acid sequence shown in FIG. 25A, for example from about 59, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween, sequence similarity with the amino acid sequence of the $S_1$-P1$a_2$-$P2_2$-P1$b_2$ fusions (see FIG. 4B), provided that the VP1 protein induces immunity to norovirus in a subject, when the VP1 protein is administered to the subject;

S(GI.1 Nor/68)+P (GI.3/S29/08/Lilla Edet) (SEQ ID NO:23, FIG. 26A; S(GI.1)+P(GI.3)): comprising an S domain from GI.1 Nor/68 (SEQ ID NO:1) and a P domain from GI.3/S29/08/Lilla Edet (SEQ ID NO:3), or a sequence that exhibits from about 59-100% or any amount therebetween (see FIG. 4B), sequence similarity with the amino acid sequence of the GI.1 VP1 protein, or the $S_1$-P1$a_2$-$P2_2$-P1$b_2$ fusion amino acid sequence shown in FIG. 26A, for example from about 59, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween, sequence similarity with the amino acid sequence of the $S_1$-P1$a_2$-$P2_2$-P1$b_2$ fusions (see FIG. 4B), provided that the VP1 protein induces immunity to norovirus in a subject, when the VP1 protein is administered to the subject;

S(GI.1 Nor/68)+P (GII.4/Sydney/NSW0514/12) (SEQ ID NO:24, FIG. 27A; S(GI.1)+P(GII.4)): comprising an S domain from GI.1 Nor/68 (SEQ ID NO:1) and a P domain from GII.4/Sydney/NSW0514/12 (SEQ ID NO:4), or a sequence that exhibits from about 59-100% or any amount therebetween (see FIG. 4B), sequence similarity with the amino acid sequence of the GI.1 VP1 protein, or the $S_1$-P1$a_2$-$P2_2$-P1$b_2$ fusion amino acid sequence shown in FIG. 27A, for example from about 59, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween, sequence similarity with the amino acid sequence of the $S_1$-P1$a_2$-$P2_2$-P1$b_2$ fusions (see FIG. 4B), provided that the VP1 protein induces immunity to norovirus in a subject, when the VP1 protein is administered to the subject;

S(GI.1 Nor/68)+P (GII.6/Ohio/490/12) (SEQ ID NO:25, FIG. 28A; S(GI.1)+P(GII.6)): comprising an S domain from GI.1 Nor/68 (SEQ ID NO: 1) and a P domain from GII.6/Ohio/490/12 (SEQ ID NO:5), or a sequence that exhibits from about 59-100% or any amount therebetween, sequence similarity with the amino acid sequence of the GI.1 VP1 protein, or the $S_1$-P1$a_2$-$P2_2$-P1$b_2$ fusion shown in FIG. 28A, for example from about 59, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween, sequence similarity with the amino acid sequence of the $S_1$-P1$a_2$-P22-P1$b_2$ fusions, provided that the VP1 protein induces immunity to norovirus in a subject, when the VP1 protein is administered to the subject;

S(GI.1 Nor/68)+P (GII.12/HS206/2010/USA) (SEQ ID NO:71, FIG. 31A; S(GI.1)+P(GII.12)): comprising an S domain from GI.1 Nor/68 (SEQ ID NO:1) and a P domain from GII.12/HS206/2010/USA (SEQ ID NO:28), or a sequence that exhibits from about 59-100% or any amount therebetween (see FIG. 4B), sequence similarity with the amino acid sequence of the GI.1 VP1 protein, or the $S_1$-P1$a_2$-P22-P1$b_2$ fusion amino acid sequence shown in FIG. 31A, for example from about 59, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween, sequence similarity with the amino acid sequence of the $S_1$-P1$a_2$-P$2_2$-P1$b_2$ fusions (see FIG. 4B), provided that the VP1 protein induces immunity to norovirus in a subject, when the VP1 protein is administered to the subject;

(GI.1 Nor/68)+P (GII.13/VA173/10) (SEQ ID NO:26, FIG. 29A; S(GI.1)+P(GII.13): comprising an S domain from GI.1 Nor/68 (SEQ ID NO:1) and a P domain from GII.13/VA173/10 (SEQ ID NO:6), or a sequence that exhibits from about 59-100% or any amount therebetween (see FIG. 4B), sequence similarity with the amino acid sequence of the GI.1 VP1 protein, or the $S_1$-P1$a_2$-P$2_2$-P1$b_2$ fusion amino acid sequence shown in FIG. 29A, for example from about 59, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween, sequence similarity with the amino acid sequence of the $S_1$-P1$a_2$-P$2_2$-P1$b_2$ fusions (see FIG. 4B), provided that the VP1 protein induces immunity to norovirus in a subject, when the VP1 protein is administered to the subject; or (GI.1 Nor/68)+P (GII.17/Kawasaki323/14) (SEQ ID NO:27, FIG. 30A; S(GI.1)+P(GII.17): comprising an S domain from GI.1 Nor/68 (SEQ ID NO:1) and a P domain from GII.17/Kawasaki323/14 (SEQ ID NO: 7), or a sequence that exhibits from about 59-100% or any amount therebetween (see FIG. 4B), sequence similarity with the amino acid sequence of the GI.1 VP1 protein, or the $S_1$-P1$a_2$-P$2_2$-P1$b_2$ fusion amino acid sequence shown in FIG. 30A, for example from about 59, 60, 62, 64, 66, 68, 70, 72, 74, 76, 77, 78, 79, 80, 81, 82, 83, 84, 85, 86, 87, 88, 89, 90, 91, 92, 93, 94, 95, 96, 97, 98, 99, 100% or any amount therebetween, sequence similarity with the amino acid sequence of the $S_1$-P1$a_2$-P$2_2$-P1$b_2$ fusions (see FIG. 4B), provided that the VP1 protein induces immunity to norovirus in a subject, when the VP1 protein is administered to the subject.

The VP1 fusion protein is heterologous (or chimeric) in that the fusion protein comprises an S domain from a first VP1 protein and a P domain from a second VP1 protein. The heterologous VP1 fusion protein may comprise an amino acid sequence that falls within, or the amino acid sequence is found within (or maps against) the consensus sequence of the VP1 sequence shown in FIG. 16G (S-P boundary underlined and indicated by "||"; SEQ ID NO:70), provided that the S and P domains of the VP1 fusion protein is heterologous, and that the VP1 fusion protein induces immunity to norovirus in a subject, when the VP1 protein is administered to the subject.

Additional non-limiting examples of VP1 fusion proteins include those that comprise an S domain from: GI.1, for example but not limited to, the VP1 fusion shown in FIGS. 32A-32C (SEQ ID NO's:49-51); GI.5, for example but not limited to, the VP1 fusion shown in FIG. 31B (SEQ ID NO:48); GII.12, for example but not limited to, the VP1 fusion as shown in FIGS. 33A-33O (SEQ ID NO's:29-43), GII.14 for example, but not limited to, the VP1 fusion shown in FIG. 34A (SEQ ID NO:52), GII.21 for example but not limited to, the VP1 fusion shown in FIG. 34B (SEQ ID NO:53), or a sequence that exhibits from about 40-100% or any amount therebetween, sequence similarity with the amino acid sequence of the S domain provided that the VP1 protein induces immunity to norovirus in a subject, when the VP1 protein is administered to the subject. Furthermore, the VP1 fusion protein may comprise an S domain that comprises an amino acid sequence that falls within (i.e. the amino acid sequence is found within, or maps against) the consensus sequence of the S domain as shown in FIG. 16G (i.e. the N terminal portion of the consensus sequence; S-P boundary underlined and indicated by "II"; SEQ ID NO:70), provided that the VP1 protein induces immunity to norovirus in a subject, when the VP1 protein is administered to the subject.

VP1 fusion proteins may also comprise a P domain obtained from GI.1/Norwalk/1968/US (SEQ ID NO:1); GI.5 Siklos/Hun5407/2013/HUN (SEQ ID NO:44); GII.1 Ascension 208/2010/USA (SEQ ID NO:45); GII.2 CGMH47/2011/TW (SEQ ID NO:66); GII.3 Jingzhou/2013402/CHN (SEQ ID NO:67); GII.4/Dresden174/1997/DE(variant: US1995/96); GII.4/FarmingtonHills/2002/US (SEQ ID NO:9); GII.4/Hunter-NSW504D/2004/AU (SEQ ID NO:10); GII.4/Shellharbour-NSW696T/2006/AU (11); GII.4/Orange-NSW001P/2008/AU (variant New Orleans 2009) (SEQ ID NO:12); GII.5 AlbertaEI390/2013/CA (SEQ ID NO:68); GII.7 Musashimurayama/2010/JP (SEQ ID NO:69; GII.14 8610/Saga/2008/JPN (SEQ ID NO:46); GII.21 Salisbury150/2011/USA (SEQ ID NO:47), or a sequence that exhibits from about 40-100% or any amount therebetween, sequence similarity with the amino acid sequence of the P domain from any one of GI.1/Norwalk/1968/US; GI.5 Siklos/Hun5407/2013/HUN; GII.1 Ascension 208/2010/USA; GII.2 CGMH47/2011/TW; GII.3 Jingzhou/2013402/CHN; GII.4/Dresden174/1997/DE(variant:US1995/96); GII.4/FarmingtonHills/2002/US; GII.4/Hunter-NSW504D/2004/AU; GII.4/Shellharbour-NSW696T/2006/AU (11); GII.4/Orange-NSW001P/2008/AU (variant New Orleans 2009); GII.5 AlbertaEI390/2013/CA; GII.7 Musashimurayama/2010/JP; GII.14 8610/Saga/2008/JPN; GII.21 Salisbury150/2011/USA, for example from about 40, 42, 44, 46, 48, 50, 52, 54, 56, 58, 60, 62, 64, 66, 68, 70, 72, 74, 76, 78, 80, 81, 82, 83, 84, 85, 86, 87, 88, 89, 90, 91, 92, 93, 94, 95, 96, 97, 98, 99, 100% or any amount therebetween sequence similarity with the amino acid sequence of the P or the P2 domain from any one of GI.1/Norwalk/1968/US; GI.5 Siklos/Hun5407/2013/HUN; GII.1 Ascension 208/2010/USA; GII.2 CGMH47/2011/TW; GII.3 Jingzhou/2013402/CHN; GII.4/Dresden174/1997/DE (variant:US1995/96); GII.4/FarmingtonHills/2002/US; GII.4/Hunter-NSW504D/2004/AU; GII.4/Shellharbour-NSW696T/2006/AU (11); GII.4/Orange-NSW001P/2008/AU (variant New Orleans 2009); GII.5 AlbertaEI390/2013/CA; GII.7 Musashimurayama/2010/JP; GII.14 8610/Saga/2008/JPN; GII.21 Salisbury150/2011/USA, provided that the VP1 protein induces immunity to norovirus in a subject, when the VP1 protein is administered to the subject. Furthermore, the VP1 fusion protein may comprise a P domain that comprises an amino acid sequence that falls within (i.e. the amino acid sequence maps against, or is found within) the consensus sequence of the P domain as shown in FIG. 16G (i.e. the C terminal portion of the consensus sequence; S-P boundary underlined and indicated by "||"; SEQ ID NO:70), provided that the VP1 protein induces immunity to norovirus in a subject, when the VP1 protein is administered to the subject.

In the VP1 fusion protein examples provided above, the S domain may comprise an amino acid sequence that exhibits from about 80-100%, or any amount therebetween, sequence similarity with the amino acid sequence of the S domain from any norovirus, for example but not limited to, the S domain from GI.1 Nor/68 (SEQ ID NO:1; see FIGS. 13A, and 4B), GII.12/HS206/2010/USA (SEQ ID NO:28; see FIGS. 22A and 4C), or GI.5 Siklos/Hun5407/2013/HUN (SEQ ID NO:44; see FIGS. 16A and 4D). For example the S domain may comprise an amino acid sequence that exhibits from about 80, 81, 82, 83, 84, 85, 86, 87, 88, 89, 90, 91, 92, 93, 94, 95, 96, 97, 98, 99, 100% or any amount therebetween sequence similarity with the amino acid sequence of the S domain from GI.1 Nor/68 (SEQ ID NO:1), GII.12/HS206/2010/USA (SEQ ID NO:28), or GI.5 Siklos/Hun5407/2013/HUN (SEQ ID NO:44), provided that the VP1 protein induces immunity to norovirus in a subject, when the VP1 protein is administered to the subject.

As shown in FIGS. 5A, 5B, 6A, 6B and 6C, VP1 fusion proteins comprising S(GI.1)+P(GI.2), S(GI.1)+P(GI.3), S(GI.1)+P(GII.4), S(GI.1)+P(GII.13), S(GI.1)+P(GII.17) resulted in VP1 fusion protein production in plants (as determined using a SDS-Comassie stained gel, or Western analysis) that was similar to or greater than the yield of the native VP1 protein that comprised the corresponding P domain (as determined using a SDS-Comassie stained gel, or Western analysis).

Figure 5A:
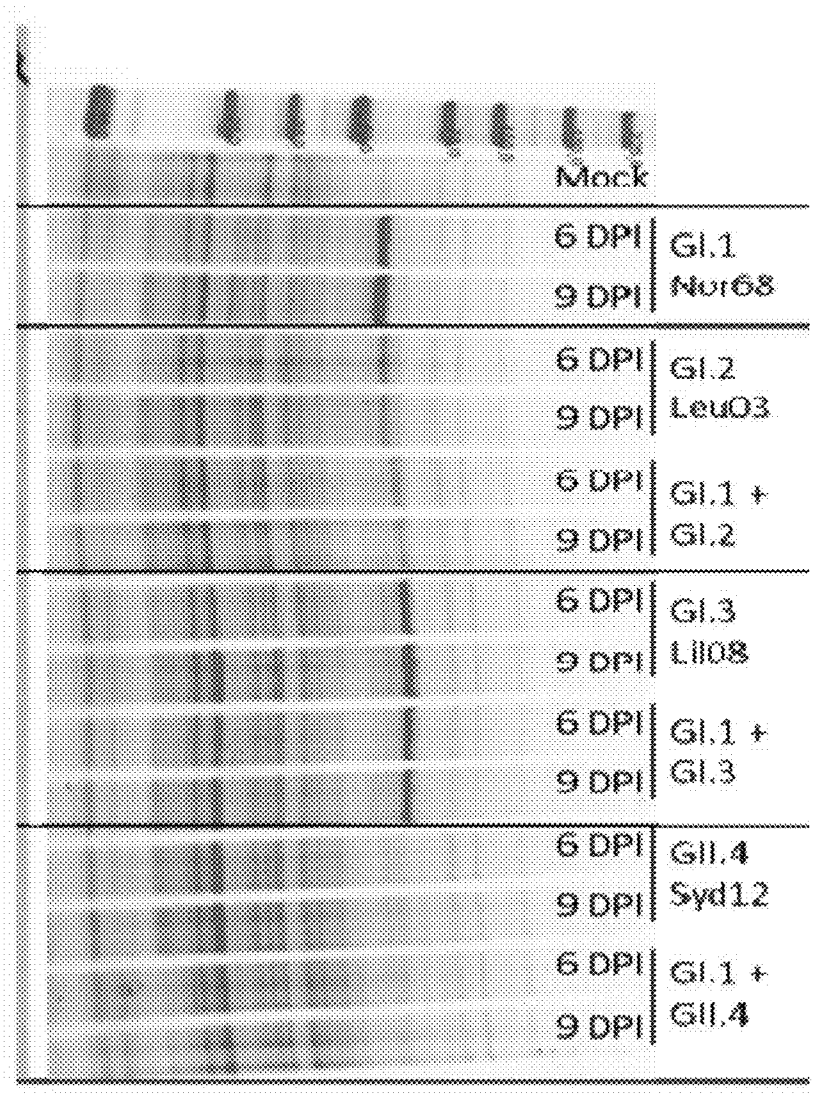
FIG. 5A shows Coomassie-stained SDS-PAGE analysis of crude protein extracts prepared from *N. benthamiana* leaves producing native norovirus VP1 and VP1 fusion proteins, six and nine days post infiltration (DPI) with expression vectors encoding human codon optimized (hCod) norovirus native VP1 (GI.1, construct #2724, SEQ ID NO's:1 (aa) and 18 (na); GI.2, construct #3300, SEQ ID NO's:2 (aa) and 54(na); GI.3, construct #3302, SEQ ID NO's:3(aa) and 55(na): GII.4, construct #3304, SEQ ID NO's:4(aa) and 56(na)) or norovirus VP1 fusion proteins (GI.1+GI.2, construct #3360, SEQ ID NO's:22(aa) and 57(na); GI.1+GI.3, construct #3361, SEQ ID NO's:23(aa) and 58(na); GI.1+GII.4, construct #3362, SEQ ID NO's:24 (aa) and 59(na)).
Figure 5B:
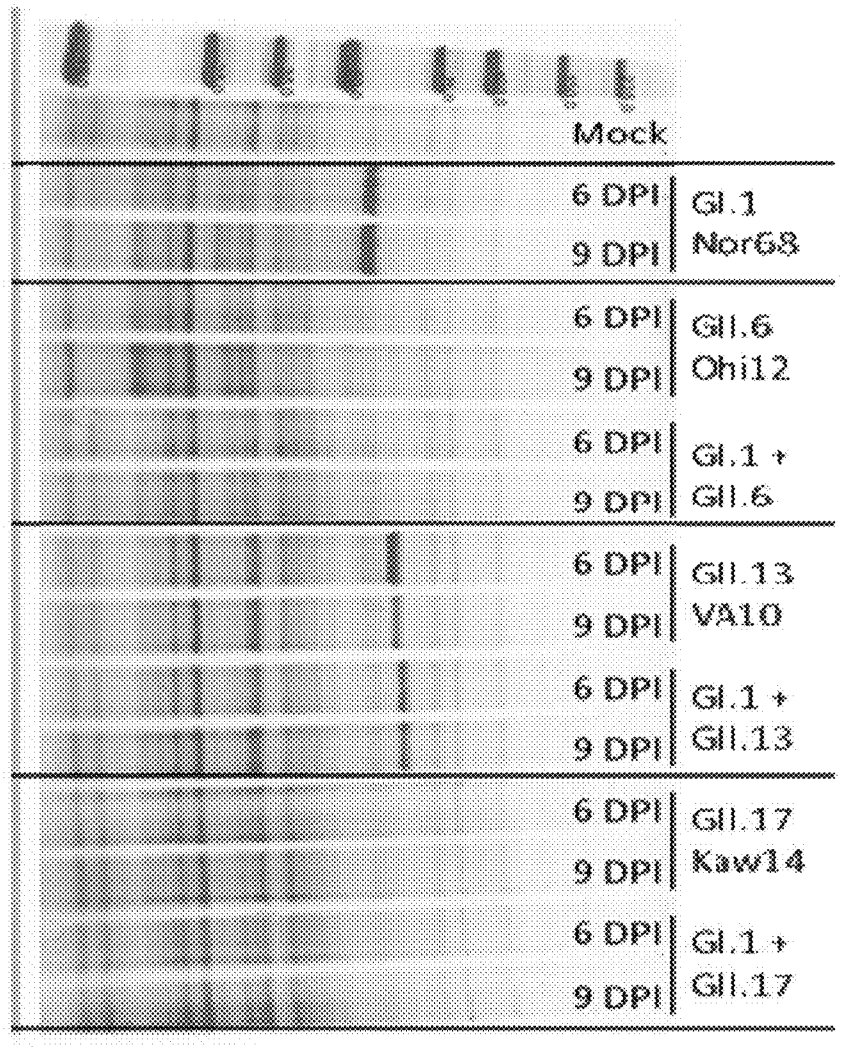
FIG. 5B shows Coomassie-stained SDS-PAGE analysis of crude protein extracts prepared from *N. benthamiana* leaves, producing native norovirus VP1 and VP1 fusion proteins, six and nine days post infiltration (DPI) with expression vectors encoding native (wildtype) norovirus VP1 (GI.1, construct #2724, SEQ ID NO's:1(aa) and 18(na); GII.6, construct #3306, SEQ ID NO's:5(aa) and 60(na); GII.13, construct #3308, SEQ ID NO's:6(aa) and 61(na): GII.17, construct #3310, SEQ ID NO"s:7(aa) and 62(na)) or norovirus VP1 fusion proteins (GI.1+GII.6, construct #3363, SEQ ID NO's:25(aa) and 63(na); GI.1+GII.13, construct #3364, SEQ ID NO's:26(aa) and 64(na); GI.1+GII.17, construct #3365, SEQ ID NO's:27(aa) and 65(na)).

Expression of native GII.6/Ohio/490/12 VP1 protein has proven to be challenging (e.g. FIG. 5B) and VP1 protein production varies from below detectable levels to detectable levels (see Example 4 below). Additionally expression of a VP1 fusion protein comprising an S domain from GI.1 Nor/68 (SEQ ID NO: 1) and a P domain from GII.6/Ohio/490/12 (SEQ ID NO: 5), was also bellow detection levels (FIG. 5B).

The term "virus-like particle", VLP, "virus-like particles", or "VLPs", as used herein, refers to a norovirus virus like particles that comprise one or more than one type of norovirus VP1 protein, one or more than one type of VP1 fusion protein, or a combination thereof, and that self-assemble into non-replicating, non-enveloped, non-infectious viral capsid structures lacking all parts of the norovirus genome. For example, the VLP may comprise one type of VP1 fusion protein, or the VLP may comprise two or more different VP1 fusion proteins. Furthermore the VLP may comprise a VP2 protein. VLPs comprising VP1 protein, VP1+VP2 protein, VP1 fusion protein, or VP1 fusion protein+VP2 protein are of the size from about 15 nm to 50 nm or any amount therebetween, for example 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nm, or any amount therebetween. For example, for T=1 icosahedral symmetry, VLPs may about 23 nm, or for T=3 icosahedral symmetry, VLPs may be from about 38 to about 40 nm.

Figure 6A:
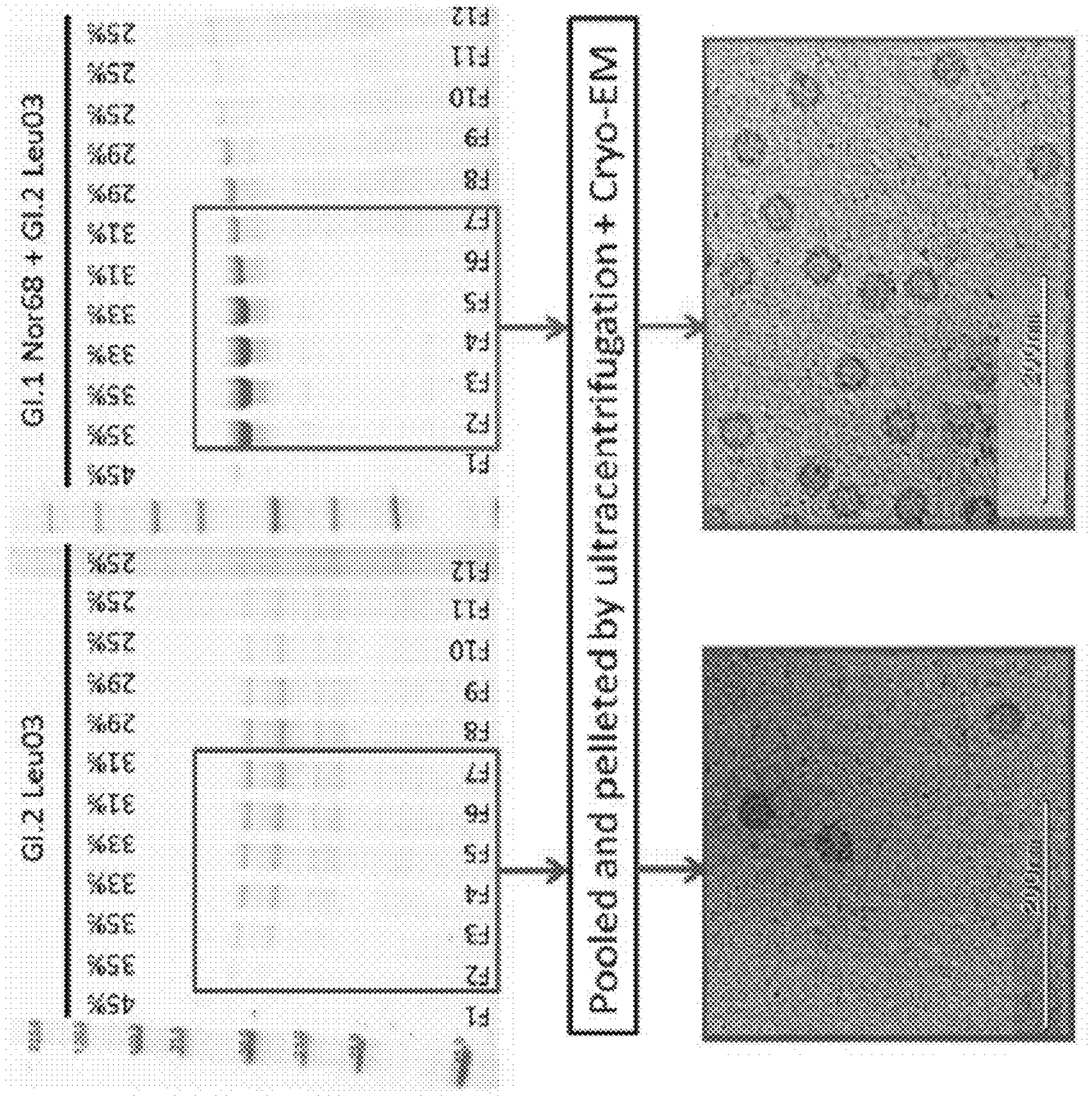
FIG. 6A upper panel shows production of native norovirus VP1, native norovirus VLPs, VP1 fusion proteins and VLPs comprising VP1 fusion proteins using Coomassie-stained SDS-PAGE analysis of fractions from density gradients using crude protein extracts prepared from *N. benthamiana* leaves, nine days post infiltration (DPI) with expression vectors encoding human codon optimized norovirus VP1 (GI.2, construct #3300, SEQ ID NO's:2(aa) and 54(na)) or norovirus human codon optimized VP1 fusion (GI.1+GI.2, construct #3360, SEQ ID NO's:22(aa) and 57(na)). Lower panel shows electron micrographs of wildtype norovirus GI.2 VLPs and VLPs comprising norovirus GI.1+GI.2 VP1 fusions proteins from iodixanol gradient fractions.
Figure 6B:
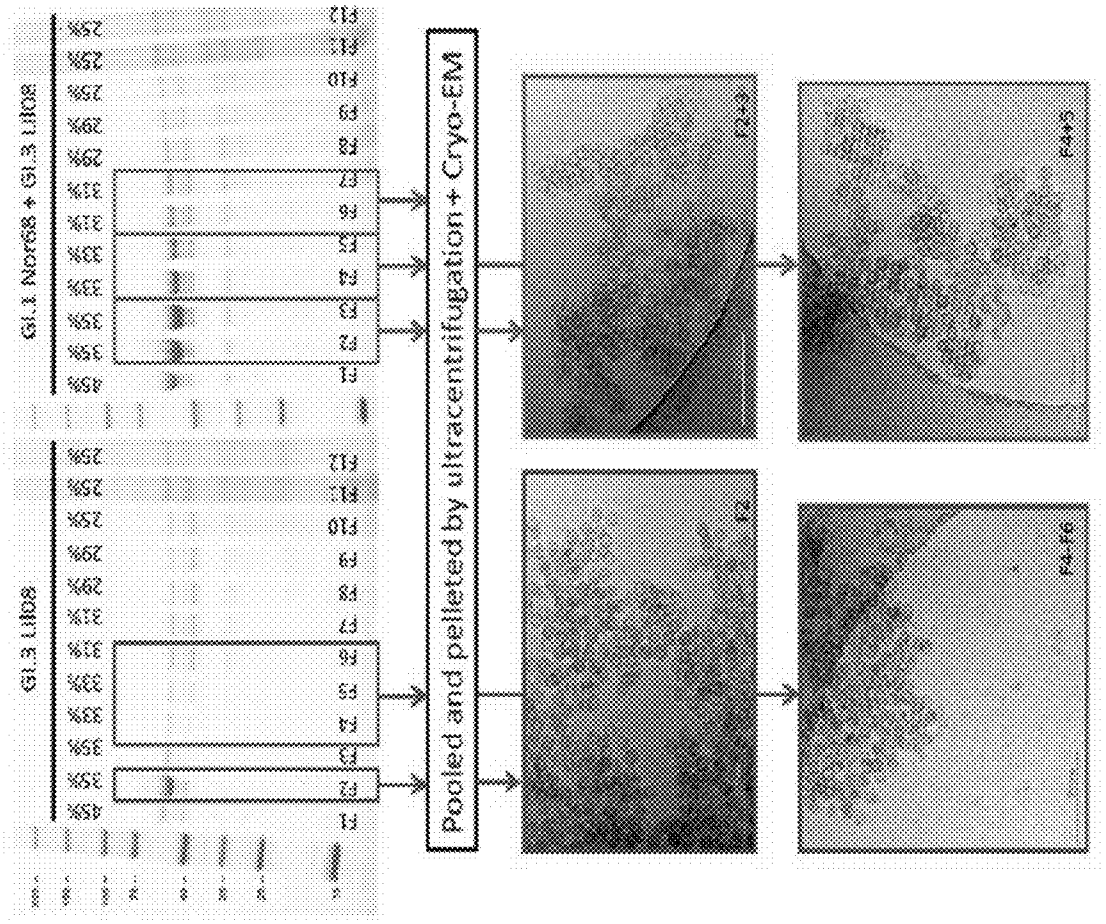
FIG. 6B upper panel shows production of native norovirus VP1, native norovirus VLPs, VP1 fusion proteins and VLPs comprising VP1 fusion proteins using Coomassie-stained SDS-PAGE analysis of fractions from density gradients using crude protein extracts prepared from *N. benthamiana* leaves, nine days post infiltration (DPI) with expression vectors encoding norovirus human codon optimized VP1 (GI.3, construct #3302, SEQ ID NO's:3(aa) and 55(na)) or norovirus VP1 fusion (GI.1+GI.3, construct #3361, SEQ ID NO's:23(aa) and 58(na)). Lower panel shows electron micrographs of wildtype norovirus GI.3 VLPs and VLPs comprising norovirus GI.1+GI.3 VP1 fusions proteins from iodixanol gradient fractions.
Figure 6C:
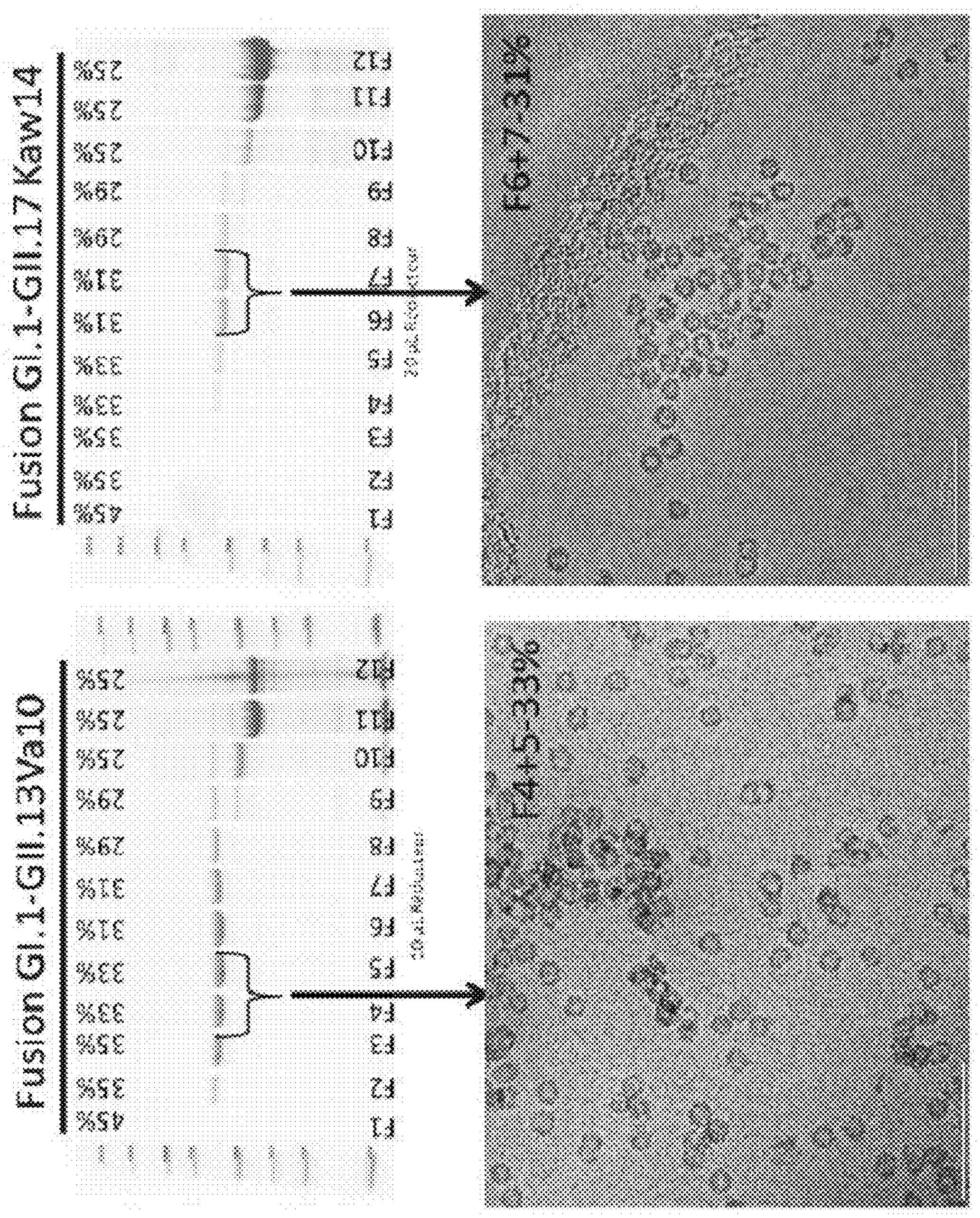
FIG. 6C upper panel shows production of VP1 fusion proteins and VLPs comprising VP1 fusion proteins using Coomassie-stained SDS-PAGE analysis of fractions from density gradients using crude protein extracts prepared from *N. benthamiana* leaves, nine days post infiltration (DPI) with expression vectors encoding norovirus human codon optimized VP1 fusion (GI.1+GII.13, construct #3364, SEQ ID NO's; 26(aa) and 64(na) GI.1+GII.17, construct #3365, SEQ ID NO's:27(aa) and 65(na)). Lower panel shows electron micrographs of VLPs comprising norovirus GI.1+GII.13 or GI.1+GII.17 VP1 fusions proteins from iodixanol gradient fractions.

As shown in FIGS. 6A, 6B, 6C, VLPS may be produced in plants from expressing human codon optimized nucleotide sequences encoding VP1 fusion proteins described herein. For example, VLPs were produced comprising an S domain from GI.1 Nor/68 (SEQ ID NO:1) and a P domain from GI.2/Leuven/03 (SEQ ID NO:2; FIG. 6A), an S domain from GI.1 Nor/68 (SEQ ID NO:1) and a P domain from GI.3/S29/08/Lilla Edet (SEQ ID NO:3; FIG. 6B), an S domain from GI.1 Nor/68 (SEQ ID NO: 1) and a P domain from GII.13/VA173/10 (SEQ ID NO:6; FIG. 6C), and an S domain from GI.1 Nor/68 (SEQ ID NO:1) and a P domain from GII.17/Kawasaki323/14 (SEQ ID NO:7; FIG. 6C).

Figure 3A:
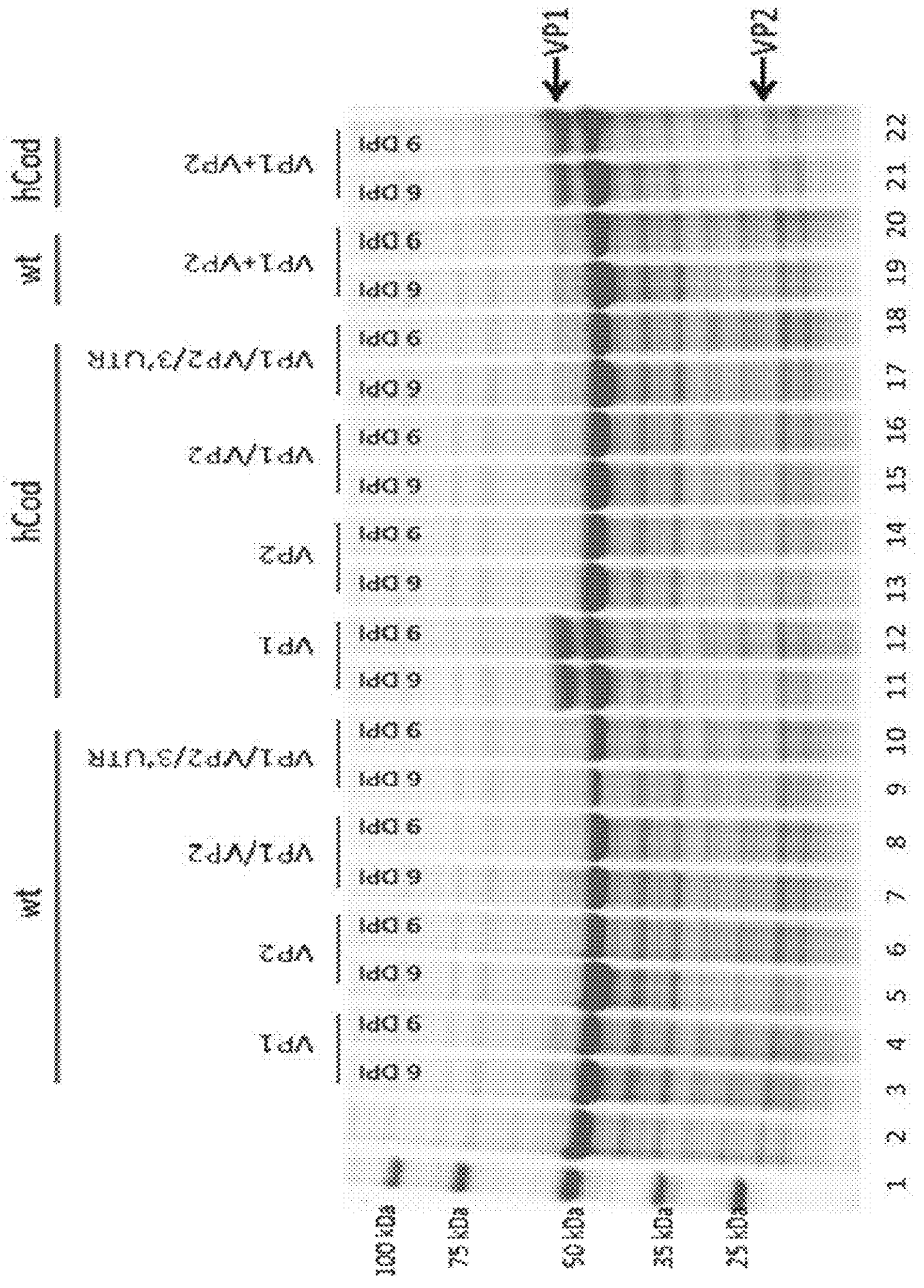
FIG. 3A shows norovirus protein production. Crude protein extracts prepared from *N. benthamiana* leaves, six and nine days post infiltration (DPI) of native (wildtype; wt) GI.1/United States/Norwalk/1968 ORF2 alone (VP1) (SEQ ID NO's: 1 (aa) and 13 (na); construct #2720) and ORF 3 alone (VP2) (SEQ ID NO's: 14 (aa) and 15 (na); construct #2721), ORF2/ORF3 (VP1/VP2; SEQ ID NO:16 (na); construct #2722) and ORF2/ORF3/3'UTR (VP1/VP2/3'UTR; SEQ ID NO:17 (na); construct #2723), and human codon-optimized (hCod) GI.1/United States/Norwalk/1968 ORF2 alone (VP1) (SEQ ID NO:18; construct #2724), ORF3 alone (hCod VP2) (SEQ ID NO:19 (na); construct #2725), ORF2/ORF3 (hCod VP1/VP2; in cis, on the same construct; SEQ ID NO:20 (na); construct #2726) and ORF2/ORF3/3'UTR (hCod VP1/PV2/3'UTR; SEQ ID NO:21; construct #2727), expression constructs. VP1+VP2: ORF2 (SEQ ID NO's: 1 (aa) and 13 (na); construct #2720) and ORF 3 (SEQ ID NO's: 14 (aa) and 15 (na); construct #2721) expressed on separated constructs, in trans. Proteins were analyzed by Coomassie-stained SDS-PAGE.

An aspect of the present disclosure provides for the production of norovirus VP1 protein in plants. As shown in FIG. 3A, leaves (from *N. benthamiana*) were vacuum infiltrated with *Agrobacterium tumefaciens* comprising expression vectors encoding GI.1 VP1 as a single nucleic acid construct, GI.1 VP2 as a single nucleic acid construct, both GI.1 VP1 and VP2, with VP1 and VP2 nucleic acid sequences introduced in separate vectors ("VP1+VP2"; dual constructs), or on the same vector ("VP1/VP2" or "VP1/VP2/3'UTR"; single nucleic acid constructs) to permit co-expression of the VP1 and/or VP2 sequences and the leaves examined for VP1 and VP2 production. After 6 or 9 days post infiltration (6 DPI and 9 DPI, respectively), total crude protein extracts were prepared from leaf homogenates, separated by SDS-PAGE, and stained with Coomassie Brilliant Blue dye. As seen in lanes 3-4, 7-10 and 19-20, leaves infiltrated with expression vectors comprising nucleotide sequences that correspond to wildtype GI.1 ORF2, encoding the VP1 protein, produced low or non-detectable levels of GI.1 VP1 as determined using Coomassie stained gels (VP1 expression was observed when expression was assayed by Western analysis, data not provided). In contrast, leaves infiltrated with expression vectors comprising GI.1 VP1 nucleotide sequences that were codon optimized for human expression (hCod), or enriched for GC content when compared to the GC content of the wildtype VP1 nucleic acid sequence, produced increased amounts of GI.1 VP1 protein (see lanes 11, 12, 21, 22; "VP1", 55-70 kDa band) in Coomassie stained gels. These results show that hCod VP1 may be produced in plants when VP1 is expressed on its own.

Furthermore, as seen in lanes 7-10 and 15-18 of FIG. 3A, leaves infiltrated with vectors comprising either wildtype GI.1 VP1 and VP2 (lanes 7-10) or human codon optimized GI.1 VP1 and VP2 (lanes 15-18; dual nucleic acid constructs) produced low or non-detectable levels of GI.1 VP1 protein in Coomassie stained gels, suggesting that expression of VP1 is not enhanced by the presence of VP2 when co-expressed in cis on the same vector, using the same organization as found in the viral genome (using one promoter to control expression). However, when VP1 or human codon optimized VP1 was co-expressed in trans (on a separate construct) along with VP2 or hCod VP2 (hCod VP1+VP2), respectively, an increase in VP1 protein (approx. 55-60 kDa band) was observed (see lanes 15, 16, and 21, 22; FIG. 3A). In this example, VP1 and VP2 nucleic acid segments, with each nucleic acid segment comprising a regulatory region and a terminator, were introduced into the plants as a nucleic acid complex, and this resulted in a corresponding increase in VP1 protein yield.

This observation is in contrast to that observed in insect and mammalian cells (Bertolotti-Ciarlet A., Crawford S. E., Hutson A. M., Estes M. K. 2003, J. Virol. 77:11603-11615), who reported that an increase in VP1 expression was only observed when VP1 and VP2 (or VP1+VP2+3'UTR) resided in cis, and were co-expressed using the same organization as that found in the viral genome, under the control of one promoter and terminator. No increase in VP1 expression was observed by Bertolotti-Ciarlet (2003) in insect or mammalian cells, when VP1 and VP2 were co-expressed in trans.

As described in more detail below (see "Norovirus VP1 Fusion Proteins"; reference to FIG. 5E), when VP1 fusion proteins are expressed in plants, it is preferred that the ORF3 sequence encoding VP2 is obtained from the same norovirus genotype and strain as that used to obtain the S domain of fusion VP1 sequence.

The data presented in FIG. 3A show that in plants, hCod VP1 may be expressed on its own, and that if hCod VP1 is co-expressed along with VP2, then both VP1 and VP2 should be expressed using separate expression systems, for example, on separate plasmids, or VP1 and VP2 may be expressed on the same vector but each of the sequences encoding VP1 and VP2 should be under the control of separate promoter and terminator sequences, so that they have a separate expression system.

Assembly of Plant-Produced Norovirus VP1 into VLPs

Figure 3B:
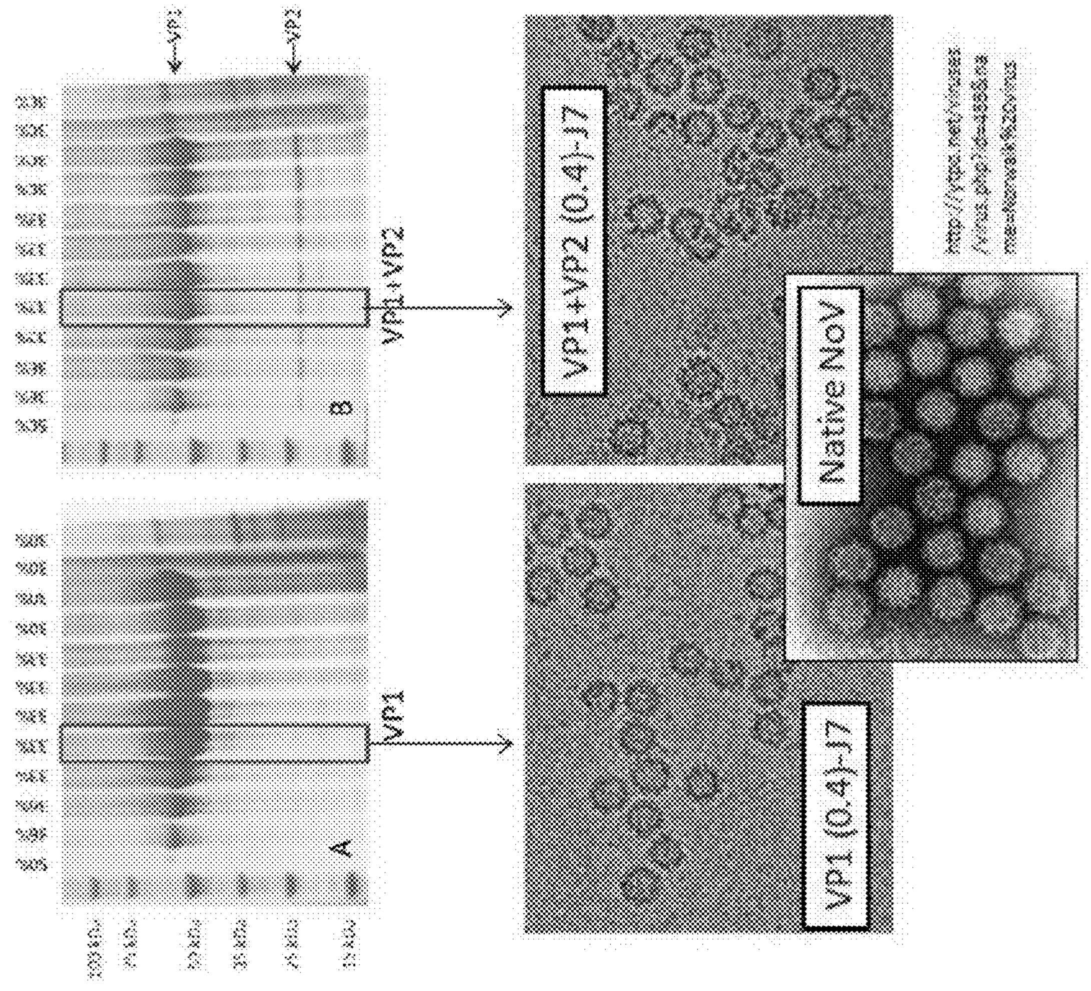
FIG. 3B upper panel shows norovirus protein expression and VLP assembly using Coomassie-stained SDS-PAGE analysis of fractions from an iodixanol density gradient separation of crude protein extracts prepared from *N. benthamiana* leaves expressing human codon-optimized GI.1/United States/Norwalk/1968 VP1 (construct #2724), or human codon-optimized VP1 (construct #2724) and co-expressed with human codon-optimized VP2 (construct #2725). Lower panel shows electron micrographs of norovirus VLPs purified from 33% iodixanol gradient fractions of VP1 or co-expression of VP1 and VP2 proteins. An electron micrograph of native norovirus VLP is shown for comparison.

FIG. 3B (upper panel) shows a Coomassie-stained SDS-PAGE analysis of fractions from an iodixanol density gradient separation of crude protein extracts prepared from *N. benthamiana* leaves expressing GI.1 VP1 (single nucleic acid human codon optimized constructs), or VP1 and VP2 (dual nucleic acid human codon optimized constructs). Norovirus VP1 proteins (approx. 55-60 kDa band) in high density fractions were analyzed by scanning electron microscopy. As seen in FIG. 3B (lower panel), norovirus VP1 proteins and norovirus VP1+VP2 proteins self-assemble into VLPs in plants. The isolated VLPs exhibit a structural conformation similar to that of wildtype norovirus GI.1 virion particles (insert, FIG. 3B).

Differential Expression of Norovirus VP1 in Plants

The expression levels of norovirus VP1 protein derived from six norovirus strains having the highest occurrence of outbreaks between Sep. 1, 2013 and Aug. 31, 2015 (as reported by the Centers for Disease Control and Prevention) were compared in *N benthamiana.*

VP1 protein production was determined using Coomassie-stained SDS-PAGE analysis (approx. 55-60 kDa band) of extracts obtained from plant leaves vacuum infiltrated with expression vectors comprising human codon optimized sequences of VP1 derived from GI.1/Norwalk/1968/US (SEQ ID NO:18), GI.2/Leuven/2003/Bel (SEQ ID NO:54), GI.3/S29/2008/Lilla Edet/Sweden (SEQ ID NO:55), GII.4/Sydney/NSW0514/2012/AU (SEQ ID NO:56), GII.6/Ohio/490/12 (SEQ ID NO:60), GII.13/VA173/2010/USA (SEQ ID NO:61), GII.17/Kawasaki323/2014/JP (SEQ ID NO:62), strains. As shown in FIGS. 5A and 5B, VP1 protein production was observed in plant leaves expressing GI.1/Norwalk/1968/US (SEQ ID NO:1), GI.2/Leuven/2003/Bel (SEQ ID NO:2), GI.3/S29/2008/Lilla Edet/Sweden (SEQ ID NO:3), and GII.13/VA173/2010/USA (SEQ ID NO:6). A low or non-detectable amount of VP1 protein production was observed in plant leaves expressing GII.4/Sydney/NSW0514/2012/AU (SEQ ID NO:4), GII.6/Ohio/490/12 (SEQ ID NO:5), and GII.17/Kawasaki323/2014/JP (SEQ ID NO7).

VP1 protein expression was also observed when GI.3 (/S29/2008/Lilla Edet/Sweden; SEQ ID NO:3, FIG. 15A), GI.5 (Siklos/Hun5407/2013/HUN; SEQ ID NO: 44, FIG. 16A), GII.1 (Ascension208/2010/USA; SEQ ID NO: 45, FIG. 16B), GII.2 (CGMH47/2011/TW; SEQ ID NO: 66, FIG. 16C), GII.3 (Jingzhou/2013402/CHN; SEQ ID NO:67, FIG. 16D), GII.5 (AlbertaEI390/2013/CA; SEQ ID NO: 68, FIG. 16E), GII.6 (Ohio/490/12; SEQ ID NO: 60, FIG. 18B), GII.7 (Musahimurayama/2010/JP; SEQ ID NO: 69, FIG. 16F), GII.12 (HS206/2010/USA; SEQ ID NO:28, FIG. 22A), GII.14 (8610/Saga/2008/JP; SEQ ID NO: 46, FIG. 22B), and GII.21 (Salisbury150/2011/USA; SEQ ID NO: 47, FIG. 22C), were expressed in plants (see Example 4 below).

As shown in the electron micrographs of FIGS. 3B, 5C, 5D, 6A and 6B, plant produced VP1 proteins derived from several norovirus strains self-assembled into VLPs. VLPs were observed in plant extracts following expression of strains GI.2/Leuven/2003/Bel (SEQ ID NO:54, FIG. 14B), GI.3 S29/2008/Lilla Edet/Sweeden (SEQ ID NO's:3 (aa); 55 (na); FIG. 15B), GI.5 Siklos/HUN5407/2013/HUN (SEQ ID NO:44: FIG. 16A), GII.1 Ascension208/2010/USA SEQ ID NO:45; FIG. 16B); GII.7 Musashimurayama/2010/JP (SEQ I NO:69; FIG. 16F), GII.12 HS206/2010/USA (SEQ ID NO:28, FIG. 22A), GII.13 VA173/2010/USA (SEQ ID NO:61, FIG. 19B), GII.14 8610/Saga/2008/JPN (SEQ ID NO:46, FIG. 22B), and GII.21 Salisbury150/2011/USA (SEQ ID NO:47, FIG. 22B). The VLPs have a structural conformation and diameter of about 15 nm to 50 nm, for example, of either about 23 nm, for T=1 icosahedral symmetry; or about 38 to 40 nm, for T=3 icosahedral symmetry, similar to that of wildtype norovirus.

Even though expression levels of VP1 protein in leaves infiltrated with vectors expressing GII.4/Sydney/NSW0514/2012/AU (SEQ ID NO:4), GII.6/Ohio/490/12 (SEQ ID NO:5), GII.17/Kawasaki323/2014/JP (SEQ ID NO:7), was either low or undetectable using Coomassie-stained SDS-PAGE analysis (see FIGS. 5A and 5B), expression of these VP1 proteins was observed at low levels (see Example 4, below).

Norovirus VP1 Fusion Proteins

Expression vectors were constructed which encoded norovirus VP1 fusion proteins wherein the S domain of GI.1 was fused to the following P domains:

GI.2 (S(GI.1)+P(GI.2); S(GI.1 Nor/68)+P (GI.2/Leuven/03); SEQ ID NO's:22(aa), 57(na), FIGS. 25A, 25B; construct 3360; SEQ ID NO:87; FIG. 12C, GI.3 (S(GI.1)+P(GI.3); GI.3 S(GI.1 Nor/68)+P (GI.3/S29/08/Lilla Edet) SEQ ID NO:23(aa), 58(na), FIGS. 26A, 26B; construct 3361), GII.4 (S(GI.1)+P(GII.4); S(GI.1 Nor/68)+P (GII.4/Sydney/NSW0514/12) SEQ ID NO:24(aa), 59na), FIGS. 27A, 27B; construct 3362), GII.6 (S(GI.1)+P(GII.6); S(GI.1 Nor/68)+P(GII.6/Ohio/490/12) SEQ ID NO:25(aa), 63(na), FIGS. 28A, 28B; construct 3363), GII.13 (S(GI.1)+P(GII.13); S(GI.1 Nor/68)+P (GII.13/VA173/10) SEQ ID NO:26(aa); 64(na), FIGS. 29A, 29B; construct 3364), and GII.17 (S(GI.1)+P(GII.17); S(GI.1 Nor/68)+P (GII.17/Kawasaki323/14) SEQ ID NO:27(aa), 65(na), FIGS. 30A, 30B; construct 3365)

VP1 fusion protein production was determined using Coomassie-stained SDS-PAGE analysis (approx. 55-60 kDa band) of extracts obtained from plant leaves vacuum infiltrated with expression vectors comprising the above nucleotide sequences encoding the various VP1 fusion proteins, and VP2. As shown in FIGS. 5A and 5B, the fusion of the GI.1 Norwalk S domain to the P domain of GI.2 (GI.1S-GI.2P), GI.3 (GI.1S-GI.3P), or GII.13 (GI.1S-GII.13P), resulted in similar levels of expression of norovirus VP1 fusion proteins as compared to their native non-fusion counterparts. Demonstrating that VP1 fusion proteins may be expressed in a plant, portion of a plant, or a plant cell.

Figure 6D:
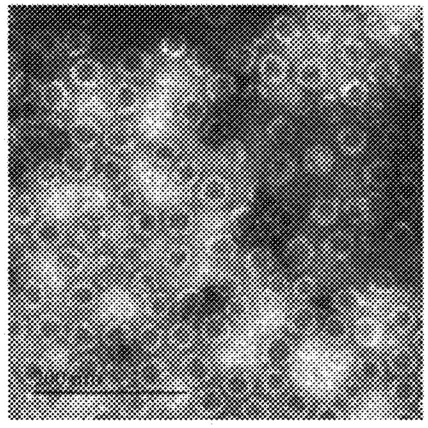
FIG. 6D shows an electron micrographs of a human codon optimized norovirus VLP from iodixanol gradient fractions, the VLP comprising the VP1 fusion S(GI.1)+P(GII.4) (S(GI.1 Nor/68)+P (GII.4/Sydney/NSW0514/12; SEQ ID NO:59, FIG. 27B).

Even though protein product was not observed using SDS-PAGE analysis for the VP1 fusion S(GI.1)+P(GII.4) (S(GI.1 Nor/68)+P (GII.4/Sydney/NSW0514/12; SEQ ID NO:59, FIG. 27B), and S(GI.1)+P(GII.17) (S(GI.1 Nor/68)+P (GII.17/Kawasaki323/14; SEQ ID NO:65, FIG. 30B), electron micrograph analysis of S(GI.1)+P(GII.4) and GII.17 (GI.1S-GII.17P), revealed that VLPs were produced (see FIGS. 6C and 6D).

The fusion of the GI.1 Norwalk S domain to the P domains of low-expressing GII.6 (GI.1S-GII.6P) did not result in enhanced expression of norovirus VP1 fusion protein as compared to their native non-fusion counterparts. Without wishing to be bound by theory, these results suggest that the S domain may not be responsible for the low-level of expression in plants for these particular norovirus strains.

When VP1 fusion proteins are expressed in plants, it is preferred that the ORF3 sequence encoding VP2 is obtained from the same norovirus strain as used to obtain the S domain of fusion VP1 sequence. Support for this observation may be found with reference to Panels B and C of FIG. 5E, which show that, in this example, the level of expression of a VP1 fusion protein, when co-expressed with VP2 obtained from the same genotype and strain as the S domain of the VP1 fusion, results in greater VLP yield (Panel B; FIG. 5E, right hand side), then co-expression of the same VP1 fusion protein with a VP2 obtained from a different genotype and strain (FIG. 5E; Panel C, right hand side). Rather, the VLP yield observed following co-expression of the VP1 fusion along with a heterologous VP2 (i.e. the S domain of the VP1 fusion and VP2 are from different genotypes and strains) decreased and approximated the VLP yield observed when VP1 was expressed alone (FIG. 5E, Panel A, left hand side).

It is also of interest to note that the VLP yield obtained from co-expressing a VP1 fusion along with a VP2, where the S domain and the VP2 area obtained from the same genotype and strain (Panel B; FIG. 5E, right hand side), is greater than the VLP yield observed following expression of the VP1 fusion when expressed alone (Panel B; FIG. 5E, left hand side).

As shown in the electron micrographs of FIGS. 6A and 6B, VP1 fusion proteins derived from several of the strains including GI.1 Nor68+GI.2/Leuven/2003/Bel (FIG. 6A, right hand side); GI.1 Nor68+GI.3/S29/2008/Lilla Edet/Sweden (FIG. 6B, right hand side), GI.1+GII.13Vas10 (FIG. 6C left hand side), GI.1+GII.17Kaw14 (FIG. 6C right hand side), self-assembled into VLPs having a structural conformation and diameter of about 15 nm to 50 nm, for example, for T=1 icosahedral symmetry, about 23 nm, or for T=3 icosahedral symmetry, about 38 to about 40 nm, similar to that of wildtype norovirus. Of note is that the VP1 fusion product encoded by GI.1+GII.17Kaw14 resulted in a low yield (FIG. 5B), however, VLPs comprising this VP1 protein could be purified from plant extracts.

However, no VLPs were obtained from plant extracts expressing the VP1 fusion protein GI.1+GII.6/Ohio/490/12 (also see Example 5), consistent with the low or undetectable expression levels of this VP1 fusion protein as shown in FIG. 5B.

Additional human codon optimized VP1 fusion proteins were prepared and co-expressed with VP2 in *N. benthamiana* leaves, as described in Example 5 below.

The VP1 fusion proteins included:

S(GI.1)+P(X), where X=GI.2, GI.3, GII.4, GII.6, GII.12, GII.13, GII.17;

S(GI.5)+P(Y), where Y=GII.4;

S(GII.1)+P(Z), where Z=GI.3, GII.4, GII.17;

S(GII.12)+P(W), where W=GI.1, GI.2, GI.3, GI.5, GII.1, GII.2, GII.3, GII.4, GII.5, GII.6, GII.7, GII.13, GII.14, GII.17, GII.21;

S(GII.14)+P(T), where T=GII.4;

S(GII.21)+P(Q), where Q=GII.4

Expression of VP1 fusion proteins in a plant, a portion of a plant or a plant cell was observed (see Example 5) with the following VP1 fusion constructs:

S(GI.1)+P(GI.2), S(GI.1)+P(GI.3), S(GI.1)+P(GII.4), S(GI.1)+P(GII.6), S(GI.1)+P(GII.12), S(GI.1)+P(GII.13), S(GI.1)+P(GII.17),

S(GI.5)+P(GII.4),

S(GII.1)+P(GI.3), S(GII.1)+P(GII.4),

S(GII.12)+P(GI.1), S(GII.12)+P(GI.2), S(GII.12)+P(GI.3), S(GII.12)+P(GI.5), S(GII.12)+P(GII.1), S(GII.12)+P(GII.2), S(GII.12)+P(GII.4), S(GII.12)+P(GII.7), S(GII.12)+P(GII.13), S(GII.12)+P(GII.14), S(GII.12)+P(GII.17), S(GII.12)+P(GII.21).

Enhanced Stability of VLPs Comprising Norovirus VP1 Fusion Proteins

Figure 3C:
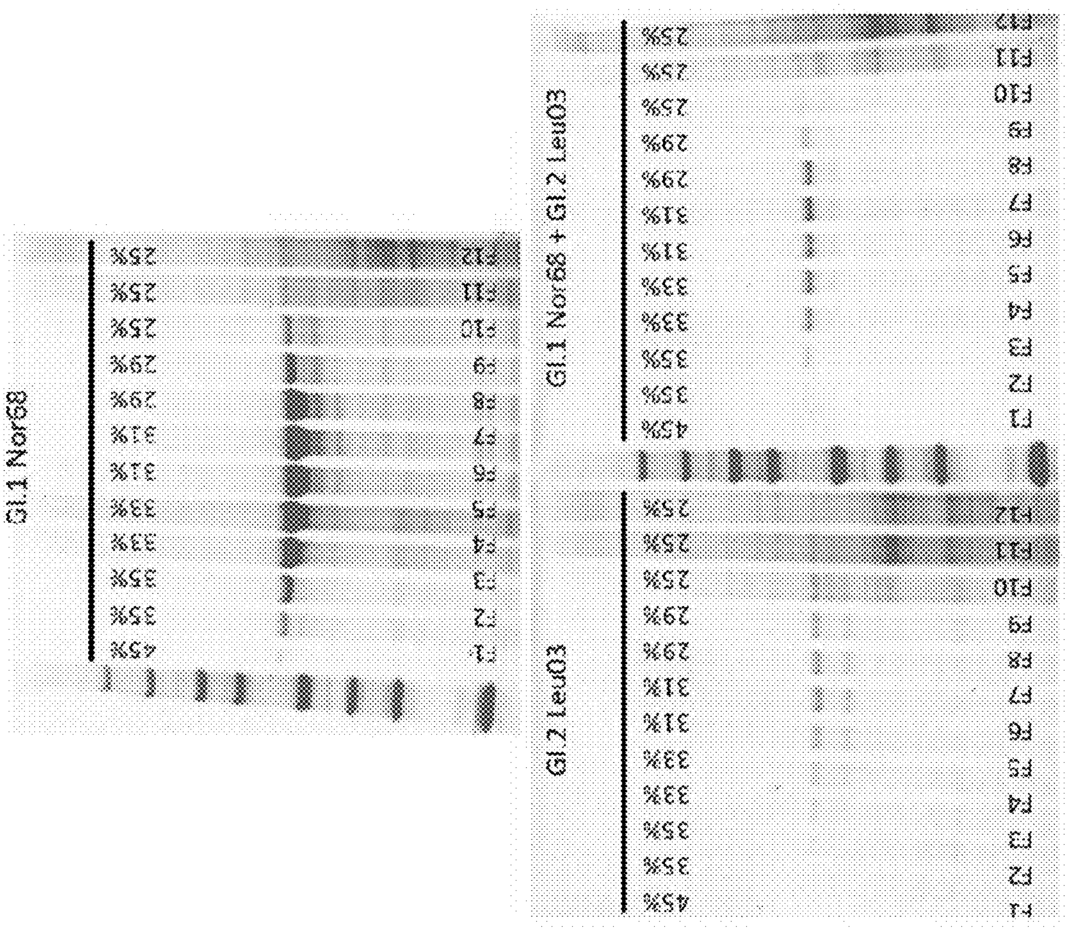
FIG. 3C shows norovirus protein expression and VLP assembly using Coomassie-stained SDS-PAGE analysis of fractions from an iodixanol density gradient separation of crude protein extracts prepared from *N. benthamiana* leaves expressing: upper panel—human codon optimized GI.1/United States/Norwalk/1968 native VP1 (construct #2724); lower panel (left hand side)—human codon optimized GI.2 Leu03 native VP1 (construct #3300); lower panel (right hand side) human codon optimized VP1 S(GI.1)+P (GI.2) fusion protein (construct 3360).

As shown in FIG. 3C (upper panel), the levels of VLPs comprising of high-expressing native GI.1 VP1 protein (encoded by construct 2724) peaked in fractions four through eight following iodixanol gradient centrifugation. In contrast, VLPs comprising of native GI.2 VP1 protein (encoded by construct 3300) FIG. 3C lower panel, left hand side) peaked in lower-density fractions six through nine. These results indicate that the assembly of native GI.2 VLPs may be less stable than GI.1 VLPs and may be more susceptible to malformed capsid particles and the generation of fragmentation products.

However, VLPs comprising S(GI.1 Nor68)+P(GI.2 Leu03) norovirus VP1 fusion proteins (encoded by construct 3360; FIG. 3C, lower panel, right hand side), peaked in fractions four through eight, indicating that VLPs comprising norovirus VP1 fusion proteins having a GI.1 S domain core may be more stable than their native VLP counterparts where the S domain is not derived from GI.1.

A similar shift in density was also observed in VLPs comprising of S(GI.1)+P(GI.3P) norovirus VP1 fusion proteins (FIG. 6B; GI.1 Nor68+GI.3 Lil08, encoded by construct 3360).

Additionally, as shown with reference to FIG. 5E, when a VP1 fusion protein is co-expressed with a VP2 minor structural protein that is obtained from the same genotype and strain as the S domain of the VP1 fusion, then the VP2 protein is incorporated on the VLPs (see high-molecular weight fractions of the density gradient that contain Norovirus VLPs, band of 21-24 kDa, indicated by a square; FIG. 5E; Panel B right hand side, and Panel C left hand side). The VP2 band is absent when the VP2 protein is obtained from a different genotype and strain as the S domain of the VP1 fusion (FIG. 5E, Panel C, right hand side). Without wishing to be bound by theory, these results are consistent with the proposal that VP2 is located on the inside of the viral particle and that VP2 may play a role in particle stability.

Induction of Immunity Against Norovirus Infection

An "immune response" generally refers to a response of the adaptive immune system of a subject. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity may be of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-norovirus antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be quantified in a number of ways, including: enumeration of lysis plaques (plaque assay) following crystal violent fixation/coloration of cells; microscopic observation of cell lysis in in vitro culture; and 2) ELISA and spectrophotometric detection of norovirus.

The term "epitope" or "epitopes", as used herein, refers to a structural part of an antigen to which an antibody specifically binds.

Figure 6E:
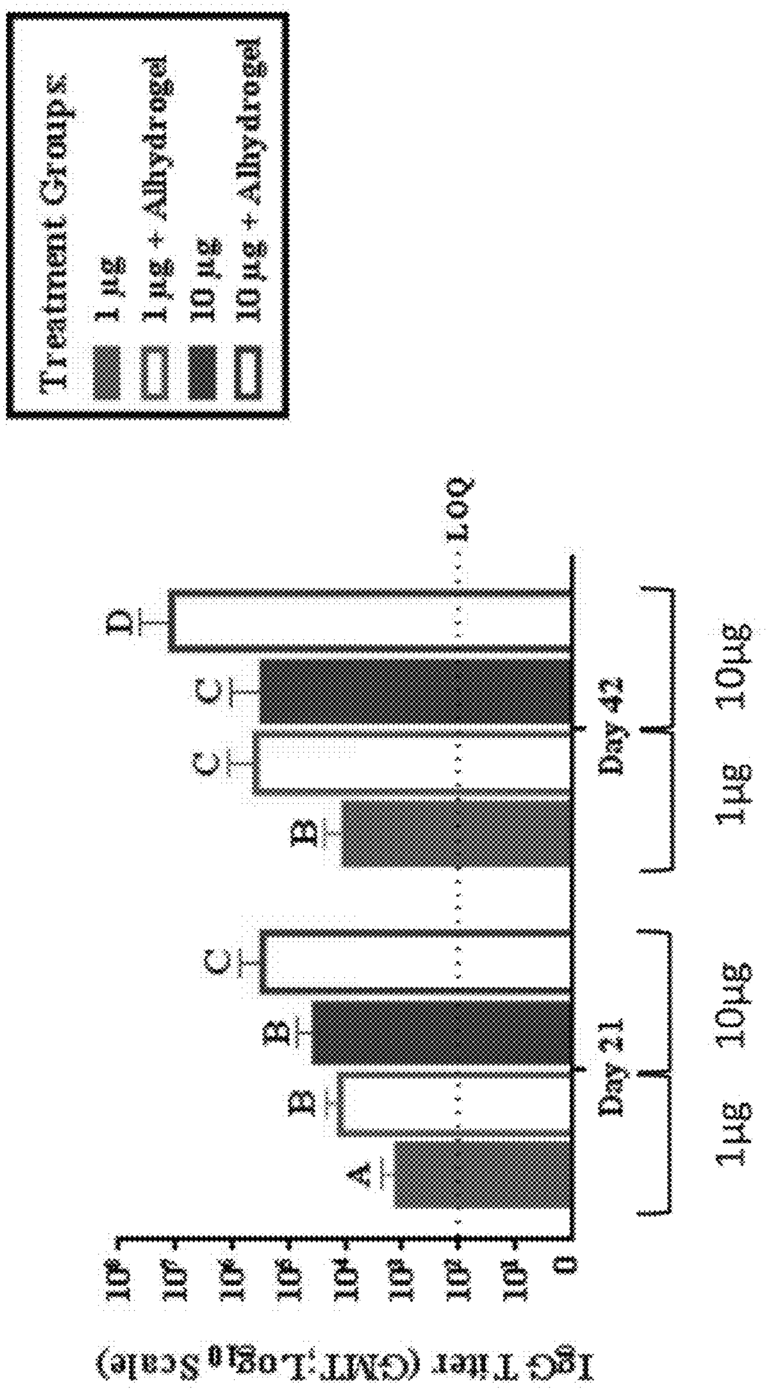
FIG. 6E shows GI.1 VLP-specific total IgG titers measured in serum samples from animals after IM immunization with one dose (Day 21) and two doses (Day 42) of 1 μg or 10 μg of each formulation. Total IgG titers were measured by ELISA using GI.1 VLP-coated plates (LOQ=100). Total IgG titers per treatment group (n=8 animals/group) are represented by geometric mean titer (GMT) with a 95% confidence interval. Same letter (A, B, C, D): no significant difference detected between treatment groups ($p>0.05$).

With reference to FIG. 6E, an immune response is observed following the administration of GI.1 VP1 VLPs, produced as described herein, to mice. Mice immunized with plant-made Norovirus native VP1 VLPs from GI.1 genotype exhibited GI.1 VLP-specific IgG antibody titers in sera on Days 21 and 42. IgG titer levels induced by each treatment on Days 21 and 42 were statistically higher than the titers quantified for the placebo group ($p<0.05$). IgG titer level increased in a dose-dependent manner with a significant difference observed between the 1 μg and 10 μg treatments. The addition of Alhydrogel® (aluminum hydroxide) to the Norovirus VLP vaccine enhanced the immune response. These results demonstrate the ability of plant produced Norovirus native VP1 VLPs to elicit a robust immune response in mice. Similar results are observed with the administration of VP1 fusion proteins produced as described herein.

Plant Expression

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. D T. Dennis, D H Turpin, D D Lefebrvre, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (1991, *Gene* 100: 247-250), Scheid et al. (1991, *Mol. Gen. Genet.* 228: 104-112), Guerche et al. (1987, *Plant Science* 52: 111-116), Neuhause et al. (1987, *Theor. Appl Genet.* 75: 30-36), Klein et al. (2987, *Nature* 327: 70-73); Freeman et al. (1984, *Plant Cell Physiol.* 29: 1353), Howell et al. (1980, *Science* 208: 1265), Horsch et al. (1985, *Science* 227: 1229-1231), DeBlock et al. (1989, *Plant Physiology* 91: 694-701), Methods for Plant Molecular Biology (Weissbach and Weissbach, eds., Academic Press Inc., 1988), Methods in Plant Molecular Biology (Schuler and Zielinski, eds., Academic Press Inc., 1989), WO 92/09696, WO 94/00583, EP 331083, EP 175966, Liu and Lomonossoff (2002, *J Virol Meth,* 105:343-348), EP 290395; WO 8706614; U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient expression methods may be used to express the constructs of the present invention (see D'Aoust et al., 2009, *Methods in molecular biology*, Vol 483, pages 41-50; Liu and Lomonossoff, 2002, *Journal of Virological Methods,* 105:343-348; which is incorporated herein by reference). Alternatively, a vacuum-based transient expression method, as described by Kapila et al. (1997, *Plant Sci.* 122, 101-108; which is incorporated herein by reference), or WO 00/063400, WO 00/037663 (which are incorporated herein by reference) may be used. These methods may include, for example, but are not limited to, a method of Agro-inoculation or Agro-infiltration, syringe infiltration, however, other transient methods may also be used as noted above. With Agro-inoculation, Agro-infiltration, or syringe infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacteria* infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the gene construct of the present invention that may be used as a platform plant suitable for transient protein expression described herein. Methods of regenerating whole plants from plant cells are also known in the art (for example see Guerineau and Mullineaux (1993, Plant transformation and expression vectors. In: Plant Molecular Biology Labfax (Croy RRD ed) Oxford, BIOS Scientific Publishers, pp 121-148). In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue culture. Methods for stable transformation, and regeneration of these organisms are established in the art and known to one of skill in the art. Available techniques are reviewed in Vasil et al. (Cell Culture and Somatic Cell Genetics of Plants, Vol I, II and III, Laboratory Procedures and Their Applications, Academic Press, 1984), and Weissbach and Weissbach (Methods for Plant Molecular Biology, Academic Press, 1989). The method of obtaining transformed and regenerated plants is not critical to the present invention.

If plants, plant portions or plant cells are to be transformed or co-transformed by two or more nucleic acid constructs, the nucleic acid construct may be introduced into the *Agrobacterium* in a single transfection event so that the nucleic acids are pooled, and the bacterial cells transfected. Alternatively, the constructs may be introduced serially. In this case, a first construct is introduced into the *Agrobacterium* as described, the cells are grown under selective conditions (e.g. in the presence of an antibiotic) where only the singly transformed bacteria can grow. Following this first selection step, a second nucleic acid construct is introduced into the *Agrobacterium* as described, and the cells are grown under doubly-selective conditions, where only the doubly-transformed bacteria can grow. The doubly-transformed bacteria may then be used to transform a plant, plant portion or plant cell as described herein, or may be subjected to a further transformation step to accommodate a third nucleic acid construct.

Alternatively, if plants, plant portions, or plant cells are to be transformed or co-transformed by two or more nucleic acid constructs, the nucleic acid construct may be introduced into the plant by co-infiltrating a mixture of *Agrobacterium* cells with the plant, plant portion, or plant cell, each *Agrobacterium* cell may comprise one or more constructs to be introduced within the plant. In order to vary the relative expression levels within the plant, plant portion or plant cell, of a nucleotide sequence of interest within a construct, during the step of infiltration, the concentration of the various *Agrobacteria* populations comprising the desired constructs may be varied.

TABLE 1

Norovirus strains and constructs.

| Trivial name | strain | SEQ ID NO: | Construct # | FIG. # |
|---|---|---|---|---|
| VP1 | | | | |
| GI.1 (VP1; aa) | GI.1/Norwalk/1968/US | 1 | — | 13A |
| GI.1 (VP1; na) | Wild type GI.1/Norwalk/1968/US | 13 | | 13B |
| GI.1 hCod (VP1; na) | VP1-hCod GI.1/US/Norwalk/1968 | 18 | 2724 | 13C |
| GI.2 (VP1; aa) | GI.2/Leuven/2003/Bel | 2 | — | 14A |
| GI.2 (VP1; (na) | hCod GI.2/Leuven/2003/Bel | 54 | 3300 | 14B |
| GI.3 (VP1; aa) | GI.3/S29/2008/Lilla Edet/Sweden | 3 | — | 15A |
| GI.3 (VP1; na) | hCod VP1 GI.3/S29/2008/Lilla Edet/Sweden | 55 | 3302 | 15B |
| GI.5 (VP1; aa) | GI.5/Siklos/Hun5407/2013/HUN | 44 | | 16A |
| GII.1 (VP1; aa) | GII.1/Ascension208/2010/USA | 45 | | 16B |
| GII.2 (VP1; aa) | GII.2/CGMH47/2011/TW | 66 | | 16C |
| GII.3 (VP1; aa) | GII.3/Jingzhou/2013402/CHN | 67 | | 16D |
| GII.4 Syd12 (VP1; aa) | GII.4/Sydney/NSW0514/2012/AU | 4 | — | 17A |
| GII.4 (VP1; na) | hCod VP1 GII.4/Sydney/NSW0514/2012/AU | 56 | 3304 | 17B |
| GII.4 US96 (VP1; aa) | GII.4/Dresden174/1997/DE (variant: US 1995/96) | 8 | — | 21A |
| GII.4 FH02 (VP1; aa) | GII.4/FarmingtonHills/2002/US | 9 | — | 21B |
| GII.4 Hnt04 (VP1; aa) | GII.4/Hunter-NSW504D/2004/AU | 10 | — | 21C |
| GII.4 2006b (VP1; aa) | GII.4/Shellharbour-NSW696T/2006/AU | 11 | — | 21D |
| GII.4 NO09 (VP1; aa) | GII.4/Orange-NSW001P/2008/AU (variant New Orleans 2009) | 12 | — | 21E |
| GII.5 (VP1; aa) | GII.5/AlbertaEI390/2013/CA | 68 | | 16E |
| GII.6 (VP1; aa) | GII.6/Ohio/490/12 | 5 | | 18A |
| GII.6 (VP1 ;na) | hCod GII.6/Ohio/490/12 | 60 | 3306 | 18B |
| GII.7 (VP1; aa) | GII.7/Musahimurayama/2010/JP | 69 | | 16F |
| GII.12 (VP1; aa) | GII.12/HS206/2010/USA | 28 | | 22A |
| GII.13 (VP1; aa) | GII.13/VA173/2010/USA | 6 | | 19A |
| GII.13 (VP1; na) | hCod GII.13/VA173/2010/USA | 61 | 3308 | 19B |
| GII.14 (VP1; aa) | GII.14/8610/Saga/2008/JP | 46 | | 22B |
| GII.17 (VP1; aa) | GII.17/Kawasaki323/2014/JP | 7 | | 20A |
| GII.17 (VP1; na) | hCod GII.17/Kawasaki323/2014/JP | 62 | 3310 | 20B |
| GII.21 (VP1; aa) | GII.21/Salisbury150/2011/USA | 47 | | 22C |
| VP1 consensus (aa) | VP1 consensus sequence | 70 | — | 16G |
| VP2 | | | | |
| GI.1 (VP2; aa) | VP2 GI.1/US/Norwalk/1968 | 14 | | 23A |
| GI.1 (VP2; na) | VP2-GI.1/US/Norwalk/1968 | 15 | 2721 | 23B |
| GI.1 hCod (VP2; na) | VP2-hCod GI.1/US/Norwalk/1968 | 19 | 2725 | 23C |
| GII.4 hCod (VP2; na) | VP2 hCod GII.4/Sydney/NSW0514/2012/AU | 120 | 3305 | 23D |
| GII.4 (VP2; aa) | VP2 GII.4/ Sydney/NSW0514/2012/AU | 121 | | 23E |
| VP1 fusions | | | | |
| S(GI.1) + P(GI.2) (aa) | S(GI.1 Nor/68) + P (GI.2/Leuven/03) | 22 | | 25A |
| S(GI.1) + P(GI.2) (na) | hCod S(GI.1 Nor/68) + P (GI.2/Leuven/03) | 57 | 3360 | 25B |
| S(GI.1) + P(GI.3) (aa) | S(GI.1 Nor/68) + P (GI.3/S29/08/Lilla Edet) | 23 | — | 26A |
| S(GI.1) + P(GI.3) (na) | hCod S(GI.1 Nor/68) + P (GI.3/S29/08/Lilla Edet) | 58 | 3361 | 26B |

TABLE 1-continued

Norovirus strains and constructs.

| Trivial name | strain | SEQ ID NO: | Construct # | FIG. # |
|---|---|---|---|---|
| S(GI.1) + P(GII.4) (aa) | S(GI.1 Nor/68) + P (GII.4/Sydney/NSW0514/12 | 24 | — | 27A |
| S(GI.1) + P(GII.4) (na) | hCod S(GI.1 Nor/68) + P (GII.4/Sydney/NSW0514/12 | 59 | 3362 | 27B |
| S(GI.1) + P(GII.6) (aa) | S(GI.1 Nor/68) + P (GII.6/Ohio/490/12) | 25 | — | 28A |
| S(GI.1) + P(GII.6) (na) | hCod S(GI.1 Nor/68) + P (GII.6/Ohio/490/12) | 63 | 3363 | 28B |
| S(GI.1) + P(GII.12)(aa) | S(GI.1 Nor/68) + P (GII.12/HS206/2010/USA) | 71 | — | 31A |
| S(GI.1) + P(GII.13) (aa) | S(GI.1 Nor/68) + P (GII.13/VA173/10) | 26 | — | 29A |
| S(GI.1) + P(GII.13) (na) | hCod S(GI.1 Nor/68) + P (GII.13/VA173/10) | 64 | 3364 | 29B |
| S(GI.1) + P(GII.17) (aa) | S(GI.1 Nor/68) + P (GII.17/Kawasaki323/14) | 27 | — | 30A |
| S(GI.1) + P(GII.17) (na) | hCod S(GI.1 Nor/68) + P (GII.17/Kawasaki323/14) | 65 | 3365 | 30B |
| S(GI.5) + P(GII.4) (aa) | | 48 | | 31B |
| S(GII.1) + P(GI.3) (aa) | | 49 | | 32A |
| S(GII. 1) + P(GII.4) (aa) | | 50 | | 32B |
| S(GII.1) + P(GII.17) (aa) | | 51 | | 32C |
| S(GII.12) + P(GI.1) (aa) | | 29 | — | 33A |
| S(GII. 12) + P(GI.2) (aa) | | 30 | — | 33B |
| S(GII.12) + P(GI.3) (aa) | | 31 | — | 33C |
| S(GII.12) + P(GI.5) (aa) | | 32 | — | 33D |
| S(GII.12) + P(GII.1) (aa) | | 33 | — | 33E |
| S(GII.12) + P(GII.2) (aa) | | 34 | — | 33F |
| S(GII.12) + P(GII.3) (aa) | | 35 | — | 33G |
| S(GII.12) + P(GII.4) (aa) | | 36 | — | 33H |
| S(GII.12) + P(GII.5) (aa) | | 37 | — | 33I |
| S(GII.12) + P(GII.6) (aa) | | 38 | — | 33J |
| S(GII.12) + P(GII.7) (aa) | | 39 | — | 33K |
| S(GII.12) + P(GII.13) (aa) | | 40 | — | 33L |
| S(GII.12) + P(GII.14) (aa) | | 41 | — | 33M |
| S(GII.12) + P(GII.17) (aa) | | 42 | — | 33N |
| S(GII.12) + P(GII.21) (aa) | | 43 | — | 33O |
| S(GII.14) + P(II.4) (aa) | | 52 | | 34A |
| S9GII.21) + P(GII.4) (aa) | | 53 | | 34B |
| S-P boundary | | | | |
| S-P GI.1 | S-P GI.1/Norwalk/1968/US | 88 | — | 4A |
| S-P GI.2 | S-P GI.2/Leuven/2003/Bel | 89 | — | 4A |
| S-P GI.3 | S-P GI.3/S29/2008/Lilla Edet/Sweden | 90 | — | 4A |
| S-P GII.4 | S-P GII.4/Sydney/NSW0514/2012/AU | 91 | — | 4A |
| S-P GII.6 | S-P GII.6/Ohio/490/12 | 92 | — | 4A |
| S-P GII.13 | S-P GII.13/VA173/2010/USA | 93 | — | 4A |
| S-P GII.17 | S-P GII.17/Kawasaki323/2014/JP | 94 | — | 4A |
| S-P boundary consensus | | 95 | | 4A |
| ORF2/ORF3 | | | | |
| GI.1 VP1/VP2 (na) | GI.1/US/Norwalk/1968 | 16 | 2722 | 24A |
| GI.1 VP1/VP2/3'UTR (na) | GI.1/US/Norwalk/1968 | 17 | 2723 | 24B |
| GI.1 hCod VP1/VP2 (na) | hCod GI.1/US/Norwalk/1968 | 20 | 2726 | 24C |
| GI.1 hCod VP1/VP2/3'UTR (na) | hCod GI.1/US/Norwalk/1968 | 21 | 2727 | 24D |
| Primers | | | | |
| IF NoV(US68)VP1(ORF2).c | | 72 | | 7A |
| IF-NoV(US68)VP1(ORF2).r | | 73 | | 7B |
| IF-NoV(US68)VP1(ORF2)(hCod).c | | 76 | | 9A |
| IF-NoV(US68)VP1(ORF2)(hCod).r | | 77 | | 9B |
| IF-NoV(US68)VP2(ORF3)(hCod).c | | 79 | | 10A |
| IF-NoV(US68)VP2(ORF3)(hCod).r | | 80 | | 10B |
| IF-GI2Leu03VP1.c | | 82 | | 11A |
| IF-GI2Leu03VP1.r | | 83 | | 11B |
| GI2Leu + GI1VP1.r | | 85 | | 12A |
| GI1VP1 + GI2Leu.c | | 86 | | 12B |
| IF-GI3Lil08VP1.c | | 111 | | 35 |
| IF-GI3Lil08VP1.r | | 98 | | 35 |
| IF-GII4Syd12VP1.c | | 112 | | 35 |
| IF-GII4Syd12VP1.r | | 101 | | 35 |
| IF-GII6Ohi12VP1.c | | 113 | | 35 |
| IF-GII6Ohi12VP1.r | | 104 | | 35 |
| IF-GII13VA10VP1.c | | 114 | | 35 |
| IF-GII13VA10VP1.r | | 107 | | 35 |

TABLE 1-continued

| Norovirus strains and constructs. | | | | |
|---|---|---|---|---|
| Trivial name | strain | SEQ ID NO: | Construct # | FIG. # |
| IF-GII17Kaw14VP1.c | | 115 | | 35 |
| IF-GII17Kaw14VP1.r | | 110 | | 35 |
| GI3Lil + GI1VP1.r | | 96 | | 35 |
| GI1VP1 + GI3Lil.c | | 97 | | 35 |
| GII4Syd + GI1VP1.r | | 99 | | 35 |
| GIlVP1 + GII4Syd.c | | 100 | | 35 |
| GII6Ohi + GI1VP1.r | | 102 | | 35 |
| GI1VP1 + GII6Ohi.c | | 103 | | 35 |
| GII13Va + GI1VP1.r | | 105 | | 35 |
| GI1VP1 + GII13Va.c | | 106 | | 35 |
| GII17Kaw + GI1VP1.r | | 108 | | 35 |
| GI1VP1 + GII17Kaw.c | | 109 | | 35 |
| IF-GII4Syd12VP2.c | | 117 | | 35 |
| IF-GII4Syd12VP2.r | | 119 | | 35 |
| IF-NoV(US68)VP2(ORF3).c | | 116 | | 35 |
| IF-NoV(US68)VP2(ORF3).r | | 122 | | |
| IF- NoV(US68)VP1/VP2 (ORF3)NoV3'UTR.r | | 118 | | 35 |
| Constructs | | | | |
| 2X35S/CPMV-160/NOS (na) | 2X35S/CPMV-160/NOS with Plastocyanine-P19-Plastocyanine silencing inhibitor | 74 | 1190 | 7C |
| 2X35S-WT VP1 GI.1/Norwalk/1968/US-NOS terminator (na) | 2X35S promoter to NOS terminator. Wild-type VP1 from Norovirus GI.1/Norwalk/1968/US strain | 75 | 2720 | 8A |
| 2X35S-hCod-optimized VP1 GI.1/Norwalk/1968/US-NOS terminator | 2X35S promoter to NOS terminator. Human codon-optimized VP1 from Norovirus GI.1/Norwalk/1968/US | 78 | 2724 | 9C |
| 2X35S-hCod-optimized VP2 GI.1/Norwalk/1968/US-NOS terminator | 2X35S promoter to NOS terminator. Human codon-optimized VP2 from Norovirus GI.1/Norwalk/1968/US | 81 | 2725 | 10C |
| 2X35S-hCod optimized VP1 GI.2/Leuven/2003/Bel-NOS terminator | 2X35S promoter to NOS terminator. Human codon-optimized VP1 from Norovirus GI.2/Leuven/2003/Bel | 84 | 3300 | 11C |
| 2X35S-hCod-optimized fusion VP1 S(GI.1) + P (GI.2)-NOS terminator | 2X35S promoter to NOS terminator. Human codon-optimized fusion VP1 S(GI.1) + P(GI.2) | 87 | 3360 | 12C |

The present invention will be further illustrated in the following examples.

Example 1: Norovirus VP1 Constructs

The candidate sequences for VP1 and VP2 are available in Genbank (see FIGS. 2A and 2B). Non-limiting examples of these sequences are:

- GI.1/Norwalk/1968/US (GI.1) NCBI M87661 (SEQ ID NO: 1); VP1
- GI.2/Leuven/2003/Bel (GI.2) NCBI FJ515294 (SEQ ID NO:2)
- GI.3/S29/2008/Lilla Edet/Sweden NCBI JN603244 (SEQ ID NO:3)
- GI.5/Siklos/Hun5407/2013/HUN (SEQ ID NO:44)
- GII.1/Ascension208/2010/USA (SEQ ID NO: 45)
- GII.2/CGMH47/2011/TW (SEQ ID NO:66)
- GII.3/Jingzhou/2013402/CHN (SEQ ID NO:67)
- GII.4/Sydney/NSW0514/2012/AU NCBI JX459908 (SEQ ID NO:4)
- GII.5/AlbertaEI390/2013/CA (SEQ ID NO:68)
- GII.6/Ohio/490/2012/USA NCBI KC464321 (SEQ ID NO:5; VP1), NCBI J407072 (VP2)
- GII.7/Musahimurayama/2010/JP (SEQ ID NO:69)
- GII.12/HS206/2010/USA (SEQ ID NO:28)
- GII.13/VA173/2010/USA NCBI JN899242 (SEQ ID NO:6)
- GII.14/8610/Saga/2008/JP (SEQ ID NO:46)
- GII.17/Kawasaki323/2014/JP NCBI AB983218 (SEQ ID NO:7)
- GII.21/Salisbury150/2011/USA NCBI XX (SEQ ID NO:47)

A2X35S/CPMV 160/wt VP1 GI.1/NOS (Construct Number 2720)

Figures 8A, 8B:
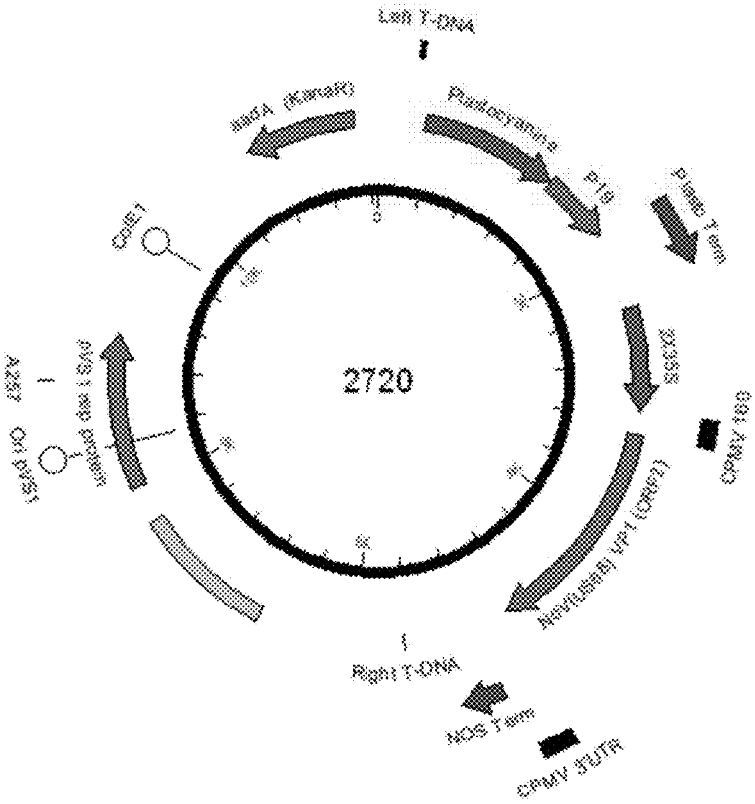
FIG. 8A shows the nucleotide sequence of construct 2720 from 2X35S promoter to NOS terminator. Wild-type VP1 from Norovirus GI.1/Norwalk/1968/US strain is underlined. (SEQ ID NO: 75)
FIG. 8B shows a schematic representation of construct 2720.

A wild-type sequence encoding VP1 from Norovirus strain GI.1/Norwalk/1968/US was cloned into 2X35S/CPMV 160/NOS expression system using the following PCR-based method. A fragment containing the GI.1 VP1 coding sequence was amplified using primers IF-NoV(US68)VP1(ORF2).c (SEQ ID NO: 72) and IF-NoV(US68)VP1(ORF2).r (SEQ ID NO: 73), using native GI.1 VP1 gene sequence (SEQ ID NO: 13; FIG. 13B) as template. The PCR product was cloned in 2X35S/CPMV 160/NOS expression system using In-Fusion cloning system (Clontech, Mountain View, CA). Construct number 1190 (FIG. 7D) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette (for a description of CMPV 160 see WO2015/103704 and WO2015/143567; both of which are incorporated herein by reference). It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 74 (FIG. 7C). The resulting construct was given number 2720 (SEQ ID NO: 75; FIG. 8A). The amino acid sequence of native VP1 from Norovirus strain GI.1/Norwalk/1968/US is presented in SEQ ID NO: 1. A representation of plasmid 2720 is presented in FIG. 8B.

2X35S/CPMV 160/VP1 GI.1 (hCod)/NOS (Construct Number 2724)

A human codon-optimized sequence encoding VP1 from Norovirus strain GI.1/Norwalk/1968/US was cloned into 2X35S/CPMV 160/NOS expression system using the following PCR-based method. A fragment containing the GI.1 VP1 coding sequence was amplified using primers IF-NoV (US68)VP1(ORF2)(hCod).c (SEQ ID NO: 76) and IF-NoV (US68)VP1(ORF2)(hCod).r (SEQ ID NO: 77), using human codon-optimized GI.1 VP1 gene sequence (SEQ ID NO: 18; FIG. 13C) as template. For sequence optimization, GI.1/Norwalk/1968/US VP1 protein sequence (Genbank accession number NP_056821) was backtranslated and optimized for human codon usage, GC content and mRNA structure. The PCR product was cloned in 2X35S/CPMV 160/NOS expression system using In-Fusion cloning system (Clontech, Mountain View, CA). Construct number 1190 (FIGS. 7C and 7D) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette (For a description of CMPV 160 see WO2015/103704 and WO2015/143567; both of which are incorporated herein by reference). It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 74. The resulting construct was given number 2724 (SEQ ID NO: 78; FIG. 9C). The amino acid sequence of native VP1 from Norovirus strain GI.1/Norwalk/1968/US is presented in SEQ ID NO: 1. A representation of plasmid 2724 is presented in FIG. 9D.

2X35S/CPMV 160/VP2 GI.1 (hCod)/NOS (Construct Number 2725)

Figures 10C, 10D:
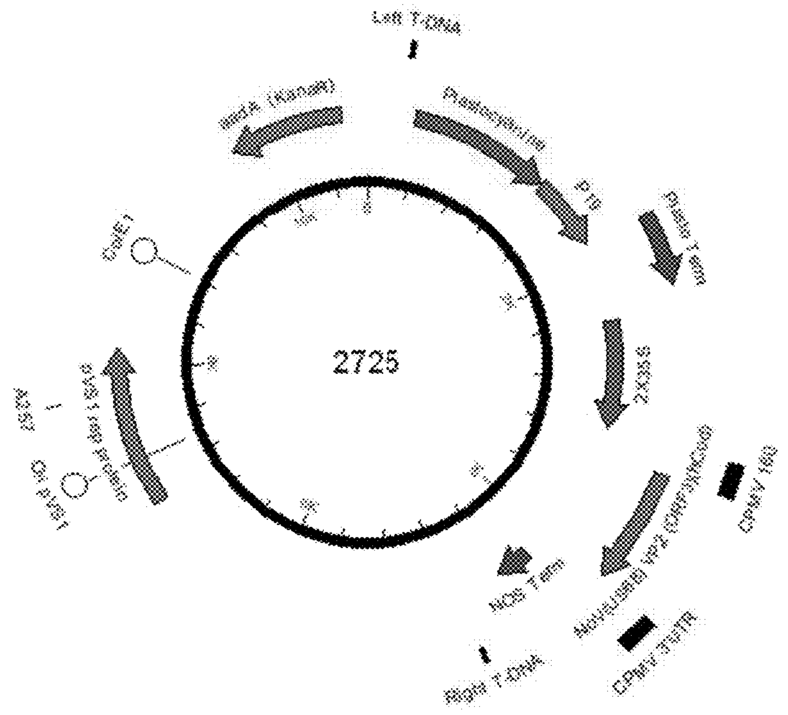
FIG. 10C shows the nucleotide sequence of construct 2725 from 2X35S promoter to NOS terminator. Human codon-optimized VP2 from Norovirus GI.1/Norwalk/1968/US strain is underlined. (SEQ ID NO: 81)
FIG. 10D shows a schematic representation of construct 2725.

A human codon-optimized sequence encoding VP2 from Norovirus strain GI.1/Norwalk/1968/US was cloned into 2X35S/CPMV 160/NOS expression system using the following PCR-based method. A fragment containing the GI.1 VP2 coding sequence was amplified using primers IF-NoV (US68)VP2(ORF3)(hCod).c (SEQ ID NO: 79) and IF-NoV (US68)VP2(ORF3)(hCod).r (SEQ ID NO: 80), using human codon-optimized GI.1 VP2 gene sequence (SEQ ID NO: 19; FIG. 23C) as template. For sequence optimization, GI.1/Norwalk/1968/US VP2 protein sequence (Genbank accession number NP_056822) was backtranslated and optimized for human codon usage, GC content and mRNA structure. The PCR product was cloned in 2X35S/CPMV 160/NOS expression system using In-Fusion cloning system (Clontech, Mountain View, CA). Construct number 1190 (FIGS. 7C and 7D) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette (for a description of CMPV 160 see WO2015/103704 and WO2015/143567; both of which are incorporated herein by reference). It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 74. The resulting construct was given number 2725 (SEQ ID NO: 81; FIG. 10C). The amino acid sequence of native VP2 from Norovirus strain GI.1/Norwalk/1968/US is presented in SEQ ID NO: 14. A representation of plasmid 2725 is presented in FIG. 10D.

2X35S/CPMV 160/VP1 GI.2 (hCod)/NOS (Construct Number 3300)

A human codon-optimized sequence encoding VP1 from Norovirus strain GI.2/Leuven/2003/Bel was cloned into 2X35S/CPMV 160/NOS expression system using the following PCR-based method. A fragment containing the GI.2 VP1 coding sequence was amplified using primers IF-GI2Leu03VP1.c (SEQ ID NO: 82) and IF-GI2Leu03VP1.r (SEQ ID NO: 83), using human codon-optimized GI.2 VP1 gene sequence (SEQ ID NO: 54; FIG. 14B) as template. For sequence optimization, GI.2/Leuven/2003/Bel VP1 protein sequence (Genbank accession number ACU56258) was backtranslated and optimized for human codon usage, GC content and mRNA structure. The PCR product was cloned in 2X35S/CPMV 160/NOS expression system using In-Fusion cloning system (Clontech, Mountain View, CA). Construct number 1190 (FIGS. 7C and 7D) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette (for a description of CMPV 160 see WO2015/103704 and WO2015/143567; both of which are incorporated herein by reference). It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 74. The resulting construct was given number 3300 (SEQ ID NO: 84; FIG. 11C). The amino acid sequence of native VP1 from Norovirus strain GI.2/Leuven/2003/Bel is presented in SEQ ID NO: 2. A representation of plasmid 3300 is presented in FIG. 11D.

A summary of the primers and templates used to preparer the above VP1 and VP2 constructs described above is provided in Table 2 below.

Norovirus VP1 Fusion Constructs

2X35S/CPMV 160/Fusion VP1 S(GI.1)+P(GI.2) (hCod)/NOS (Construct Number 3360)

A human codon-optimized sequence encoding fusion VP1 comprising of S domain from Norovirus strain GI.1/Norwalk/1968/US fused to P domain from Norovirus strain GI.2/Leuven/2003/Bel (VP1 S(GI.1)+P(GI.2)) was cloned into 2X35S/CPMV 160/NOS expression system using the following PCR-based method. In a first round of PCR, a fragment containing S domain from Norovirus strain GI.1/Norwalk/1968/US was amplified using primers IF-NoV (US68)VP1(ORF2).c (SEQ ID NO: 72) and GI2Leu+

GI1VP1.r (SEQ ID NO: 85), using human codon-optimized GI.1 VP1 gene sequence (SEQ ID NO: 18; FIG. 13C) as template. A second fragment containing the P domain of GI.2/Leuven/2003/Bel was amplified using GI1VP1+GI2Leu.c (SEQ ID NO: 86) and IF-GI2Leu03VP1.r (SEQ ID NO: 83), using human codon-optimized GI.2 VP1 gene sequence (SEQ ID NO: 54; FIG. 14B) as template. For sequence optimization, GI.1/Norwalk/1968/US VP1 protein sequence (Genbank accession number NP_056821) and GI.2/Leuven/2003/Bel VP1 protein sequence (Genbank accession number ACU56258) were backtranslated and optimized for human codon usage, GC content and mRNA structure. The PCR products from both amplifications were then mixed and used as template for a second round of amplification using IF-NoV(US68)VP1(ORF2).c (SEQ ID NO: 72) and IF-GI2Leu03VP1.r (SEQ ID NO: 83) as primers. The final PCR product was cloned in 2X35S/CPMV 160/NOS expression system using In-Fusion cloning system (Clontech, Mountain View, CA). Construct number 1190 (FIG. 7D) was digested with SacII and StuI restriction enzyme and the linearized plasmid was used for the In-Fusion assembly reaction. Construct number 1190 is an acceptor plasmid intended for "In Fusion" cloning of genes of interest in a 2X35S/CPMV 160/NOS-based expression cassette (for a description of CMPV 160 see WO2015/103704 and WO2015/143567; both of which are incorporated herein by reference). It also incorporates a gene construct for the co-expression of the TBSV P19 suppressor of silencing under the alfalfa Plastocyanin gene promoter and terminator. The backbone is a pCAMBIA binary plasmid and the sequence from left to right t-DNA borders is presented in SEQ ID NO: 74, FIG. 7C. The resulting construct was given number 3360 (SEQ ID NO: 87; FIG. 12C). The amino acid sequence of fusion VP1, VP1 S(GI.1)+P(GI.2) is presented in SEQ ID NO: 22 (FIG. 25A). A representation of plasmid 3360 is presented in FIG. 12D.

A summary of the VP1 fusion proteins, primers, templates and products is provided in Table 2 below. The VP1 fusion proteins were constructed using the same methods as described above, with reference to construct #3360.

TABLE 2

Summary of VP1 and VP2 proteins of interest, primers, templates, construct numbers, and final sequence identifiers of the resulting proteins. Rach construct also comprises a 2X 35S promoter, a CPMV-160 5'UTR*^, a CPMV 3" UTR, a Poly-A linker and a NOS terminator.

| Protein of Interest | Construct No | Primer 1* | Primer 2** | Primer 3*** | Primer 4^ | Template ^^ | Resulting protein (s) |
|---|---|---|---|---|---|---|---|
| NoV (GI.1/US/68) VP1 (hCod) | 2724 | 76 | N/Ap~ | N/Ap | 77 | 18 | SEQ ID NO: 1 |
| NoV (GI.2 Leu03) VP1 (Opt) | 3300 | 82 | N/Ap | N/Ap | 83 | 54 | SEQ ID NO: 2 |
| NoV (GI.3 Lil08) VP1 (Opt) | 3302 | 111 | N/Ap | N/Ap | 98 | 55 | SEQ ID NO: 3 |
| NoV (GII.4 Syd12) VP1 (Opt) | 3304 | 112 | N/Ap | N/Ap | 101 | 56 | SEQ ID NO: 4 |
| NoV (GII.6 Ohi12) VP1 (Opt) | 3306 | 113 | N/Ap | N/Ap | 104 | 60 | SEQ ID NO: 5 |
| NoV (GII.13 VA10) VP1 (Opt) | 3308 | 114 | N/Ap | N/Ap | 107 | 61 | SEQ ID NO: 6 |
| NoV (GII.17 Kaw14) VP1 (Opt) | 3310 | 115 | N/Ap | N/Ap | 110 | 62 | SEQ ID NO: 7 |
| NoV (GI.1/US/68) VP2 | 2721 | 116 | N/Ap | N/Ap | 122 | 13 | SEQ ID NO: 14 |
| NoV (GI.1/US/68) VP2 (hCod) | 2725 | 79 | N/Ap | N/Ap | 80 | 19 | SEQ ID NO: 14 |
| VP1 S(GI.1) + P(GI.2) | 3360 | 76 | 85 | 86 | 83 | 18 (S) and 54 (P) | SEQ ID NO: 22 |
| VP1 S(GI.1) + P(GI.3) | 3361 | 76 | 96 | 97 | 98 | 18 (S) and 55 (P) | SEQ ID NO: 23 |
| VP1 S(GI.1) + P(GII.4) | 3362 | 76 | 99 | 100 | 101 | 18 (S) and 56 (P) | SEQ ID NO: 24 |
| VP1 S(GI.1) + P(GII.6) | 3363 | 76 | 102 | 103 | 104 | 18 (S) and 60 (P) | SEQ ID NO: 25 |
| VP1 S(GI.1) + P(GII.13) | 3364 | 76 | 105 | 106 | 107 | 18 (S) and 61 (P) | SEQ ID NO: 26 |
| VP1 S(GI.1) + P(GII.17) | 3365 | 76 | 108 | 109 | 110 | 18 (S) and 62 (P) | SEQ ID NO: 27 |
| NoV (GI.1/US/68) VP1/2 | 2722 | 72 | N/Ap | N/Ap | 122 | 17 | SEQ ID NO: 1 and 14 |
| NoV (GI.1/US/68) VP1/2/3'UTR | 2723 | 72 | N/Ap | N/Ap | 118 | 17 | SEQ ID NO: 1 and 14 |
| NoV (GI.1/US/68) VP 1/2 (hCod) | 2726 | 76 | N/Ap | N/Ap | 80 | 21 | SEQ ID NO: 1 and 14 |
| NoV (GI.1/US/68) VP1/2 (hCod)/3'UTR | 2727 | 76 | N/Ap | N/Ap | 118 | 21 | SEQ ID NO: 1 and 14 |
| NoV (GI.1/US/68) VP1 | 2720 | 72 | N/Ap | N/Ap | 73 | 13 | SEQ ID NO: 1 |
| NoV (GII.4 Syd12) VP2 (Opt) | 3305 | 117 | N/Ap | N/Ap | 119 | 120 | SEQ ID NO: 121 |

*^For a description of CMPV 160 see WO2015/103704 and WO2015/143567 (both of which are incorporated herein by reference)
*For In-fusion cloning; SEQ ID NO:
**To amplify S domain with primer 1; SEQ ID NO:
***To amplify P domain with primer 4; SEQ ID NO:
^For In-fusion cloning; SEQ ID NO:
^^ Complete VP1, S domain or P domain; SEQ ID NO:)
~Not Applicable

Example 2: Methods

*Agrobacterium tumefaciens* Transfection

*Agrobacterium tumefaciens* strain AGL1 was transfected by electroporation with the native norovirus VP1, native norovirus VP2, or norovirus VP1 fusion protein expression vectors using the methods described by D'Aoust et al., 2008 (*Plant Biotech. J* 6:930-40). Transfected *Agrobacterium* were grown in YEB medium supplemented with 10 mM 2-(N-morpholino)ethanesulfonic acid (MES), 20 μM acetosyringone, 50 μg/ml kanamycin and 25 μg/ml of carbenicillin pH5.6 to an $OD_{600}$ between 0.6 and 1.6. *Agrobacterium* suspensions were centrifuged before use and resuspended in infiltration medium (10 mM $MgCl_2$ and 10 mM MES pH 5.6).

Preparation of Plant Biomass, Inoculum and Agroinfiltration

*N. benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions

*Agrobacteria* transfected with each native norovirus VP1, native norovirus VP2, or norovirus VP1 fusion expression vector were grown in a YEB medium supplemented with 10 mM 2-(N-morpholino)ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6) and stored overnight at 4° C. On the day of infiltration, culture batches were diluted in 2.5 culture volumes and allowed to warm before use. Whole plants of *N. benthamiana* were placed upside down in the bacterial suspension in an air-tight stainless steel tank under a vacuum of 20-40 Torr for 2-min. Plants were returned to the greenhouse for a 6 or 9 day incubation period until harvest.

Leaf Harvest and Total Protein Extraction

Following incubation, the aerial part of plants was harvested, frozen at −80° C. and crushed into pieces. Total soluble proteins were extracted by homogenizing (Polytron) each sample of frozen-crushed plant material in 3 volumes of cold 100 mM NaOAc pH 5.2+150 mM NaCl, 0.4 μg/ml Metabisulfite and 1 mM phenylmethanesulfonyl fluoride. After homogenization, the slurries were centrifuged at 10,000 g for 10 min at 4° C. and these clarified crude extracts (supernatant) kept for analyses.

The total protein content of clarified crude extracts was determined by the Bradford assay (Bio-Rad, Hercules, California) using bovine serum albumin as the reference standard. Proteins were separated by SDS-PAGE under reducing conditions using Criterion™ TGX Stain-Free™ precast gels (Bio-Rad Laboratories, Hercules, CA) and proteins were visualized with Gel Doc™ EZ imaging system (Bio-Rad Laboratories, Hercules, CA) and electrotransferred onto polyvinylene difluoride (PVDF) membranes (Roche Diagnostics Corporation, Indianapolis, Indiana) for immunodetection. Prior to immunoblotting, the membranes were blocked with 5% skim milk and 0.1% Tween-20 in Tris-buffered saline (TBS-T) for 16-18 h at 4° C.

Protein Analysis and Immunoblotting

Immunoblotting was performed with a first incubation with a primary mAb 242P antibody specific to VP1 from GI and GII genotypes, diluted 1/500 in 2% skim milk in TBS-Tween 20 0.1%. Peroxydase-conjugated goat anti-mouse (Jackson Immunoresearch, cat #115-035-146) diluted 1/10000 was used as secondary antibody for chemiluminescence detection were as indicated in Table 4, diluted as indicated in 2% skim milk in TBS-Tween 20 0.1% Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

Analysis of VLP Formation/Iodixanol Gradients

Proteins were extracted from frozen biomass by mechanical extraction in a blender with 2 volumes of extraction buffer (100 mM NaOAc pH 5.2+150 mM NaCl). The slurry was filtered through a large pore nylon filter to remove large debris and centrifuged 5000 g for 5 min at 4° C. The supernatant was collected and centrifuged again at 5000 g for 30 min (4° C.) to remove additional debris. The supernatant is then loaded on a discontinuous iodixanol density gradient. Analytical density gradient centrifugation was performed as follows: 38 ml tubes containing discontinuous iodixanol density gradient in acetate buffer (1 ml at 45%, 2 ml at 35%, 2 ml at 33%. 2 ml at 31%, 2 ml at 29% and 5 ml at 25% of iodixanol) were prepared and overlaid with 25 ml of the extracts containing the rotavirus-like particles. The gradients were centrifuged at 175 000 g for 4 hours (4° C.). After centrifugation, 1 ml fractions were collected from the bottom to the top and fractions were analyzed by SDS-PAGE combined with protein staining or Western blot.

Electron Microscopy

Following centrifugation of partially clarified plant extracts on discontinuous iodixanol density gradients, as described above, fractions (1 ml/fraction) containing the samples were pooled, mixed with 100 mM PBS pH 7.2+150 mM NaCl buffer to completely fill the tube and centrifuged 120 minutes at 100000 g. The pellets were re-suspended in 300-1000 μl of buffer depending of the VP1 quantity.

Carbon-coated copper grids with a 200 nm mesh size were made hydrophilic by placing the carbon side face up on a Whatman paper in a petri dish and incubating overnight at 4 deg C. Pooled fractions (20 μl) from density gradient centrifugation to be observed by transmission electron microscopy (TEM) were deposited on a Parafilm and grids were floated with the carbon side facing down and incubated at room temperature for 5 minutes. Grids were washed 4 times on 20 μl water droplet and the excess water from the last wash drained by touching a Whatman paper with the side of the grid. Grids were incubated 1 minute on a 20 μl droplet of 2% uranyl acetate in water. Grids were allowed to dry 5 minutes on a Whatman paper. Observation was performed under transmission electron microscopy at magnifications ranging from 10,000× to 150,000×.

Example 3: VP1 Protein Production in Plants

*N. benthamiana* leaves were, vacuum infiltrated, as described in Example 2, with *Agrobacterium tumifaciens* comprising expression vectors encoding wildtype GI.1 VP1 as a single nucleic acid construct, GI.1 VP2 (GI.1/Norwalk/1968/US; SEQ ID NO:15, FIG. 23B) as a single nucleic acid construct, both GI.1 VP1 and VP2, with VP1 and VP2 nucleic acid sequences introduced in separate vectors ("VP1+/VP2"; dual constructs), or on the same vector ("VP1/VP2" or "VP1/VP2/3'UTR"; single nucleic acid constructs) to permit co-expression of the VP1 and/or VP2 sequences, and the leaves examined for VP1 and VP2 production.

After 6 or 9 days post infiltration (6 DPI and 9 DPI, respectively), total crude protein extracts were prepared from leaf homogenates, separated by SDS-PAGE, and stained with Coomassie Brilliant Blue dye. The results are shown in FIG. 3A, Leaves infiltrated with expression vectors comprising nucleotide sequences that correspond to wildtype GI.1 VP1

(GI.1/Norwalk/1968/US; SEQ ID NO: 13; FIG. 13B), produced low or non-detectable levels of GI.1 VP1 as determined using Coomassie stained gels. See lanes 3-4, 7-10 and 19-20 of FIG. 3A. VP1 expression was observed when expression was assayed by Western analysis (data not provided).

Leaves infiltrated with expression vectors comprising GI.1 VP1 nucleotide sequences that were codon optimized for human expression (hCod GI.1/Norwalk/1968/US; SEQ ID NO:18; FIG. 13C), or enriched for GC content when compared to the GC content of the wildtype VP1 nucleic acid sequence (hCod), produced increased amounts of GI.1 VP1 protein (see lanes 11, 12, 21, 22; "VP1", 55-70 kDa band, FIG. 3A).

Leaves infiltrated with vectors comprising either wildtype GI.1 VP1 (GI.1/Norwalk/1968/US; SEQ ID NO: 13; FIG. 13B) and VP2 (GI.1/Norwalk/1968/US; SEQ ID NO:15, FIG. 23B; see lanes 7-10, FIG. 3A) or human codon optimized GI.1 VP1 and VP2 (lanes 15-18, FIG. 3A; dual nucleic acid constructs) produced low or non-detectable levels of GI.1 VP1 protein in Coomassie stained gels.

Co-expression of human codon optimized GI.1 VP1 (GI.1/Norwalk/1968/US; SEQ ID NO:13; FIG. 13B) and GI.1 VP2 (GI.1/Norwalk/1968/US; SEQ ID NO: 15, FIG. 23B) using separate vectors resulted in production of increased amounts of VP1 protein of approx. 55-60 kDa (lanes 21-22, FIG. 3A; single nucleic acid constructs). These data show that VP1 protein can be expressed in plants in the presence or absence of VP2 co-expression.

Norovirus VP1 VLPs

Components of crude plant extracts prepared from *N. benthamiana* leaves expressing GI.1 VP1 (single nucleic acid human codon optimized constructs; hCod GI.1/Norwalk/1968/US; SEQ ID NO:18; FIG. 13C), or single nucleic acid human codon optimized constructs one vector comprising VP1 (hCod GI.1/Norwalk/1968/US; SEQ ID NO:18; FIG. 13C) and the second vector comprising VP2 (GI.1/Norwalk/1968/US; SEQ ID NO:19, FIG. 23C), were separated using discontinuous iodixanol density gradients as described in Example 2. Fractions following density gradient centrifugation were examined using Coomassie-stained SDS-PAGE analysis. The results are shown in FIG. 3B (upper panel), with norovirus VP1 proteins, of approx. 55-60 kDa band, observed in in high density (33% and 36%) fractions.

The protein components from the high density iodixanol gradient fractions were analyzed by scanning electron microscopy FIG. 3B; lower panel). Norovirus VP1 proteins and norovirus VP1+VP2 proteins were found to self-assemble into VLPs in plants. The isolated VLPs exhibit a structural conformation similar to that of wildtype norovirus GI.1 virion particles (insert, FIG. 3B).

Example 4: Differential Expression of Norovirus VP1 in Plants

The expression levels of norovirus human codon optimized sequences encoding VP1 protein from norovirus strains, GI.1/Norwalk/1968/US (SEQ ID NO:18; FIG. 13C), GI.2/Leuven/2003/Bel (SEQ ID NO:54; FIG. 14B), GI.3/S29/2008/Lilla Edet/Sweden (SEQ ID NO:55; FIG. 15B), GII.4/Sydney/NSW0514/2012/AU (SEQ ID NO:56; FIG. 17B), GII.6/Ohio/490/12 (SEQ ID NO:60; FIG. 18B), GII.13/VA173/2010/USA (SEQ ID NO:61; FIG. 19B), and GII.17/Kawasaki323/2014/JP (SEQ ID NO:62; FIG. 20B), were compared in *N. benthamiana*. VP1 protein production was determined using Coomassie-stained SDS-PAGE analysis of extracts obtained from plant leaves vacuum infiltrated with expression vectors as described in Example 2. The results are presented in FIGS. 5A and 5B Strong, or high, VP1 protein production was observed when human codon optimized GI.1/Norwalk/1968/US (SEQ ID NO:18), GI.3/S29/2008/Lilla Edet/Sweden (SEQ ID NO:55), GII.13/VA173/2010/USA (SEQ ID NO:61), and good, or medium, expression of VP1 was observed when GI.2/Leuven/2003/Bel (SEQ ID NO:54), were expressed in plant leaves (FIGS. 5A and 5B). Low or non-detectable amount of VP1 protein production was observed in plant leaves expressing human codon optimized GII.4/Sydney/NSW0514/2012/AU (SEQ ID NO:56), GII.6/Ohio/490/12 (SEQ ID NO:60), and GII.17/Kawasaki323/2014/JP (SEQ ID NO:62).

Strong, or high expression of GI.5/Siklos/HUN5407/2013/HUN; GII.1/Ascension208/2010/USA; GII.12/HS206/2010/USA; GII.12/HS206/2010/USA; and GII.21/Salisbury150/2011/USA, and good or medium expression of GII.2/CGMH47/2011/TW; GII.5/AlbertaE1390/2013/CA; GII.7/Musashimurayama/2010/JP, was also observed in plants.

Figure 5C:
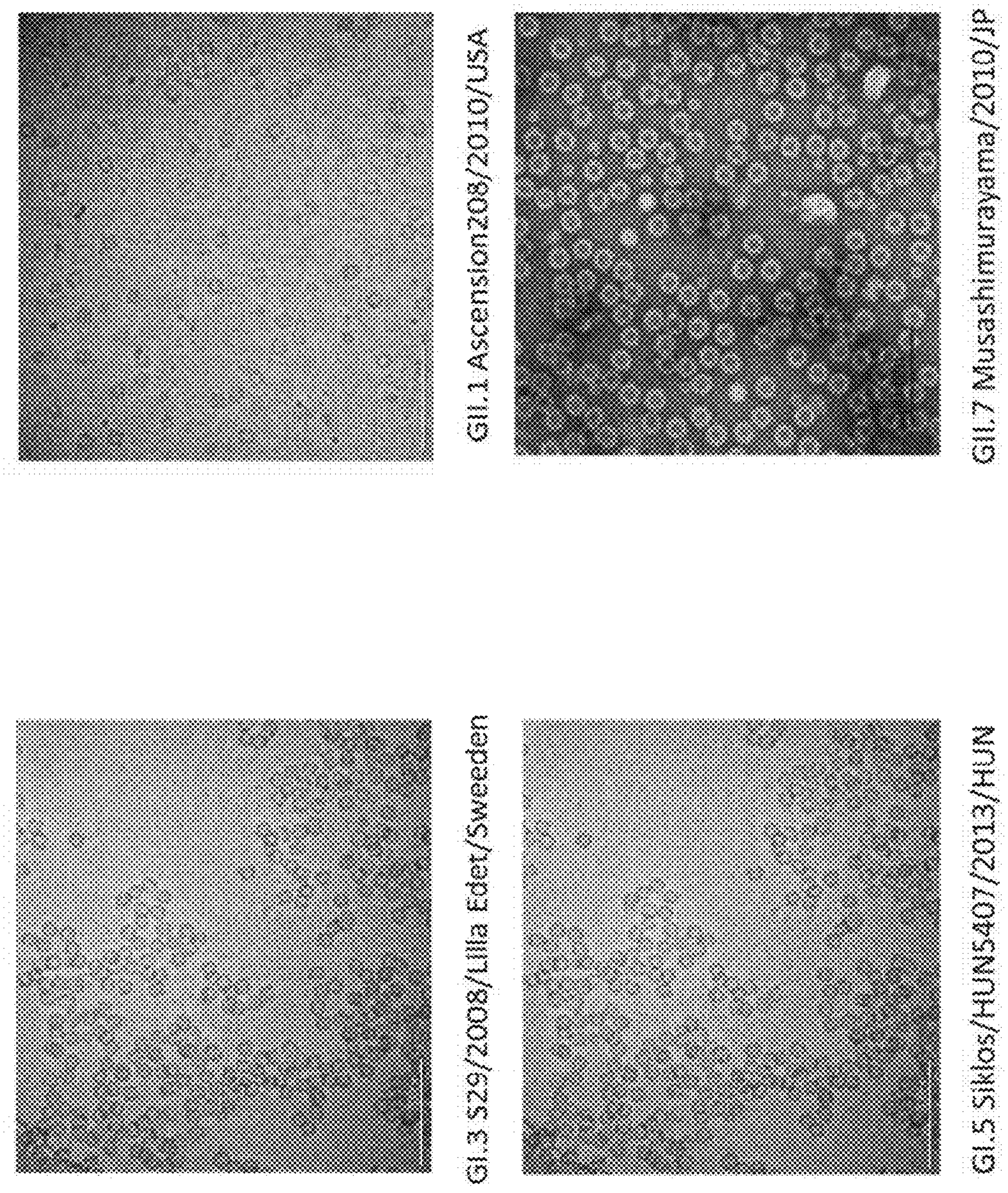
FIG. 5C shows electron micrographs of human codon optimized native norovirus VLPs from iodixanol gradient fractions. GI.3 S29/2008/Lilla Edet/Sweeden (SEQ ID NO:3 (aa); 55 (na)
Figure 5D:
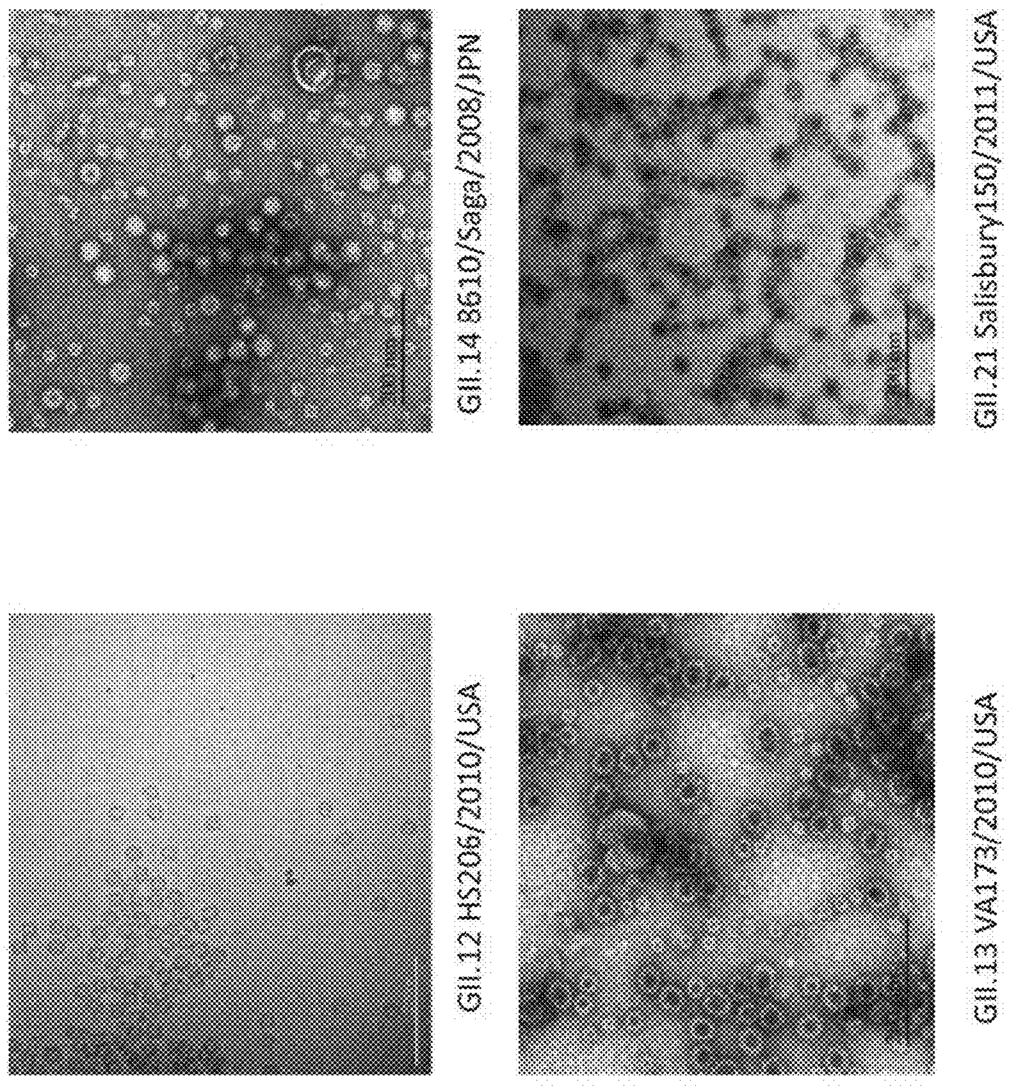
FIG. 5D shows electron micrographs of human codon optimized native norovirus VLPs from iodixanol gradient fractions. GII.12 HS206/2010/USA (SEQ ID NO:28, FIG. 22A); GII.13 VA173/2010/USA (SEQ ID NO:61, FIG. 19B); GII.14 8610/Saga/2008/JPN (SEQ ID NO:46, FIG. 22B); GII.21 Salisbury150/2011/USA (SEQ ID NO:47, FIG. 22B).
Figure 5E:
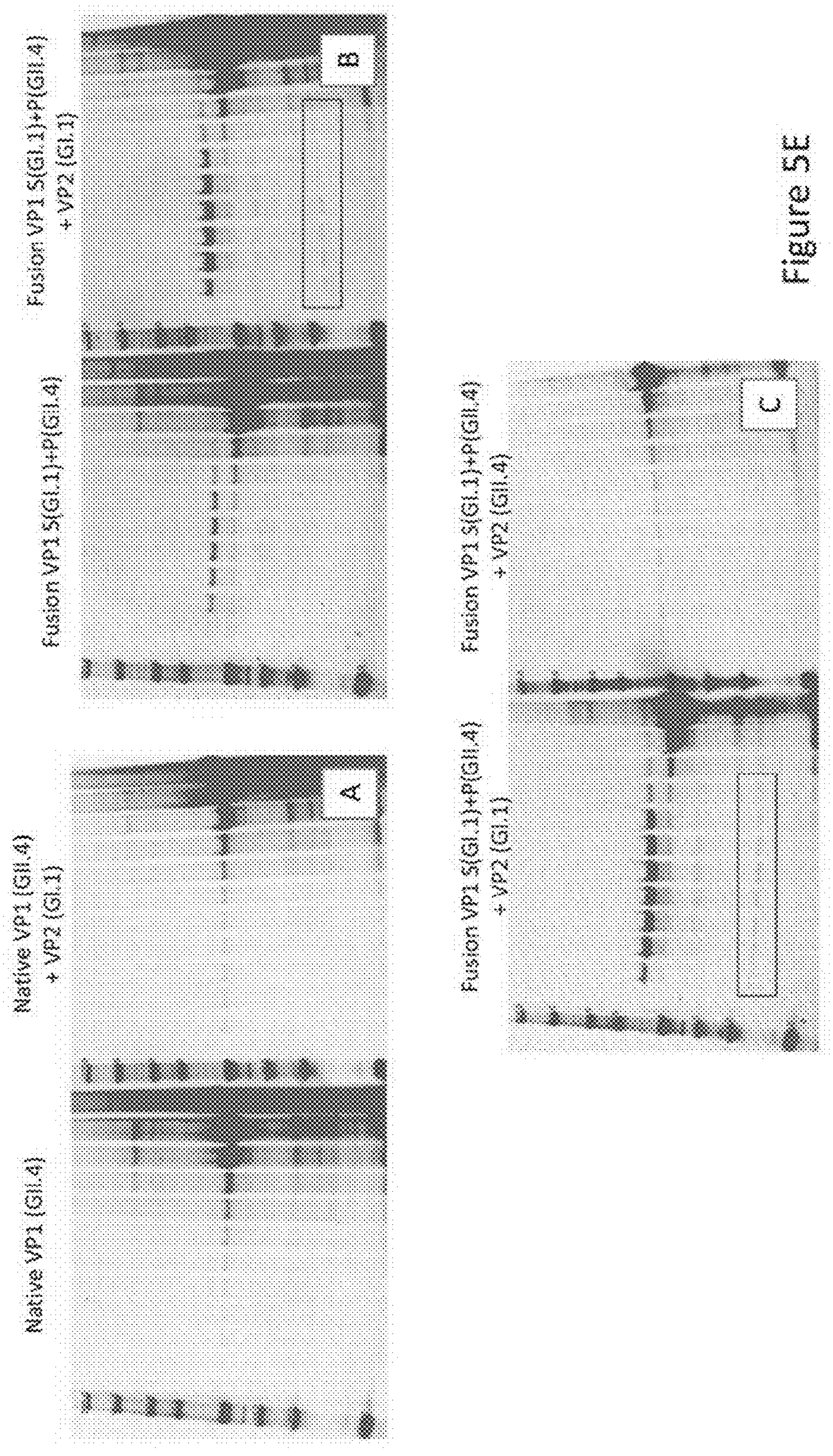
FIG. 5E shows norovirus protein expression and VLP assembly using Coomassie-stained SDS-PAGE analysis of fractions from an iodixanol density gradient separation of crude protein extracts prepared from *N. benthamiana* leaves expressing: Panel A (left hand side)—human codon optimized GII.4/Sydney/NSW0514/2012/AU native VP1 (construct #3304); Panel A (right hand side)—human codon optimized GII.4/Sydney/NSW0514/2012/AU (construct #3304; SEQ ID NO:56.

Electron micrographs (prepared as described in Example 2), of high density iodixanol gradient fractions of several human codon optimized VP1 preparations were observed following expression of the following norovirus strains in plants (see FIGS. 5C, 5D, 6A (left hand panel) and FIG. 6B (left hand panel):

GI.2/Leuven/2003/Bel (SEQ ID NO's: 2 (aa) and 54 (na); FIG. 14B);

GI.3 S29/2008/Lilla Edet/Sweeden (SEQ ID NO:3 (aa); 55 (na); FIG. 15B);

GI.5 Siklos/HUN5407/2013/HUN (SEQ ID NO:44: FIG. 16A);

GII.1 Ascension208/2010/USA SEQ ID NO:45; FIG. 16B);

GII.7 Musashimurayama/2010/JP (SEQ I NO:69; FIG. 16F)

GII.12 HS206/2010/USA (SEQ ID NO:28, FIG. 22A);

GII.13 VA173/2010/USA (SEQ ID NO:61, FIG. 19B);

GII.14 8610/Saga/2008/JPN (SEQ ID NO:46, FIG. 22B); and

GII.21 Salisbury150/2011/USA (SEQ ID NO:47, FIG. 22B).

VP1 proteins derived from the above strains were observed to self-assembled into VLPs having a structural conformation and diameter of about 15 nm to 50 nm (for example, of either about 23 nm, for T=1 icosahedral symmetry; or about 38 to 40 nm, for T=3 icosahedral symmetry), similar to that of wildtype norovirus.

Example 5: VP1 Fusion Protein Production in Plants

*N. benthamiana* leaves were, vacuum infiltrated, as described in Example 2, with *Agrobacterium tumifaciens* comprising expression vectors encoding VP1 fusion proteins described below were co-expressed with VP2 (GI.1/Norwalk/1968/US; SEQ ID NO:15, FIG. 23B). Nucleic acid segments encoding VP1 fusion proteins and VP2 were provided to the plants as a nucleic acid complex. After 6 or 9 days post infiltration (6 DPI and 9 DPI, respectively), total crude protein extracts were prepared from leaf homogenates, separated by SDS-PAGE, and stained with Coomassie Brilliant Blue dye to determine VP1 fusion protein production. Additionally electron micrographs of high density iodixanol gradient fractions of several VP1 fusion products were also prepared. The results are shown in FIGS. 5A, 5B, 5E, 6A (right hand panel), 6B (right hand panel), FIGS. 6C and 6D.

Leaves were infiltrated with expression vectors (nucleic acid complex) comprising human codon optimized nucleotide sequences encoding VP1 fusion of the GI.1 Norwalk S domain (GI.1/Norwalk/1968/US (SEQ ID NO:18; FIG. 13C), to the P domain of

- GI.2/Leuven/2003/Bel (SEQ ID NO:54; FIG. 14B); to produce "GI.1-GI.2", comprising S(GI.1)+P(GI.2); SEQ ID NO's 22(aa), 57(na);
- GI.3/S29/2008/Lilla Edet/Sweden (SEQ ID NO:55; FIG. 15B); to produce "GI.1-GI.3", comprising S(GI.1)+P (GI.3); SEQ ID NO's: 23 (aa) and 58 (na);
- GII.4/Sydney/NSW0514/2012/AU (SEQ ID NO:56; FIG. 17B); to produce "GI.1+GII.4", comprising S(GI.1)+P (GII.4); SEQ ID NO's: 24 (aa) and 59 (na);
- GII.6/Ohio/490/12 (SEQ ID NO:60; FIG. 18B); to produce "GI.1+GII.6", comprising S(GI.1)+P(GII.6); SEQ ID NO's:25 (aa) and 63(na);
- GII.13/VA173/2010/USA (SEQ ID NO:61; FIG. 19B); to produce "GI.1S+GII.13P", comprising S(GI.1)+P (GII.13); SEQ ID NO's:26 (aa) and 64 (na); and
- GII.17/Kawasaki323/2014/JP (SEQ ID NO:62; FIG. 20B); to produce "GI.1+GII.17", comprising S(GI.1)+ P(GII.17); SEQ ID NO's:27 (aa) and 65 (na).

In this example, VP1 and VP2 nucleic acid segments, with each nucleic acid segment comprising a regulatory region and a terminator, were introduced into the plants as a nucleic acid complex. As described below, with reference to FIG. 5E, when VP1 fusion proteins are expressed in plants, it is preferred that the ORF3 sequence encoding VP2 is obtained from the same norovirus strain as used to obtain the S domain of fusion VP1 sequence.

Expression of VP1 fusion proteins comprising S(GI.1)+ P(GI.2), S(GI.1)+P(GI.3), S(GI.1)+P(GII.4), S(GI.1)+P (GII.13), S(GI.1)+P(GII.17), when co-expressed with VP2, resulted in similar or greater levels of expression of norovirus VP1 fusion proteins as compared to their native non-fusion counterparts (see Example 3; FIGS. 5A and 5B). These results demonstrate that VP1 fusion proteins may be expressed in a plant, portion of a plant, or a plant cell. Expression of the VP1 fusion proteins S(GI.1)+P(GII.6) was bellow detection levels (FIG. 5B).

Electron micrographs (prepared as described in Example 2), of high density iodixanol gradient fractions of several human codon optimized VP1 fusion preparations were prepared as shown in FIG. 6A (right hand panel), FIG. 6B (right hand panel), FIG. 6C (left and right hand panel) and 6D. VP1 fusion proteins derived from S(GI.1)+P(GI.2), S(GI.1)+P(GII.3), S(GI.1)+P(GII.13), S(GI.1)+P(GII.17) and S(GI.1)+P(GII.4), and co-expressed with VP2, were observed to self-assembled into VLPs having a structural conformation and diameter of about 15 nm to 50 nm, for example, of either about 23 nm, for T=1 icosahedral symmetry; or about 38 to 40 nm, for T=3 icosahedral symmetry, similar to that of wildtype norovirus.

Even though protein product was below detectable levels using SDS-PAGE analysis for the VP1 fusion S(GI.1)+P (GII.4) (S(GI.1 Nor/68)+P (GII.4/Sydney/NSW0514/12; SEQ ID NO:59, FIG. 27B) in FIG. 5A, and for S(GI.1)+P (GII.17) (S(GI.1 Nor/68)+P (GII.17/Kawasaki323/14; SEQ ID NO:65, FIG. 30B) in FIG. 5B, VLPs comprising S(GI.1)+P(GII.4) and S(GI.1)+P(GII.17) VP1 fusion protein could be purified from plant extracts (see FIGS. 6C and 6D). However, no VLPs were detected from plant extracts expressing S(GI.1)+P(GII.6) consistent with the low or undetectable expression levels of this VP1 fusion protein (FIG. 5B).

Additional nucleic acid segments encoding human codon optimized VP1 fusion proteins were prepared and co-expressed with nucleic acid segments encoding VP2, in *N. benthamiana* leaves, as described above. These VP1 fusion proteins included:

- S(GI.1)+P(X), where X=GI.2, GI.3, GII.4, GII.6, GII.12, GII.13, GII.17;
- S(GI.5)+P(Y), where Y=GII.4;
- S(GII.1)+P(Z), where Z=GI.3, GII.4, GII.17;
- S(GII.12)+P(W), where W=GI.1, GI.2, GI.3, GI.5, GII.1, GII.2, GII.3, GII.4, GII.5, GII.6, GII.7, GII.13, GII.14, GII.17, GII.21;
- S(GII.14)+P(T), where T=GII.4;
- S(GII.21)+P(Q), where Q=GII.4

After 6 or 9 days post infiltration (6 DPI and 9 DPI, respectively) with the nucleic acid complex, total crude protein extracts were prepared from leaf homogenates, separated by SDS-PAGE, and stained with Coomassie Brilliant Blue dye to determine VP1 fusion protein production. Expression levels of the various VP1 fusion proteins was determined from the Coomassie stained gels. Additionally electron micrographs of high density iodixanol gradient fractions of several VP1 fusion products were also prepared.

Expression of various a nucleic acid segments encoding VP1 fusion proteins, comprising an S domain fused with heterologous P domain, with both domains obtained from VP1 proteins from a range of norovirus strains was observed, including, an S domain from GI.1, GI.5, GII.1, GII.12, GII.14 and GII.21, and a P domain obtained from GI.1, GI.2, GI.3, GI.5, GII.1, GII.2, GII.4, GII.6, GII.7, GII.12, GII.13, GII.14, GII.17 and GII.21. For example S(GI.1)+P(GI.2), S(GI.1)+P(GI.3), S(GI.1)+P(GII.4), S(GI.1)+P(GII.6), S(GI.1)+P(GII.12), S(GI.1)+P(GII.13), S(GI.1)+P(GII.17); S(GI.5)+P(GII.4); S(GII.1)+P(GI.3), S(GII.1)+P(GII.4), S(GII.12)+P(GI.1), S(GII.12)+P(GI.2), S(GII.12)+P(GI.3), S(GII.12)+P(GI.5), S(GII.12)+P(GII.1), S(GII.12)+P(GII.2), S(GII.12)+P(GII.4), S(GII.12)+P (GII.7), S(GII.12)+P(GII.13), S(GII.12)+P(GII.14), S(GII.12)+P(GII.17), S(GII.12)+P(GII.21), when co-expressed with a nucleic acid segment encoding VP2.

For example, strong, or high levels of expression of VP1 fusion protein in plants was observed using nucleic acid segments encoding: S(GI.1/US/68)+P(X); or S(GI.5/Siklos/HUN5407/2013/HUN)+P(Y), or S(GII.1/Ascension208/2010/USA)+P(Z); S(GII.12/HS206/2010/USA)+P(W); where:

X=P(GI.2/Leuven/2003/BEL); P(GII.4/Sydney/NSW0514/2012/AU); P(GII.12/HS206/2010/USA); P(GII.13/VA173/2010/USA);

Y=P(GII.4/Sydney/NSW0514/2012/AU);

Z=P(GI.3/S29/2008/Lilla Edet/Sweeden); or

W=P(GI.1/US/68): P(GI.3/S29/2008/Lilla Edet/Sweeden); P(GI.5/Siklos/HUN5407/2013/HUN); P(GII.1/Ascension208/2010/USA); P(GII.13/VA173/2010/USA); P(GII.14/8610/Saga/2008/JPN); P(GII.21/Salisbury150/2011/USA).

Good, or medium levels of expression levels in plants were observed using nucleic acid segments encoding VP1 fusion proteins comprising: S(GI.1/US/68)+P(X); S(GII.12/HS206/2010/USA)+P(W); or S(GII.14/8610/Saga/2008/JPN)+P(T), where:

X=P(GI.3/S29/2008/Lilla Edet/Sweeden); P(GII.6/Ohio/490/2012/USA); P(GII.17/Kawasaki323/2014/JP);

W=P(GI.2/Leuven/2003/BEL); P(GII.2/CGMH47/2011/TW); P(GII.7/Musashimurayama/2010/JP); P(GII.17/Kawasaki323/2014/JP); or T=P(GII.4/Sydney/NSW0514/2012/AU).

Expression that was below detectable levels was observed with nucleic acid segments encoding VP1 fusion proteins comprising: S(GII.12/HS206/2010/USA)+P(GII.4/Sydney/NSW0514/2012/AU); S(GII.1/Ascension208/2010/USA+P (GII.4/Sydney/NSW0514/2012/AU); or S(GII.21/Salisbury150/2011/USA)+P(GII.4/Sydney/NSW0514/2012/AU).

These results demonstrate that VP1 fusion proteins comprising various combinations of S domains and P domains may be produced when expressed in plants.

Increased Expression of VLPs Comprising Norovirus VP1 Fusion Proteins and VP2 Native Proteins from the S Domain Genotype The expression of a nucleic acid complex comprising norovirus nucleic acid segments encoding VP1 protein or VP1 fusion proteins co-expressed with a nucleic acid segment encoding VP2, were compared in *N. benthamiana* as described in Example 2. VP1 or VP1 fusion protein production was determined using Coomassie-stained SDS-PAGE analysis of extracts obtained from plant leaves vacuum infiltrated with expression vectors were loaded onto discontinuous iodixanol density gradients. Fractions collected from the bottom to the top and fractions were analyzed by SDS-PAGE. The following constructs were expressed and analyzed:

VP1 GII.4: human codon optimized native VP1 GII.4/Sydney/NSW0514/2012/AU (construct #3304; SEQ ID NO:56; FIG. 17B)

VP1 GII.4 and VP2 GII.4: human codon optimized native VP1 co-expressed with human codon optimized native VP2 GII.4/Sydney/NSW0514/2012/AU (construct #3305; SEQ ID NO:120; FIG. 23D);

VP1 fusion S(GI.1)+P(GII.4): human codon optimized VP1 S(GI.1)+P(GII.4) fusion protein (construct 3362; SEQ ID NO:59; FIG. 27B);

VP1 fusion S(GI.1)+P(GII.4) and VP2 GI.1: human codon optimized native VP1 S(GI.1)+P(GII.4) fusion protein (construct 3362; SEQ ID NO:59; FIG. 27B) co-expressed with human codon optimized native VP2 GI.1/Norwalk (construct #2725; SEQ ID NO:19; FIG. 23C);

VP1 fusion S(GI.1)+P(GII.4) and VP2 GII.4: human codon optimized VP1 S(GI.1)+P(GII.4) fusion protein (construct 3362; SEQ ID NO:59; FIG. 27B) co-expressed with human codon optimized native VP2 GII.4/Sydney (construct #3305; SEQ ID NO:133; FIG. 23D).

The results are presented in FIG. 5E.

The level of expression of the human codon-optimized GII.4/Sydney native VP1 protein (construct #3304) is low when the GII.4 VP1 construct is expressed alone (FIG. 5E; Panel A, left hand side). The level of expression of the same GII.4 VP1 (construct #3304) remains low when co-expressed with human codon-optimized native minor structural VP2 protein from the GII.4 genotype and strain (construct #3305; FIG. 5E Panel A, left hand side). T The level of expression of the VP1 fusion, human codon optimized VP1 S (GI.1)+P (GII.4; construct #3362), is greatly increased when compared to the native VP1 of the GII.4 genotype (Panel B, FIG. 5E, left hand side). Furthermore, the level of expression of the VP1 fusion S(GI.1)+P (GII.4; construct #3362), when co-expressed with human codon-optimized VP2 from GI.1/Norwalk (construct #2725), that is where the S domain of the VP1 fusion and the VP2 protein are obtained from the same genotype and strain, resulted in even higher VLP yield (Panel B; FIG. 5E, right hand side) when compared to the expression of the VP1 fusion S(GI.1)+P(GII.4). Additionally, the VP2 minor structural protein is incorporated on the VLPs as it is visible at the correct protein size (21-24 kDa; indicated by a square; FIG. 5E; Panel B right hand side, and Panel C left hand side) in the high-molecular weight fractions of the density gradient that contain Norovirus VLPs.

This production of VLPs when co-expressing a VP1 fusion having an S domain and VP2 from same genotype and strain is to be contrast with the co-expression of a VP1 fusion, human codon optimized VP1 S (GI.1)+P (GII.4; construct #3362) with human codon-optimized VP2 from GII.4/Sydney (construct #3305), where the S domain of the VP1 fusion and the VP2 protein are obtained from different genotypes and strains. Co-expression of VP1 fusion comprising an S domain with a VP2 obtained from a different genotype and strain resulted in a dramatic decrease in VLP production (Panel C; FIG. 5E, right hand side), when compared to the co-expression of the VP1 fusion S(GI.1)+P(GII.4) and VP2 from GI.1/Norwalk, construct #2725; Panel C; FIG. 5E, left hand side) where the S domain and the VP2 are obtained from the same genotype and strain.

Without wishing to be bound by theory, these results are consistent with the proposal that VP2 is located on the inside of the viral particle and that VP2 may play a role in particle stability. When VP1 fusion proteins are expressed in plants, it is preferred that the ORF3 sequence encoding VP2 is obtained from the same norovirus strain as used to obtain the S domain of fusion VP1 sequence.

Enhanced Stability of VLPs Comprising Norovirus VP1 Fusion Proteins

Levels of VLPs comprising of high-expressing native VP1 GI.1/Norwalk/1968/US (encoded by construct 2724; SEQ ID NO:78; FIG. 9C) peaked in fractions four through eight following iodixanol gradient centrifugation (see FIG. 3C upper panel). In contrast, VLPs comprising of native VP1 GI.2/Leuven/2003/Bel (encoded by construct 3300; SEQ ID NO:84; FIG. 11C) FIG. 3C lower panel, left hand side) peaked in lower-density fractions six through nine, suggesting that native GI.2 VLPs may be less stable, more susceptible to malformed capsid particles and the generation of fragmentation products, or a combination thereof, when compared to GI.1 VLPs.

In contrast, increased stability of VP1 fusion protein was observed with VLPs comprising S(GI.1 Nor68)+P(GI.2 Leu03) norovirus VP1 fusion proteins (encoded by construct 3360; SEQ ID NO:87; FIG. 12C). As shown in FIG. 3C, (lower panel, right hand side) VP1 fusion protein peaked in fractions four through eight, indicating that VLPs comprising norovirus VP1 fusion proteins having a GI.1 S domain core maybe more stable than their native VLP counterparts where the S domain is not derived from GI.1.

A similar shift in density was also observed in VLPs comprising S(GI.1)+P(GI.3) norovirus VP1 fusion proteins GI.1 Nor68+GI.3 Lil08 (see FIG. 6B, right hand panel), encoded by construct 33601; SEQ ID NO:58; FIG. 26B) when compared to expression of VP1 GI.3 Lil08 (SEQ ID NO: 55; FIG. 15B) as shown in FIG. 6B (left hand panel).

Example 6: Immune Response Using VP1

Studies on the immune response to Norovirus native GI.1 (SEQ ID NO:1) VLP administration were performed with 6-8 week old female BALB/c mice (Charles River Laboratories). Thirty seven mice were randomly divided into four groups of eight animals for Norovirus VLP vaccine and a group of five animals for placebo. All groups were injected using intramuscular immunization. All groups were immunized in a two-dose regimen, the boost immunization being administered 3 weeks following the first immunization.

For intramuscular administration in hind legs, two groups (eight animals) of unanaesthetized mice were immunized with the plant-made VLP native VP1 from Norovirus GI.1 genotype vaccine (1 or 10 μg). Placebo group (five animals) was immunized using the same route and regimen as the candidate vaccine using vaccine buffer (PBS at pH 6.0). In a similar manner plant-produced VP1 fusion proteins as described herein, for example VP1 fusion proteins produced using construct #3360, 3361, 3361, 3363, 3364, 3365, or SEQ ID NO's: 22 to 27, 29 to 43, 49 to 53, and 71, may also administered to mice following the same protocol as described in this example.

To measure the potential benefit of adjuvant, two groups of animals (8 animals) were immunized by intramuscular administration in hind legs on unanaesthetized mice with 1 or 10 μg plant-made VLP Norovirus vaccine plus one volume Alhydrogel® (aluminum hydroxide) 2% (alum, Cedarlane Laboratories Ltd., Burlington, Ontario, Canada). All groups were immunized according to a prime-boost regimen with the boost immunization performed 3 weeks following the first immunization.

Mice were evaluated through clinical observations during the in-life period as followed: daily monitoring for mortality and clinical signs, weekly detailed examinations, injection site observations and body weight measurements. All animals were under observation and sacrinced on Day 42 for gross examination. Blood was collected from all animals prior to dosing on Day 0, on Days 21 and 42 (21 days after each immunization). Samples were processed to isolate the serum for specific antibody response analyses.

Serum samples from blood collected on Days 21 and 42 from all animals were analyzed individually by ELISA for GI.1 VLP-specific total IgG and IgA antibodies using GI.1 VLP-coated plates. Pre-immune serum samples (Day 0—prior dosing) collected from all animals were pooled by treatment group and each pool was analyzed to insure that they were negative (or below the cut-off value of the analytical test).

Descriptive statistics were performed using GraphPad Prism software (Version 6.05; GraphPad Software, La Jolla, CA, USA). Antibody titers measured for each group were reported as geometric mean titer (GMT) with 95% confidence intervals (CI). Half of the value of the limit of detection was attributed to antibody titers below the limit of detection of the method specific to the tested antibodies. Therefore, in this study, an animal was considered to be a positive responder if its GMT value for a determined condition was equal or above the limit of detection of the method (LOQ=100). Statistical comparisons between IgG titers of treatment groups were performed using one-way ANOVA followed by a Tukey's test on log 10-transformed data. A comparison between the placebo group and each treatment group was also performed using oneway ANOVA followed by a post hoc Dunnett's test on log 10-transformed data.

The GI.1 VLP-specific total IgG titers that were measured in serum samples from all animals after IM immunization with one dose (Day 21) and two doses (Day 42) of 1 μg or 10 μg of each formulation. Total IgG titers were measured by ELISA using GI.1 VLP-coated plates (LOQ=100). The results are present in FIG. 6E. Total IgG titers per treatment group (n=8 animals/group) are represented by geometric mean titer (GMT) with a 95% confidence interval. Statistical comparisons between IgG titers of treatment groups were performed using one-way ANOVA followed by a Tukey's test on log 10-transformed data. A comparison between the placebo group and each treatment group was also performed using one-way ANOVA followed by a post-hoc Dunnett's test on log 10-transformed data. Significant differences were annotated as letters in FIG. 6E (the same letter indicates that no significant difference was detected between treatment groups; $p>0.05$).

Mouse Immune Response to Norovirus Native VP1 VLPs

As demonstrated in FIG. 6E, mice immunized with plant-made Norovirus native VP1 VLPs from GI.1 genotype had shown GI.1 VLP-specific IgG antibody titers in sera and were detected for each treatment group on Days 21 and 42. IgG titer levels that were induced by each treatment on Days 21 and 42 were statistically higher than the titers quantified for the placebo group ($p<0.05$). On each day, IgG titer level increased in a dose-dependent manner as demonstrated by the significant differences detected between the 1 μg and 10 μg treatments formulated with Alhydrogel® (aluminum hydroxide) or not ($p<0.05$) and the addition of Alhydrogel® (aluminum hydroxide) to the NoV VLP vaccine enhanced significantly the induced immune response at doses of 1 μg and 10 μg ($p<0.05$). A significant increase of IgG titer level was also detected for each treatment group between Days 21 and 42 ($p<0.05$). These results collectively demonstrate the ability of plant produced Norovirus native VP1 VLPs to elicit a robust immune response in mice.

Similar results area observed with the administration of VP1 fusion proteins, VP1 fusion proteins produced for example, using construct #3360, 3361, 3361, 3363, 3364, 3365, or SEQ ID NO's: 22 to 27, 29 to 43, 49 to 53, and 71, as described herein.

All citations are hereby incorporated by reference.

The present invention has been described with regard to one or more embodiments. However, it will be apparent to persons skilled in the art that a number of variations and modifications can be made to the described subject matter. The scope of the claims should not be limited by the preferred embodiments set forth in the examples, but should be given the broadest interpretation consistent with the description as a whole.

What is claimed is:

1. A method of producing a norovirus VP1 fusion protein in a plant, a portion of the plant, or a plant cell comprising, introducing into the plant, the portion of the plant, or the plant cell a nucleic acid comprising a first sequence encoding an S domain derived from a first norovirus strain and a second sequence encoding a P domain derived from a second norovirus strain, the first norovirus strain selected from norovirus genotypes GI.1, GI.5, GII.1, GII.12, GII.14, and GII.21, and the second norovirus strain selected from norovirus genogroups GI, and GIV or selected from norovirus genotypes GII.1, GII.2, GII.3, GII.4, GII.5, GII.7, GII.12, GII.13, GII.14, GII.17 and GII.21, and incubating the plant, the portion of the plant, or the plant cell under conditions that permit the expression and production of the norovirus VP1 fusion protein.

2. The method of claim 1, wherein the second norovirus strain is selected from norovirus genotypes GI.1, GI.2, GI.3, GI.4, GI.5, GII.1, GII.2, GII.3, GII.4, GII.5, GII.7, GII.12, GII.13, GII.14, GII.17 and GII.21.

3. The method of claim 1, wherein the first norovirus strain and the second norovirus strain are selected from norovirus subtypes GI.1/US/Norwalk/1968; GI.2/Leuven/2003/Bel; GI.3/S29/2008/Lilla Edet/Sweden; GII.5/AlbertaEI390/2013/CA; GII.1/Ascension208/2010/USA; GII.12/H5206/2010/USA; GII.13/VA173/2010/USA; GII.14/8610/Saga/2008/JPN; and GII.21/Salisbury150/2011/USA.

4. The method of claim 1, wherein the nucleic acid further comprises a third sequence encoding a Cowpea Mosaic Virus (CPMV) enhancer, the CPMV enhancer operatively linked with the first and second sequences.

5. The method of claim 1, wherein the first, the second, or both the first and second, sequence is optimized for human codon usage, increased GC content, or a combination thereof.

6. The method of claim 1, wherein the method further comprises a step of harvesting the plant, the portion of the plant, or the plant cell.

7. The method of claim 6, wherein the method further comprises a step of extracting, purifying, or both extracting and purifying, the norovirus VP1 fusion protein from the plant, the portion of the plant, or the plant cell.

8. The method of claim 6, wherein the method further comprises a step of extracting, purifying, or both extracting and purifying a virus like particle (VLP) from the plant, the portion of the plant, or the plant cell, wherein the VLP comprises the norovirus VP1 fusion protein and has a diameter of about 15 nm to 50 nm.

9. The method of claim 8, wherein the VLP has a diameter of either about 23 nm or about 38 nm.

10. The method of claim 1, wherein in the step of introducing, a second nucleic acid sequence encoding a norovirus VP2 protein is introduced in the plant, the portion of the plant, or the plant cell, and in the step of incubating, the conditions permit co-expression and co-production, of both the norovirus VP1 fusion protein and the norovirus VP2 protein in the plant, the portion of the plant, or the plant cell.

11. The method of claim 10, further comprising a step of harvesting the plant, the portion of the plant, or the plant cell.

12. The method of claim 11, further comprising a step of extracting, purifying, or both extracting and purifying, the norovirus VP1 fusion protein and norovirus VP2 protein.

13. The method of claim 11, further comprising a step of extracting, purifying, or both extracting and purifying a virus like particle (VLP) from the plant, the portion of the plant, or the plant cell, wherein the VLP comprises the norovirus VP1 fusion protein and the norovirus VP2 protein, and has a diameter of about 15 nm to 50 nm.

14. The method of claim 13, wherein the VLP has a diameter of either about 23 nm or about 38 nm.

15. A plant, a portion of the plant or plant cell comprising the norovirus VP1 fusion protein produced by the method of claim 1.

16. A plant, a portion of the plant or plant cell comprising a VLP comprising the VP1 fusion protein produced by the method of claim 1.

17. A plant, a portion of the plant or plant cell comprising a VLP comprising the VP1 fusion protein and the VP2 protein produced by the method of claim 10.

18. A plant extract comprising the norovirus VP1 fusion protein produced by the method of claim 1.

19. A plant extract comprising a VLP comprising the VP1 fusion protein produced by the method of claim 1.

20. A plant extract comprising a VLP comprising the VP1 fusion protein and the VP2 protein produced by the method of claim 10.

* * * * *

SEQUENCE LISTING

```
<160> NUMBER OF SEQ ID NOS: 122

<210> SEQ ID NO 1
<211> LENGTH: 530
<212> TYPE: PRT
<213> ORGANISM: Norovirus GI.1/Norwalk/1968/US

<400> SEQUENCE: 1
```

-continued

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
```

```
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530


<210> SEQ ID NO 2
<211> LENGTH: 546
<212> TYPE: PRT
<213> ORGANISM: Norovirus GI.2/Leuven/2003/Bel

<400> SEQUENCE: 2

Met Met Met Ala Ser Lys Asp Ala Pro Gln Ser Ala Asp Gly Ala Ser
1               5                   10                  15

Gly Ala Gly Gln Leu Val Pro Glu Val Asn Thr Ala Asp Pro Leu Pro
            20                  25                  30

Met Glu Pro Val Ala Gly Pro Thr Thr Ala Val Ala Thr Ala Gly Gln
        35                  40                  45

Val Asn Met Ile Asp Pro Trp Ile Val Asn Asn Phe Val Gln Ser Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ser His Leu
                85                  90                  95

Ser Gln Met Tyr Asn Gly Trp Val Gly Asn Met Arg Val Arg Ile Leu
            100                 105                 110

Leu Ala Gly Asn Ala Phe Ser Ala Gly Lys Ile Ile Val Cys Cys Val
        115                 120                 125

Pro Pro Gly Phe Thr Ser Ser Ser Leu Thr Ile Ala Gln Ala Thr Leu
    130                 135                 140

Phe Pro His Val Ile Ala Asp Val Arg Thr Leu Glu Pro Ile Glu Met
145                 150                 155                 160

Pro Leu Glu Asp Val Arg Asn Val Leu Tyr His Thr Asn Asp Asn Gln
                165                 170                 175

Pro Thr Met Arg Leu Val Cys Met Leu Tyr Thr Pro Leu Arg Thr Gly
            180                 185                 190

Gly Gly Ser Gly Asn Ser Asp Ser Phe Val Val Ala Gly Arg Val Leu
        195                 200                 205

Thr Ala Pro Ser Ser Asp Phe Ser Phe Leu Phe Leu Val Pro Pro Thr
    210                 215                 220

Ile Glu Gln Lys Thr Arg Ala Phe Thr Val Pro Asn Ile Pro Leu Gln
225                 230                 235                 240

Thr Leu Ser Asn Ser Arg Phe Pro Ser Leu Ile Gln Gly Met Ile Leu
                245                 250                 255
```

```
Ser Pro Asp Ala Ser Gln Val Val Gln Phe Gln Asn Gly Arg Cys Leu
            260                 265                 270

Ile Asp Gly Gln Leu Leu Gly Thr Thr Pro Ala Thr Ser Gly Gln Leu
        275                 280                 285

Phe Arg Val Arg Gly Lys Ile Asn Gln Gly Ala Arg Thr Leu Asn Leu
    290                 295                 300

Thr Glu Val Asp Gly Lys Pro Phe Met Ala Phe Asp Ser Pro Ala Pro
305                 310                 315                 320

Val Gly Phe Pro Asp Phe Gly Lys Cys Asp Trp His Met Arg Ile Ser
                325                 330                 335

Lys Thr Pro Asn Asn Thr Ser Ser Gly Asp Pro Met Arg Ser Val Asp
            340                 345                 350

Val Gln Thr Asp Val Gln Gly Phe Val Pro His Leu Gly Ser Ile Gln
        355                 360                 365

Phe Asp Glu Val Phe Asn His Pro Thr Gly Asp Tyr Ile Gly Thr Ile
    370                 375                 380

Glu Trp Ile Ser Gln Pro Ser Thr Pro Pro Gly Thr Asp Ile Asn Leu
385                 390                 395                 400

Trp Glu Ile Pro Asp Tyr Gly Ser Ser Leu Ser Gln Ala Ala Asn Leu
                405                 410                 415

Ala Pro Pro Val Phe Pro Pro Gly Phe Gly Glu Ala Leu Val Tyr Phe
            420                 425                 430

Val Ser Ala Phe Pro Gly Pro Asn Asn Arg Ser Ala Pro Asn Asp Val
        435                 440                 445

Pro Cys Leu Leu Pro Gln Glu Tyr Val Thr His Phe Val Ser Glu Gln
    450                 455                 460

Ala Pro Thr Met Gly Asp Ala Ala Leu Leu His Tyr Val Asp Pro Asp
465                 470                 475                 480

Thr Asn Arg Asn Leu Gly Glu Phe Lys Leu Tyr Pro Gly Gly Tyr Leu
                485                 490                 495

Thr Cys Val Pro Asn Gly Val Gly Ala Gly Pro Gln Gln Leu Pro Leu
            500                 505                 510

Asn Gly Val Phe Leu Phe Val Ser Trp Val Ser Arg Phe Tyr Gln Leu
        515                 520                 525

Lys Pro Val Gly Thr Ala Ser Thr Ala Arg Gly Arg Leu Gly Val Arg
    530                 535                 540

Arg Ile
545
```

<210> SEQ ID NO 3
<211> LENGTH: 543
<212> TYPE: PRT
<213> ORGANISM: Norovirus GI.3/S29/2008/Lilla Edet/Sweden

<400> SEQUENCE: 3

```
Met Met Met Ala Ser Lys Asp Ala Pro Thr Asn Met Asp Gly Thr Ser
1               5                   10                  15

Gly Ala Gly Gln Leu Val Pro Glu Val Ser Thr Ala Glu Pro Ile Ser
            20                  25                  30

Met Glu Pro Val Ala Gly Ala Ala Thr Ala Ala Ala Thr Ala Gly Gln
        35                  40                  45

Val Asn Met Ile Asp Pro Trp Ile Met Ser Asn Tyr Val Gln Ala Pro
    50                  55                  60

Gln Gly Glu Phe Thr Ile Ser Pro Asn Asn Thr Pro Gly Asp Ile Leu
65                  70                  75                  80
```

-continued

```
Phe Asp Leu Gln Leu Gly Pro His Leu Asn Pro Phe Leu Ser His Leu
                85                  90                  95

Ala Gln Met Tyr Asn Gly Trp Val Gly Asn Met Lys Val Arg Val Leu
            100                 105                 110

Leu Ala Gly Asn Ala Phe Thr Ala Gly Lys Ile Ile Ile Ser Cys Val
        115                 120                 125

Pro Pro Gly Phe Ala Ala Gln Asn Val Ser Ile Ala Gln Ala Thr Met
    130                 135                 140

Phe Pro His Val Ile Ala Asp Val Arg Val Leu Glu Pro Ile Glu Val
145                 150                 155                 160

Pro Leu Glu Asp Val Arg Asn Val Leu Phe His Asn Asn Asp Ser Thr
                165                 170                 175

Pro Thr Met Arg Leu Ile Cys Met Leu Tyr Thr Pro Leu Arg Ala Ser
            180                 185                 190

Gly Ser Ser Ser Gly Thr Asp Pro Phe Val Ile Ala Gly Arg Val Leu
        195                 200                 205

Thr Cys Pro Ser Pro Asp Phe Asn Phe Leu Phe Leu Val Pro Pro Asn
    210                 215                 220

Val Glu Gln Lys Thr Lys Pro Phe Ser Val Pro Asn Leu Pro Leu Asn
225                 230                 235                 240

Val Leu Ser Asn Ser Arg Val Pro Ser Leu Ile Lys Ser Met Met Val
                245                 250                 255

Ser Gln Asp His Gly Gln Met Val Gln Phe Gln Asn Gly Arg Val Thr
            260                 265                 270

Leu Asp Gly Gln Leu Gln Gly Thr Thr Pro Thr Ser Ala Ser Gln Leu
        275                 280                 285

Cys Lys Ile Arg Gly Thr Val Tyr His Ala Thr Gly Gly Gln Gly Leu
    290                 295                 300

Asn Leu Thr Glu Ile Asp Gly Thr Pro Tyr His Ala Phe Glu Ser Pro
305                 310                 315                 320

Ala Pro Ile Gly Phe Pro Asp Leu Gly Glu Cys Asp Trp His Ile Asn
                325                 330                 335

Ala Ser Pro Ala Asn Ala Phe Thr Asp Gly Ser Ile Ile His Arg Ile
            340                 345                 350

Asp Val Ala Gln Asp Ser Thr Phe Ala Pro His Leu Gly Thr Ile His
        355                 360                 365

Tyr Thr Asn Ala Asp Tyr Asn Ala Asn Val Gly Leu Ile Cys Ser Leu
    370                 375                 380

Glu Trp Leu Ser Pro Pro Ser Gly Gly Ala Pro Lys Val Asn Pro Trp
385                 390                 395                 400

Ala Ile Pro Arg Tyr Gly Ser Thr Leu Thr Glu Ala Ala Gln Leu Ala
                405                 410                 415

Pro Pro Ile Tyr Pro Pro Gly Phe Gly Glu Ala Ile Val Phe Phe Met
            420                 425                 430

Ser Asp Phe Pro Ile Ala Asn Gly Ser Asp Gly Leu Ser Val Pro Cys
        435                 440                 445

Thr Ile Pro Gln Glu Phe Val Thr His Phe Val Asn Glu Gln Ala Pro
    450                 455                 460

Thr Arg Gly Glu Ala Ala Leu Leu His Tyr Val Asp Pro Asp Thr His
465                 470                 475                 480

Arg Asn Leu Gly Glu Phe Lys Leu Tyr Pro Glu Gly Phe Met Thr Cys
                485                 490                 495
```

```
Val Pro Asn Ser Ser Gly Ser Gly Pro Gln Thr Leu Pro Ile Asn Gly
            500                 505                 510

Val Phe Thr Phe Ile Ser Trp Val Ser Arg Phe Tyr Gln Leu Lys Pro
        515                 520                 525

Val Gly Thr Thr Gly Pro Val Arg Arg Leu Gly Ile Arg Arg Ser
    530                 535                 540


<210> SEQ ID NO 4
<211> LENGTH: 540
<212> TYPE: PRT
<213> ORGANISM: Norovirus GII.4/Sydney/NSW0514/2012/AU

<400> SEQUENCE: 4

Met Lys Met Ala Ser Ser Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Val Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335
```

```
Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540
```

<210> SEQ ID NO 5
<211> LENGTH: 547
<212> TYPE: PRT
<213> ORGANISM: Norovirus GII.6/Ohio/490/12

<400> SEQUENCE: 5

```
Met Lys Met Ala Ser Asn Asp Ala Ala Pro Ser Asn Asp Gly Ala Ala
1               5                   10                  15

Asn Leu Val Pro Glu Ala Asn Asn Glu Val Met Ala Leu Glu Pro Val
            20                  25                  30

Val Gly Ala Ser Ile Ala Ala Pro Val Val Gly Gln Gln Asn Ile Ile
        35                  40                  45

Asp Pro Trp Ile Arg Glu Asn Phe Val Gln Ala Pro Gln Gly Glu Phe
    50                  55                  60

Thr Val Ser Pro Arg Asn Ser Pro Gly Glu Met Leu Leu Asn Leu Glu
65                  70                  75                  80

Leu Gly Pro Glu Leu Asn Pro Tyr Leu Ser His Leu Ser Arg Met Tyr
                85                  90                  95

Asn Gly Tyr Ala Gly Gly Met Gln Val Gln Val Val Leu Ala Gly Asn
            100                 105                 110

Ala Phe Thr Ala Gly Lys Ile Ile Phe Ala Ala Val Pro Pro His Phe
        115                 120                 125

Pro Val Glu Asn Ile Asn Ala Ala Gln Ile Thr Met Cys Pro His Val
    130                 135                 140

Ile Val Asp Val Arg Gln Leu Glu Pro Val Leu Leu Pro Leu Pro Asp
145                 150                 155                 160

Ile Arg Asn Arg Phe Phe His Tyr Asn Gln Glu Asn Thr Ser Arg Met
```

-continued

```
                165                 170                 175

Arg Leu Val Ala Met Leu Tyr Thr Pro Leu Arg Ala Asn Ser Gly Glu
            180                 185                 190

Asp Val Phe Thr Val Ser Cys Arg Val Leu Thr Arg Pro Ala Pro Asp
        195                 200                 205

Phe Glu Phe Thr Phe Leu Val Pro Pro Thr Val Glu Ser Lys Thr Lys
    210                 215                 220

Pro Phe Ser Leu Pro Ile Leu Thr Leu Gly Glu Leu Ser Asn Ser Arg
225                 230                 235                 240

Phe Pro Ala Pro Ile Asp Met Leu Tyr Thr Asp Pro Asn Glu Gly Ile
                245                 250                 255

Val Val Gln Pro Gln Asn Gly Arg Cys Thr Leu Asp Gly Thr Leu Gln
            260                 265                 270

Gly Thr Thr Gln Leu Val Pro Thr Gln Ile Cys Ala Phe Arg Gly Thr
        275                 280                 285

Leu Ile Gly Gln Thr Ser Arg Ser Pro Asp Ser Thr Asp Ser Ala Pro
    290                 295                 300

Arg Arg Arg Asp His Pro Leu His Val Gln Leu Lys Asn Leu Asp Gly
305                 310                 315                 320

Thr Gln Tyr Asp Pro Thr Asp Glu Val Pro Ala Val Leu Gly Ala Ile
                325                 330                 335

Asp Phe Lys Gly Thr Val Phe Gly Val Ala Ser Gln Arg Asp Val Ser
            340                 345                 350

Gly Gln Gln Val Gly Ala Thr Arg Ala His Glu Val His Ile Asn Thr
        355                 360                 365

Thr Asp Pro Arg Tyr Thr Pro Lys Leu Gly Ser Ile Leu Met Tyr Ser
    370                 375                 380

Glu Ser Asp Asp Phe Val Thr Gly Gln Pro Val Arg Phe Thr Pro Ile
385                 390                 395                 400

Gly Met Gly Asp Asn Asp Trp His Gln Trp Glu Leu Pro Asp Tyr Pro
                405                 410                 415

Gly His Leu Thr Leu Asn Met Asn Leu Ala Pro Ala Val Ala Pro Ala
            420                 425                 430

Phe Pro Gly Glu Arg Ile Leu Phe Phe Arg Ser Ile Val Pro Ser Ala
        435                 440                 445

Gly Gly Tyr Gly Ser Gly Gln Ile Asp Cys Leu Ile Pro Gln Glu Trp
    450                 455                 460

Val Gln His Phe Tyr Gln Glu Ala Ala Pro Ser Gln Ser Ala Val Ala
465                 470                 475                 480

Leu Ile Arg Tyr Val Asn Pro Asp Thr Gly Arg Asn Ile Phe Glu Ala
                485                 490                 495

Lys Leu His Arg Glu Gly Phe Ile Thr Val Ala Asn Ser Gly Asn Asn
            500                 505                 510

Pro Ile Val Val Pro Pro Asn Gly Tyr Phe Arg Phe Glu Ala Trp Val
        515                 520                 525

Asn Gln Phe Tyr Thr Leu Thr Pro Met Gly Thr Gly Gln Gly Arg Arg
    530                 535                 540

Arg Asp Gln
545
```

<210> SEQ ID NO 6
<211> LENGTH: 542
<212> TYPE: PRT
<213> ORGANISM: Norovirus GII.13/VA173/2010/USA -continued

<400> SEQUENCE: 6

Met Lys Met Ala Ser Asn Asp Ala Ala Pro Ser Asn Asp Gly Ala Ala
1               5                   10                  15

Ser Leu Val Pro Glu Ala Ile Asn Glu Thr Met Pro Leu Glu Pro Val
            20                  25                  30

Ala Gly Ala Ser Ile Ala Ala Pro Val Ala Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Ile Pro Pro Asn Phe
        115                 120                 125

Pro Val Asp Met Ile Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Val Phe Tyr His Phe Asn Asn Gln Pro Gln Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Ile Tyr Leu Val Pro Pro Ser Val Glu Ser Lys Thr
    210                 215                 220

Lys Pro Phe Thr Leu Pro Ile Leu Thr Ile Ser Glu Leu Thr Asn Ser
225                 230                 235                 240

Arg Phe Pro Ile Ser Ile Glu Gln Leu Tyr Thr Ala Pro Asn Glu Asn
                245                 250                 255

Asn Val Val Gln Cys Gln Asn Gly Arg Cys Thr Leu Asp Gly Glu Leu
            260                 265                 270

Gln Gly Thr Thr Gln Leu Leu Ser Ser Ala Val Cys Ser Tyr Arg Gly
        275                 280                 285

Arg Thr Val Ala Asn Ser Gly Asp Asn Trp Asp Gln Asn Val Leu Gln
    290                 295                 300

Leu Thr Tyr Pro Ser Gly Ala Ser Tyr Asp Pro Thr Asp Glu Val Pro
305                 310                 315                 320

Ala Pro Leu Gly Thr Gln Asp Phe Ser Gly Ile Leu Tyr Gly Val Leu
                325                 330                 335

Thr Gln Asp Asn Val Arg Glu Asn Thr Gly Glu Ala Lys Asn Ala Lys
            340                 345                 350

Gly Val Tyr Ile Ser Thr Thr Ser Gly Lys Phe Thr Pro Lys Ile Gly
        355                 360                 365

Ser Ile Gly Leu His Ser Ile Thr Glu Asp Val Arg Pro Asn Gln Gln
    370                 375                 380

Ser Arg Phe Thr Pro Val Gly Val Ala Gln Asn Glu Asn Thr Pro Phe
385                 390                 395                 400

Gln Gln Trp Val Leu Pro His Tyr Ala Gly Ala Leu Ala Leu Asn Thr

-continued

```
                405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Gln Gly Gln Asp
        435                 440                 445

Ala Phe Ile Asp Cys Leu Leu Pro Gln Glu Trp Val Asn His Phe Tyr
    450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
            485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
        515                 520                 525

Leu Ala Pro Met Gly Thr Gly Asn Gly Arg Arg Arg Val Gln
    530                 535                 540


<210> SEQ ID NO 7
<211> LENGTH: 538
<212> TYPE: PRT
<213> ORGANISM: Norovirus GII.17/Kawasaki323/2014/JP

<400> SEQUENCE: 7

Met Lys Met Ala Ser Asn Asp Ala Ala Pro Ser Asn Asp Gly Ala Ala
1               5                   10                  15

Gly Leu Val Pro Glu Gly Asn Asn Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Leu Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Glu Phe Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Thr Phe Phe His Tyr Asn Asn Gln Pro Asn Ser Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Ser Leu Pro Ile Leu Thr Leu Ser Glu Leu Thr Asn Ser
225                 230                 235                 240
```

-continued

```
Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535


<210> SEQ ID NO 8
<211> LENGTH: 539
<212> TYPE: PRT
<213> ORGANISM: Artificial
<220> FEATURE:
<223> OTHER INFORMATION: Amino acid sequence of VP1 US96:
      GII.4/Dresden174/1997/DE_AY741811

<400> SEQUENCE: 8

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60
```

```
Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Val Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Lys Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Ser Asn Ser
225                 230                 235                 240

Arg Phe Pro Ile Pro Leu Glu Lys Leu Tyr Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Ala Val Asn Ile Cys Thr Phe Arg Gly
        275                 280                 285

Asp Val Thr His Ile Ala Gly Ser His Asp Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Met Leu Thr Gln
                325                 330                 335

Thr Thr Arg Glu Asp Gly Ser Thr Arg Ala His Lys Ala Thr Val Ser
            340                 345                 350

Thr Gly Ser Val His Phe Thr Pro Lys Leu Gly Ser Val Gln Tyr Thr
        355                 360                 365

Thr Asp Thr Asn Asn Asp Phe Gln Thr Gly Gln Asn Thr Lys Phe Thr
    370                 375                 380

Pro Val Gly Val Ile Gln Asp Gly Asn Asn His Gln Asn Glu Pro Gln
385                 390                 395                 400

Gln Trp Val Leu Pro Asn Tyr Ser Gly Arg Thr Gly His Asn Val His
                405                 410                 415

Leu Ala Pro Ala Val Ala Pro Thr Phe Pro Gly Glu Gln Leu Leu Phe
            420                 425                 430

Phe Arg Ser Thr Met Pro Gly Cys Ser Gly Tyr Pro Asn Met Asn Leu
        435                 440                 445

Asp Cys Leu Leu Pro Gln Glu Trp Val Gln His Phe Tyr Gln Glu Ala
    450                 455                 460

Ala Pro Ala Gln Ser Asp Val Ala Leu Leu Arg Phe Val Asn Pro Asp
465                 470                 475                 480
```

```
Thr Gly Arg Val Leu Phe Glu Cys Lys Leu His Lys Ser Gly Tyr Val
                485                 490                 495

Thr Val Ala His Thr Gly Pro His Asp Leu Val Ile Pro Pro Asn Gly
            500                 505                 510

Tyr Phe Arg Phe Asp Ser Trp Val Asn Gln Phe Tyr Thr Leu Ala Pro
        515                 520                 525

Met Gly Asn Gly Ala Gly Arg Arg Arg Ala Leu
    530                 535


<210> SEQ ID NO 9
<211> LENGTH: 540
<212> TYPE: PRT
<213> ORGANISM: Norovirus GII.4/Dresden174/1997/DE

<400> SEQUENCE: 9

Met Lys Met Ala Ser Asn Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Leu Asn Asp Pro Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr His Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320
```

```
Leu Gly Thr Pro Asp Phe Val Gly Arg Ile Gln Gly Met Leu Thr Gln
                325                 330                 335

Thr Thr Arg Gly Asp Gly Ser Thr Arg Gly His Lys Ala Thr Val Ser
            340                 345                 350

Thr Gly Asp Val His Phe Thr Pro Lys Leu Gly Ser Ile Gln Phe Asn
        355                 360                 365

Thr Asp Thr Asn Asn Asp Phe Glu Thr Gly Gln Asn Thr Lys Phe Thr
    370                 375                 380

Pro Val Gly Val Val Gln Asp Gly Asn Gly Thr His Gln Asn Glu Pro
385                 390                 395                 400

Gln Gln Trp Val Leu Pro Ser Tyr Ser Gly Arg Thr Gly His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 10
<211> LENGTH: 540
<212> TYPE: PRT
<213> ORGANISM: Norovirus GII.4/Hunter-NSW504D/2004/AU

<400> SEQUENCE: 10

Met Lys Met Ala Ser Asn Asp Ala Thr Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Val Leu Ser Pro Ser Gln Val Thr Met Phe Pro His Ile
    130                 135                 140

Ile Val Asp Val Arg Gln Leu Glu Pro Val Leu Ile Pro Leu Pro Asp
```

```
145                 150                 155                 160

Val Arg Asn Asn Leu Tyr His Tyr Asn Gln Ser Asn Asp Pro Thr Ile
                165                 170                 175

Arg Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Thr Gln Asn Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Arg Ile Gln Gly Val Leu Thr Gln
                325                 330                 335

Thr Thr Arg Arg Asp Gly Ser Thr Arg Gly His Lys Ala Thr Val Ser
            340                 345                 350

Thr Gly Ser Val His Phe Thr Pro Lys Leu Gly Ser Val Gln Phe Ser
        355                 360                 365

Thr Asp Thr Ser Asn Asp Phe Glu Thr Gly Gln Asn Thr Arg Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asn
        435                 440                 445

Leu Asp Cys Leu Leu Pro Gln Glu Trp Val Gln His Phe Tyr Gln Glu
    450                 455                 460

Ser Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Ala Gly Arg Arg Arg Ala Leu
    530                 535                 540
```

<210> SEQ ID NO 11
<211> LENGTH: 540
<212> TYPE: PRT
<213> ORGANISM: Norovirus GII.4/Shellharbour-NSW696T/2006/AU

<400> SEQUENCE: 11

Met Lys Met Ala Ser Asn Asp Ala Asn Pro Ser Asp Gly Ser Ala Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Ser Thr Ile
                165                 170                 175

Lys Leu Ile Ala Met Leu Tyr Thr Pro Leu Arg Ala Asn Asn Ala Gly
            180                 185                 190

Glu Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Leu Lys Trp Asn Lys Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Lys Gly Asp Gly Ser Thr Arg Gly His Lys Ala Thr Ile Tyr
            340                 345                 350

Thr Gly Ser Ala Pro Phe Thr Pro Lys Leu Gly Ser Val Gln Phe Ser
        355                 360                 365

Thr Asp Thr Glu Asn Asp Phe Glu Thr His Gln Asn Thr Lys Phe Thr
    370                 375                 380

Pro Val Gly Val Thr Gln Asp Gly Ser Thr Thr His Arg Asn Glu Pro
385                 390                 395                 400

Gln Gln Trp Val Leu Pro Ser Tyr Ser Gly Arg Asn Val His Asn Val

```
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln His Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 12
<211> LENGTH: 540
<212> TYPE: PRT
<213> ORGANISM: Norovirus GII.4/Orange-NSW001P/2008/AU

<400> SEQUENCE: 12

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Met Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
            180                 185                 190

Asp Asp Val Phe Thr Val Ser Cys Arg Val Leu Thr Arg Pro Ser Pro
        195                 200                 205

Asp Phe Asp Phe Ile Phe Leu Val Pro Pro Thr Val Glu Ser Arg Thr
    210                 215                 220

Lys Pro Phe Ser Val Pro Ile Leu Thr Val Glu Glu Met Thr Asn Ser
225                 230                 235                 240
```

-continued

```
Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Ala Gly Ser Arg Asn Tyr Thr Met Asn Leu Ala
    290                 295                 300

Ser Gln Asn Trp Asn Ser Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ser Pro Lys Leu Gly Arg Val Gln Phe Ala
        355                 360                 365

Thr Asp Thr Asp Asn Asp Phe Asp Ala Asn Gln Asn Thr Lys Phe Thr
    370                 375                 380

Pro Val Gly Val Ile Gln Asp Gly Asn Thr Ala His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
    530                 535                 540


<210> SEQ ID NO 13
<211> LENGTH: 1593
<212> TYPE: PRT
<213> ORGANISM: Norovirus GI.1/Norwalk/1968/US

<400> SEQUENCE: 13

Ala Thr Gly Ala Thr Gly Ala Thr Gly Gly Cys Gly Thr Cys Thr Ala
1               5                   10                  15

Ala Gly Gly Ala Cys Gly Cys Thr Ala Cys Ala Thr Cys Ala Ala Gly
            20                  25                  30

Cys Gly Thr Gly Gly Ala Thr Gly Gly Cys Gly Cys Thr Ala Gly Thr
        35                  40                  45

Gly Gly Cys Gly Cys Thr Gly Gly Thr Cys Ala Gly Thr Thr Gly Gly
    50                  55                  60

Thr Ala Cys Cys Gly Gly Ala Gly Gly Thr Thr Ala Ala Thr Gly Cys
65                  70                  75                  80
```

```
Thr Thr Cys Thr Gly Ala Cys Cys Cys Thr Cys Thr Thr Gly Cys Ala
                85                  90                  95

Ala Thr Gly Gly Ala Thr Cys Cys Thr Gly Thr Ala Gly Cys Ala Gly
            100                 105                 110

Gly Thr Thr Cys Thr Thr Cys Gly Ala Cys Ala Gly Cys Ala Gly Thr
        115                 120                 125

Cys Gly Cys Gly Ala Cys Thr Gly Cys Thr Gly Gly Ala Cys Ala Ala
    130                 135                 140

Gly Thr Thr Ala Ala Thr Cys Cys Thr Ala Thr Thr Gly Ala Thr Cys
145                 150                 155                 160

Cys Cys Thr Gly Gly Ala Thr Ala Ala Thr Thr Ala Ala Thr Ala Ala
                165                 170                 175

Thr Thr Thr Thr Gly Thr Gly Cys Ala Ala Gly Cys Cys Cys Cys Cys
            180                 185                 190

Cys Ala Ala Gly Gly Thr Gly Ala Ala Thr Thr Thr Ala Cys Thr Ala
        195                 200                 205

Thr Thr Thr Cys Cys Cys Cys Ala Ala Ala Thr Ala Ala Thr Ala Cys
    210                 215                 220

Cys Cys Cys Cys Gly Gly Thr Gly Ala Thr Gly Thr Thr Thr Thr Gly
225                 230                 235                 240

Thr Thr Thr Gly Ala Thr Thr Thr Gly Ala Gly Thr Thr Thr Gly Gly
                245                 250                 255

Gly Thr Cys Cys Cys Cys Ala Thr Cys Thr Thr Ala Ala Thr Cys Cys
            260                 265                 270

Thr Thr Thr Cys Thr Thr Gly Cys Thr Cys Cys Ala Thr Cys Thr Ala
        275                 280                 285

Thr Cys Ala Cys Ala Ala Ala Thr Gly Thr Ala Thr Ala Ala Thr Gly
    290                 295                 300

Gly Thr Thr Gly Gly Gly Thr Thr Gly Gly Thr Ala Ala Cys Ala Thr
305                 310                 315                 320

Gly Ala Gly Ala Gly Thr Cys Ala Gly Gly Ala Thr Thr Ala Thr Gly
                325                 330                 335

Cys Thr Ala Gly Cys Thr Gly Gly Thr Ala Ala Thr Gly Cys Cys Thr
            340                 345                 350

Thr Thr Ala Cys Thr Gly Cys Gly Gly Gly Gly Ala Ala Gly Ala Thr
        355                 360                 365

Ala Ala Thr Ala Gly Thr Thr Thr Cys Cys Thr Gly Cys Ala Thr Ala
    370                 375                 380

Cys Cys Cys Cys Cys Thr Gly Gly Thr Thr Thr Thr Gly Gly Thr Thr
385                 390                 395                 400

Cys Ala Cys Ala Thr Ala Ala Thr Cys Thr Thr Ala Cys Thr Ala Thr
                405                 410                 415

Ala Gly Cys Ala Cys Ala Ala Gly Cys Ala Ala Cys Thr Cys Thr Cys
            420                 425                 430

Thr Thr Thr Cys Cys Ala Cys Ala Thr Gly Thr Gly Ala Thr Thr Gly
        435                 440                 445

Cys Thr Gly Ala Thr Gly Thr Thr Ala Gly Gly Ala Cys Thr Cys Thr
    450                 455                 460

Ala Gly Ala Cys Cys Cys Cys Ala Thr Thr Gly Ala Gly Gly Thr Gly
465                 470                 475                 480

Cys Cys Thr Thr Thr Gly Gly Ala Ala Gly Ala Thr Gly Thr Thr Ala
                485                 490                 495
```

Gly Gly Ala Ala Thr Gly Thr Thr Cys Thr Cys Thr Thr Thr Cys Ala
500 505 510

Thr Ala Ala Thr Ala Ala Thr Gly Ala Thr Ala Gly Ala Ala Ala Thr
515 520 525

Cys Ala Ala Cys Ala Ala Ala Cys Cys Ala Thr Gly Cys Gly Cys Cys
530 535 540

Thr Thr Gly Thr Gly Thr Gly Cys Ala Thr Gly Cys Thr Gly Thr Ala
545 550 555 560

Cys Ala Cys Cys Cys Cys Cys Cys Thr Cys Cys Gly Cys Ala Cys Thr
565 570 575

Gly Gly Thr Gly Gly Thr Gly Gly Thr Ala Cys Thr Gly Gly Thr Gly
580 585 590

Ala Thr Thr Cys Thr Thr Thr Thr Gly Thr Ala Gly Thr Thr Gly Cys
595 600 605

Ala Gly Gly Gly Cys Gly Ala Gly Thr Thr Ala Thr Gly Ala Cys Thr
610 615 620

Thr Gly Cys Cys Cys Cys Ala Gly Thr Cys Cys Thr Gly Ala Thr Thr
625 630 635 640

Thr Thr Ala Ala Thr Thr Thr Cys Thr Thr Gly Thr Thr Thr Thr Thr
645 650 655

Ala Gly Thr Cys Cys Cys Thr Cys Cys Thr Ala Cys Gly Gly Thr Gly
660 665 670

Gly Ala Gly Cys Ala Gly Ala Ala Ala Ala Cys Cys Ala Gly Gly Cys
675 680 685

Cys Cys Thr Thr Cys Ala Cys Ala Cys Thr Cys Cys Cys Ala Ala Ala
690 695 700

Thr Cys Thr Gly Cys Cys Ala Thr Thr Gly Ala Gly Thr Thr Cys Thr
705 710 715 720

Cys Thr Gly Thr Cys Thr Ala Ala Cys Thr Cys Ala Cys Gly Thr Gly
725 730 735

Cys Cys Cys Cys Thr Cys Thr Cys Cys Cys Ala Ala Thr Cys Ala Gly
740 745 750

Thr Ala Gly Thr Ala Thr Gly Gly Gly Cys Ala Thr Thr Thr Cys Cys
755 760 765

Cys Cys Ala Gly Ala Cys Ala Ala Thr Gly Thr Cys Cys Ala Gly Ala
770 775 780

Gly Thr Gly Thr Gly Cys Ala Gly Thr Thr Cys Cys Ala Ala Ala Ala
785 790 795 800

Thr Gly Gly Thr Cys Gly Gly Thr Gly Thr Ala Cys Thr Cys Thr Gly
805 810 815

Gly Ala Thr Gly Gly Cys Cys Gly Cys Cys Thr Gly Gly Thr Thr Gly
820 825 830

Gly Cys Ala Cys Cys Ala Cys Cys Cys Cys Ala Gly Thr Thr Thr Cys
835 840 845

Ala Thr Thr Gly Thr Cys Ala Cys Ala Thr Gly Thr Thr Gly Cys Cys
850 855 860

Ala Ala Gly Ala Thr Ala Ala Gly Ala Gly Gly Gly Ala Cys Cys Thr
865 870 875 880

Cys Cys Ala Ala Thr Gly Gly Cys Ala Cys Thr Gly Thr Ala Ala Thr
885 890 895

Cys Ala Ala Cys Cys Thr Thr Ala Cys Thr Gly Ala Ala Thr Thr Gly
900 905 910

Gly Ala Thr Gly Gly Cys Ala Cys Ala Cys Cys Cys Thr Thr Thr Cys

-continued

```
        915                 920                 925

Ala Cys Cys Cys Thr Thr Thr Thr Gly Ala Gly Gly Gly Cys Cys Cys
    930                 935                 940

Thr Gly Cys Cys Cys Cys Cys Ala Thr Thr Gly Gly Gly Thr Thr Thr
945                 950                 955                 960

Cys Cys Ala Gly Ala Cys Cys Thr Cys Gly Gly Thr Gly Gly Thr Thr
                965                 970                 975

Gly Thr Gly Ala Thr Thr Gly Gly Cys Ala Thr Ala Thr Cys Ala Ala
            980                 985                 990

Thr Ala Thr Gly Ala Cys Ala Cys  Ala Gly Thr Thr Thr  Gly Gly Cys
        995                 1000                1005

Cys Ala  Thr Thr Cys Thr Ala  Gly Cys Cys Ala Gly  Ala Cys Cys
    1010                1015                1020

Cys Ala  Gly Thr Ala Thr Gly  Ala Thr Gly Thr Ala  Gly Ala Cys
    1025                1030                1035

Ala Cys  Cys Ala Cys Cys Cys  Cys Thr Gly Ala Cys  Ala Cys Thr
    1040                1045                1050

Thr Thr  Thr Gly Thr Cys Cys  Cys Cys Cys Ala Thr  Cys Thr Thr
    1055                1060                1065

Gly Gly  Thr Thr Cys Ala Ala  Thr Thr Cys Ala Gly  Gly Cys Ala
    1070                1075                1080

Ala Ala  Thr Gly Gly Cys Ala  Thr Thr Gly Gly Cys  Ala Gly Thr
    1085                1090                1095

Gly Gly  Thr Ala Ala Thr Thr  Ala Thr Gly Thr Thr  Gly Gly Thr
    1100                1105                1110

Gly Thr  Thr Cys Thr Thr Ala  Gly Cys Thr Gly Gly  Ala Thr Thr
    1115                1120                1125

Thr Cys  Cys Cys Cys Cys Cys  Cys Ala Thr Cys Ala  Cys Ala Cys
    1130                1135                1140

Cys Cys  Gly Thr Cys Thr Gly  Gly Cys Thr Cys Cys  Cys Ala Ala
    1145                1150                1155

Gly Thr  Thr Gly Ala Cys Cys  Thr Thr Thr Gly Gly  Ala Ala Gly
    1160                1165                1170

Ala Thr  Cys Cys Cys Cys Ala  Ala Thr Thr Ala Thr  Gly Gly Gly
    1175                1180                1185

Thr Cys  Ala Ala Gly Thr Ala  Thr Thr Ala Cys Gly  Gly Ala Gly
    1190                1195                1200

Gly Cys  Ala Ala Cys Ala Cys  Ala Thr Cys Thr Ala  Gly Cys Cys
    1205                1210                1215

Cys Cys  Thr Thr Cys Thr Gly  Thr Ala Thr Ala Cys  Cys Cys Cys
    1220                1225                1230

Cys Cys  Thr Gly Gly Thr Thr  Thr Cys Gly Gly Ala  Gly Ala Gly
    1235                1240                1245

Gly Thr  Ala Thr Thr Gly Gly  Thr Cys Thr Thr Thr  Thr Thr Cys
    1250                1255                1260

Ala Thr  Gly Thr Cys Ala Ala  Ala Ala Ala Thr Gly  Cys Cys Ala
    1265                1270                1275

Gly Gly  Thr Cys Cys Thr Gly  Gly Thr Gly Cys Thr  Thr Ala Thr
    1280                1285                1290

Ala Ala  Thr Thr Thr Gly Cys  Cys Cys Thr Gly Thr  Cys Thr Ala
    1295                1300                1305

Thr Thr  Ala Cys Cys Ala Cys  Ala Ala Gly Ala Gly  Thr Ala Cys
    1310                1315                1320
```

```
Ala Thr  Thr Thr Cys Ala Cys  Ala Thr Cys Thr Thr  Gly Cys Thr
    1325                 1330                 1335

Ala Gly  Thr Gly Ala Ala Cys  Ala Ala Gly Cys Cys  Cys Cys Thr
    1340                 1345                 1350

Ala Cys  Thr Gly Thr Ala Gly  Gly Thr Gly Ala Gly  Gly Cys Thr
    1355                 1360                 1365

Gly Cys  Cys Cys Thr Gly Cys  Thr Cys Cys Ala Cys  Thr Ala Thr
    1370                 1375                 1380

Gly Thr  Thr Gly Ala Cys Cys  Cys Thr Gly Ala Thr  Ala Cys Cys
    1385                 1390                 1395

Gly Gly  Thr Cys Gly Gly Ala  Ala Thr Cys Thr Thr  Gly Gly Gly
    1400                 1405                 1410

Gly Ala  Ala Thr Thr Cys Ala  Ala Ala Gly Cys Ala  Thr Ala Cys
    1415                 1420                 1425

Cys Cys  Thr Gly Ala Thr Gly  Gly Thr Thr Thr Cys  Cys Thr Cys
    1430                 1435                 1440

Ala Cys  Thr Thr Gly Thr Gly  Thr Cys Cys Cys Cys  Ala Ala Thr
    1445                 1450                 1455

Gly Gly  Gly Gly Cys Thr Ala  Gly Cys Thr Cys Gly  Gly Gly Thr
    1460                 1465                 1470

Cys Cys  Ala Cys Ala Ala Cys  Ala Gly Cys Thr Gly  Cys Cys Gly
    1475                 1480                 1485

Ala Thr  Cys Ala Ala Thr Gly  Gly Gly Gly Thr Cys  Thr Thr Thr
    1490                 1495                 1500

Gly Thr  Cys Thr Thr Thr Gly  Thr Thr Thr Cys Ala  Thr Gly Gly
    1505                 1510                 1515

Gly Thr  Gly Thr Cys Cys Ala  Gly Ala Thr Thr Thr  Thr Ala Thr
    1520                 1525                 1530

Cys Ala  Ala Thr Thr Ala Ala  Ala Gly Cys Cys Thr  Gly Thr Gly
    1535                 1540                 1545

Gly Gly  Ala Ala Cys Thr Gly  Cys Cys Ala Gly Cys  Thr Cys Gly
    1550                 1555                 1560

Gly Cys  Ala Ala Gly Ala Gly  Gly Thr Ala Gly Gly  Cys Thr Thr
    1565                 1570                 1575

Gly Gly  Thr Cys Thr Gly Cys  Gly Cys Cys Gly Ala  Thr Ala Ala
    1580                 1585                 1590


<210> SEQ ID NO 14
<211> LENGTH: 212
<212> TYPE: PRT
<213> ORGANISM: Norovirus GI.1/US/Norwalk/1968

<400> SEQUENCE: 14

Met Ala Gln Ala Ile Ile Gly Ala Ile Ala Ala Ser Thr Ala Gly Ser
1               5                   10                  15

Ala Leu Gly Ala Gly Ile Gln Val Gly Gly Glu Ala Ala Leu Gln Ser
            20                  25                  30

Gln Arg Tyr Gln Gln Asn Leu Gln Leu Gln Glu Asn Ser Phe Lys His
        35                  40                  45

Asp Arg Glu Met Ile Gly Tyr Gln Val Glu Ala Ser Asn Gln Leu Leu
    50                  55                  60

Ala Lys Asn Leu Ala Thr Arg Tyr Ser Leu Leu Arg Ala Gly Gly Leu
65                  70                  75                  80

Thr Ser Ala Asp Ala Ala Arg Ser Val Ala Gly Ala Pro Val Thr Arg
```

-continued

```
                85                  90                  95

Ile Val Asp Trp Asn Gly Val Arg Val Ser Ala Pro Glu Ser Ser Ala
            100                 105                 110

Thr Thr Leu Arg Ser Gly Gly Phe Met Ser Val Pro Ile Pro Phe Ala
        115                 120                 125

Ser Lys Gln Lys Gln Val Gln Ser Ser Gly Ile Ser Asn Pro Asn Tyr
    130                 135                 140

Ser Pro Ser Ser Ile Ser Arg Thr Thr Ser Trp Val Glu Ser Gln Asn
145                 150                 155                 160

Ser Ser Arg Phe Gly Asn Leu Ser Pro Tyr His Ala Glu Ala Leu Asn
                165                 170                 175

Thr Val Trp Leu Thr Pro Pro Gly Ser Thr Ala Ser Ser Thr Leu Ser
            180                 185                 190

Ser Val Pro Arg Gly Tyr Phe Asn Thr Asp Arg Leu Pro Leu Phe Ala
        195                 200                 205

Asn Asn Arg Arg
    210

<210> SEQ ID NO 15
<211> LENGTH: 639
<212> TYPE: DNA
<213> ORGANISM: Norovirus GI.1/US/Norwalk/1968

<400> SEQUENCE: 15
atggcccaag ccataattgg tgcaattgct gcttccacag caggtagtgc tctgggagcg     60
ggcatacagg ttggtggcga agcggccctc caaagccaaa ggtatcaaca aaatttgcaa    120
ctgcaagaaa attcttttaa acatgacagg gaaatgattg ggtatcaggt tgaagcttca    180
aatcaattat tggctaaaaa tttggcaact agatattcac tcctccgtgc tgggggtttg    240
accagtgctg atgcagcaag atctgtggca ggagctccag tcacccgcat tgtagattgg    300
aatggcgtga gagtgtctgc tcccgagtcc tctgctacca cattgagatc cggtggcttc    360
atgtcagttc ccataccatt tgcctctaag caaaaacagg ttcaatcatc tggtattagt    420
aatccaaatt attccccttc atccatttct cgaaccacta gttgggtcga gtcacaaaac    480
tcatcgagat ttggaaatct ttctccatac cacgcggagg ctctcaatac agtgtggttg    540
actccacccg gttcaacagc ctcttctaca ctgtcttctg tgccacgtgg ttatttcaat    600
acagacaggt tgccattatt cgcaaataat aggcgatga                           639

<210> SEQ ID NO 16
<211> LENGTH: 2231
<212> TYPE: DNA
<213> ORGANISM: Norovirus GI.1/US/Norwalk/1968

<400> SEQUENCE: 16
atgatgatgg cgtctaagga cgctacatca agcgtggatg gcgctagtgg cgctggtcag     60
ttggtaccgg aggttaatgc ttctgaccct cttgcaatgg atcctgtagc aggttcttcg    120
acagcagtcg cgactgctgg acaagttaat cctattgatc cctggataat taataatttt    180
gtgcaagccc cccaaggtga atttactatt tccccaaata ataccccccgg tgatgttttg    240 tttgatttga gtttgggtcc ccatcttaat cctttcttgc tccatctatc acaaatgtat    300
aatggttggg ttggtaacat gagagtcagg attatgctag ctggtaatgc ctttactgcg    360
gggaagataa tagtttcctg cataccccct ggttttggtt cacataatct tactatagca    420
caagcaactc tctttccaca tgtgattgct gatgttagga ctctagaccc cattgaggtg    480
```

```
cctttggaag atgttaggaa tgttctcttt cataataatg atagaaatca acaaaccatg    540
cgccttgtgt gcatgctgta cacccccctc cgcactggtg gtggtactgg tgattctttt    600
gtagttgcag ggcgagttat gacttgcccc agtcctgatt ttaatttctt gtttttagtc    660
cctcctacgg tggagcagaa aaccaggccc ttcacactcc caaatctgcc attgagttct    720
ctgtctaact cacgtgcccc tctcccaatc agtagtatgg gcatttcccc agacaatgtc    780
cagagtgtgc agttccaaaa tggtcggtgt actctggatg gccgcctggt tggcaccacc    840
ccagtttcat tgtcacatgt tgccaagata agagggacct ccaatggcac tgtaatcaac    900
cttactgaat tggatggcac accctttcac ccttttgagg gccctgcccc cattgggttt    960
ccagacctcg gtggttgtga ttggcatatc aatatgacac agtttggcca ttctagccag   1020
acccagtatg atgtagacac cacccctgac acttttgtcc cccatcttgg ttcaattcag   1080
gcaaatggca ttggcagtgg taattatgtt ggtgttctta gctggatttc ccccccatca   1140
cacccgtctg gctcccaagt tgacctttgg aagatcccca attatgggtc aagtattacg   1200
gaggcaacac atctagcccc ttctgtatac ccccctggtt tcggagaggt attggtcttt   1260
ttcatgtcaa aaatgccagg tcctggtgct tataatttgc cctgtctatt accacaagag   1320
tacatttcac atcttgctag tgaacaagcc cctactgtag gtgaggctgc cctgctccac   1380
tatgttgacc ctgataccgg tcggaatctt ggggaattca aagcataccc tgatggtttc   1440
ctcacttgtg tccccaatgg ggctagctcg ggtccacaac agctgccgat caatggggtc   1500
tttgtctttg tttcatgggt gtccagattt tatcaattaa agcctgtggg aactgccagc   1560
tcggcaagag gtaggcttgg tctgcgccga taatggccca agccataatt ggtgcaattg   1620
ctgcttccac agcaggtagt gctctgggag cgggcataca ggttggtggc gaagcggccc   1680
tccaaagcca aaggtatcaa caaaatttgc aactgcaaga aaattctttt aaacatgaca   1740
gggaaatgat tgggtatcag gttgaagctt caaatcaatt attggctaaa aatttggcaa   1800
ctagatattc actcctccgt gctggggggtt tgaccagtgc tgatgcagca agatctgtgg   1860
caggagctcc agtcacccgc attgtagatt ggaatggcgt gagagtgtct gctcccgagt   1920
cctctgctac cacattgaga tccggtggct tcatgtcagt tcccatacca tttgcctcta   1980
agcaaaaaca ggttcaatca tctggtatta gtaatccaaa ttattcccct tcatccattt   2040
ctcgaaccac tagttgggtc gagtcacaaa actcatcgag atttggaaat ctttctccat   2100
accacgcgga ggctctcaat acagtgtggt tgactccacc cggttcaaca gcctcttcta   2160
cactgtcttc tgtgccacgt ggttatttca atacagacag gttgccatta ttcgcaaata   2220
ataggcgatg a                                                        2231
```

<210> SEQ ID NO 17
<211> LENGTH: 2297
<212> TYPE: DNA
<213> ORGANISM: Norovirus GI.1/US/Norwalk/1968

<400> SEQUENCE: 17

```
atgatgatgg cgtctaagga cgctacatca agcgtggatg gcgctagtgg cgctggtcag     60
ttggtaccgg aggttaatgc ttctgaccct cttgcaatgg atcctgtagc aggttcttcg    120
acagcagtcg cgactgctgg acaagttaat cctattgatc cctggataat taataatttt    180
gtgcaagccc cccaaggtga atttactatt tccccaaata atacccccgg tgatgttttg    240
tttgatttga gtttgggtcc ccatcttaat cctttcttgc tccatctatc acaaatgtat    300
```

-continued

```
aatggttggg ttggtaacat gagagtcagg attatgctag ctggtaatgc ctttactgcg    360

gggaagataa tagtttcctg catacccccct ggttttggtt cacataatct tactatagca    420

caagcaactc tctttccaca tgtgattgct gatgttagga ctctagaccc cattgaggtg    480

cctttggaag atgttaggaa tgttctcttt cataataatg atagaaatca acaaaccatg    540

cgccttgtgt gcatgctgta cacccccctc cgcactggtg gtggtactgg tgattctttt    600

gtagttgcag ggcgagttat gacttgcccc agtcctgatt ttaatttctt gtttttagtc    660

cctcctacgg tggagcagaa aaccaggccc ttcacactcc caaatctgcc attgagttct    720

ctgtctaact cacgtgcccc tctcccaatc agtagtatgg gcatttcccc agacaatgtc    780

cagagtgtgc agttccaaaa tggtcggtgt actctggatg gccgcctggt tggcaccacc    840

ccagtttcat tgtcacatgt tgccaagata agagggacct ccaatggcac tgtaatcaac    900

cttactgaat tggatggcac acccttcac cctttttgagg gccctgcccc cattgggttt    960

ccagacctcg gtggttgtga ttggcatatc aatatgacac agtttggcca ttctagccag   1020

acccagtatg atgtagacac cacccctgac actttttgtcc cccatcttgg ttcaattcag   1080

gcaaatggca ttggcagtgg taattatgtt ggtgttctta gctggatttc ccccccatca   1140

cacccgtctg gctcccaagt tgacctttgg aagatcccca attatgggtc aagtattacg   1200

gaggcaacac atctagcccc ttctgtatac ccccctggtt tcggagaggt attggtcttt   1260

ttcatgtcaa aaatgccagg tcctggtgct tataatttgc cctgtctatt accacaagag   1320

tacatttcac atcttgctag tgaacaagcc cctactgtag gtgaggctgc cctgctccac   1380

tatgttgacc ctgataccgg tcggaatctt ggggaattca aagcataccc tgatggtttc   1440

ctcacttgtg tccccaatgg ggctagctcg ggtccacaac agctgccgat caatggggtc   1500

tttgtctttg tttcatgggt gtccagattt tatcaattaa agcctgtggg aactgccagc   1560

tcggcaagag gtaggcttgg tctgcgccga taatggccca agccataatt ggtgcaattg   1620

ctgcttccac agcaggtagt gctctgggag cgggcataca ggttggtggc gaagcggccc   1680

tccaaagcca aaggtatcaa caaaatttgc aactgcaaga aaattctttt aaacatgaca   1740

gggaaatgat tgggtatcag gttgaagctt caaatcaatt attggctaaa aatttggcaa   1800

ctagatattc actcctccgt gctgggggtt tgaccagtgc tgatgcagca agatctgtgg   1860

caggagctcc agtcacccgc attgtagatt ggaatggcgt gagagtgtct gctcccgagt   1920

cctctgctac cacattgaga tccggtggct tcatgtcagt tcccatacca tttgcctcta   1980

agcaaaaaca ggttcaatca tctggtatta gtaatccaaa ttattcccct tcatccattt   2040

ctcgaaccac tagttgggtc gagtcacaaa actcatcgag atttggaaat ctttctccat   2100

accacgcgga ggctctcaat acagtgtggt tgactccacc cggttcaaca gcctcttcta   2160

cactgtcttc tgtgccacgt ggttatttca atacagacag gttgccatta ttcgcaaata   2220

ataggcgatg atgttgtaat atgaaatgtg ggcatcatat tcatttaatt aggtttaatt   2280

aggtttaatt tgatgtt                                                   2297
```

<210> SEQ ID NO 18
<211> LENGTH: 1593
<212> TYPE: DNA
<213> ORGANISM: Artificial
<220> FEATURE:
<223> OTHER INFORMATION: Nucleic acid sequence of human codon-optimized
      VP1 G1.1

<400> SEQUENCE: 18

```
atgatgatgg ctagtaaaga tgcgacctcc tctgtggatg gtgcgtcagg ggcaggacaa     60
ctcgtacccg aggtaaacgc cagcgaccca cttgccatgg accccgttgc cggaagttcc    120
acagcagtgg ccacagccgg tcaagtgaat ccaattgatc cgtggattat caacaatttc    180
gtccaggcac cccagggcga gttcacaatt tcaccaaaca atacaccggg cgatgtgcta    240
ttcgatcttt ccttgggtcc tcaccttaac ccttttctac tccatctctc acagatgtac    300
aatggttggg taggaaacat gagagtccgg atcatgctgg ctggcaatgc ctttaccgct    360
ggcaagatca tcgtcagttg tattcctccc ggatttggat ctcataatct gaccattgct    420
caagcgactc tctttcccca tgtcatcgcc gacgttagga ccctggaccc catcgaggtg    480
cccctggagg acgtccggaa tgttttgttc cacaacaacg acagaaacca gcagacgatg    540
agacttgtct gtatgctcta taccccactg cggactggag gcgggactgg agactccttc    600
gttgtggcag gaagagtgat gacatgcccc tcccccgact tcaactttct ttttctggtc    660
ccaccaaccg ttgagcagaa gacgcggccc tttacactgc ccaatctccc gctttcaagt    720
ctgagtaatt cacgggcccc attgccgatc tcctcaatgg gaatctcccc cgacaacgtc    780
cagtctgtcc aattccaaaa tgggagatgc acactggacg gtcgcctggt gggaacaact    840
ccggtgtccc tctcacatgt cgccaaaatc cgcggcacat caaatggtac cgtaatcaat    900
ctgacagaac ttgatggcac gcccttccat ccctttgaag gaccagcccc tattggattt    960
cctgatctgg gaggttgcga ctggcacata aacatgacac agtttggcca ctccagccag   1020
acacagtatg atgtcgatac aaccccagat accttcgtgc cacacctggg atctattcaa   1080
gctaacggta ttggatccgg caactacgtg ggagtcttat cttggatctc accaccatcc   1140
cacccctcag gatcccaggt tgacttgtgg aagataccga attatggatc ctcgatcact   1200
gaagccacgc acctcgcacc ttccgtctac ccaccaggtt ttggagaagt cttggtgttt   1260
ttcatgagca aaatgcccgg ccctggagcc tacaatctcc cttgcctact ccctcaagag   1320
tatattagtc acctcgcatc tgagcaggcc ccgaccgttg gcgaggcagc cctgctgcat   1380
tatgtggatc cggacaccgg caggaacctg ggtgagttca aagcttatcc tgacggtttt   1440
ctaacatgtg taccaaatgg cgcttccagc ggccctcaac agctcccaat caatggcgtg   1500
ttcgtttttg tcagctgggt aagccgcttc taccagctga agcccgtggg gacagcttct   1560
tctgcccgcg gacgcctcgg tctgcggaga taa                                1593
```

<210> SEQ ID NO 19
<211> LENGTH: 639
<212> TYPE: DNA
<213> ORGANISM: Artificial
<220> FEATURE:
<223> OTHER INFORMATION: Nucleic acid sequence of human codon-optimized VP2 G1.1

<400> SEQUENCE: 19

```
atggctcagg ccattattgg cgccatcgct gcaagtacag ccgggagtgc attgggggcc     60
ggaatacagg tgggcgggga agctgcattg cagagccagc ggtaccagca aaacctgcag    120
ttacaggaga atagctttaa acacgacagg gagatgattg gatatcaggt ggaggccagc    180
aatcagctgc tcgccaaaaa cttggctact cgatactcat tactgcgcgc cggggggttg    240
actagcgccg acgccgcacg atctgtcgca ggcgcccccg tgactcggat cgtagactgg    300
aacggggtac gagtctcggc tcccgagtcg tctgcaacca ccctgaggtc gggagggttt    360
atgtccgtgc ccatcccatt cgctagcaaa cagaaacagg tccagagctc cggaatctcc    420
```

aatcccaatt actcccctag ctctatctct cgtaccactt cctgggtcga gagtcagaac 480
agcagtagat ttggcaacct gagcccctac catgctgaag ccctgaacac tgtgtggttg 540
actccacctg gtagcacggc ctcctcaacc ctgagttccg tgcctcgcgg gtacttcaat 600
accgacagac ttcctctgtt cgctaacaac cgccgctga 639

<210> SEQ ID NO 20
<211> LENGTH: 2231
<212> TYPE: DNA
<213> ORGANISM: Artificial
<220> FEATURE:
<223> OTHER INFORMATION: Nucleic acid sequence of human codon-optimized VP1/VP2 G1.1

<400> SEQUENCE: 20
atgatgatgg ctagtaaaga tgcgacctcc tctgtggatg gtgcgtcagg ggcaggacaa 60
ctcgtacccg aggtaaacgc cagcgaccca cttgccatgg accccgttgc cggaagttcc 120
acagcagtgg ccacagccgg tcaagtgaat ccaattgatc cgtggattat caacaatttc 180
gtccaggcac cccagggcga gttcacaatt tcaccaaaca atacaccggg cgatgtgcta 240
ttcgatcttt ccttgggtcc tcaccttaac ccttttctac tccatctctc acagatgtac 300
aatggttggg taggaaacat gagagtccgg atcatgctgg ctggcaatgc ctttaccgct 360
ggcaagatca tcgtcagttg tattcctccc ggatttggat ctcataatct gaccattgct 420
caagcgactc tctttcccca tgtcatcgcc gacgttagga ccctggaccc catcgaggtg 480
cccctggagg acgtccggaa tgttttgttc cacaacaacg acagaaacca gcagacgatg 540
agacttgtct gtatgctcta taccccactg cggactggag gcgggactgg agactccttc 600
gttgtggcag gaagagtgat gacatgcccc tcccccgact tcaactttct ttttctggtc 660
ccaccaaccg ttgagcagaa gacgcggccc tttacactgc ccaatctccc gctttcaagt 720
ctgagtaatt cacgggcccc attgccgatc tcctcaatgg gaatctcccc cgacaacgtc 780
cagtctgtcc aattccaaaa tgggagatgc acactggacg gtcgcctggt gggaacaact 840
ccggtgtccc tctcacatgt cgccaaaatc cgcggcacat caaatggtac cgtaatcaat 900
ctgacagaac ttgatggcac gcccttccat ccctttgaag gaccagcccc tattggattt 960
cctgatctgg gaggttgcga ctggcacata aacatgacac agtttggcca ctccagccag 1020
acacagtatg atgtcgatac aaccccagat accttcgtgc cacacctggg atctattcaa 1080
gctaacggta ttggatccgg caactacgtg ggagtcttat cttggatctc accaccatcc 1140
cacccctcag gatcccaggt tgacttgtgg aagataccga attatggatc ctcgatcact 1200
gaagccacgc acctcgcacc ttccgtctac ccaccaggtt ttggagaagt cttggtgttt 1260
ttcatgagca aaatgcccgg ccctggagcc tacaatctcc cttgcctact ccctcaagag 1320
tatattagtc acctcgcatc tgagcaggcc ccgaccgttg gcgaggcagc cctgctgcat 1380
tatgtggatc cggacaccgg caggaacctg ggtgagttca aagcttatcc tgacggtttt 1440
ctaacatgtg taccaaatgg cgcttccagc ggccctcaac agctcccaat caatggcgtg 1500
ttcgtttttg tcagctgggt aagccgcttc taccagctga agcccgtggg gacagcttct 1560
tctgcccgcg gacgcctcgg tctgcggaga taatggctca ggccattatt ggcgccatcg 1620
ctgcaagtac agccgggagt gcattggggg ccggaataca ggtgggcggg gaagctgcat 1680
tgcagagcca gcggtaccag caaaacctgc agttacagga gaatagcttt aaacacgaca 1740
gggagatgat tggatatcag gtggaggcca gcaatcagct gctcgccaaa aacttggcta 1800
ctcgatactc attactgcgc gccggggggt tgactagcgc cgacgccgca cgatctgtcg 1860
caggcgcccc cgtgactcgg atcgtagact ggaacggggt acgagtctcg gctcccgagt 1920
cgtctgcaac caccctgagg tcgggagggt ttatgtccgt gcccatccca ttcgctagca 1980
aacagaaaca ggtccagagc tccggaatct ccaatcccaa ttactcccct agctctatct 2040
ctcgtaccac ttcctgggtc gagagtcaga acagcagtag atttggcaac ctgagcccct 2100
accatgctga agccctgaac actgtgtggt tgactccacc tggtagcacg gcctcctcaa 2160
ccctgagttc cgtgcctcgc gggtacttca ataccgacag acttcctctg ttcgctaaca 2220
accgccgctg a 2231

<210> SEQ ID NO 21
<211> LENGTH: 2297
<212> TYPE: DNA
<213> ORGANISM: Artificial
<220> FEATURE:
<223> OTHER INFORMATION: Nucleic acid sequence of human codon-optimized VP1/VP2/3'UTR G1.1

<400> SEQUENCE: 21
atgatgatgg ctagtaaaga tgcgacctcc tctgtggatg gtgcgtcagg ggcaggacaa 60
ctcgtacccg aggtaaacgc cagcgaccca cttgccatgg accccgttgc cggaagttcc 120
acagcagtgg ccacagccgg tcaagtgaat ccaattgatc cgtggattat caacaatttc 180
gtccaggcac cccagggcga gttcacaatt tcaccaaaca atacaccggg cgatgtgcta 240
ttcgatcttt ccttgggtcc tcaccttaac ccttttctac tccatctctc acagatgtac 300
aatggttggg taggaaacat gagagtccgg atcatgctgg ctggcaatgc ctttaccgct 360
ggcaagatca tcgtcagttg tattcctccc ggatttggat ctcataatct gaccattgct 420
caagcgactc tctttcccca tgtcatcgcc gacgttagga ccctggaccc catcgaggtg 480
cccctggagg acgtccggaa tgttttgttc cacaacaacg acagaaacca gcagacgatg 540
agacttgtct gtatgctcta taccccactg cggactggag gcgggactgg agactccttc 600
gttgtggcag gaagagtgat gacatgcccc tcccccgact tcaactttct ttttctggtc 660
ccaccaaccg ttgagcagaa gacgcggccc tttacactgc ccaatctccc gctttcaagt 720
ctgagtaatt cacgggcccc attgccgatc tcctcaatgg gaatctcccc cgacaacgtc 780
cagtctgtcc aattccaaaa tgggagatgc acactggacg gtcgcctggt gggaacaact 840
ccggtgtccc tctcacatgt cgccaaaatc cgcggcacat caaatggtac cgtaatcaat 900
ctgacagaac ttgatggcac gcccttccat ccctttgaag gaccagcccc tattggattt 960
cctgatctgg gaggttgcga ctggcacata aacatgacac agtttggcca ctccagccag 1020
acacagtatg atgtcgatac aaccccagat accttcgtgc cacacctggg atctattcaa 1080
gctaacggta ttggatccgg caactacgtg ggagtcttat cttggatctc accaccatcc 1140
cacccctcag gatcccaggt tgacttgtgg aagataccga attatggatc ctcgatcact 1200
gaagccacgc acctcgcacc ttccgtctac ccaccaggtt ttggagaagt cttggtgttt 1260
ttcatgagca aaatgcccgg ccctggagcc tacaatctcc cttgcctact ccctcaagag 1320
tatattagtc acctcgcatc tgagcaggcc ccgaccgttg gcgaggcagc cctgctgcat 1380
tatgtggatc cggacaccgg caggaacctg ggtgagttca aagcttatcc tgacggtttt 1440
ctaacatgtg taccaaatgg cgcttccagc ggccctcaac agctcccaat caatggcgtg 1500
ttcgtttttg tcagctgggt aagccgcttc taccagctga agcccgtggg gacagcttct 1560
tctgcccgcg gacgcctcgg tctgcggaga taatggctca ggccattatt ggcgccatcg 1620
ctgcaagtac agccgggagt gcattggggg ccggaataca ggtgggcggg gaagctgcat 1680
tgcagagcca gcggtaccag caaaacctgc agttacagga gaatagcttt aaacacgaca 1740
gggagatgat tggatatcag gtggaggcca gcaatcagct gctcgccaaa aacttggcta 1800
ctcgatactc attactgcgc gccggggggt tgactagcgc cgacgccgca cgatctgtcg 1860
caggcgcccc cgtgactcgg atcgtagact ggaacggggt acgagtctcg gctcccgagt 1920
cgtctgcaac caccctgagg tcgggagggt ttatgtccgt gcccatccca ttcgctagca 1980
aacagaaaca ggtccagagc tccggaatct ccaatcccaa ttactcccct agctctatct 2040
ctcgtaccac ttcctgggtc gagagtcaga acagcagtag atttggcaac ctgagcccct 2100
accatgctga agccctgaac actgtgtggt tgactccacc tggtagcacg gcctcctcaa 2160
ccctgagttc cgtgcctcgc gggtacttca ataccgacag acttcctctg ttcgctaaca 2220
accgccgctg atgttgtaat atgaaatgtg ggcatcatat tcatttaatt aggtttaatt 2280
aggtttaatt tgatgtt 2297

<210> SEQ ID NO 22
<211> LENGTH: 545
<212> TYPE: PRT
<213> ORGANISM: Artificial
<220> FEATURE:
<223> OTHER INFORMATION: Amino acid sequence of S(GI.1)+P(GI.2) fusion VP1

<400> SEQUENCE: 22

Met Met Met Ala Ser Lys Asp Ala Thr Ser Ser Val Asp Gly Ala Ser
1 5 10 15

Gly Ala Gly Gln Leu Val Pro Glu Val Asn Ala Ser Asp Pro Leu Ala
20 25 30

Met Asp Pro Val Ala Gly Ser Ser Thr Ala Val Ala Thr Ala Gly Gln
35 40 45

Val Asn Pro Ile Asp Pro Trp Ile Ile Asn Asn Phe Val Gln Ala Pro
50 55 60

Gln Gly Glu Phe Thr Ile Ser Pro Asn Asn Thr Pro Gly Asp Val Leu
65 70 75 80

Phe Asp Leu Ser Leu Gly Pro His Leu Asn Pro Phe Leu Leu His Leu
85 90 95

Ser Gln Met Tyr Asn Gly Trp Val Gly Asn Met Arg Val Arg Ile Met
100 105 110

Leu Ala Gly Asn Ala Phe Thr Ala Gly Lys Ile Ile Val Ser Cys Ile
115 120 125

Pro Pro Gly Phe Gly Ser His Asn Leu Thr Ile Ala Gln Ala Thr Leu
130 135 140

Phe Pro His Val Ile Ala Asp Val Arg Thr Leu Asp Pro Ile Glu Val
145 150 155 160

Pro Leu Glu Asp Val Arg Asn Val Leu Phe His Asn Asn Asp Arg Asn
165 170 175

Gln Gln Thr Met Arg Leu Val Cys Met Leu Tyr Thr Pro Leu Arg Thr
180 185 190

Gly Gly Gly Thr Gly Asp Ser Phe Val Val Ala Gly Arg Val Met Thr
195 200 205

Cys Pro Ser Pro Asp Phe Asn Phe Leu Phe Leu Val Pro Pro Thr Val
210 215 220

-continued

```
Glu Gln Lys Thr Arg Ala Phe Thr Val Pro Asn Ile Pro Leu Gln Thr
225                 230                 235                 240

Leu Ser Asn Ser Arg Phe Pro Ser Leu Ile Gln Gly Met Ile Leu Ser
                245                 250                 255

Pro Asp Ala Ser Gln Val Val Gln Phe Gln Asn Gly Arg Cys Leu Ile
            260                 265                 270

Asp Gly Gln Leu Leu Gly Thr Thr Pro Ala Thr Ser Gly Gln Leu Phe
        275                 280                 285

Arg Val Arg Gly Lys Ile Asn Gln Gly Ala Arg Thr Leu Asn Leu Thr
    290                 295                 300

Glu Val Asp Gly Lys Pro Phe Met Ala Phe Asp Ser Pro Ala Pro Val
305                 310                 315                 320

Gly Phe Pro Asp Phe Gly Lys Cys Asp Trp His Met Arg Ile Ser Lys
                325                 330                 335

Thr Pro Asn Asn Thr Ser Ser Gly Asp Pro Met Arg Ser Val Asp Val
            340                 345                 350

Gln Thr Asp Val Gln Gly Phe Val Pro His Leu Gly Ser Ile Gln Phe
        355                 360                 365

Asp Glu Val Phe Asn His Pro Thr Gly Asp Tyr Ile Gly Thr Ile Glu
    370                 375                 380

Trp Ile Ser Gln Pro Ser Thr Pro Pro Gly Thr Asp Ile Asn Leu Trp
385                 390                 395                 400

Glu Ile Pro Asp Tyr Gly Ser Ser Leu Ser Gln Ala Ala Asn Leu Ala
                405                 410                 415

Pro Pro Val Phe Pro Pro Gly Phe Gly Glu Ala Leu Val Tyr Phe Val
            420                 425                 430

Ser Ala Phe Pro Gly Pro Asn Asn Arg Ser Ala Pro Asn Asp Val Pro
        435                 440                 445

Cys Leu Leu Pro Gln Glu Tyr Val Thr His Phe Val Ser Glu Gln Ala
    450                 455                 460

Pro Thr Met Gly Asp Ala Ala Leu Leu His Tyr Val Asp Pro Asp Thr
465                 470                 475                 480

Asn Arg Asn Leu Gly Glu Phe Lys Leu Tyr Pro Gly Gly Tyr Leu Thr
                485                 490                 495

Cys Val Pro Asn Gly Val Gly Ala Gly Pro Gln Gln Leu Pro Leu Asn
            500                 505                 510

Gly Val Phe Leu Phe Val Ser Trp Val Ser Arg Phe Tyr Gln Leu Lys
        515                 520                 525

Pro Val Gly Thr Ala Ser Thr Ala Arg Gly Arg Leu Gly Val Arg Arg
    530                 535                 540

Ile
545
```

<210> SEQ ID NO 23
<211> LENGTH: 542
<212> TYPE: PRT
<213> ORGANISM: Artificial
<220> FEATURE:
<223> OTHER INFORMATION: Amino acid sequence of S(GI.1)+P(GI.3) fusion VP1

<400> SEQUENCE: 23

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30
```

```
Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Lys Pro Phe Ser Val Pro Asn Leu Pro Leu Asn Val
225                 230                 235                 240

Leu Ser Asn Ser Arg Val Pro Ser Leu Ile Lys Ser Met Met Val Ser
                245                 250                 255

Gln Asp His Gly Gln Met Val Gln Phe Gln Asn Gly Arg Val Thr Leu
            260                 265                 270

Asp Gly Gln Leu Gln Gly Thr Thr Pro Thr Ser Ala Ser Gln Leu Cys
        275                 280                 285

Lys Ile Arg Gly Thr Val Tyr His Ala Thr Gly Gly Gln Gly Leu Asn
    290                 295                 300

Leu Thr Glu Ile Asp Gly Thr Pro Tyr His Ala Phe Glu Ser Pro Ala
305                 310                 315                 320

Pro Ile Gly Phe Pro Asp Leu Gly Glu Cys Asp Trp His Ile Asn Ala
                325                 330                 335

Ser Pro Ala Asn Ala Phe Thr Asp Gly Ser Ile Ile His Arg Ile Asp
            340                 345                 350

Val Ala Gln Asp Ser Thr Phe Ala Pro His Leu Gly Thr Ile His Tyr
        355                 360                 365

Thr Asn Ala Asp Tyr Asn Ala Asn Val Gly Leu Ile Cys Ser Leu Glu
    370                 375                 380

Trp Leu Ser Pro Pro Ser Gly Gly Ala Pro Lys Val Asn Pro Trp Ala
385                 390                 395                 400

Ile Pro Arg Tyr Gly Ser Thr Leu Thr Glu Ala Ala Gln Leu Ala Pro
                405                 410                 415

Pro Ile Tyr Pro Pro Gly Phe Gly Glu Ala Ile Val Phe Phe Met Ser
            420                 425                 430

Asp Phe Pro Ile Ala Asn Gly Ser Asp Gly Leu Ser Val Pro Cys Thr
        435                 440                 445
```

```
Ile Pro Gln Glu Phe Val Thr His Phe Val Asn Glu Gln Ala Pro Thr
    450                 455                 460

Arg Gly Glu Ala Ala Leu Leu His Tyr Val Asp Pro Asp Thr His Arg
465                 470                 475                 480

Asn Leu Gly Glu Phe Lys Leu Tyr Pro Glu Gly Phe Met Thr Cys Val
                485                 490                 495

Pro Asn Ser Ser Gly Ser Gly Pro Gln Thr Leu Pro Ile Asn Gly Val
            500                 505                 510

Phe Thr Phe Ile Ser Trp Val Ser Arg Phe Tyr Gln Leu Lys Pro Val
        515                 520                 525

Gly Thr Thr Gly Pro Val Arg Arg Leu Gly Ile Arg Arg Ser
    530                 535                 540


<210> SEQ ID NO 24
<211> LENGTH: 544
<212> TYPE: PRT
<213> ORGANISM: Artificial
<220> FEATURE:
<223> OTHER INFORMATION: Amino acid sequence of S(GI.1)+P(GII.4) fusion
      VP1

<400> SEQUENCE: 24

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Ser Arg Thr Lys Pro Phe Ser Val Pro Val Leu Thr Val Glu Glu
225                 230                 235                 240

Met Thr Asn Ser Arg Phe Pro Ile Pro Leu Glu Lys Leu Phe Thr Gly
                245                 250                 255

Pro Ser Ser Ala Phe Val Val Gln Pro Gln Asn Gly Arg Cys Thr Thr
            260                 265                 270
```

```
Asp Gly Val Leu Leu Gly Thr Thr Gln Leu Ser Pro Val Asn Ile Cys
        275                 280                 285

Thr Phe Arg Gly Asp Val Thr His Ile Thr Gly Ser Arg Asn Tyr Thr
    290                 295                 300

Met Asn Leu Ala Ser Gln Asn Trp Asn Asp Tyr Asp Pro Thr Glu Glu
305                 310                 315                 320

Ile Pro Ala Pro Leu Gly Thr Pro Asp Phe Val Gly Lys Ile Gln Gly
                325                 330                 335

Val Leu Thr Gln Thr Thr Arg Thr Asp Gly Ser Thr Arg Gly His Lys
            340                 345                 350

Ala Thr Val Tyr Thr Gly Ser Ala Asp Phe Ala Pro Lys Leu Gly Arg
        355                 360                 365

Val Gln Phe Glu Thr Asp Thr Asp Arg Asp Phe Glu Ala Asn Gln Asn
    370                 375                 380

Thr Lys Phe Thr Pro Val Gly Val Ile Gln Asp Gly Gly Thr Thr His
385                 390                 395                 400

Arg Asn Glu Pro Gln Gln Trp Val Leu Pro Ser Tyr Ser Gly Arg Asn
                405                 410                 415

Thr His Asn Val His Leu Ala Pro Ala Val Ala Pro Thr Phe Pro Gly
            420                 425                 430

Glu Gln Leu Leu Phe Phe Arg Ser Thr Met Pro Gly Cys Ser Gly Tyr
        435                 440                 445

Pro Asn Met Asp Leu Asp Cys Leu Leu Pro Gln Glu Trp Val Gln Tyr
    450                 455                 460

Phe Tyr Gln Glu Ala Ala Pro Ala Gln Ser Asp Val Ala Leu Leu Arg
465                 470                 475                 480

Phe Val Asn Pro Asp Thr Gly Arg Val Leu Phe Glu Cys Lys Leu His
                485                 490                 495

Lys Ser Gly Tyr Val Thr Val Ala His Thr Gly Gln His Asp Leu Val
            500                 505                 510

Ile Pro Pro Asn Gly Tyr Phe Arg Phe Asp Ser Trp Val Asn Gln Phe
        515                 520                 525

Tyr Thr Leu Ala Pro Met Gly Asn Gly Thr Gly Arg Arg Arg Ala Val
    530                 535                 540


<210> SEQ ID NO 25
<211> LENGTH: 552
<212> TYPE: PRT
<213> ORGANISM: Artificial
<220> FEATURE:
<223> OTHER INFORMATION: Amino acid sequence of S(GI.1)+P(GII.6) fusion
      VP1

<400> SEQUENCE: 25

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
```

-continued

```
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Ser Lys Thr Lys Pro Phe Ser Leu Pro Ile Leu Thr Leu Gly Glu
225                 230                 235                 240

Leu Ser Asn Ser Arg Phe Pro Ala Pro Ile Asp Met Leu Tyr Thr Asp
                245                 250                 255

Pro Asn Glu Gly Ile Val Val Gln Pro Gln Asn Gly Arg Cys Thr Leu
            260                 265                 270

Asp Gly Thr Leu Gln Gly Thr Thr Gln Leu Val Pro Thr Gln Ile Cys
        275                 280                 285

Ala Phe Arg Gly Thr Leu Ile Gly Gln Thr Ser Arg Ser Pro Asp Ser
    290                 295                 300

Thr Asp Ser Ala Pro Arg Arg Arg Asp His Pro Leu His Val Gln Leu
305                 310                 315                 320

Lys Asn Leu Asp Gly Thr Gln Tyr Asp Pro Thr Asp Glu Val Pro Ala
                325                 330                 335

Val Leu Gly Ala Ile Asp Phe Lys Gly Thr Val Phe Gly Val Ala Ser
            340                 345                 350

Gln Arg Asp Val Ser Gly Gln Gln Val Gly Ala Thr Arg Ala His Glu
        355                 360                 365

Val His Ile Asn Thr Thr Asp Pro Arg Tyr Thr Pro Lys Leu Gly Ser
    370                 375                 380

Ile Leu Met Tyr Ser Glu Ser Asp Asp Phe Val Thr Gly Gln Pro Val
385                 390                 395                 400

Arg Phe Thr Pro Ile Gly Met Gly Asp Asn Asp Trp His Gln Trp Glu
                405                 410                 415

Leu Pro Asp Tyr Pro Gly His Leu Thr Leu Asn Met Asn Leu Ala Pro
            420                 425                 430

Ala Val Ala Pro Ala Phe Pro Gly Glu Arg Ile Leu Phe Phe Arg Ser
        435                 440                 445

Ile Val Pro Ser Ala Gly Gly Tyr Gly Ser Gly Gln Ile Asp Cys Leu
    450                 455                 460

Ile Pro Gln Glu Trp Val Gln His Phe Tyr Gln Glu Ala Ala Pro Ser
465                 470                 475                 480

Gln Ser Ala Val Ala Leu Ile Arg Tyr Val Asn Pro Asp Thr Gly Arg
                485                 490                 495

Asn Ile Phe Glu Ala Lys Leu His Arg Glu Gly Phe Ile Thr Val Ala
            500                 505                 510
```

```
Asn Ser Gly Asn Asn Pro Ile Val Val Pro Pro Asn Gly Tyr Phe Arg
        515                 520                 525

Phe Glu Ala Trp Val Asn Gln Phe Tyr Thr Leu Thr Pro Met Gly Thr
    530                 535                 540

Gly Gln Gly Arg Arg Arg Asp Gln
545                 550


<210> SEQ ID NO 26
<211> LENGTH: 546
<212> TYPE: PRT
<213> ORGANISM: Artificial
<220> FEATURE:
<223> OTHER INFORMATION: Amino acid sequence of S(GI.1)+P(GII.13)
      fusion VP1

<400> SEQUENCE: 26

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Ser Lys Thr Lys Pro Phe Thr Leu Pro Ile Leu Thr Ile Ser Glu
225                 230                 235                 240

Leu Thr Asn Ser Arg Phe Pro Ile Ser Ile Glu Gln Leu Tyr Thr Ala
                245                 250                 255

Pro Asn Glu Asn Asn Val Val Gln Cys Gln Asn Gly Arg Cys Thr Leu
            260                 265                 270

Asp Gly Glu Leu Gln Gly Thr Thr Gln Leu Leu Ser Ser Ala Val Cys
        275                 280                 285

Ser Tyr Arg Gly Arg Thr Val Ala Asn Ser Gly Asp Asn Trp Asp Gln
    290                 295                 300

Asn Val Leu Gln Leu Thr Tyr Pro Ser Gly Ala Ser Tyr Asp Pro Thr
```

```
305                 310                 315                 320

Asp Glu Val Pro Ala Pro Leu Gly Thr Gln Asp Phe Ser Gly Ile Leu
                325                 330                 335

Tyr Gly Val Leu Thr Gln Asp Asn Val Arg Glu Asn Thr Gly Glu Ala
            340                 345                 350

Lys Asn Ala Lys Gly Val Tyr Ile Ser Thr Thr Ser Gly Lys Phe Thr
        355                 360                 365

Pro Lys Ile Gly Ser Ile Gly Leu His Ser Ile Thr Glu Asp Val Arg
    370                 375                 380

Pro Asn Gln Gln Ser Arg Phe Thr Pro Val Gly Val Ala Gln Asn Glu
385                 390                 395                 400

Asn Thr Pro Phe Gln Gln Trp Val Leu Pro His Tyr Ala Gly Ala Leu
                405                 410                 415

Ala Leu Asn Thr Asn Leu Ala Pro Ala Val Ala Pro Thr Phe Pro Gly
            420                 425                 430

Glu Gln Leu Leu Phe Phe Arg Ser Arg Val Pro Cys Val Gln Gly Leu
        435                 440                 445

Gln Gly Gln Asp Ala Phe Ile Asp Cys Leu Leu Pro Gln Glu Trp Val
    450                 455                 460

Asn His Phe Tyr Gln Glu Ala Ala Pro Ser Gln Ala Asp Val Ala Leu
465                 470                 475                 480

Ile Arg Tyr Val Asn Pro Asp Thr Gly Arg Thr Leu Phe Glu Ala Lys
                485                 490                 495

Leu His Arg Ser Gly Phe Ile Thr Val Ser His Thr Gly Ala Tyr Pro
            500                 505                 510

Leu Val Val Pro Pro Asn Gly His Phe Arg Phe Asp Ser Trp Val Asn
        515                 520                 525

Gln Phe Tyr Ser Leu Ala Pro Met Gly Thr Gly Asn Gly Arg Arg Arg
    530                 535                 540

Val Gln
545


<210> SEQ ID NO 27
<211> LENGTH: 520
<212> TYPE: PRT
<213> ORGANISM: Artificial
<220> FEATURE:
<223> OTHER INFORMATION: Amino acid sequence of S(GI.1)+P(GII.17)
      fusion VP1

<400> SEQUENCE: 27

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110
```

```
Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Gln Leu Leu Pro Ser Gly Ile Cys
        275                 280                 285

Ala Phe Arg Gly Arg Val Thr Ala Glu Thr Asp His Arg Asp Lys Trp
    290                 295                 300

His Met Gln Leu Gln Asn Leu Asn Gly Thr Thr Tyr Asp Pro Thr Asp
305                 310                 315                 320

Asp Val Pro Ala Pro Leu Gly Thr Pro Asp Phe Lys Gly Val Val Phe
                325                 330                 335

Gly Val Ala Ser Gln Arg Asn Val Gly Asn Asp Ala Pro Gly Ser Thr
            340                 345                 350

Arg Ala His Glu Ala Val Ile Ser Thr Tyr Ser Pro Gln Phe Val Pro
        355                 360                 365

Lys Leu Gly Ser Val Asn Phe Arg Ser Asn Asp Asn Asp Phe Gln Leu
    370                 375                 380

Gln Pro Thr Lys Phe Thr Pro Val Gly Ile Asn Asp Asp Gly Asp His
385                 390                 395                 400

Pro Phe Arg Gln Trp Glu Leu Pro Asp Tyr Ser Gly Leu Leu Thr Leu
                405                 410                 415

Asn Met Asn Leu Ala Pro Ser Val Tyr Pro Pro Gly Phe Gly Glu Val
            420                 425                 430

Leu Val Phe Phe Met Ser Lys Met Pro Gly Pro Gly Ala Tyr Asn Leu
        435                 440                 445

Pro Cys Leu Leu Pro Gln Glu Tyr Ile Ser His Leu Ala Ser Glu Gln
    450                 455                 460

Ala Pro Thr Val Gly Glu Ala Ala Leu Leu His Tyr Val Asp Pro Asp
465                 470                 475                 480

Thr Gly Arg Asn Leu Gly Glu Phe Lys Ala Tyr Pro Asp Gly Phe Leu
                485                 490                 495

Thr Cys Val Pro Asn Gly Ala Ser Ser Gly Pro Gln Gln Leu Pro Ile
            500                 505                 510

Asn Gly Val Phe Val Phe Val Ser
        515                 520
```

```
<210> SEQ ID NO 28
<211> LENGTH: 535
<212> TYPE: PRT
<213> ORGANISM: Norovirus GII.12/HS206/2010/USA

<400> SEQUENCE: 28

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Val Pro Ile Asp Glu Leu Tyr Thr Ser Pro Asn Glu Ser
                245                 250                 255

Leu Val Val Gln Pro Gln Asn Gly Arg Cys Ala Leu Asp Gly Glu Leu
            260                 265                 270

Gln Gly Thr Thr Gln Leu Leu Pro Thr Ala Ile Cys Ser Phe Arg Gly
        275                 280                 285

Arg Ile Asn Gln Lys Val Ser Gly Glu Asn His Val Trp Asn Met Gln
    290                 295                 300

Val Thr Asn Ile Asp Gly Thr Pro Phe Asp Pro Thr Glu Asp Val Pro
305                 310                 315                 320

Ala Pro Leu Gly Thr Pro Asp Phe Ser Gly Lys Leu Phe Gly Val Leu
                325                 330                 335

Ser Gln Arg Asp His Asp Asn Ala Cys Arg Ser His Asp Ala Val Ile
            340                 345                 350

Ala Thr Asn Ser Ala Lys Phe Thr Pro Lys Leu Gly Ala Ile Gln Ile
        355                 360                 365

Gly Thr Trp Glu Gln Asp Asp Val His Ile Asn Gln Pro Thr Lys Phe
    370                 375                 380
```

Thr Pro Val Gly Leu Phe Glu Ser Glu Gly Phe Asn Gln Trp Thr Leu
385 390 395 400

Pro Asn Tyr Ser Gly Ala Leu Thr Leu Asn Met Gly Leu Ala Pro Pro
405 410 415

Val Ala Pro Thr Phe Pro Gly Glu Gln Ile Leu Phe Phe Arg Ser His
420 425 430

Ile Pro Leu Lys Gly Gly Val Ala Asp Pro Val Ile Asp Cys Leu Leu
435 440 445

Pro Gln Glu Trp Ile Gln His Leu Tyr Gln Glu Ser Ala Pro Ser Gln
450 455 460

Thr Asp Val Ala Leu Ile Arg Phe Thr Asn Pro Asp Thr Gly Arg Val
465 470 475 480

Leu Phe Glu Ala Lys Leu His Arg Ser Gly Tyr Ile Thr Val Ala Asn
485 490 495

Thr Gly Ser Arg Pro Ile Val Val Pro Ala Asn Gly Tyr Phe Arg Phe
500 505 510

Asp Ser Trp Val Asn Gln Phe Tyr Ser Leu Ala Pro Met Gly Thr Gly
515 520 525

Asn Gly Arg Arg Arg Val Gln
530 535

<210> SEQ ID NO 29
<211> LENGTH: 526
<212> TYPE: PRT
<213> ORGANISM: Artificial
<220> FEATURE:
<223> OTHER INFORMATION: Amino acid sequence of S(GII.12)+P(GI.1) fusion VP1

<400> SEQUENCE: 29

Met Lys Met Ala Ser Asn Asp Ala Ala Pro Ser Asn Asp Gly Ala Ala
1 5 10 15

Gly Leu Val Pro Glu Val Asn Asn Glu Thr Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Leu Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Leu Val Phe Ala Ala Val Pro Pro His Phe
115 120 125

Pro Leu Glu Asn Ile Ser Pro Gly Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Gln Asn Glu Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Ser Pro
195 200 205

Asp Phe Asp Phe Asn Tyr Leu Val Pro Pro Thr Val Glu Gln Lys Thr
    210                 215                 220

Arg Pro Phe Thr Leu Pro Asn Leu Pro Leu Ser Ser Leu Ser Asn Ser
225                 230                 235                 240

Arg Ala Pro Leu Pro Ile Ser Ser Met Gly Ile Ser Pro Asp Asn Val
                245                 250                 255

Gln Ser Val Gln Phe Gln Asn Gly Arg Cys Thr Leu Asp Gly Arg Leu
            260                 265                 270

Val Gly Thr Thr Pro Val Ser Leu Ser His Val Ala Lys Ile Arg Gly
        275                 280                 285

Thr Ser Asn Gly Thr Val Ile Asn Leu Thr Glu Leu Asp Gly Thr Pro
    290                 295                 300

Phe His Pro Phe Glu Gly Pro Ala Pro Ile Gly Phe Pro Asp Leu Gly
305                 310                 315                 320

Gly Cys Asp Trp His Ile Asn Met Thr Gln Phe Gly His Ser Ser Gln
                325                 330                 335

Thr Gln Tyr Asp Val Asp Thr Thr Pro Asp Thr Phe Val Pro His Leu
            340                 345                 350

Gly Ser Ile Gln Ala Asn Gly Ile Gly Ser Gly Asn Tyr Val Gly Val
        355                 360                 365

Leu Ser Trp Ile Ser Pro Pro Ser His Pro Ser Gly Ser Gln Val Asp
    370                 375                 380

Leu Trp Lys Ile Pro Asn Tyr Gly Ser Ser Ile Thr Glu Ala Thr His
385                 390                 395                 400

Leu Ala Pro Ser Val Tyr Pro Pro Gly Phe Gly Glu Val Leu Val Phe
                405                 410                 415

Phe Met Ser Lys Met Pro Gly Pro Gly Ala Tyr Asn Leu Pro Cys Leu
            420                 425                 430

Leu Pro Gln Glu Tyr Ile Ser His Leu Ala Ser Glu Gln Ala Pro Thr
        435                 440                 445

Val Gly Glu Ala Ala Leu Leu His Tyr Val Asp Pro Asp Thr Gly Arg
    450                 455                 460

Asn Leu Gly Glu Phe Lys Ala Tyr Pro Asp Gly Phe Leu Thr Cys Val
465                 470                 475                 480

Pro Asn Gly Ala Ser Ser Gly Pro Gln Gln Leu Pro Ile Asn Gly Val
                485                 490                 495

Phe Val Phe Val Ser Trp Val Ser Arg Phe Tyr Gln Leu Lys Pro Val
            500                 505                 510

Gly Thr Ala Ser Ser Ala Arg Gly Arg Leu Gly Leu Arg Arg
        515                 520                 525

<210> SEQ ID NO 30
<211> LENGTH: 541
<212> TYPE: PRT
<213> ORGANISM: Artificial
<220> FEATURE:
<223> OTHER INFORMATION: Amino acid sequence of S(GII.12)+P(GI.2)fusion
      VP1

<400> SEQUENCE: 30

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile

-continued

```
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Gln Lys Thr
    210                 215                 220

Arg Ala Phe Thr Val Pro Asn Ile Pro Leu Gln Thr Leu Ser Asn Ser
225                 230                 235                 240

Arg Phe Pro Ser Leu Ile Gln Gly Met Ile Leu Ser Pro Asp Ala Ser
                245                 250                 255

Gln Val Val Gln Phe Gln Asn Gly Arg Cys Leu Ile Asp Gly Gln Leu
            260                 265                 270

Leu Gly Thr Thr Pro Ala Thr Ser Gly Gln Leu Phe Arg Val Arg Gly
        275                 280                 285

Lys Ile Asn Gln Gly Ala Arg Thr Leu Asn Leu Thr Glu Val Asp Gly
    290                 295                 300

Lys Pro Phe Met Ala Phe Asp Ser Pro Ala Pro Val Gly Phe Pro Asp
305                 310                 315                 320

Phe Gly Lys Cys Asp Trp His Met Arg Ile Ser Lys Thr Pro Asn Asn
                325                 330                 335

Thr Ser Ser Gly Asp Pro Met Arg Ser Val Asp Val Gln Thr Asp Val
            340                 345                 350

Gln Gly Phe Val Pro His Leu Gly Ser Ile Gln Phe Asp Glu Val Phe
        355                 360                 365

Asn His Pro Thr Gly Asp Tyr Ile Gly Thr Ile Glu Trp Ile Ser Gln
    370                 375                 380

Pro Ser Thr Pro Pro Gly Thr Asp Ile Asn Leu Trp Glu Ile Pro Asp
385                 390                 395                 400

Tyr Gly Ser Ser Leu Ser Gln Ala Ala Asn Leu Ala Pro Pro Val Phe
                405                 410                 415

Pro Pro Gly Phe Gly Glu Ala Leu Val Tyr Phe Val Ser Ala Phe Pro
            420                 425                 430

Gly Pro Asn Asn Arg Ser Ala Pro Asn Asp Val Pro Cys Leu Leu Pro
        435                 440                 445

Gln Glu Tyr Val Thr His Phe Val Ser Glu Gln Ala Pro Thr Met Gly
    450                 455                 460
```

Asp Ala Ala Leu Leu His Tyr Val Asp Pro Asp Thr Asn Arg Asn Leu
465 470 475 480

Gly Glu Phe Lys Leu Tyr Pro Gly Gly Tyr Leu Thr Cys Val Pro Asn
485 490 495

Gly Val Gly Ala Gly Pro Gln Gln Leu Pro Leu Asn Gly Val Phe Leu
500 505 510

Phe Val Ser Trp Val Ser Arg Phe Tyr Gln Leu Lys Pro Val Gly Thr
515 520 525

Ala Ser Thr Ala Arg Gly Arg Leu Gly Val Arg Arg Ile
530 535 540

<210> SEQ ID NO 31
<211> LENGTH: 538
<212> TYPE: PRT
<213> ORGANISM: Artificial
<220> FEATURE:
<223> OTHER INFORMATION: Amino acid sequence of S(GII.12)+P(GI.3) fusion VP1

<400> SEQUENCE: 31

Met Lys Met Ala Ser Asn Asp Ala Ala Pro Ser Asn Asp Gly Ala Ala
1 5 10 15

Gly Leu Val Pro Glu Val Asn Asn Glu Thr Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Leu Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Leu Val Phe Ala Ala Val Pro Pro His Phe
115 120 125

Pro Leu Glu Asn Ile Ser Pro Gly Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Gln Asn Glu Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Ser Pro
195 200 205

Asp Phe Asp Phe Asn Tyr Leu Val Pro Pro Thr Val Glu Gln Lys Thr
210 215 220

Lys Pro Phe Ser Val Pro Asn Leu Pro Leu Asn Val Leu Ser Asn Ser
225 230 235 240

Arg Val Pro Ser Leu Ile Lys Ser Met Met Val Ser Gln Asp His Gly
245 250 255

Gln Met Val Gln Phe Gln Asn Gly Arg Val Thr Leu Asp Gly Gln Leu
260 265 270

Gln Gly Thr Thr Pro Thr Ser Ala Ser Gln Leu Cys Lys Ile Arg Gly

```
        275                 280                 285

Thr Val Tyr His Ala Thr Gly Gly Gln Gly Leu Asn Leu Thr Glu Ile
    290                 295                 300

Asp Gly Thr Pro Tyr His Ala Phe Glu Ser Pro Ala Pro Ile Gly Phe
305                 310                 315                 320

Pro Asp Leu Gly Glu Cys Asp Trp His Ile Asn Ala Ser Pro Ala Asn
                325                 330                 335

Ala Phe Thr Asp Gly Ser Ile Ile His Arg Ile Asp Val Ala Gln Asp
            340                 345                 350

Ser Thr Phe Ala Pro His Leu Gly Thr Ile His Tyr Thr Asn Ala Asp
        355                 360                 365

Tyr Asn Ala Asn Val Gly Leu Ile Cys Ser Leu Glu Trp Leu Ser Pro
    370                 375                 380

Pro Ser Gly Gly Ala Pro Lys Val Asn Pro Trp Ala Ile Pro Arg Tyr
385                 390                 395                 400

Gly Ser Thr Leu Thr Glu Ala Ala Gln Leu Ala Pro Pro Ile Tyr Pro
                405                 410                 415

Pro Gly Phe Gly Glu Ala Ile Val Phe Phe Met Ser Asp Phe Pro Ile
            420                 425                 430

Ala Asn Gly Ser Asp Gly Leu Ser Val Pro Cys Thr Ile Pro Gln Glu
        435                 440                 445

Phe Val Thr His Phe Val Asn Glu Gln Ala Pro Thr Arg Gly Glu Ala
    450                 455                 460

Ala Leu Leu His Tyr Val Asp Pro Asp Thr His Arg Asn Leu Gly Glu
465                 470                 475                 480

Phe Lys Leu Tyr Pro Glu Gly Phe Met Thr Cys Val Pro Asn Ser Ser
                485                 490                 495

Gly Ser Gly Pro Gln Thr Leu Pro Ile Asn Gly Val Phe Thr Phe Ile
            500                 505                 510

Ser Trp Val Ser Arg Phe Tyr Gln Leu Lys Pro Val Gly Thr Thr Gly
        515                 520                 525

Pro Val Arg Arg Leu Gly Ile Arg Arg Ser
    530                 535


<210> SEQ ID NO 32
<211> LENGTH: 538
<212> TYPE: PRT
<213> ORGANISM: Artificial
<220> FEATURE:
<223> OTHER INFORMATION: Amino acid sequence of S(GII.12)+P(GI.5)
      fusion VP1

<400> SEQUENCE: 32

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95
```

```
Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Gln Lys Thr
    210                 215                 220

Arg Pro Phe Ser Val Pro Asn Ile Pro Leu Gln Leu Leu Ser Asn Ser
225                 230                 235                 240

Arg Val Pro Asn Leu Ile Gln Ser Met Val Leu Ser Pro Asp Gln Ala
                245                 250                 255

Gln Asn Val Gln Phe Gln Asn Gly Arg Cys Thr Thr Asp Gly Gln Leu
            260                 265                 270

Leu Gly Thr Thr Pro Val Ser Val Ser Gln Ile Leu Lys Phe Arg Gly
        275                 280                 285

Lys Val Ser Ala Gly Ser Lys Val Ile Asn Leu Thr Glu Leu Asp Gly
    290                 295                 300

Ser Pro Phe Leu Ala Phe Glu Ala Pro Ala Pro Thr Gly Phe Pro Asp
305                 310                 315                 320

Leu Gly Thr Ser Asp Trp His Val Glu Met Ser Leu Asn Ser Asn Ser
                325                 330                 335

Gln Ser Ser Gly Asn Pro Ile Leu Leu Arg Asp Ile His Pro Asn Ser
            340                 345                 350

Ser Glu Phe Val Pro His Leu Gly Ser Val Cys Val Thr Ala Ala Ile
        355                 360                 365

Glu Val Ala Gly Asp Tyr Thr Gly Thr Ile Gln Trp Thr Ser Gln Pro
    370                 375                 380

Ser Asn Val Thr Pro Val Pro Asp Val Asn Phe Trp Thr Ile Pro His
385                 390                 395                 400

Tyr Gly Ser Asn Leu Ala Glu Ala Ser Gln Leu Ala Pro Val Val Tyr
                405                 410                 415

Pro Pro Gly Phe Gly Glu Ala Ile Val Tyr Phe Met Ser Pro Ile Pro
            420                 425                 430

Gly Pro Asn Thr Ala His Lys Pro Asn Leu Val Pro Cys Leu Leu Pro
        435                 440                 445

Gln Glu Phe Val Thr His Phe Val Ser Glu Gln Ala Pro Ser Met Gly
    450                 455                 460

Glu Ala Ala Leu Val His Tyr Val Asp Pro Asp Thr Asn Arg Asn Leu
465                 470                 475                 480

Gly Glu Phe Lys Leu Tyr Pro Glu Gly Phe Ile Thr Cys Val Pro Asn
                485                 490                 495

Gly Thr Gly Pro Gln Gln Leu Pro Leu Asn Gly Val Phe Val Phe Ala
            500                 505                 510

Ser Trp Val Ser Arg Phe Tyr Gln Leu Lys Pro Val Gly Thr Ala Ser
```

```
        515                 520                 525

Ser Ala Arg Gly Arg Leu Gly Val Arg Arg
    530                 535


<210> SEQ ID NO 33
<211> LENGTH: 535
<212> TYPE: PRT
<213> ORGANISM: Artificial
<220> FEATURE:
<223> OTHER INFORMATION: Amino acid sequence of S(GII.12)+P(GII.1)
      fusion VP1

<400> SEQUENCE: 33

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Ser Asn Ser
225                 230                 235                 240

Arg Phe Pro Val Pro Ile Asp Glu Leu Tyr Thr Ser Pro Asn Glu Gly
                245                 250                 255

Val Val Val Gln Pro Gln Asn Gly Arg Ser Thr Leu Asp Gly Glu Leu
            260                 265                 270

Leu Gly Thr Thr Gln Leu Val Pro Ser Asn Ile Cys Ala Leu Arg Gly
        275                 280                 285

Arg Ile Asn Ala Gln Val Pro Asp Asp His His Gln Trp Asn Leu Gln
    290                 295                 300

Val Thr Asn Ala Asn Gly Thr Ser Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335
```

```
Ser Gln Arg Asn Pro Asp Asn Thr Cys Arg Ala His Asp Gly Val Leu
            340                 345                 350

Ala Thr Trp Ser Pro Lys Phe Thr Pro Lys Leu Gly Ser Val Val Leu
        355                 360                 365

Gly Thr Trp Glu Glu Ser Asp Leu Asp Leu Asn Gln Pro Thr Arg Phe
    370                 375                 380

Thr Pro Val Gly Leu Tyr Asp Thr Gly His Phe Asp Gln Trp Val Leu
385                 390                 395                 400

Pro Asn Tyr Ser Gly Arg Leu Thr Leu Asn Met Asn Leu Ala Pro Ser
                405                 410                 415

Val Ala Pro Leu Phe Pro Gly Glu Gln Ile Leu Phe Phe Arg Ser His
            420                 425                 430

Ile Pro Leu Lys Gly Gly Thr Ser Asn Gly Ala Ile Asp Cys Leu Leu
        435                 440                 445

Pro Gln Glu Trp Ile Gln His Phe Tyr Gln Glu Ser Ala Pro Ser Pro
    450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495

Ser Gly Ser Arg Pro Ile Val Val Pro Pro Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535


<210> SEQ ID NO 34
<211> LENGTH: 542
<212> TYPE: PRT
<213> ORGANISM: Artificial
<220> FEATURE:
<223> OTHER INFORMATION: Amino acid sequence of S(GII.12)+P(GII.2)
      fusion VP1

<400> SEQUENCE: 34

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160
```

Val Arg Asn Asn Phe Phe His Tyr Asn Gln Gln Asn Glu Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Ser Pro
195 200 205

Asp Phe Asp Phe Asn Tyr Leu Val Pro Pro Thr Val Glu Ser Lys Thr
210 215 220

Lys Pro Phe Thr Leu Pro Ile Leu Thr Leu Gly Glu Leu Ser Asn Ser
225 230 235 240

Arg Phe Pro Val Ser Ile Asp Gln Met Tyr Thr Ser Pro Asn Glu Val
245 250 255

Ile Ser Val Gln Cys Gln Asn Gly Arg Cys Thr Leu Asp Gly Glu Leu
260 265 270

Gln Gly Thr Thr Gln Leu Gln Val Ser Gly Ile Cys Ala Phe Lys Gly
275 280 285

Glu Val Thr Ala His Leu His Asp Asn Asp His Leu Tyr Asn Val Thr
290 295 300

Ile Thr Asn Leu Asn Gly Ser Pro Phe Asp Pro Ser Glu Asp Ile Pro
305 310 315 320

Ala Pro Leu Gly Val Pro Asp Phe Gln Gly Arg Val Phe Gly Val Ile
325 330 335

Ser Gln Arg Asp Lys His Asn Thr Pro Gly His Asn Glu Pro Ala Asn
340 345 350

Arg Ala His Asp Ala Val Val Pro Thr Tyr Thr Ala Gln Tyr Thr Pro
355 360 365

Lys Leu Gly Gln Ile Gln Ile Gly Thr Trp Gln Thr Asp Asp Leu Thr
370 375 380

Val Asn Gln Pro Val Lys Phe Thr Pro Val Gly Leu Asn Asp Thr Asp
385 390 395 400

His Phe Asn Gln Trp Val Val Pro Arg Tyr Ala Gly Ala Leu Asn Leu
405 410 415

Asn Thr Asn Leu Ala Pro Ser Val Ala Pro Val Phe Pro Gly Glu Arg
420 425 430

Leu Leu Phe Phe Arg Ser Tyr Ile Pro Leu Lys Gly Gly Tyr Gly Thr
435 440 445

Pro Ala Ile Asp Cys Leu Leu Pro Gln Glu Trp Val Gln His Phe Tyr
450 455 460

Gln Glu Ala Ala Pro Ser Met Ser Glu Val Ala Leu Val Arg Tyr Ile
465 470 475 480

Asn Pro Asp Thr Gly Arg Ala Leu Phe Glu Ala Lys Leu His Arg Ala
485 490 495

Gly Phe Met Thr Val Ser Ser Asn Thr Ser Ala Pro Val Val Val Pro
500 505 510

Ala Asn Gly Tyr Phe Arg Phe Asp Ser Trp Val Asn Gln Phe Tyr Ser
515 520 525

Leu Ala Pro Met Gly Thr Gly Asn Gly Arg Arg Arg Ile Gln
530 535 540

<210> SEQ ID NO 35
<211> LENGTH: 548
<212> TYPE: PRT
<213> ORGANISM: Artificial
<220> FEATURE:

<223> OTHER INFORMATION: Amino acid sequence of S(GII.12)+P(GII.3) fusion VP1

<400> SEQUENCE: 35

Met Lys Met Ala Ser Asn Asp Ala Ala Pro Ser Asn Asp Gly Ala Ala
1 5 10 15

Gly Leu Val Pro Glu Val Asn Asn Glu Thr Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Leu Asn Phe Val Gln Ala Pro Asn Gly Glu Phe
50 55 60

Thr Val Ser Pro Arg Asn Ser Pro Gly Glu Val Leu Leu Asn Leu Glu
65 70 75 80

Leu Gly Pro Glu Leu Asn Pro Tyr Leu Ala His Leu Ser Arg Met Tyr
85 90 95

Asn Gly Tyr Ala Gly Gly Val Glu Val Gln Val Leu Leu Ala Gly Asn
100 105 110

Ala Phe Thr Ala Gly Lys Leu Val Phe Ala Ala Val Pro Pro His Phe
115 120 125

Pro Leu Glu Asn Ile Ser Pro Gly Gln Ile Thr Met Phe Pro His Val
130 135 140

Ile Ile Asp Val Arg Thr Leu Glu Pro Val Leu Leu Pro Leu Pro Asp
145 150 155 160

Val Arg Asn Asn Phe Phe His Tyr Asn Gln Gln Asn Glu Pro Arg Met
165 170 175

Arg Leu Val Ala Met Leu Tyr Thr Pro Leu Arg Ser Asn Gly Ser Gly
180 185 190

Asp Asp Val Phe Thr Val Ser Cys Arg Val Leu Thr Arg Pro Ser Pro
195 200 205

Asp Phe Asp Phe Asn Tyr Leu Val Pro Pro Thr Val Glu Ser Lys Thr
210 215 220

Lys Pro Phe Ser Leu Pro Ile Leu Thr Ile Ser Glu Met Ser Asn Ser
225 230 235 240

Arg Phe Pro Val Pro Ile Asp Ser Leu His Thr Ser Pro Thr Glu Asn
245 250 255

Ile Val Val Gln Cys Gln Asn Gly Arg Val Thr Leu Asp Gly Glu Leu
260 265 270

Met Gly Thr Thr Gln Leu Leu Pro Ser Gln Ile Cys Ala Phe Arg Gly
275 280 285

Thr Leu Thr Arg Ser Thr Ser Arg Ala Ser Asp Gln Ala Asp Thr Ala
290 295 300

Thr Pro Arg Leu Phe Asn Tyr Tyr Trp His Ile Gln Leu Asp Asn Leu
305 310 315 320

Asn Gly Thr Pro Tyr Asp Pro Ala Glu Asp Ile Pro Ala Pro Leu Gly
325 330 335

Thr Pro Asp Phe Arg Gly Lys Val Phe Gly Val Ala Ser Gln Arg Asn
340 345 350

Pro Asp Ala Thr Thr Arg Ala His Glu Ala Lys Ile Asp Thr Thr Ser
355 360 365

Gly Arg Phe Thr Pro Lys Leu Gly Ser Leu Glu Ile Ser Thr Glu Ser
370 375 380

Gly Asp Phe Asp Gln Asn Gln Pro Thr Arg Phe Thr Pro Val Gly Ile
385 390 395 400

```
Gly Val Asp His Glu Pro Asp Phe Gln Gln Trp Ala Leu Pro Asp Tyr
                405                 410                 415

Ala Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ser Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Arg Phe Met Thr Ile Ala Lys Ser Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545


<210> SEQ ID NO 36
<211> LENGTH: 540
<212> TYPE: PRT
<213> ORGANISM: Artificial
<220> FEATURE:
<223> OTHER INFORMATION: Amino acid sequence of S(GII.12)+P(GII.4)
      fusion VP1

<400> SEQUENCE: 36

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
```

```
        195                 200                 205

Asp Phe Asp Phe Asn Tyr Leu Val Pro Pro Thr Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540


<210> SEQ ID NO 37
<211> LENGTH: 540
<212> TYPE: PRT
<213> ORGANISM: Artificial
<220> FEATURE:
<223> OTHER INFORMATION: Amino acid sequence of S(GII.12)+P(GII.5)
      fusion VP1

<400> SEQUENCE: 37

Met Lys Met Ala Ser Asn Asp Ala Ala Pro Ser Asn Asp Gly Ala Ala
1               5                   10                  15
```

-continued

```
Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Val Leu Thr Leu Gly Glu Leu Ser Asn Ser
225                 230                 235                 240

Arg Phe Pro Leu Ser Ile Asp Glu Met Val Thr Ser Pro Asn Glu Ser
                245                 250                 255

Ile Val Val Gln Pro Gln Asn Gly Arg Val Thr Leu Asp Gly Glu Leu
            260                 265                 270

Leu Gly Thr Thr Gln Leu Gln Ala Cys Asn Ile Cys Ser Ile Arg Gly
        275                 280                 285

Lys Val Thr Gly Gln Val Pro Asn Glu Gln His Met Trp Asn Leu Glu
    290                 295                 300

Ile Thr Asn Leu Asn Gly Thr Gln Phe Asp Pro Thr Asp Asp Val Pro
305                 310                 315                 320

Ala Pro Leu Gly Val Pro Asp Phe Ala Gly Glu Val Phe Gly Val Leu
                325                 330                 335

Ser Gln Arg Asn Arg Gly Glu Ser Asn Pro Ala Asn Arg Ala His Asp
            340                 345                 350

Ala Val Val Ala Thr Tyr Ser Asp Lys Tyr Thr Pro Lys Leu Gly Leu
        355                 360                 365

Val Gln Ile Gly Thr Trp Asn Thr Asn Asp Val Glu Asn Gln Pro Thr
    370                 375                 380

Lys Phe Thr Pro Ile Gly Leu Asn Glu Val Ala Asn Gly His Arg Phe
385                 390                 395                 400

Glu Gln Trp Thr Leu Pro Arg Tyr Ser Gly Ala Leu Thr Leu Asn Met
                405                 410                 415

Asn Leu Ala Pro Ala Val Ala Pro Leu Phe Pro Gly Glu Arg Leu Leu
            420                 425                 430

Phe Phe Arg Ser Tyr Val Pro Leu Lys Gly Gly Phe Gly Asn Pro Ala
```

```
        435                 440                 445

Ile Asp Cys Leu Val Pro Gln Glu Trp Val Gln His Phe Tyr Gln Glu
    450                 455                 460

Ser Ala Pro Ser Leu Gly Asp Val Ala Leu Val Arg Tyr Val Asn Pro
465                 470                 475                 480

Asp Thr Gly Arg Val Leu Phe Glu Ala Lys Leu His Lys Gly Gly Phe
                485                 490                 495

Leu Thr Val Ser Ser Thr Ser Thr Gly Pro Val Val Val Pro Ala Asn
            500                 505                 510

Gly Tyr Phe Arg Phe Asp Ser Trp Val Asn Gln Phe Tyr Ser Leu Ala
        515                 520                 525

Pro Met Gly Thr Gly Asn Gly Arg Arg Arg Phe Gln
    530                 535                 540


<210> SEQ ID NO 38
<211> LENGTH: 548
<212> TYPE: PRT
<213> ORGANISM: Artificial
<220> FEATURE:
<223> OTHER INFORMATION: Amino acid sequence of S(GII.12)+P(GII.6)
      fusion VP1

<400> SEQUENCE: 38

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Ser Leu Pro Ile Leu Thr Leu Gly Glu Leu Ser Asn Ser
225                 230                 235                 240

Arg Phe Pro Ala Pro Ile Asp Met Leu Tyr Thr Asp Pro Asn Glu Gly
                245                 250                 255
```

Ile Val Val Gln Pro Gln Asn Gly Arg Cys Thr Leu Asp Gly Thr Leu
260 265 270

Gln Gly Thr Thr Gln Leu Val Pro Thr Gln Ile Cys Ala Phe Arg Gly
275 280 285

Thr Leu Ile Gly Gln Thr Ser Arg Ser Pro Asp Ser Thr Asp Ser Ala
290 295 300

Pro Arg Arg Arg Asp His Pro Leu His Val Gln Leu Lys Asn Leu Asp
305 310 315 320

Gly Thr Gln Tyr Asp Pro Thr Asp Glu Val Pro Ala Val Leu Gly Ala
325 330 335

Ile Asp Phe Lys Gly Thr Val Phe Gly Val Ala Ser Gln Arg Asp Val
340 345 350

Ser Gly Gln Gln Val Gly Ala Thr Arg Ala His Glu Val His Ile Asn
355 360 365

Thr Thr Asp Pro Arg Tyr Thr Pro Lys Leu Gly Ser Ile Leu Met Tyr
370 375 380

Ser Glu Ser Asp Asp Phe Val Thr Gly Gln Pro Val Arg Phe Thr Pro
385 390 395 400

Ile Gly Met Gly Asp Asn Asp Trp His Gln Trp Glu Leu Pro Asp Tyr
405 410 415

Pro Gly His Leu Thr Leu Asn Met Asn Leu Ala Pro Ala Val Ala Pro
420 425 430

Ala Phe Pro Gly Glu Arg Ile Leu Phe Phe Arg Ser Ile Val Pro Ser
435 440 445

Ala Gly Gly Tyr Gly Ser Gly Gln Ile Asp Cys Leu Ile Pro Gln Glu
450 455 460

Trp Val Gln His Phe Tyr Gln Glu Ala Ala Pro Ser Gln Ser Ala Val
465 470 475 480

Ala Leu Ile Arg Tyr Val Asn Pro Asp Thr Gly Arg Asn Ile Phe Glu
485 490 495

Ala Lys Leu His Arg Glu Gly Phe Ile Thr Val Ala Asn Ser Gly Asn
500 505 510

Asn Pro Ile Val Val Pro Pro Asn Gly Tyr Phe Arg Phe Glu Ala Trp
515 520 525

Val Asn Gln Phe Tyr Thr Leu Thr Pro Met Gly Thr Gly Gln Gly Arg
530 535 540

Arg Arg Asp Gln
545

<210> SEQ ID NO 39
<211> LENGTH: 540
<212> TYPE: PRT
<213> ORGANISM: Artificial
<220> FEATURE:
<223> OTHER INFORMATION: Amino acid sequence of S(GII.12)+P(GII.7) fusion VP1

<400> SEQUENCE: 39

Met Lys Met Ala Ser Asn Asp Ala Ala Pro Ser Asn Asp Gly Ala Ala
1 5 10 15

Gly Leu Val Pro Glu Val Asn Asn Glu Thr Met Ala Leu Glu Pro Val
20 25 30

Ala Gly Ala Ser Ile Ala Ala Pro Leu Thr Gly Gln Asn Asn Val Ile
35 40 45

Asp Pro Trp Ile Arg Leu Asn Phe Val Gln Ala Pro Asn Gly Glu Phe
50 55 60

```
Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Gln Phe Thr Leu Pro Ile Leu Lys Ile Ser Glu Met Thr Asn Ser
225                 230                 235                 240

Arg Phe Pro Val Pro Val Glu Met Met Tyr Thr Ala Arg Asn Glu Asn
                245                 250                 255

Gln Val Val Gln Pro Gln Asn Gly Arg Val Thr Leu Asp Gly Glu Leu
            260                 265                 270

Leu Gly Thr Thr Pro Leu Leu Ala Val Asn Ile Cys Lys Phe Lys Gly
        275                 280                 285

Glu Val Ile Ala Lys Asn Gly Asp Val Arg Ser Tyr Arg Met Asp Met
    290                 295                 300

Glu Ile Thr Asn Thr Asp Gly Thr Pro Ile Asp Pro Thr Glu Asp Thr
305                 310                 315                 320

Pro Gly Pro Ile Gly Ser Pro Asp Phe Gln Gly Ile Leu Phe Gly Val
                325                 330                 335

Ala Ser Gln Arg Asn Lys Asn Glu Gln Asn Pro Ala Thr Arg Ala His
            340                 345                 350

Glu Ala Asn Ile Asn Thr Gly Gly Asp Gln Tyr Ala Pro Lys Leu Ala
        355                 360                 365

Gln Val Lys Phe Phe Ser Glu Ser Gln Asp Phe Glu Val His Gln Pro
    370                 375                 380

Thr Val Phe Thr Pro Val Gly Val Ala Gly Asp Thr Ser His Pro Phe
385                 390                 395                 400

Arg Gln Trp Val Leu Pro Arg Tyr Gly Gly His Leu Thr Asn Asn Thr
                405                 410                 415

His Leu Ala Pro Ala Val Ala Pro Leu Phe Pro Gly Glu Gln Ile Leu
            420                 425                 430

Phe Phe Arg Ser Gln Ile Pro Ser Ser Gly Gly His Glu Leu Gly Tyr
        435                 440                 445

Met Asp Cys Leu Val Pro Gln Glu Trp Val Gln His Phe Tyr Gln Glu
    450                 455                 460

Ala Ala Thr Ala Gln Ser Glu Val Ala Leu Ile Arg Phe Ile Asn Pro
465                 470                 475                 480
```

```
Asp Thr Gly Arg Val Leu Phe Glu Ala Lys Leu His Lys Gln Gly Phe
            485                 490                 495

Ile Thr Val Ala His Thr Gly Asp Asn Pro Ile Val Met Pro Pro Asn
            500                 505                 510

Gly Tyr Phe Arg Phe Glu Ala Trp Val Asn Gln Phe Tyr Ser Leu Ala
        515                 520                 525

Pro Val Gly Thr Gly Asn Gly Arg Arg Arg Ile Gln
    530                 535                 540


<210> SEQ ID NO 40
<211> LENGTH: 542
<212> TYPE: PRT
<213> ORGANISM: Artificial
<220> FEATURE:
<223> OTHER INFORMATION: Amino acid sequence of S(GII.12)+P(GII.13)
      fusion VP1

<400> SEQUENCE: 40

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Ser Glu Leu Thr Asn Ser
225                 230                 235                 240

Arg Phe Pro Ile Ser Ile Glu Gln Leu Tyr Thr Ala Pro Asn Glu Asn
                245                 250                 255

Asn Val Val Gln Cys Gln Asn Gly Arg Cys Thr Leu Asp Gly Glu Leu
            260                 265                 270

Gln Gly Thr Thr Gln Leu Leu Ser Ser Ala Val Cys Ser Tyr Arg Gly
        275                 280                 285

Arg Thr Val Ala Asn Ser Gly Asp Asn Trp Asp Gln Asn Val Leu Gln
    290                 295                 300
```

```
Leu Thr Tyr Pro Ser Gly Ala Ser Tyr Asp Pro Thr Asp Glu Val Pro
305                 310                 315                 320

Ala Pro Leu Gly Thr Gln Asp Phe Ser Gly Ile Leu Tyr Gly Val Leu
                325                 330                 335

Thr Gln Asp Asn Val Arg Glu Asn Thr Gly Glu Ala Lys Asn Ala Lys
            340                 345                 350

Gly Val Tyr Ile Ser Thr Thr Ser Gly Lys Phe Thr Pro Lys Ile Gly
        355                 360                 365

Ser Ile Gly Leu His Ser Ile Thr Glu Asp Val Arg Pro Asn Gln Gln
    370                 375                 380

Ser Arg Phe Thr Pro Val Gly Val Ala Gln Asn Glu Asn Thr Pro Phe
385                 390                 395                 400

Gln Gln Trp Val Leu Pro His Tyr Ala Gly Ala Leu Ala Leu Asn Thr
                405                 410                 415

Asn Leu Ala Pro Ala Val Ala Pro Thr Phe Pro Gly Glu Gln Leu Leu
            420                 425                 430

Phe Phe Arg Ser Arg Val Pro Cys Val Gln Gly Leu Gln Gly Gln Asp
        435                 440                 445

Ala Phe Ile Asp Cys Leu Leu Pro Gln Glu Trp Val Asn His Phe Tyr
    450                 455                 460

Gln Glu Ala Ala Pro Ser Gln Ala Asp Val Ala Leu Ile Arg Tyr Val
465                 470                 475                 480

Asn Pro Asp Thr Gly Arg Thr Leu Phe Glu Ala Lys Leu His Arg Ser
                485                 490                 495

Gly Phe Ile Thr Val Ser His Thr Gly Ala Tyr Pro Leu Val Val Pro
            500                 505                 510

Pro Asn Gly His Phe Arg Phe Asp Ser Trp Val Asn Gln Phe Tyr Ser
        515                 520                 525

Leu Ala Pro Met Gly Thr Gly Asn Gly Arg Arg Arg Val Gln
    530                 535                 540


<210> SEQ ID NO 41
<211> LENGTH: 536
<212> TYPE: PRT
<213> ORGANISM: Artificial
<220> FEATURE:
<223> OTHER INFORMATION: Amino acid sequence of S(GII.12)+P(GII.14)
      fusion VP1

<400> SEQUENCE: 41

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
```

```
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Asn Phe Thr Leu Pro Val Leu Arg Val Ser Glu Met Thr Asn Ser
225                 230                 235                 240

Arg Phe Pro Val Val Leu Asp Gln Met Tyr Thr Ser Arg Asn Glu Asn
                245                 250                 255

Ile Ile Val Gln Pro Gln Asn Gly Arg Cys Thr Thr Asp Gly Glu Leu
            260                 265                 270

Leu Gly Thr Thr Ile Leu Gln Ser Val Ser Ile Cys Asn Phe Lys Gly
        275                 280                 285

Thr Met Gln Ala Lys Leu Asn Glu Glu Pro Arg Tyr Gln Leu Gln Leu
    290                 295                 300

Thr Asn Leu Asp Gly Ser Pro Ile Asp Pro Thr Asp Asp Met Pro Ala
305                 310                 315                 320

Pro Leu Gly Thr Pro Asp Phe Gln Ala Met Leu Tyr Gly Val Ala Ser
                325                 330                 335

Gln Arg Ser Ser Ile Asp Asn Ala Thr Arg Ala His Asp Ala Gln Ile
            340                 345                 350

Asp Thr Ala Gly Asp Thr Phe Ala Pro Lys Ile Gly Gln Val Arg Phe
        355                 360                 365

Lys Ser Ser Ser Asn Asp Phe Asp Leu His Asp Pro Thr Lys Phe Thr
    370                 375                 380

Pro Ile Gly Val Asn Val Asp Asp Gln His Pro Phe Arg Gln Trp Ser
385                 390                 395                 400

Leu Pro Asn Tyr Gly Gly His Leu Ala Leu Asn Asn His Leu Ala Pro
                405                 410                 415

Ala Val Thr Pro Leu Phe Pro Gly Glu Gln Ile Leu Phe Phe Arg Ser
            420                 425                 430

Tyr Ile Pro Ser Ala Gly Gly His Thr Asp Gly Ala Met Asp Cys Leu
        435                 440                 445

Leu Pro Gln Glu Trp Val Glu His Phe Tyr Gln Glu Ala Ala Pro Ser
    450                 455                 460

Gln Ser Asp Ile Ala Leu Val Arg Phe Ile Asn Pro Asp Thr Gly Arg
465                 470                 475                 480

Val Leu Phe Glu Ala Lys Leu His Lys Gln Gly Phe Leu Thr Ile Ala
                485                 490                 495

Ala Ser Gly Asp His Pro Ile Val Met Pro Thr Asn Gly Tyr Phe Arg
            500                 505                 510

Phe Glu Ala Trp Val Asn Pro Phe Tyr Thr Leu Ala Pro Val Gly Thr
        515                 520                 525

Gly Ser Gly Arg Arg Arg Ile Gln
    530                 535
```

<210> SEQ ID NO 42
<211> LENGTH: 538
<212> TYPE: PRT
<213> ORGANISM: Artificial
<220> FEATURE:
<223> OTHER INFORMATION: Amino acid sequence of S(GII.12)+P(GII.17) fusion VP1

<400> SEQUENCE: 42

```
Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
```

-continued

```
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460

Pro Ser Gln Ser Asp Val Ala Leu Ile Arg Tyr Val Asn Pro Asp Thr
465                 470                 475                 480

Gly Arg Thr Leu Phe Glu Ala Lys Leu His Arg Ser Gly Tyr Ile Thr
                485                 490                 495

Val Ala His Ser Gly Asp Tyr Pro Leu Val Val Pro Ala Asn Gly Tyr
            500                 505                 510

Phe Arg Phe Asp Ser Trp Val Asn Gln Phe Tyr Ser Leu Ala Pro Met
        515                 520                 525

Gly Thr Gly Asn Gly Arg Arg Arg Ala Gln
    530                 535


<210> SEQ ID NO 43
<211> LENGTH: 539
<212> TYPE: PRT
<213> ORGANISM: Artificial
<220> FEATURE:
<223> OTHER INFORMATION: Amino acid sequence of S(GII.12)+P(GII.21)
      fusion VP1

<400> SEQUENCE: 43

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Leu Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Val Pro Pro His Phe
        115                 120                 125

Pro Leu Glu Asn Ile Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Asn Glu Pro Arg Met
                165                 170                 175
```

-continued

```
Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Ala Pro Ile Asp Gln Leu Tyr Thr Ser Pro Asn Ala Asp
                245                 250                 255

Val Val Val Gln Pro Gln Asn Gly Arg Cys Thr Leu Asp Gly Glu Leu
            260                 265                 270

Gln Gly Thr Thr Gln Leu Leu Thr Thr Ala Ile Cys Ser Tyr Arg Gly
        275                 280                 285

Met Thr Ser Asn Pro Thr Ser Asp Tyr Trp Asp Asp His Leu Leu His
    290                 295                 300

Leu Val His Pro Asn Gly Ala Thr Tyr Asp Pro Thr Glu Asp Val Pro
305                 310                 315                 320

Ala Pro Phe Gly Thr Gln Asp Phe Arg Gly Ile Leu Tyr Gly Met Leu
                325                 330                 335

Thr Gln Asn Pro Arg Thr Ser Gly Asp Glu Ala Ala Asn Ser His Gly
            340                 345                 350

Ile Tyr Ile Ser Ser Thr Ser Glu Lys Phe Thr Pro Lys Leu Gly Thr
        355                 360                 365

Ile Gly Leu His Gln Val Gln Gly Asp Ile Ala Ser Asn Gln Gln Ser
    370                 375                 380

Lys Phe Thr Pro Val Gly Ile Ala Val Asn Gly Asn Thr Pro Phe Arg
385                 390                 395                 400

Gln Trp Glu Leu Pro Asn Tyr Ser Gly Ala Leu Thr Leu Asn Thr Asn
                405                 410                 415

Leu Ala Pro Ala Val Gly Pro Asn Phe Pro Gly Glu Gln Ile Leu Phe
            420                 425                 430

Phe Arg Ser Asn Val Pro Ser Val Gln Gly Gly Gln Pro Ile Glu Ile
        435                 440                 445

Asp Cys Leu Ile Pro Gln Glu Trp Val Ser His Phe Tyr Gln Glu Ser
    450                 455                 460

Ala Pro Ser Gln Ser Asp Val Ala Leu Val Arg Tyr Val Asn Pro Asp
465                 470                 475                 480

Thr Gly Arg Thr Ile Phe Glu Ala Lys Leu His Arg Gln Gly Phe Ile
                485                 490                 495

Thr Ile Ala Ala Thr Gly Ser Asn Pro Val Val Val Pro Pro Asn Gly
            500                 505                 510

Tyr Phe Arg Phe Asp Ser Trp Val Asn Gln Phe Tyr Ala Leu Ala Pro
        515                 520                 525

Met Gly Thr Gly Asn Gly Arg Arg Arg Val Gln
    530                 535
```

<210> SEQ ID NO 44
<211> LENGTH: 543
<212> TYPE: PRT
<213> ORGANISM: Norovirus GI.5/Siklos/Hun5407/2013/HUN

<400> SEQUENCE: 44

```
Met Met Met Ala Ser Lys Asp Ala Pro Ser Ser Ala Asp Gly Ala Asn
1               5                   10                  15
```

```
Gly Ala Gly Gln Leu Val Pro Glu Val Asn Asn Ala Glu Pro Leu Pro
            20                  25                  30

Leu Asp Pro Val Ala Gly Ala Ser Thr Ala Leu Ala Thr Ala Gly Gln
        35                  40                  45

Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Val Ile
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Ile Ile Ala Asp Val Arg Thr Leu Glu Pro Ile Glu Ile
145                 150                 155                 160

Pro Leu Glu Asp Val Arg Asn Thr Leu Tyr His Thr Asn Asp Asn Gln
                165                 170                 175

Pro Thr Met Arg Leu Leu Cys Met Leu Tyr Thr Pro Leu Arg Thr Gly
            180                 185                 190

Gly Gly Ser Gly Gly Thr Asp Ala Phe Val Val Ala Gly Arg Val Leu
        195                 200                 205

Thr Cys Pro Ser Ser Asp Phe Asn Phe Leu Phe Leu Val Pro Pro Thr
    210                 215                 220

Val Glu Gln Lys Thr Arg Pro Phe Ser Val Pro Asn Ile Pro Leu Gln
225                 230                 235                 240

Leu Leu Ser Asn Ser Arg Val Pro Asn Leu Ile Gln Ser Met Val Leu
                245                 250                 255

Ser Pro Asp Gln Ala Gln Asn Val Gln Phe Gln Asn Gly Arg Cys Thr
            260                 265                 270

Thr Asp Gly Gln Leu Leu Gly Thr Thr Pro Val Ser Val Ser Gln Ile
        275                 280                 285

Leu Lys Phe Arg Gly Lys Val Ser Ala Gly Ser Lys Val Ile Asn Leu
    290                 295                 300

Thr Glu Leu Asp Gly Ser Pro Phe Leu Ala Phe Glu Ala Pro Ala Pro
305                 310                 315                 320

Thr Gly Phe Pro Asp Leu Gly Thr Ser Asp Trp His Val Glu Met Ser
                325                 330                 335

Leu Asn Ser Asn Ser Gln Ser Ser Gly Asn Pro Ile Leu Leu Arg Asp
            340                 345                 350

Ile His Pro Asn Ser Ser Glu Phe Val Pro His Leu Gly Ser Val Cys
        355                 360                 365

Val Thr Ala Ala Ile Glu Val Ala Gly Asp Tyr Thr Gly Thr Ile Gln
    370                 375                 380

Trp Thr Ser Gln Pro Ser Asn Val Thr Pro Val Pro Asp Val Asn Phe
385                 390                 395                 400

Trp Thr Ile Pro His Tyr Gly Ser Asn Leu Ala Glu Ala Ser Gln Leu
                405                 410                 415

Ala Pro Val Val Tyr Pro Pro Gly Phe Gly Glu Ala Ile Val Tyr Phe
            420                 425                 430
```

```
Met Ser Pro Ile Pro Gly Pro Asn Thr Ala His Lys Pro Asn Leu Val
        435                 440                 445

Pro Cys Leu Leu Pro Gln Glu Phe Val Thr His Phe Val Ser Glu Gln
    450                 455                 460

Ala Pro Ser Met Gly Glu Ala Ala Leu Val His Tyr Val Asp Pro Asp
465                 470                 475                 480

Thr Asn Arg Asn Leu Gly Glu Phe Lys Leu Tyr Pro Glu Gly Phe Ile
                485                 490                 495

Thr Cys Val Pro Asn Gly Thr Gly Pro Gln Gln Leu Pro Leu Asn Gly
            500                 505                 510

Val Phe Val Phe Ala Ser Trp Val Ser Arg Phe Tyr Gln Leu Lys Pro
        515                 520                 525

Val Gly Thr Ala Ser Ser Ala Arg Gly Arg Leu Gly Val Arg Arg
    530                 535                 540


<210> SEQ ID NO 45
<211> LENGTH: 535
<212> TYPE: PRT
<213> ORGANISM: Norovirus GII.1/Ascension208/2010/USA

<400> SEQUENCE: 45

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Leu Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Thr Leu Pro Ile Leu Thr Ile Gly Glu Leu Ser Asn Ser
225                 230                 235                 240

Arg Phe Pro Val Pro Ile Asp Glu Leu Tyr Thr Ser Pro Asn Glu Gly
                245                 250                 255

Val Val Val Gln Pro Gln Asn Gly Arg Ser Thr Leu Asp Gly Glu Leu
            260                 265                 270
```

```
Leu Gly Thr Thr Gln Leu Val Pro Ser Asn Ile Cys Ala Leu Arg Gly
        275                 280                 285

Arg Ile Asn Ala Gln Val Pro Asp Asp His His Gln Trp Asn Leu Gln
    290                 295                 300

Val Thr Asn Ala Asn Gly Thr Ser Phe Asp Pro Thr Glu Asp Val Pro
305                 310                 315                 320

Ala Pro Leu Gly Thr Pro Asp Phe Leu Ala Asn Ile Tyr Gly Val Thr
                325                 330                 335

Ser Gln Arg Asn Pro Asp Asn Thr Cys Arg Ala His Asp Gly Val Leu
            340                 345                 350

Ala Thr Trp Ser Pro Lys Phe Thr Pro Lys Leu Gly Ser Val Val Leu
        355                 360                 365

Gly Thr Trp Glu Glu Ser Asp Leu Asp Leu Asn Gln Pro Thr Arg Phe
    370                 375                 380

Thr Pro Val Gly Leu Tyr Asp Thr Gly His Phe Asp Gln Trp Val Leu
385                 390                 395                 400

Pro Asn Tyr Ser Gly Arg Leu Thr Leu Asn Met Asn Leu Ala Pro Ser
                405                 410                 415

Val Ala Pro Leu Phe Pro Gly Glu Gln Ile Leu Phe Phe Arg Ser His
            420                 425                 430

Ile Pro Leu Lys Gly Gly Thr Ser Asn Gly Ala Ile Asp Cys Leu Leu
        435                 440                 445

Pro Gln Glu Trp Ile Gln His Phe Tyr Gln Glu Ser Ala Pro Ser Pro
    450                 455                 460

Thr Asp Val Ala Leu Ile Arg Tyr Thr Asn Pro Asp Thr Gly Arg Val
465                 470                 475                 480

Leu Phe Glu Ala Lys Leu His Arg Gln Gly Phe Ile Thr Val Ala Asn
                485                 490                 495

Ser Gly Ser Arg Pro Ile Val Val Pro Pro Asn Gly Tyr Phe Arg Phe
            500                 505                 510

Asp Ser Trp Val Asn Gln Phe Tyr Ser Leu Ala Pro Met Gly Thr Gly
        515                 520                 525

Asn Gly Arg Arg Arg Val Gln
    530                 535


<210> SEQ ID NO 46
<211> LENGTH: 536
<212> TYPE: PRT
<213> ORGANISM: Norovirus GII.14/8610/Saga/2008/JP

<400> SEQUENCE: 46

Met Lys Met Ala Ser Asn Asp Ala Thr Pro Ser Asp Asp Gly Ala Ala
1               5                   10                  15

Gly Leu Val Pro Glu Ile Asn Asn Glu Val Met Ala Leu Glu Pro Val
            20                  25                  30

Ala Gly Ala Ser Ile Ala Ala Pro Val Val Gly Gln Gln Asn Ile Ile
        35                  40                  45

Asp Pro Trp Ile Arg Asn Asn Phe Val Gln Ala Pro Ala Gly Glu Phe
    50                  55                  60

Thr Val Ser Pro Arg Asn Ser Pro Gly Glu Leu Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
```

-continued

```
            100                 105                 110

Ala Phe Thr Ala Gly Lys Ile Leu Phe Ala Ala Ile Pro Pro Ser Phe
        115                 120                 125

Pro Tyr Glu Asn Leu Ser Pro Ala Gln Leu Thr Met Cys Pro His Val
    130                 135                 140

Ile Val Asp Val Arg Gln Leu Glu Pro Val Leu Leu Pro Met Pro Asp
145                 150                 155                 160

Ile Arg Asn Val Phe Tyr His Tyr Asn Gln Asn Asn Ser Pro Lys Leu
                165                 170                 175

Arg Leu Val Ala Met Leu Tyr Thr Pro Leu Arg Ala Asn Asn Ser Gly
            180                 185                 190

Asp Asp Val Phe Thr Val Ser Cys Arg Val Leu Thr Arg Pro Ser Pro
        195                 200                 205

Asp Phe Gln Phe Thr Phe Leu Val Pro Pro Thr Val Glu Ser Lys Thr
    210                 215                 220

Lys Asn Phe Thr Leu Pro Val Leu Arg Val Ser Glu Met Thr Asn Ser
225                 230                 235                 240

Arg Phe Pro Val Val Leu Asp Gln Met Tyr Thr Ser Arg Asn Glu Asn
                245                 250                 255

Ile Ile Val Gln Pro Gln Asn Gly Arg Cys Thr Thr Asp Gly Glu Leu
            260                 265                 270

Leu Gly Thr Thr Ile Leu Gln Ser Val Ser Ile Cys Asn Phe Lys Gly
        275                 280                 285

Thr Met Gln Ala Lys Leu Asn Glu Glu Pro Arg Tyr Gln Leu Gln Leu
    290                 295                 300

Thr Asn Leu Asp Gly Ser Pro Ile Asp Pro Thr Asp Asp Met Pro Ala
305                 310                 315                 320

Pro Leu Gly Thr Pro Asp Phe Gln Ala Met Leu Tyr Gly Val Ala Ser
                325                 330                 335

Gln Arg Ser Ser Ile Asp Asn Ala Thr Arg Ala His Asp Ala Gln Ile
            340                 345                 350

Asp Thr Ala Gly Asp Thr Phe Ala Pro Lys Ile Gly Gln Val Arg Phe
        355                 360                 365

Lys Ser Ser Ser Asn Asp Phe Asp Leu His Asp Pro Thr Lys Phe Thr
    370                 375                 380

Pro Ile Gly Val Asn Val Asp Asp Gln His Pro Phe Arg Gln Trp Ser
385                 390                 395                 400

Leu Pro Asn Tyr Gly Gly His Leu Ala Leu Asn Asn His Leu Ala Pro
                405                 410                 415

Ala Val Thr Pro Leu Phe Pro Gly Glu Gln Ile Leu Phe Phe Arg Ser
            420                 425                 430

Tyr Ile Pro Ser Ala Gly Gly His Thr Asp Gly Ala Met Asp Cys Leu
        435                 440                 445

Leu Pro Gln Glu Trp Val Glu His Phe Tyr Gln Glu Ala Ala Pro Ser
    450                 455                 460

Gln Ser Asp Ile Ala Leu Val Arg Phe Ile Asn Pro Asp Thr Gly Arg
465                 470                 475                 480

Val Leu Phe Glu Ala Lys Leu His Lys Gln Gly Phe Leu Thr Ile Ala
                485                 490                 495

Ala Ser Gly Asp His Pro Ile Val Met Pro Thr Asn Gly Tyr Phe Arg
            500                 505                 510

Phe Glu Ala Trp Val Asn Pro Phe Tyr Thr Leu Ala Pro Val Gly Thr
        515                 520                 525
```

```
Gly Ser Gly Arg Arg Arg Ile Gln
    530                 535


<210> SEQ ID NO 47
<211> LENGTH: 539
<212> TYPE: PRT
<213> ORGANISM: Norovirus GII.21/Salisbury150/2011/USA

<400> SEQUENCE: 47

Met Lys Met Ala Ser Asn Asp Ala Ala Pro Ser Asn Asp Gly Ala Thr
1               5                   10                  15

Gly Leu Val Pro Glu Ile Asn Thr Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Asn Asn Phe Val Gln Ala Pro Asn Gly Glu Phe
    50                  55                  60

Thr Val Ser Pro Arg Asn Ser Pro Gly Glu Ile Leu Met Asn Leu Glu
65                  70                  75                  80

Leu Gly Pro Asp Leu Asn Pro Tyr Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Asp Met Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Val Phe Tyr His Phe Asn Asn Gln Pro Ala Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Lys Thr
    210                 215                 220

Lys Pro Phe Thr Leu Pro Ile Leu Thr Ile Gly Glu Leu Thr Asn Ser
225                 230                 235                 240

Arg Phe Pro Ala Pro Ile Asp Gln Leu Tyr Thr Ser Pro Asn Ala Asp
                245                 250                 255

Val Val Val Gln Pro Gln Asn Gly Arg Cys Thr Leu Asp Gly Glu Leu
            260                 265                 270

Gln Gly Thr Thr Gln Leu Leu Thr Thr Ala Ile Cys Ser Tyr Arg Gly
        275                 280                 285

Met Thr Ser Asn Pro Thr Ser Asp Tyr Trp Asp Asp His Leu Leu His
    290                 295                 300

Leu Val His Pro Asn Gly Ala Thr Tyr Asp Pro Thr Glu Asp Val Pro
305                 310                 315                 320

Ala Pro Phe Gly Thr Gln Asp Phe Arg Gly Ile Leu Tyr Gly Met Leu
                325                 330                 335

Thr Gln Asn Pro Arg Thr Ser Gly Asp Glu Ala Ala Asn Ser His Gly
            340                 345                 350

Ile Tyr Ile Ser Ser Thr Ser Glu Lys Phe Thr Pro Lys Leu Gly Thr
```

```
        355                 360                 365

Ile Gly Leu His Gln Val Gln Gly Asp Ile Ala Ser Asn Gln Gln Ser
    370                 375                 380

Lys Phe Thr Pro Val Gly Ile Ala Val Asn Gly Asn Thr Pro Phe Arg
385                 390                 395                 400

Gln Trp Glu Leu Pro Asn Tyr Ser Gly Ala Leu Thr Leu Asn Thr Asn
                405                 410                 415

Leu Ala Pro Ala Val Gly Pro Asn Phe Pro Gly Glu Gln Ile Leu Phe
            420                 425                 430

Phe Arg Ser Asn Val Pro Ser Val Gln Gly Gly Gln Pro Ile Glu Ile
        435                 440                 445

Asp Cys Leu Ile Pro Gln Glu Trp Val Ser His Phe Tyr Gln Glu Ser
    450                 455                 460

Ala Pro Ser Gln Ser Asp Val Ala Leu Val Arg Tyr Val Asn Pro Asp
465                 470                 475                 480

Thr Gly Arg Thr Ile Phe Glu Ala Lys Leu His Arg Gln Gly Phe Ile
                485                 490                 495

Thr Ile Ala Ala Thr Gly Ser Asn Pro Val Val Val Pro Pro Asn Gly
            500                 505                 510

Tyr Phe Arg Phe Asp Ser Trp Val Asn Gln Phe Tyr Ala Leu Ala Pro
        515                 520                 525

Met Gly Thr Gly Asn Gly Arg Arg Arg Val Gln
    530                 535


<210> SEQ ID NO 48
<211> LENGTH: 545
<212> TYPE: PRT
<213> ORGANISM: Artificial
<220> FEATURE:
<223> OTHER INFORMATION: Amino acid sequence of S(GI.5)+P(GII.4) fusion
      VP1

<400> SEQUENCE: 48

Met Met Met Ala Ser Lys Asp Ala Pro Ser Ser Ala Asp Gly Ala Asn
1               5                   10                  15

Gly Ala Gly Gln Leu Val Pro Glu Val Asn Asn Ala Glu Pro Leu Pro
            20                  25                  30

Leu Asp Pro Val Ala Gly Ala Ser Thr Ala Leu Ala Thr Ala Gly Gln
        35                  40                  45

Val Asn Met Ile Asp Pro Trp Ile Phe Asn Asn Phe Val Gln Ala Pro
    50                  55                  60

Gln Gly Glu Phe Thr Ile Ser Pro Asn Asn Thr Pro Gly Asp Ile Leu
65                  70                  75                  80

Phe Asp Leu Gln Leu Gly Pro His Leu Asn Pro Phe Leu Ala His Leu
                85                  90                  95

Ser Gln Met Tyr Asn Gly Trp Val Gly Asn Met Arg Val Arg Val Ile
            100                 105                 110

Leu Ala Gly Asn Ala Phe Thr Ala Gly Lys Val Ile Ile Cys Cys Val
        115                 120                 125

Pro Pro Gly Phe Gln Ser Arg Thr Leu Ser Ile Ala Gln Ala Thr Leu
    130                 135                 140

Phe Pro His Ile Ile Ala Asp Val Arg Thr Leu Glu Pro Ile Glu Ile
145                 150                 155                 160

Pro Leu Glu Asp Val Arg Asn Thr Leu Tyr His Thr Asn Asp Asn Gln
                165                 170                 175
```

```
Pro Thr Met Arg Leu Leu Cys Met Leu Tyr Thr Pro Leu Arg Thr Gly
            180                 185                 190

Gly Gly Ser Gly Gly Thr Asp Ala Phe Val Val Ala Gly Arg Val Leu
        195                 200                 205

Thr Cys Pro Ser Ser Asp Phe Asn Phe Leu Phe Leu Val Pro Pro Thr
    210                 215                 220

Val Glu Ser Arg Thr Lys Pro Phe Ser Val Pro Val Leu Thr Val Glu
225                 230                 235                 240

Glu Met Thr Asn Ser Arg Phe Pro Ile Pro Leu Glu Lys Leu Phe Thr
                245                 250                 255

Gly Pro Ser Ser Ala Phe Val Val Gln Pro Gln Asn Gly Arg Cys Thr
            260                 265                 270

Thr Asp Gly Val Leu Leu Gly Thr Thr Gln Leu Ser Pro Val Asn Ile
        275                 280                 285

Cys Thr Phe Arg Gly Asp Val Thr His Ile Thr Gly Ser Arg Asn Tyr
    290                 295                 300

Thr Met Asn Leu Ala Ser Gln Asn Trp Asn Asp Tyr Asp Pro Thr Glu
305                 310                 315                 320

Glu Ile Pro Ala Pro Leu Gly Thr Pro Asp Phe Val Gly Lys Ile Gln
                325                 330                 335

Gly Val Leu Thr Gln Thr Thr Arg Thr Asp Gly Ser Thr Arg Gly His
            340                 345                 350

Lys Ala Thr Val Tyr Thr Gly Ser Ala Asp Phe Ala Pro Lys Leu Gly
        355                 360                 365

Arg Val Gln Phe Glu Thr Asp Thr Asp Arg Asp Phe Glu Ala Asn Gln
    370                 375                 380

Asn Thr Lys Phe Thr Pro Val Gly Val Ile Gln Asp Gly Gly Thr Thr
385                 390                 395                 400

His Arg Asn Glu Pro Gln Gln Trp Val Leu Pro Ser Tyr Ser Gly Arg
                405                 410                 415

Asn Thr His Asn Val His Leu Ala Pro Ala Val Ala Pro Thr Phe Pro
            420                 425                 430

Gly Glu Gln Leu Leu Phe Phe Arg Ser Thr Met Pro Gly Cys Ser Gly
        435                 440                 445

Tyr Pro Asn Met Asp Leu Asp Cys Leu Leu Pro Gln Glu Trp Val Gln
    450                 455                 460

Tyr Phe Tyr Gln Glu Ala Ala Pro Ala Gln Ser Asp Val Ala Leu Leu
465                 470                 475                 480

Arg Phe Val Asn Pro Asp Thr Gly Arg Val Leu Phe Glu Cys Lys Leu
                485                 490                 495

His Lys Ser Gly Tyr Val Thr Val Ala His Thr Gly Gln His Asp Leu
            500                 505                 510

Val Ile Pro Pro Asn Gly Tyr Phe Arg Phe Asp Ser Trp Val Asn Gln
        515                 520                 525

Phe Tyr Thr Leu Ala Pro Met Gly Asn Gly Thr Gly Arg Arg Arg Ala
    530                 535                 540

Val
545
```

<210> SEQ ID NO 49
<211> LENGTH: 538
<212> TYPE: PRT
<213> ORGANISM: Artificial
<220> FEATURE:
<223> OTHER INFORMATION: Amino acid sequence of S(GII.1)+P(GI.3) fusion

VP1

<400> SEQUENCE: 49

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Leu Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Gln Lys Thr
    210                 215                 220

Lys Pro Phe Ser Val Pro Asn Leu Pro Leu Asn Val Leu Ser Asn Ser
225                 230                 235                 240

Arg Val Pro Ser Leu Ile Lys Ser Met Met Val Ser Gln Asp His Gly
                245                 250                 255

Gln Met Val Gln Phe Gln Asn Gly Arg Val Thr Leu Asp Gly Gln Leu
            260                 265                 270

Gln Gly Thr Thr Pro Thr Ser Ala Ser Gln Leu Cys Lys Ile Arg Gly
        275                 280                 285

Thr Val Tyr His Ala Thr Gly Gly Gln Gly Leu Asn Leu Thr Glu Ile
    290                 295                 300

Asp Gly Thr Pro Tyr His Ala Phe Glu Ser Pro Ala Pro Ile Gly Phe
305                 310                 315                 320

Pro Asp Leu Gly Glu Cys Asp Trp His Ile Asn Ala Ser Pro Ala Asn
                325                 330                 335

Ala Phe Thr Asp Gly Ser Ile Ile His Arg Ile Asp Val Ala Gln Asp
            340                 345                 350

Ser Thr Phe Ala Pro His Leu Gly Thr Ile His Tyr Thr Asn Ala Asp
        355                 360                 365

Tyr Asn Ala Asn Val Gly Leu Ile Cys Ser Leu Glu Trp Leu Ser Pro
    370                 375                 380

Pro Ser Gly Gly Ala Pro Lys Val Asn Pro Trp Ala Ile Pro Arg Tyr
385                 390                 395                 400

```
Gly Ser Thr Leu Thr Glu Ala Ala Gln Leu Ala Pro Pro Ile Tyr Pro
                405                 410                 415

Pro Gly Phe Gly Glu Ala Ile Val Phe Phe Met Ser Asp Phe Pro Ile
            420                 425                 430

Ala Asn Gly Ser Asp Gly Leu Ser Val Pro Cys Thr Ile Pro Gln Glu
        435                 440                 445

Phe Val Thr His Phe Val Asn Glu Gln Ala Pro Thr Arg Gly Glu Ala
    450                 455                 460

Ala Leu Leu His Tyr Val Asp Pro Asp Thr His Arg Asn Leu Gly Glu
465                 470                 475                 480

Phe Lys Leu Tyr Pro Glu Gly Phe Met Thr Cys Val Pro Asn Ser Ser
                485                 490                 495

Gly Ser Gly Pro Gln Thr Leu Pro Ile Asn Gly Val Phe Thr Phe Ile
            500                 505                 510

Ser Trp Val Ser Arg Phe Tyr Gln Leu Lys Pro Val Gly Thr Thr Gly
        515                 520                 525

Pro Val Arg Arg Leu Gly Ile Arg Arg Ser
    530                 535


<210> SEQ ID NO 50
<211> LENGTH: 540
<212> TYPE: PRT
<213> ORGANISM: Artificial
<220> FEATURE:
<223> OTHER INFORMATION: Amino acid sequence of S(GII.1)+P(GII.4)
      fusion VP1

<400> SEQUENCE: 50

Met Lys Met Ala Ser Asn Asp Ala Ala Pro Ser Asn Asp Gly Ala Ala
1               5                   10                  15

Gly Leu Val Pro Glu Val Asn Asn Glu Thr Met Ala Leu Glu Pro Val
            20                  25                  30

Ala Gly Ala Ser Ile Ala Ala Pro Leu Thr Gly Gln Asn Asn Val Ile
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Leu Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Arg Thr
    210                 215                 220
```

Lys Pro Phe Ser Val Pro Val Leu Thr Val Glu Glu Met Thr Asn Ser
225 230 235 240

Arg Phe Pro Ile Pro Leu Glu Lys Leu Phe Thr Gly Pro Ser Ser Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly
275 280 285

Asp Val Thr His Ile Thr Gly Ser Arg Asn Tyr Thr Met Asn Leu Ala
290 295 300

Ser Gln Asn Trp Asn Asp Tyr Asp Pro Thr Glu Glu Ile Pro Ala Pro
305 310 315 320

Leu Gly Thr Pro Asp Phe Val Gly Lys Ile Gln Gly Val Leu Thr Gln
325 330 335

Thr Thr Arg Thr Asp Gly Ser Thr Arg Gly His Lys Ala Thr Val Tyr
340 345 350

Thr Gly Ser Ala Asp Phe Ala Pro Lys Leu Gly Arg Val Gln Phe Glu
355 360 365

Thr Asp Thr Asp Arg Asp Phe Glu Ala Asn Gln Asn Thr Lys Phe Thr
370 375 380

Pro Val Gly Val Ile Gln Asp Gly Gly Thr Thr His Arg Asn Glu Pro
385 390 395 400

Gln Gln Trp Val Leu Pro Ser Tyr Ser Gly Arg Asn Thr His Asn Val
405 410 415

His Leu Ala Pro Ala Val Ala Pro Thr Phe Pro Gly Glu Gln Leu Leu
420 425 430

Phe Phe Arg Ser Thr Met Pro Gly Cys Ser Gly Tyr Pro Asn Met Asp
435 440 445

Leu Asp Cys Leu Leu Pro Gln Glu Trp Val Gln Tyr Phe Tyr Gln Glu
450 455 460

Ala Ala Pro Ala Gln Ser Asp Val Ala Leu Leu Arg Phe Val Asn Pro
465 470 475 480

Asp Thr Gly Arg Val Leu Phe Glu Cys Lys Leu His Lys Ser Gly Tyr
485 490 495

Val Thr Val Ala His Thr Gly Gln His Asp Leu Val Ile Pro Pro Asn
500 505 510

Gly Tyr Phe Arg Phe Asp Ser Trp Val Asn Gln Phe Tyr Thr Leu Ala
515 520 525

Pro Met Gly Asn Gly Thr Gly Arg Arg Arg Ala Val
530 535 540

<210> SEQ ID NO 51
<211> LENGTH: 538
<212> TYPE: PRT
<213> ORGANISM: Artificial
<220> FEATURE:
<223> OTHER INFORMATION: Amino acid sequence of S(GII.1)+P(GII.17)
fusion VP1

<400> SEQUENCE: 51

Met Lys Met Ala Ser Asn Asp Ala Ala Pro Ser Asn Asp Gly Ala Ala
1 5 10 15

Gly Leu Val Pro Glu Val Asn Asn Glu Thr Met Ala Leu Glu Pro Val
20 25 30

Ala Gly Ala Ser Ile Ala Ala Pro Leu Thr Gly Gln Asn Asn Val Ile

```
        35                  40                  45

Asp Pro Trp Ile Arg Met Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Phe Leu Ala His Leu Ser Arg Met Tyr
                85                  90                  95

Asn Gly Tyr Ala Gly Gly Val Glu Val Gln Val Leu Leu Ala Gly Asn
            100                 105                 110

Ala Phe Thr Ala Gly Lys Leu Val Phe Ala Ala Ile Pro Pro His Phe
        115                 120                 125

Pro Leu Glu Asn Leu Ser Pro Gly Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Gln Pro Glu Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Asn Tyr Leu Val Pro Pro Thr Val Glu Ser Lys Thr
    210                 215                 220

Lys Pro Phe Ser Leu Pro Ile Leu Thr Leu Ser Glu Leu Thr Asn Ser
225                 230                 235                 240

Arg Phe Pro Val Pro Ile Asp Ser Leu Phe Thr Ala Gln Asn Asn Val
                245                 250                 255

Leu Gln Val Gln Cys Gln Asn Gly Arg Cys Thr Leu Asp Gly Glu Leu
            260                 265                 270

Gln Gly Thr Thr Gln Leu Leu Pro Ser Gly Ile Cys Ala Phe Arg Gly
        275                 280                 285

Arg Val Thr Ala Glu Thr Asp His Arg Asp Lys Trp His Met Gln Leu
    290                 295                 300

Gln Asn Leu Asn Gly Thr Thr Tyr Asp Pro Thr Asp Asp Val Pro Ala
305                 310                 315                 320

Pro Leu Gly Thr Pro Asp Phe Lys Gly Val Val Phe Gly Val Ala Ser
                325                 330                 335

Gln Arg Asn Val Gly Asn Asp Ala Pro Gly Ser Thr Arg Ala His Glu
            340                 345                 350

Ala Val Ile Ser Thr Tyr Ser Pro Gln Phe Val Pro Lys Leu Gly Ser
        355                 360                 365

Val Asn Phe Arg Ser Asn Asp Asn Asp Phe Gln Leu Gln Pro Thr Lys
    370                 375                 380

Phe Thr Pro Val Gly Ile Asn Asp Asp Gly Asp His Pro Phe Arg Gln
385                 390                 395                 400

Trp Glu Leu Pro Asp Tyr Ser Gly Leu Leu Thr Leu Asn Met Asn Leu
                405                 410                 415

Ala Pro Pro Val Ala Pro Asn Phe Pro Gly Glu Gln Leu Leu Phe Phe
            420                 425                 430

Arg Ser Phe Val Pro Cys Ser Gly Gly Tyr Asn Gln Gly Ile Val Asp
        435                 440                 445

Cys Leu Ile Pro Gln Glu Trp Ile Gln His Phe Tyr Gln Glu Ser Ala
    450                 455                 460
```

Pro Ser Gln Ser Asp Val Ala Leu Ile Arg Tyr Val Asn Pro Asp Thr
465 470 475 480

Gly Arg Thr Leu Phe Glu Ala Lys Leu His Arg Ser Gly Tyr Ile Thr
485 490 495

Val Ala His Ser Gly Asp Tyr Pro Leu Val Val Pro Ala Asn Gly Tyr
500 505 510

Phe Arg Phe Asp Ser Trp Val Asn Gln Phe Tyr Ser Leu Ala Pro Met
515 520 525

Gly Thr Gly Asn Gly Arg Arg Arg Ala Gln
530 535

<210> SEQ ID NO 52
<211> LENGTH: 540
<212> TYPE: PRT
<213> ORGANISM: Artificial
<220> FEATURE:
<223> OTHER INFORMATION: Amino acid sequence of S(GII.14)+P(GII.4) fusion VP1

<400> SEQUENCE: 52

Met Lys Met Ala Ser Asn Asp Ala Thr Pro Ser Asp Asp Gly Ala Ala
1 5 10 15

Gly Leu Val Pro Glu Ile Asn Asn Glu Val Met Ala Leu Glu Pro Val
20 25 30

Ala Gly Ala Ser Ile Ala Ala Pro Val Val Gly Gln Gln Asn Ile Ile
35 40 45

Asp Pro Trp Ile Arg Asn Asn Phe Val Gln Ala Pro Ala Gly Glu Phe
50 55 60

Thr Val Ser Pro Arg Asn Ser Pro Gly Glu Leu Leu Leu Asp Leu Glu
65 70 75 80

Leu Gly Pro Glu Leu Asn Pro Tyr Leu Ala His Leu Ala Arg Met Tyr
85 90 95

Asn Gly His Ala Gly Gly Met Glu Val Gln Ile Val Leu Ala Gly Asn
100 105 110

Ala Phe Thr Ala Gly Lys Ile Leu Phe Ala Ala Ile Pro Pro Ser Phe
115 120 125

Pro Tyr Glu Asn Leu Ser Pro Ala Gln Leu Thr Met Cys Pro His Val
130 135 140

Ile Val Asp Val Arg Gln Leu Glu Pro Val Leu Leu Pro Met Pro Asp
145 150 155 160

Ile Arg Asn Val Phe Tyr His Tyr Asn Gln Asn Asn Ser Pro Lys Leu
165 170 175

Arg Leu Val Ala Met Leu Tyr Thr Pro Leu Arg Ala Asn Asn Ser Gly
180 185 190

Asp Asp Val Phe Thr Val Ser Cys Arg Val Leu Thr Arg Pro Ser Pro
195 200 205

Asp Phe Gln Phe Thr Phe Leu Val Pro Pro Thr Val Glu Ser Arg Thr
210 215 220

Lys Pro Phe Ser Val Pro Val Leu Thr Val Glu Glu Met Thr Asn Ser
225 230 235 240

Arg Phe Pro Ile Pro Leu Glu Lys Leu Phe Thr Gly Pro Ser Ser Ala
245 250 255

Phe Val Val Gln Pro Gln Asn Gly Arg Cys Thr Thr Asp Gly Val Leu
260 265 270

Leu Gly Thr Thr Gln Leu Ser Pro Val Asn Ile Cys Thr Phe Arg Gly

```
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Val
    530                 535                 540


<210> SEQ ID NO 53
<211> LENGTH: 540
<212> TYPE: PRT
<213> ORGANISM: Artificial
<220> FEATURE:
<223> OTHER INFORMATION: Amino acid sequence of S(GII.21)+P(GII.4)
      fusion VP1

<400> SEQUENCE: 53

Met Lys Met Ala Ser Asn Asp Ala Ala Pro Ser Asn Asp Gly Ala Thr
1               5                   10                  15

Gly Leu Val Pro Glu Ile Asn Thr Glu Thr Leu Pro Leu Glu Pro Val
            20                  25                  30

Ala Gly Ala Ala Ile Ala Ala Pro Val Thr Gly Gln Asn Asn Ile Ile
        35                  40                  45

Asp Pro Trp Ile Arg Asn Asn Phe Val Gln Ala Pro Asn Gly Glu Phe
    50                  55                  60

Thr Val Ser Pro Arg Asn Ser Pro Gly Glu Ile Leu Met Asn Leu Glu
65                  70                  75                  80

Leu Gly Pro Asp Leu Asn Pro Tyr Leu Ala His Leu Ser Arg Met Tyr
                85                  90                  95
```

```
Asn Gly Tyr Ala Gly Gly Val Glu Val Gln Val Leu Leu Ala Gly Asn
            100                 105                 110

Ala Phe Thr Ala Gly Lys Ile Leu Phe Ala Ala Val Pro Pro Asn Phe
        115                 120                 125

Pro Val Asp Met Leu Ser Pro Ala Gln Ile Thr Met Leu Pro His Leu
    130                 135                 140

Ile Val Asp Val Arg Thr Leu Glu Pro Ile Met Ile Pro Leu Pro Asp
145                 150                 155                 160

Val Arg Asn Val Phe Tyr His Phe Asn Asn Gln Pro Ala Pro Arg Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Thr Pro
        195                 200                 205

Asp Phe Glu Phe Thr Tyr Leu Val Pro Pro Ser Val Glu Ser Arg Thr
    210                 215                 220

Lys Pro Phe Ser Val Pro Val Leu Thr Val Glu Glu Met Thr Asn Ser
225                 230                 235                 240

Arg Phe Pro Ile Pro Leu Glu Lys Leu Phe Thr Gly Pro Ser Ser Ala
                245                 250                 255

Phe Val Val Gln Pro Gln Asn Gly Arg Cys Thr Thr Asp Gly Val Leu
            260                 265                 270

Leu Gly Thr Thr Gln Leu Ser Pro Val Asn Ile Cys Thr Phe Arg Gly
        275                 280                 285

Asp Val Thr His Ile Thr Gly Ser Arg Asn Tyr Thr Met Asn Leu Ala
    290                 295                 300

Ser Gln Asn Trp Asn Asp Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Thr Asp Gly Ser Thr Arg Gly His Lys Ala Thr Val Tyr
            340                 345                 350

Thr Gly Ser Ala Asp Phe Ala Pro Lys Leu Gly Arg Val Gln Phe Glu
        355                 360                 365

Thr Asp Thr Asp Arg Asp Phe Glu Ala Asn Gln Asn Thr Lys Phe Thr
    370                 375                 380

Pro Val Gly Val Ile Gln Asp Gly Gly Thr Thr His Arg Asn Glu Pro
385                 390                 395                 400

Gln Gln Trp Val Leu Pro Ser Tyr Ser Gly Arg Asn Thr His Asn Val
                405                 410                 415

His Leu Ala Pro Ala Val Ala Pro Thr Phe Pro Gly Glu Gln Leu Leu
            420                 425                 430

Phe Phe Arg Ser Thr Met Pro Gly Cys Ser Gly Tyr Pro Asn Met Asp
        435                 440                 445

Leu Asp Cys Leu Leu Pro Gln Glu Trp Val Gln Tyr Phe Tyr Gln Glu
    450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
```

```
        515                 520                 525

Pro Met Gly Asn Gly Thr Gly Arg Arg Arg Ala Val
    530                 535                 540


<210> SEQ ID NO 54
<211> LENGTH: 1641
<212> TYPE: PRT
<213> ORGANISM: Artificial
<220> FEATURE:
<223> OTHER INFORMATION: Nucleic acid sequence of human codon-optimized
      VP1 G1.2_Leuven_2003_D2DEL3

<400> SEQUENCE: 54

Ala Thr Gly Ala Thr Gly Ala Thr Gly Gly Cys Thr Thr Cys Ala Ala
1               5                   10                  15

Ala Gly Gly Ala Thr Gly Cys Thr Cys Cys Cys Cys Ala Ala Ala Gly
            20                  25                  30

Cys Gly Cys Gly Gly Ala Cys Gly Gly Ala Gly Cys Thr Ala Gly Cys
        35                  40                  45

Gly Gly Cys Gly Cys Cys Gly Gly Ala Cys Ala Gly Thr Thr Gly Gly
    50                  55                  60

Thr Thr Cys Cys Gly Gly Ala Ala Gly Thr Cys Ala Ala Cys Ala Cys
65                  70                  75                  80

Thr Gly Cys Cys Gly Ala Thr Cys Cys Ala Cys Thr Gly Cys Cys Cys
                85                  90                  95

Ala Thr Gly Gly Ala Ala Cys Cys Cys Gly Thr Ala Gly Cys Thr Gly
            100                 105                 110

Gly Thr Cys Cys Ala Ala Cys Ala Ala Cys Cys Gly Cys Thr Gly Thr
        115                 120                 125

Thr Gly Cys Cys Ala Cys Cys Gly Cys Cys Gly Gly Cys Cys Ala Gly
    130                 135                 140

Gly Thr Thr Ala Ala Cys Ala Thr Gly Ala Thr Cys Gly Ala Thr Cys
145                 150                 155                 160

Cys Ala Thr Gly Gly Ala Thr Thr Gly Thr Thr Ala Ala Thr Ala Ala
                165                 170                 175

Cys Thr Thr Thr Gly Thr Ala Cys Ala Gly Ala Gly Cys Cys Cys Cys
            180                 185                 190

Cys Ala Gly Gly Gly Gly Gly Ala Gly Thr Thr Cys Ala Cys Ala Ala
        195                 200                 205

Thr Thr Thr Cys Thr Cys Cys Gly Ala Ala Cys Ala Ala Thr Ala Cys
    210                 215                 220

Cys Cys Cys Thr Gly Gly Gly Ala Cys Ala Thr Thr Cys Thr Gly
225                 230                 235                 240

Thr Thr Cys Gly Ala Thr Cys Thr Gly Cys Ala Ala Cys Thr Gly Gly
                245                 250                 255

Gly Cys Cys Cys Ala Cys Ala Cys Thr Thr Gly Ala Ala Thr Cys Cys
            260                 265                 270

Thr Thr Thr Cys Cys Thr Gly Ala Gly Cys Cys Ala Thr Cys Thr Thr
        275                 280                 285

Thr Cys Ala Cys Ala Gly Ala Thr Gly Thr Ala Cys Ala Ala Cys Gly
    290                 295                 300

Gly Ala Thr Gly Gly Gly Thr Thr Gly Gly Gly Ala Ala Cys Ala Thr
305                 310                 315                 320

Gly Cys Gly Thr Gly Thr Thr Cys Gly Gly Ala Thr Cys Cys Thr Cys
                325                 330                 335
```

```
Cys Thr Thr Gly Cys Thr Gly Gly Cys Ala Ala Cys Gly Cys Cys Thr
            340                 345                 350

Thr Cys Ala Gly Thr Gly Cys Thr Gly Gly Cys Ala Ala Gly Ala Thr
        355                 360                 365

Thr Ala Thr Cys Gly Thr Gly Thr Gly Cys Thr Gly Cys Gly Thr Ala
    370                 375                 380

Cys Cys Ala Cys Cys Ala Gly Gly Gly Thr Thr Thr Ala Cys Cys Thr
385                 390                 395                 400

Cys Gly Ala Gly Thr Thr Cys Ala Thr Thr Ala Ala Cys Cys Ala Thr
                405                 410                 415

Thr Gly Cys Thr Cys Ala Gly Gly Cys Cys Ala Cys Cys Cys Thr Thr
            420                 425                 430

Thr Thr Cys Cys Cys Thr Cys Ala Cys Gly Thr Gly Ala Thr Cys Gly
        435                 440                 445

Cys Ala Gly Ala Cys Gly Thr Gly Cys Gly Thr Ala Cys Cys Thr Thr
    450                 455                 460

Ala Gly Ala Ala Cys Cys Ala Ala Thr Cys Gly Ala Ala Ala Thr Gly
465                 470                 475                 480

Cys Cys Cys Cys Thr Gly Gly Ala Ala Gly Ala Thr Gly Thr Ala Cys
                485                 490                 495

Gly Gly Ala Ala Cys Gly Thr Gly Cys Thr Gly Thr Ala Cys Cys Ala
            500                 505                 510

Thr Ala Cys Thr Ala Ala Thr Gly Ala Thr Ala Ala Cys Cys Ala Gly
        515                 520                 525

Cys Cys Ala Ala Cys Gly Ala Thr Gly Ala Gly Ala Thr Thr Ala Gly
    530                 535                 540

Thr Gly Thr Gly Cys Ala Thr Gly Cys Thr Gly Thr Ala Cys Ala Cys
545                 550                 555                 560

Cys Cys Cys Cys Cys Thr Gly Ala Gly Ala Ala Cys Thr Gly Gly Ala
                565                 570                 575

Gly Gly Ala Gly Gly Thr Thr Cys Thr Gly Gly Ala Ala Ala Thr Thr
            580                 585                 590

Cys Cys Gly Ala Cys Ala Gly Thr Thr Thr Thr Gly Thr Gly Gly Thr
        595                 600                 605

Gly Gly Cys Thr Gly Gly Cys Ala Gly Gly Gly Thr Cys Cys Thr Gly
    610                 615                 620

Ala Cys Cys Gly Cys Thr Cys Cys Cys Ala Gly Thr Ala Gly Cys Gly
625                 630                 635                 640

Ala Cys Thr Thr Cys Ala Gly Cys Thr Thr Thr Thr Thr Gly Thr Thr
                645                 650                 655

Cys Cys Thr Cys Gly Thr Thr Cys Cys Thr Cys Cys Thr Ala Cys Ala
            660                 665                 670

Ala Thr Cys Gly Ala Ala Cys Ala Ala Ala Ala Ala Ala Cys Ala Ala
        675                 680                 685

Gly Ala Gly Cys Ala Thr Thr Cys Ala Cys Ala Gly Thr Gly Cys Cys
    690                 695                 700

Cys Ala Ala Cys Ala Thr Thr Cys Cys Ala Cys Thr Gly Cys Ala Gly
705                 710                 715                 720

Ala Cys Thr Thr Thr Ala Ala Gly Cys Ala Ala Thr Thr Cys Cys Ala
                725                 730                 735

Gly Gly Thr Thr Thr Cys Cys Cys Ala Gly Cys Thr Thr Gly Ala Thr
            740                 745                 750

Cys Cys Ala Gly Gly Gly Thr Ala Thr Gly Ala Thr Cys Cys Thr Thr
```

```
        755                 760                 765

Thr Cys Thr Cys Cys Cys Gly Ala Cys Gly Cys Cys Thr Cys Cys Cys
    770                 775                 780

Ala Ala Gly Thr Thr Gly Thr Gly Cys Ala Gly Thr Thr Cys Cys Ala
785                 790                 795                 800

Gly Ala Ala Thr Gly Gly Gly Ala Gly Ala Thr Gly Thr Cys Thr Thr
                805                 810                 815

Ala Thr Cys Gly Ala Cys Gly Gly Thr Cys Ala Gly Cys Thr Thr Cys
            820                 825                 830

Thr Gly Gly Gly Ala Ala Cys Ala Ala Cys Cys Cys Cys Thr Gly Cys
        835                 840                 845

Cys Ala Cys Cys Thr Cys Cys Gly Gly Gly Cys Ala Ala Cys Thr Cys
    850                 855                 860

Thr Thr Cys Cys Gly Gly Gly Thr Gly Ala Gly Ala Gly Gly Cys Ala
865                 870                 875                 880

Ala Ala Ala Thr Cys Ala Ala Thr Cys Ala Gly Gly Gly Cys Gly Cys
                885                 890                 895

Cys Ala Gly Ala Ala Cys Ala Cys Thr Gly Ala Ala Thr Cys Thr Gly
            900                 905                 910

Ala Cys Ala Gly Ala Ala Gly Thr Gly Gly Ala Cys Gly Gly Gly Ala
        915                 920                 925

Ala Ala Cys Cys Cys Thr Thr Thr Ala Thr Gly Gly Cys Gly Thr Thr
    930                 935                 940

Cys Gly Ala Thr Ala Gly Cys Cys Cys Cys Gly Cys Gly Cys Cys Cys
945                 950                 955                 960

Gly Thr Thr Gly Gly Ala Thr Thr Cys Cys Cys Thr Gly Ala Cys Thr
                965                 970                 975

Thr Cys Gly Gly Cys Ala Ala Gly Thr Gly Thr Gly Ala Thr Thr Gly
            980                 985                 990

Gly Cys Ala Cys Ala Thr Gly Cys  Gly Cys Ala Thr Cys  Ala Gly Thr
        995                 1000                1005

Ala Ala  Gly Ala Cys Thr Cys  Cys Cys Ala Ala Cys  Ala Ala Cys
    1010                 1015                 1020

Ala Cys  Thr Thr Cys Ala Thr  Cys Thr Gly Gly Ala  Gly Ala Cys
    1025                 1030                 1035

Cys Cys  Cys Ala Thr Gly Ala  Gly Gly Ala Gly Cys  Gly Thr Gly
    1040                 1045                 1050

Gly Ala  Thr Gly Thr Cys Cys  Ala Gly Ala Cys Cys  Gly Ala Cys
    1055                 1060                 1065

Gly Thr  Gly Cys Ala Gly Gly  Gly Cys Thr Thr Cys  Gly Thr Gly
    1070                 1075                 1080

Cys Cys  Gly Cys Ala Cys Thr  Thr Gly Gly Gly Ala  Thr Cys Thr
    1085                 1090                 1095

Ala Thr  Cys Cys Ala Gly Thr  Thr Cys Gly Ala Thr  Gly Ala Gly
    1100                 1105                 1110

Gly Thr  Gly Thr Thr Cys Ala  Ala Thr Cys Ala Cys  Cys Cys Thr
    1115                 1120                 1125

Ala Cys  Thr Gly Gly Cys Gly  Ala Cys Thr Ala Cys  Ala Thr Ala
    1130                 1135                 1140

Gly Gly  Cys Ala Cys Ala Ala  Thr Thr Gly Ala Gly  Thr Gly Gly
    1145                 1150                 1155

Ala Thr  Ala Ala Gly Thr Cys  Ala Ala Cys Cys Ala  Thr Cys Thr
    1160                 1165                 1170
```

Ala Cys Ala Cys Cys Thr Cys Cys Ala Gly Gly Gly Ala Cys Cys
1175 1180 1185

Gly Ala Cys Ala Thr Ala Ala Ala Cys Cys Thr Gly Thr Gly Gly
1190 1195 1200

Gly Ala Ala Ala Thr Thr Cys Cys Thr Gly Ala Thr Thr Ala Cys
1205 1210 1215

Gly Gly Gly Thr Cys Ala Thr Cys Cys Cys Thr Gly Ala Gly Thr
1220 1225 1230

Cys Ala Ala Gly Cys Thr Gly Cys Cys Ala Ala Thr Cys Thr Thr
1235 1240 1245

Gly Cys Ala Cys Cys Cys Cys Cys Thr Gly Thr Cys Thr Thr Thr
1250 1255 1260

Cys Cys Cys Cys Cys Cys Gly Gly Cys Thr Thr Thr Gly Gly Thr
1265 1270 1275

Gly Ala Gly Gly Cys Thr Cys Thr Thr Gly Thr Thr Thr Ala Cys
1280 1285 1290

Thr Thr Cys Gly Thr Cys Thr Cys Thr Gly Cys Ala Thr Thr Thr
1295 1300 1305

Cys Cys Thr Gly Gly Thr Cys Cys Thr Ala Ala Cys Ala Ala Cys
1310 1315 1320

Cys Gly Cys Thr Cys Cys Gly Cys Cys Cys Cys Thr Ala Ala Cys
1325 1330 1335

Gly Ala Thr Gly Thr Thr Cys Cys Gly Thr Gly Thr Thr Thr Gly
1340 1345 1350

Thr Thr Ala Cys Cys Cys Cys Ala Gly Gly Ala Ala Thr Ala Thr
1355 1360 1365

Gly Thr Gly Ala Cys Thr Cys Ala Thr Thr Thr Cys Gly Thr Thr
1370 1375 1380

Thr Cys Cys Gly Ala Ala Cys Ala Gly Gly Cys Ala Cys Cys Cys
1385 1390 1395

Ala Cys Cys Ala Thr Gly Gly Gly Gly Gly Ala Cys Gly Cys Thr
1400 1405 1410

Gly Cys Cys Cys Thr Gly Cys Thr Ala Cys Ala Cys Thr Ala Thr
1415 1420 1425

Gly Thr Gly Gly Ala Cys Cys Cys Cys Gly Ala Cys Ala Cys Cys
1430 1435 1440

Ala Ala Thr Ala Gly Ala Ala Ala Cys Cys Thr Cys Gly Gly Cys
1445 1450 1455

Gly Ala Gly Thr Thr Cys Ala Ala Ala Cys Thr Cys Thr Ala Cys
1460 1465 1470

Cys Cys Cys Gly Gly Gly Gly Gly Ala Thr Ala Cys Cys Thr Gly
1475 1480 1485

Ala Cys Cys Thr Gly Thr Gly Thr Thr Cys Cys Ala Ala Ala Thr
1490 1495 1500

Gly Gly Ala Gly Thr Gly Gly Gly Ala Gly Cys Ala Gly Gly Cys
1505 1510 1515

Cys Cys Ala Cys Ala Ala Cys Ala Gly Cys Thr Gly Cys Cys Cys
1520 1525 1530

Cys Thr Gly Ala Ala Thr Gly Gly Gly Gly Thr Cys Thr Thr Cys
1535 1540 1545

Cys Thr Gly Thr Thr Cys Gly Thr Thr Thr Cys Thr Thr Gly Gly
1550 1555 1560

```
Gly Thr  Gly Thr Cys Ala Cys  Gly Cys Thr Thr Thr  Thr Ala Cys
    1565                1570                1575

Cys Ala  Gly Cys Thr Gly Ala  Ala Gly Cys Cys Cys  Gly Thr Thr
    1580                1585                1590

Gly Gly  Cys Ala Cys Ala Gly  Cys Thr Thr Cys Thr  Ala Cys Gly
    1595                1600                1605

Gly Cys  Ala Cys Gly Cys Gly  Gly Cys Ala Gly Gly  Cys Thr Ala
    1610                1615                1620

Gly Gly  Gly Gly Thr Cys Cys  Gly Cys Cys Gly Ala  Ala Thr Cys
    1625                1630                1635

Thr Gly  Ala
    1640


<210> SEQ ID NO 55
<211> LENGTH: 1632
<212> TYPE: DNA
<213> ORGANISM: Artificial
<220> FEATURE:
<223> OTHER INFORMATION: Nucleic acid sequence of human codon-optimized
      VP1 GI.3_LillaEdet_2008_H2DG70

<400> SEQUENCE: 55

atgatgatgg cttccaagga tgctcccaca aacatggatg gaacaagcgg cgcggggcaa     60

cttgtgccgg aggtgtccac ggcggaaccc atttccatgg aacctgtggc cggcgcagcc    120

actgctgccg ccaccgcagg acaggtaaac atgatcgacc cctggatcat gtcaaattac    180

gttcaggctc cacaggggga gtttaccata agcccaaaca acacccccggg tgacatcttg    240

tttgacctgc agctaggacc acacttgaat ccgtttctga gtcacttggc tcagatgtat    300

aatggatggg ttggaaacat gaaggtgcgc gtgctcctgg cgggcaatgc attcacagcc    360

gggaagatta ttatctcttg cgtgccacct ggatttgcag cccagaacgt gtctatcgca    420

caggcaacca tgtttccgca tgtcatcgca gatgtgcgcg tgctagagcc catcgaggtg    480

ccccttgagg acgtgcgcaa cgtcctattc cataacaatg atagcacccc caccatgcgc    540

ttgatatgta tgttatatac tcccctccgc gccagtgggt ccagctccgg gaccgatcct    600

tttgtgattg ctgggcgggt gttgacttgt cctagccctg acttcaactt cctttttctg    660

gtgcctccaa atgtagaaca gaaaacaaag ccattcagcg tgccaaacct gccccttaac    720

gtgctgtcga attcccgagt gccttccctt attaagtcca tgatggtatc tcaggatcac    780

ggtcaaatgg tgcagtttca gaacggccga gtgacgttag acgggcagct gcagggcaca    840

accccaacca gtgccagtca gctgtgtaag atcagaggca ccgtctacca cgcaactggc    900

ggacaggggc tgaatcttac tgagatcgat ggtacccccct accatgcatt cgagtcacct    960

gcacctattg gatttcccga tcttggggag tgtgattggc atatcaatgc ttcacctgcc   1020

aacgctttca cagacgggtc tattattcat cgcattgacg tagcacagga tagcacattt   1080

gccccgcacc tgggtaccat ccactatacg aacgcagatt acaacgcaaa cgtgggtctt   1140

atctgtagcc tagagtggct atctccgcca agcggtgggg cccctaaagt taacccatgg   1200

gctattcctc ggtacgggtc tacgctgact gaggccgctc agctggcacc ccccatatat   1260

ccaccaggat tcggggaagc cattgttttc tttatgtccg attttccgat agccaacggt   1320

tcagatggcc ttagtgtccc ttgcacgatt ccacaggaat ttgtgacaca cttcgtaaac   1380

gagcaggctc ctactcgggg cgaggctgcc ttgttgcatt acgtagaccc cgatacccat   1440

agaaacctgg gcgaattcaa actctaccct gaaggtttca tgacctgcgt acctaactcc   1500
```

```
tccggcagtg gccctcaaac cttgccgatc aacggcgtgt tcacgtttat cagctgggtt   1560

tcacggtttt accaactcaa gcccgtcgga acaactgggc cagttcggag gctcgggatc   1620

agacggagct ag                                                       1632
```

<210> SEQ ID NO 56
<211> LENGTH: 1623
<212> TYPE: DNA
<213> ORGANISM: Artificial
<220> FEATURE:
<223> OTHER INFORMATION: Nucleic acid sequence of human codon-optimized VP1 GII.4_Sydney_2012_K4LM89

<400> SEQUENCE: 56

```
atgaaaatgg cctcgagtga cgctaaccct agtgacggca gcgccgccaa tcttgtgcct     60

gaggttaata atgaggtgat ggccctggag cctgtggtgg gcgcagccat agcagcgccc    120

gtggccggtc agcagaatgt gattgacccg tggatacgca acaattttgt ccaagcccct    180

ggtggggagt tcaccgttag cccgagaaat gcgccaggag aaatcctgtg gtcggcccca    240

ttgggacccg atctgaaccc ctatttgtca catctcgctc ggatgtacaa cgggtatgcc    300

ggcggatttg aagtgcaggt gattctggct gggaacgcgt tcactgctgg caaagtgatc    360

tttgcagcgg tgcctcccaa cttccccact gaaggactgt ctccaagcca ggtcacaatg    420

tttccacaca tcgtggtgga cgtacggcag ctagagcctg tcctgattcc cctccctgat    480

gtacgcaata atttctacca ctacaatcaa tccaatgatc cgaccattaa actcatcgcg    540

atgttgtaca cccctctgcg cgctaacaat gctggagacg acgtattcac cgtgtcatgc    600

agagtgctca ccagaccttc accagacttt gactttatct tcttagtgcc ccccactgtt    660

gagagccgaa ccaagccctt tagtgtcccc gtactcacag tcgaggagat gacaaatagc    720

cgctttccaa tcccccttga gaaactgttc acaggacctt cctcggcatt cgtggttcag    780

ccacagaacg gacgctgcac aactgacggc gtgctgctcg gaaccaccca gcttagccct    840

gttaatatct gtacgtttag aggcgacgta actcacataa ctggctcacg gaactatacc    900

atgaatctgg catcacagaa ttggaatgac tacgacccaa ccgaagagat tcccgcacct    960

cttggaaccc ccgactttgt gggaaaaata cagggcgtcc tgacacaaac caccagaacc   1020

gatggctcca cacggggaca caaggcaacc gtctacactg gctctgccga ttttgccccg   1080

aaactgggta gagtgcagtt tgagaccgac actgaccggg actttgaagc caatcagaat   1140

actaagttca cacctgtagg agtgattcag gacgggggca ccactcaccg gaacgagccg   1200

caacaatggg tcctgccctc ttatagcggg aggaatactc ataatgtgca tttggctcct   1260

gcagtggctc ccacgtttcc cggggaacaa ctgctctttt ttcgttcaac catgcctgga   1320

tgctccggat atcccaatat ggatctcgat tgcctgctcc cacaggaatg ggtgcagtat   1380

ttttatcaag aggccgcacc agcccaatcc gacgtcgcac ttctgcggtt cgtgaatcca   1440

gacacaggcc gcgtgttgtt tgagtgcaaa ttgcacaaat caggatacgt tacagtggct   1500

catactggac agcatgacct ggtgatccca cccaacggat attttaggtt cgactcctgg   1560

gtgaatcagt tttatacatt agcccccatg ggaatggga ctggcagacg cagggctgtc   1620

tga                                                                 1623
```

<210> SEQ ID NO 57
<211> LENGTH: 1638
<212> TYPE: DNA
<213> ORGANISM: Artificial
<220> FEATURE:

-continued

<223> OTHER INFORMATION: Nucleic acid sequence of human codon optimized
S(GI.1)+P(GI.2) fusion VP1

<400> SEQUENCE: 57

```
atgatgatgg ctagtaaaga tgcgacctcc tctgtggatg gtgcgtcagg ggcaggacaa     60

ctcgtacccg aggtaaacgc cagcgaccca cttgccatgg accccgttgc cggaagttcc    120

acagcagtgg ccacagccgg tcaagtgaat ccaattgatc cgtggattat caacaatttc    180

gtccaggcac cccagggcga gttcacaatt tcaccaaaca atacaccggg cgatgtgcta    240

ttcgatcttt ccttgggtcc tcaccttaac ccttttctac tccatctctc acagatgtac    300

aatggttggg taggaaacat gagagtccgg atcatgctgg ctggcaatgc ctttaccgct    360

ggcaagatca tcgtcagttg tattcctccc ggatttggat ctcataatct gaccattgct    420

caagcgactc tctttcccca tgtcatcgcc gacgttagga ccctggaccc catcgaggtg    480

cccctggagg acgtccggaa tgttttgttc cacaacaacg acagaaacca gcagacgatg    540

agacttgtct gtatgctcta taccccactg cggactggag gcgggactgg agactccttc    600

gttgtggcag gaagagtgat gacatgcccc tcccccgact tcaactttct ttttctggtc    660

ccaccaaccg ttgagcaaaa aacaagagca ttcacagtgc ccaacattcc actgcagact    720

ttaagcaatt ccaggtttcc cagcttgatc cagggtatga tcctttctcc cgacgcctcc    780

caagttgtgc agttccagaa tgggagatgt cttatcgacg gtcagcttct gggaacaacc    840

cctgccacct ccgggcaact cttccgggtg agaggcaaaa tcaatcaggg cgccagaaca    900

ctgaatctga cagaagtgga cgggaaaccc tttatggcgt tcgatagccc cgcgcccgtt    960

ggattccctg acttcggcaa gtgtgattgg cacatgcgca tcagtaagac tcccaacaac   1020

acttcatctg gagaccccat gaggagcgtg gatgtccaga ccgacgtgca gggcttcgtg   1080

ccgcacttgg gatctatcca gttcgatgag gtgttcaatc accctactgg cgactacata   1140

ggcacaattg agtggataag tcaaccatct acacctccag ggaccgacat aaacctgtgg   1200

gaaattcctg attacgggtc atccctgagt caagctgcca atcttgcacc ccctgtcttt   1260

ccccccggct ttggtgaggc tcttgtttac ttcgtctctg catttcctgg tcctaacaac   1320

cgctccgccc ctaacgatgt tccgtgtttg ttaccccagg aatatgtgac tcatttcgtt   1380

tccgaacagg cacccaccat gggggacgct gccctgctac actatgtgga ccccgacacc   1440

aatagaaacc tcggcgagtt caaactctac cccgggggat acctgacctg tgttccaaat   1500

ggagtgggag caggcccaca acagctgccc ctgaatgggg tcttcctgtt cgtttcttgg   1560

gtgtcacgct tttaccagct gaagcccgtt ggcacagctt ctacggcacg cggcaggcta   1620

ggggtccgcc gaatctga                                                 1638
```

<210> SEQ ID NO 58
<211> LENGTH: 1629
<212> TYPE: DNA
<213> ORGANISM: Artificial
<220> FEATURE:
<223> OTHER INFORMATION: Nucleic acid sequence of human codon optimized
S(GI.1)+P(GI.3) fusion VP1

<400> SEQUENCE: 58

```
atgatgatgg ctagtaaaga tgcgacctcc tctgtggatg gtgcgtcagg ggcaggacaa     60

ctcgtacccg aggtaaacgc cagcgaccca cttgccatgg accccgttgc cggaagttcc    120

acagcagtgg ccacagccgg tcaagtgaat ccaattgatc cgtggattat caacaatttc    180

gtccaggcac cccagggcga gttcacaatt tcaccaaaca atacaccggg cgatgtgcta    240
```

ttcgatcttt ccttgggtcc tcaccttaac ccttttctac tccatctctc acagatgtac 300
aatggttggg taggaaacat gagagtccgg atcatgctgg ctggcaatgc ctttaccgct 360
ggcaagatca tcgtcagttg tattcctccc ggatttggat ctcataatct gaccattgct 420
caagcgactc tctttcccca tgtcatcgcc gacgttagga ccctggaccc catcgaggtg 480
cccctggagg acgtccggaa tgttttgttc cacaacaacg acagaaacca gcagacgatg 540
agacttgtct gtatgctcta taccccactg cggactggag gcgggactgg agactccttc 600
gttgtggcag gaagagtgat gacatgcccc tcccccgact tcaactttct ttttctggtc 660
ccaccaaccg ttgagcagaa aacaaagcca ttcagcgtgc caaacctgcc ccttaacgtg 720
ctgtcgaatt cccgagtgcc ttcccttatt aagtccatga tggtatctca ggatcacggt 780
caaatggtgc agtttcagaa cggccgagtg acgttagacg ggcagctgca gggcacaacc 840
ccaaccagtg ccagtcagct gtgtaagatc agaggcaccg tctaccacgc aactggcgga 900
caggggctga atcttactga gatcgatggt accccctacc atgcattcga gtcacctgca 960
cctattggat ttcccgatct tggggagtgt gattggcata tcaatgcttc acctgccaac 1020
gctttcacag acgggtctat tattcatcgc attgacgtag cacaggatag cacatttgcc 1080
ccgcacctgg gtaccatcca ctatacgaac gcagattaca acgcaaacgt gggtcttatc 1140
tgtagcctag agtggctatc tccgccaagc ggtggggccc ctaaagttaa cccatgggct 1200
attcctcggt acgggtctac gctgactgag gccgctcagc tggcaccccc catatatcca 1260
ccaggattcg gggaagccat tgttttcttt atgtccgatt ttccgatagc caacggttca 1320
gatggcctta gtgtcccttg cacgattcca caggaatttg tgacacactt cgtaaacgag 1380
caggctccta ctcggggcga ggctgccttg ttgcattacg tagaccccga tacccataga 1440
aacctgggcg aattcaaact ctaccctgaa ggtttcatga cctgcgtacc taactcctcc 1500
ggcagtggcc ctcaaacctt gccgatcaac ggcgtgttca cgtttatcag ctgggtttca 1560
cggttttacc aactcaagcc cgtcggaaca actgggccag ttcggaggct cgggatcaga 1620
cggagctag 1629

<210> SEQ ID NO 59
<211> LENGTH: 1635
<212> TYPE: DNA
<213> ORGANISM: Artificial
<220> FEATURE:
<223> OTHER INFORMATION: Nucleic acid sequence of human codon optimized
S(GI.1)+P(GII.4) fusion VP1

<400> SEQUENCE: 59
atgatgatgg ctagtaaaga tgcgacctcc tctgtggatg gtgcgtcagg ggcaggacaa 60
ctcgtacccg aggtaaacgc cagcgaccca cttgccatgg accccgttgc cggaagttcc 120
acagcagtgg ccacagccgg tcaagtgaat ccaattgatc cgtggattat caacaatttc 180
gtccaggcac cccagggcga gttcacaatt tcaccaaaca atacaccggg cgatgtgcta 240
ttcgatcttt ccttgggtcc tcaccttaac ccttttctac tccatctctc acagatgtac 300
aatggttggg taggaaacat gagagtccgg atcatgctgg ctggcaatgc ctttaccgct 360
ggcaagatca tcgtcagttg tattcctccc ggatttggat ctcataatct gaccattgct 420
caagcgactc tctttcccca tgtcatcgcc gacgttagga ccctggaccc catcgaggtg 480
cccctggagg acgtccggaa tgttttgttc cacaacaacg acagaaacca gcagacgatg 540
agacttgtct gtatgctcta taccccactg cggactggag gcgggactgg agactccttc 600

```
gttgtggcag gaagagtgat gacatgcccc tcccccgact tcaactttct ttttctggtc    660

ccaccaaccg ttgagagccg aaccaagccc tttagtgtcc ccgtactcac agtcgaggag    720

atgacaaata gccgctttcc aatccccctt gagaaactgt tcacaggacc ttcctcggca    780

ttcgtggttc agccacagaa cggacgctgc acaactgacg gcgtgctgct cggaaccacc    840

cagcttagcc ctgttaatat ctgtacgttt agaggcgacg taactcacat aactggctca    900

cggaactata ccatgaatct ggcatcacag aattggaatg actacgaccc aaccgaagag    960

attcccgcac ctcttggaac cccgacttt gtgggaaaaa tacagggcgt cctgacacaa   1020

accaccagaa ccgatggctc cacacgggga cacaaggcaa ccgtctacac tggctctgcc   1080

gattttgccc cgaaactggg tagagtgcag tttgagaccg acactgaccg ggactttgaa   1140

gccaatcaga atactaagtt cacacctgta ggagtgattc aggacggggg caccactcac   1200

cggaacgagc cgcaacaatg ggtcctgccc tcttatagcg ggaggaatac tcataatgtg   1260

catttggctc ctgcagtggc tcccacgttt cccggggaac aactgctctt ttttcgttca   1320

accatgcctg gatgctccgg atatcccaat atggatctcg attgcctgct cccacaggaa   1380

tgggtgcagt atttttatca agaggccgca ccagcccaat ccgacgtcgc acttctgcgg   1440

ttcgtgaatc cagacacagg ccgcgtgttg tttgagtgca aattgcacaa atcaggatac   1500

gttacagtgg ctcatactgg acagcatgac ctggtgatcc cacccaacgg atattttagg   1560

ttcgactcct gggtgaatca gttttataca ttagccccca tggggaatgg gactggcaga   1620

cgcagggctg tctga                                                    1635
```

<210> SEQ ID NO 60
<211> LENGTH: 1644
<212> TYPE: DNA
<213> ORGANISM: Artificial
<220> FEATURE:
<223> OTHER INFORMATION: Nucleic acid sequence of human codon-optimized
VP1 GII.6_Ohio_2012_M9T020

<400> SEQUENCE: 60

```
atgaagatgg caagcaacga cgcagctccc tccaatgatg gtgccgccaa cctggtcccc     60

gaagctaata atgaggtgat ggcgttagag ccggtggttg gcgcatctat tgcagcgcct    120

gtggtcggac agcagaacat cattgatccc tggattcgcg agaacttcgt acaagctcca    180

cagggggagt tcacagtctc cccccggaac tccccgggcg agatgctgct caatctggaa    240

ctcggccctg aactaaaccc ttatctgtca cacctttcac ggatgtacaa tggctacgca    300

ggaggaatgc aagttcaggt ggtcctggcc ggcaatgctt tcaccgcggg caaaatcatc    360

tttgcggccg ttcctccaca cttccctgtc gaaaatatca acgccgccca gattactatg    420

tgcccccacg tgattgtgga tgtgcgacag ttagagccag ttctgctgcc cctgcccgac    480

atcagaaacc ggttcttcca ttacaatcaa gagaatactt cacggatgag acttgttgcg    540

atgctgtaca cccctcttcg tgcaaattcc ggcgaagacg tgttcactgt gtcttgtcga    600

gtacttaccc gacccgcccc cgatttcgaa ttcaccttcc tggttccccc tactgtggag    660

agcaagacaa aacccttcag cctcccaatc ttaacactcg ggagctgtc taattcacgc    720

ttccccgcac ctattgatat gctgtatact gaccccaacg aggggatagt ggtgcagccc    780

caaaatggac ggtgtactct cgacggcacg ctccagggca caacccaact ggtgccaacc    840

cagatttgtg cattcagggg cactttgatt gggcagacat cgagatctcc agattctact    900

gattccgcgc caaggaggag ggaccaccca ctccacgttc agttaaaaaa cctggacgga    960
```

acccagtacg accctacaga cgaggtcccc gctgtcctcg gagccatcga ctttaaagga 1020
actgtatttg gagtggcatc ccaaagggat gtctcggggc agcaggtggg agctacgaga 1080
gcacatgaag tccacattaa caccacagac ccaagatata ccccaaaact agggtcaatt 1140
ttaatgtatt cggaatcaga cgattttgtt acaggtcagc ccgtgcggtt taccccgatc 1200
ggaatggggg acaacgattg gcaccagtgg gaattgcccg attaccctgg acacctcacc 1260
ttgaatatga atctggcccc agccgtcgcg cccgccttcc ccggtgagcg gatcctcttt 1320
tttagaagca tagtgccctc cgcaggtggg tatggatcag ggcagattga ttgcctgatc 1380
ccccaagaat gggtacagca tttctaccag gaagcagccc ctagccagtc cgcagtagca 1440
ctgatcagat atgttaatcc tgatacggga aggaacatct tcgaagcaaa actgcaccgt 1500
gagggcttca ttaccgtcgc caacagtggt aataacccta ttgtggtgcc tcctaatgga 1560
tacttcaggt ttgaggcatg ggtgaatcag ttttatactc tgactcccat ggggacaggc 1620
caggggcgac gccgggatca gtga 1644

<210> SEQ ID NO 61
<211> LENGTH: 1629
<212> TYPE: DNA
<213> ORGANISM: Artificial
<220> FEATURE:
<223> OTHER INFORMATION: Nucleic acid sequence of human codon-optimized
VP1 GII.13_VA173_2010_H9AWU4

<400> SEQUENCE: 61
atgaaaatgg cttctaatga tgccgcgccc agcaatgatg gtgccgccag ccttgtgccc 60
gaagcaatta acgagacaat gcccttggag ccagtcgccg gggcttctat tgcggcccca 120
gttgctggac agacgaatat catcgatcct tggatacgga ctaattttgt tcaagctcct 180
aacggagagt tcactgtctc cccccgtaat agtcctggcg agatcctgtt gaacctcgag 240
ttggggccag atctcaatcc ttacctggct catctgtcga gaatgtacaa cgggtacgcg 300
gggggggttg aggtgcaggt cttactggca ggtaacgcat tcacagcagg caagattctg 360
tttgcggcca tccctcctaa ttttccagtg gatatgatat ctccagcaca gattacaatg 420
ctgccccatt tgatagtgga tgtgcggaca cttgaaccta tcatgatccc tttgcccgat 480
gtccgaaatg tgttttatca tttcaacaac cagccgcagc caagaatgcg tctcgtcgcg 540
atgctgtaca ccccgttgcg gtccaacggc tctggcgatg atgttttcac agtgtcgtgt 600
cgagtgttaa cccgccctac cccagatttt gagtttatat atctagttcc cccttctgtg 660
gaaagcaaga ctaaaccctt tactcttccc attctgacta tatccgagct taccaactcc 720
cggttcccca tctcaatcga gcaactgtac actgcaccca acgagaacaa cgtagtccag 780
tgccagaacg ggagatgtac cctggacggg gagctccaag ggaccacgca actgttaagt 840
tcagccgttt gcagttacag aggcaggact gtggcgaact ctggtgataa ctgggatcaa 900
aatgtgttgc agctgactta cccatccggc gcaagctacg atccaacaga tgaggtgcca 960
gcgccccttg gcacacagga tttctcagga attctatacg ggtgcttac tcaggataat 1020 gtgcgagaaa atactggcga ggccaagaat gctaaaggag tgtatataag cacgacaagc 1080
ggtaagttta cccccaaaat tggcagtatt gggctccaca gcattactga ggacgtccgc 1140
ccaaaccagc agtctcgttt cactcccgtg gggtggcac agaacgagaa cacacctttc 1200
cagcagtggg tcttgcccca ttatgcaggt gctttggcgc tcaatacaaa tctggcaccc 1260
gccgtagcgc cgacatttcc tggggagcaa ttgctgttct ttagaagccg cgtcccgtgt 1320
gttcagggct tgcagggcca ggacgcgttc attgattgcc tcttgcccca ggaatgggtc 1380
aaccactttt atcaggaggc agcgccctct caagcagatg tggccctgat aagatatgtg 1440
aatcccgaca caggacggac tttgtttgag gcaaaactcc accggtcagg attcattact 1500
gtgagtcaca caggagccta tccccttgtg gttccaccta atggccactt caggttcgac 1560
tcttgggtca atcagtttta ttcgctggca ccaatgggta ccgggaatgg tcgccgtcgg 1620
gtgcaatga 1629

<210> SEQ ID NO 62
<211> LENGTH: 1617
<212> TYPE: DNA
<213> ORGANISM: Artificial
<220> FEATURE:
<223> OTHER INFORMATION: Nucleic acid sequence of human codon-optimized VP1 GII.17_Kawa_2014_A0A077KVU6

<400> SEQUENCE: 62
atgaaaatgg catctaacga cgcagccccc tcaaacgatg gcgctgctgg actcgtgccg 60
gaggggaata atgagacact tccactagag ccggttgcag gcgccgctat agctgcccca 120
gtgacagggc agaataatat tatagaccct tggattcgga caaacttcgt gcaggcaccc 180
aacggcgagt ttacagtatc cccccggaac tccccaggtg agatactcct gaatcttgag 240
ctcggccctg acctcaatcc atatctggct catctgagcc gcatgtacaa tggttacgct 300 ggggggggtcg aagtgcaggt cctcctggcc ggaaacgcct ttaccgctgg caaaattctg 360
tttgccgccg ttccaccaaa ctttccagtc gaattcctct ctcccgcgca aataaccatg 420
ctgccacatt tgatcgttga cgtgcggacc ctggagccaa taatgattcc cctgccggat 480
gtgcgtaaca cctttttcca ttataacaat cagccaaact ctcggatgag acttgttgct 540
atgctgtaca cccccctgcg gagcaacggc agtggcgatg atgtgtttac cgtgagttgc 600
agagtcctga cgcgcccaac cccggacttc gagttcacct acctggtgcc cccttctgtg 660
gaatctaaga ccaaaccgtt ttcactgcca atcttaactc tctccgaact gactaacagc 720
cggtttccag tacccataga ttctcttttt accgctcaaa acaacgtact ccaagtccag 780
tgccagaacg gccgctgtac gcttgatggt gagttgcagg ggacaacaca gctactcccc 840
agtggcatct gtgcattccg gggccgcgtg accgctgaga cagaccatcg tgacaaatgg 900
cacatgcaac tccaaaactt aaacgggacc acctacgacc caaccgacga cgtccctgct 960
ccgctaggga ctcctgactt taagggggtg gtgttcggag tggcctctca gcggaatgtt 1020
gggaatgacg cccccggctc tacccgagct cacgaggccg ttatctcaac atatagcccc 1080
caatttgtgc ccaagctcgg atccgttaat tttcgtagta acgacaacga cttccaactg 1140
caaccaacga agtttacgcc agtggggatt aatgatgatg gagaccatcc tttccgccaa 1200
tgggaactac cagattattc tgggctgctc accctcaata tgaacctcgc cccacccgtg 1260
gcccctaatt tccccggtga gcagctgctg ttttttcgga gctttgtgcc atgcagtggc 1320
ggatataatc aaggcatcgt agactgcttg attccccaag agtggataca acatttttac 1380
caggaaagtg cgccctccca gtccgatgtg gccctgatac ggtacgttaa ccccgatacc 1440
ggaagaacat tattcgaagc gaaattgcac agatcagggt acattaccgt tgcacattcc 1500
ggcgattatc ccctggtggt tcccgccaac ggttacttta ggttcgatag ttgggtcaac 1560
cagttctatt cactagcccc aatgggcacc ggtaacggca gacgccgggc tcagtag 1617

<210> SEQ ID NO 63
<211> LENGTH: 1659
<212> TYPE: DNA
<213> ORGANISM: Artificial
<220> FEATURE:
<223> OTHER INFORMATION: Nucleic acid sequence of human codon optimized S(GI.1)+P(GII.6) fusion VP1

<400> SEQUENCE: 63

```
atgatgatgg ctagtaaaga tgcgacctcc tctgtggatg gtgcgtcagg ggcaggacaa     60

ctcgtacccg aggtaaacgc cagcgaccca cttgccatgg accccgttgc cggaagttcc    120

acagcagtgg ccacagccgg tcaagtgaat ccaattgatc cgtggattat caacaatttc    180

gtccaggcac cccagggcga gttcacaatt tcaccaaaca atacaccggg cgatgtgcta    240

ttcgatcttt ccttgggtcc tcaccttaac ccttttctac tccatctctc acagatgtac    300

aatggttggg taggaaacat gagagtccgg atcatgctgg ctggcaatgc ctttaccgct    360

ggcaagatca tcgtcagttg tattcctccc ggatttggat ctcataatct gaccattgct    420

caagcgactc tctttcccca tgtcatcgcc gacgttagga ccctggaccc catcgaggtg    480

cccctggagg acgtccggaa tgttttgttc cacaacaacg acagaaacca gcagacgatg    540

agacttgtct gtatgctcta taccccactg cggactggag gcgggactgg agactccttc    600

gttgtggcag gaagagtgat gacatgcccc tcccccgact tcaactttct ttttctggtc    660

ccaccaaccg ttgagagcaa gacaaaaccc ttcagcctcc caatcttaac actcggggag    720

ctgtctaatt cacgcttccc cgcacctatt gatatgctgt atactgaccc caacgagggg    780

atagtggtgc agccccaaaa tggacggtgt actctcgacg gcacgctcca gggcacaacc    840

caactggtgc caacccagat ttgtgcattc aggggcactt tgattgggca gacatcgaga    900

tctccagatt ctactgattc cgcgccaagg aggagggacc acccactcca cgttcagtta    960

aaaaacctgg acggaaccca gtacgaccct acagacgagg tccccgctgt cctcggagcc   1020

atcgacttta aaggaactgt atttggagtg gcatcccaaa gggatgtctc ggggcagcag   1080

gtgggagcta cgagagcaca tgaagtccac attaacacca cagacccaag atataccccca   1140

aaactagggt caattttaat gtattcggaa tcagacgatt ttgttacagg tcagcccgtg   1200

cggtttaccc cgatcggaat gggggacaac gattggcacc agtgggaatt gcccgattac   1260

cctggacacc tcaccttgaa tatgaatctg gccccagccg tcgcgcccgc cttccccggt   1320

gagcggatcc tctttttag aagcatagtg ccctccgcag gtgggtatgg atcagggcag   1380

attgattgcc tgatcccccca agaatgggta cagcatttct accaggaagc agcccctagc   1440

cagtccgcag tagcactgat cagatatgtt aatcctgata cgggaaggaa catcttcgaa   1500

gcaaaactgc accgtgaggg cttcattacc gtcgccaaca gtggtaataa ccctattgtg   1560

gtgcctccta atggatactt caggtttgag gcatgggtga atcagtttta tactctgact   1620

cccatgggga caggccaggg gcgacgccgg gatcagtga                          1659
```

<210> SEQ ID NO 64
<211> LENGTH: 1641
<212> TYPE: DNA
<213> ORGANISM: Artificial
<220> FEATURE:
<223> OTHER INFORMATION: Nucleic acid sequence of human codon optimized S(GI.1)+P(GII.13) fusion VP1

<400> SEQUENCE: 64

```
atgatgatgg ctagtaaaga tgcgacctcc tctgtggatg gtgcgtcagg ggcaggacaa     60
```

```
ctcgtacccg aggtaaacgc cagcgaccca cttgccatgg accccgttgc cggaagttcc    120

acagcagtgg ccacagccgg tcaagtgaat ccaattgatc cgtggattat caacaatttc    180

gtccaggcac cccagggcga gttcacaatt tcaccaaaca atacaccggg cgatgtgcta    240

ttcgatcttt ccttgggtcc tcaccttaac ccttttctac tccatctctc acagatgtac    300

aatggttggg taggaaacat gagagtccgg atcatgctgg ctggcaatgc ctttaccgct    360

ggcaagatca tcgtcagttg tattcctccc ggatttggat ctcataatct gaccattgct    420

caagcgactc tctttcccca tgtcatcgcc gacgttagga ccctggaccc catcgaggtg    480

cccctggagg acgtccggaa tgttttgttc cacaacaacg acagaaacca gcagacgatg    540

agacttgtct gtatgctcta taccccactg cggactggag gcgggactgg agactccttc    600

gttgtggcag gaagagtgat gacatgcccc tcccccgact tcaactttct ttttctggtc    660

ccaccaaccg ttgagagcaa gactaaaccc tttactcttc ccattctgac tatatccgag    720

cttaccaact cccggttccc catctcaatc gagcaactgt acactgcacc caacgagaac    780

aacgtagtcc agtgccagaa cggagatgt acccctggacg gggagctcca agggaccacg    840

caactgttaa gttcagccgt ttgcagttac agaggcagga ctgtggcgaa ctctggtgat    900

aactgggatc aaaatgtgtt gcagctgact tacccatccg gcgcaagcta cgatccaaca    960

gatgaggtgc cagcgcccct tggcacacag gatttctcag gaattctata cggggtgctt   1020

actcaggata atgtgcgaga aaatactggc gaggccaaga atgctaaagg agtgtatata   1080

agcacgacaa gcggtaagtt tacccccaaa attggcagta ttgggctcca cagcattact   1140

gaggacgtcc gcccaaacca gcagtctcgt ttcactcccg tgggggtggc acagaacgag   1200

aacacacctt tccagcagtg ggtcttgccc cattatgcag gtgctttggc gctcaataca   1260

aatctggcac ccgccgtagc gccgacattt cctggggagc aattgctgtt ctttagaagc   1320

cgcgtcccgt gtgttcaggg cttgcagggc caggacgcgt tcattgattg cctcttgccc   1380

caggaatggg tcaaccactt ttatcaggag gcagcgccct ctcaagcaga tgtggccctg   1440

ataagatatg tgaatcccga cacaggacgg actttgtttg aggcaaaact ccaccggtca   1500

ggattcatta ctgtgagtca cacaggagcc tatccccttg tggttccacc taatggccac   1560

ttcaggttcg actcttgggt caatcagttt tattcgctgg caccaatggg taccgggaat   1620

ggtcgccgtc gggtgcaatg a                                              1641
```

<210> SEQ ID NO 65
<211> LENGTH: 1629
<212> TYPE: DNA
<213> ORGANISM: Artificial
<220> FEATURE:
<223> OTHER INFORMATION: Nucleic acid sequence of human codon optimized S(GI.1)+P(GII.17) fusion VP1

<400> SEQUENCE: 65

```
atgatgatgg ctagtaaaga tgcgacctcc tctgtggatg gtgcgtcagg ggcaggacaa     60

ctcgtacccg aggtaaacgc cagcgaccca cttgccatgg accccgttgc cggaagttcc    120

acagcagtgg ccacagccgg tcaagtgaat ccaattgatc cgtggattat caacaatttc    180

gtccaggcac cccagggcga gttcacaatt tcaccaaaca atacaccggg cgatgtgcta    240

ttcgatcttt ccttgggtcc tcaccttaac ccttttctac tccatctctc acagatgtac    300

aatggttggg taggaaacat gagagtccgg atcatgctgg ctggcaatgc ctttaccgct    360

ggcaagatca tcgtcagttg tattcctccc ggatttggat ctcataatct gaccattgct    420
```

-continued

```
caagcgactc tctttcccca tgtcatcgcc gacgttagga ccctggaccc catcgaggtg    480

cccctggagg acgtccggaa tgttttgttc cacaacaacg acagaaacca gcagacgatg    540

agacttgtct gtatgctcta taccccactg cggactggag gcgggactgg agactccttc    600

gttgtggcag gaagagtgat gacatgcccc tcccccgact tcaactttct ttttctggtc    660

ccaccaaccg ttgagtctaa gaccaaaccg ttttcactgc caatcttaac tctctccgaa    720

ctgactaaca gccggtttcc agtacccata gattctcttt ttaccgctca aaacaacgta    780

ctccaagtcc agtgccagaa cggccgctgt acgcttgatg gtgagttgca ggggacaaca    840

cagctactcc ccagtggcat ctgtgcattc cggggccgcg tgaccgctga gacagaccat    900

cgtgacaaat ggcacatgca actccaaaac ttaaacggga ccacctacga cccaaccgac    960

gacgtccctg ctccgctagg gactcctgac tttaaggggg tggtgttcgg agtggcctct   1020

cagcggaatg ttgggaatga cgcccccggc tctacccgag ctcacgaggc cgttatctca   1080

acatatagcc cccaatttgt gcccaagctc ggatccgtta attttcgtag taacgacaac   1140

gacttccaac tgcaaccaac gaagtttacg ccagtgggga ttaatgatga tggagaccat   1200

cctttccgcc aatgggaact accagattat tctgggctgc tcaccctcaa tatgaacctc   1260

gccccacccg tggcccctaa tttccccggt gagcagctgc tgtttttcg  gagctttgtg   1320

ccatgcagtg gcggatataa tcaaggcatc gtagactgct tgattcccca agagtggata   1380

caacattttt accaggaaag tgcgccctcc cagtccgatg tggccctgat acggtacgtt   1440

aaccccgata ccggaagaac attattcgaa gcgaaattgc acagatcagg gtacattacc   1500

gttgcacatt ccggcgatta tcccctggtg gttcccgcca acggttactt taggttcgat   1560

agttgggtca accagttcta ttcactagcc ccaatgggca ccggtaacgg cagacgccgg   1620

gctcagtag                                                           1629
```

```
<210> SEQ ID NO 66
<211> LENGTH: 542
<212> TYPE: PRT
<213> ORGANISM: Norovirus GII.2/CGMH47/2011/TW

<400> SEQUENCE: 66

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ser Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160
```

-continued

```
Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255

Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu His Asp Asn Asp His Leu Tyr Asn Val Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Ser Gln Arg Asp Lys His Asn Thr Pro Gly His Asn Glu Pro Ala Asn
            340                 345                 350

Arg Ala His Asp Ala Val Val Pro Thr Tyr Thr Ala Gln Tyr Thr Pro
        355                 360                 365

Lys Leu Gly Gln Ile Gln Ile Gly Thr Trp Gln Thr Asp Asp Leu Thr
    370                 375                 380

Val Asn Gln Pro Val Lys Phe Thr Pro Val Gly Leu Asn Asp Thr Asp
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Ile Pro Leu Lys Gly Gly Tyr Gly Thr
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540
```

<210> SEQ ID NO 67
<211> LENGTH: 548
<212> TYPE: PRT
<213> ORGANISM: Norovirus GII.3/Jingzhou/2013402/CHN -continued

<400> SEQUENCE: 67

Met Lys Met Ala Ser Asn Asp Ala Ala Pro Ser Asn Asp Gly Ala Ala
1 5 10 15

Gly Leu Val Pro Glu Ile Ser Ser Glu Ala Met Ala Leu Glu Pro Val
20 25 30

Ala Gly Ala Ala Ile Ala Ala Pro Leu Thr Gly Gln Gln Asn Ile Ile
35 40 45

Asp Pro Trp Ile Met Asn Asn Phe Val Gln Ala Pro Gly Gly Glu Phe
50 55 60

Thr Val Ser Pro Arg Asn Ser Pro Gly Glu Val Leu Leu Asn Leu Glu
65 70 75 80

Leu Gly Pro Glu Ile Asn Pro Tyr Leu Ala His Leu Ala Arg Met Tyr
85 90 95

Asn Gly Tyr Ala Gly Gly Phe Glu Val Gln Val Val Leu Ala Gly Asn
100 105 110

Ala Phe Thr Ala Gly Lys Ile Ile Phe Ala Ala Ile Pro Pro Asn Phe
115 120 125

Pro Ile Asp Asn Leu Ser Ala Ala Gln Ile Thr Met Cys Pro His Val
130 135 140

Ile Val Asp Val Arg Gln Leu Glu Pro Val Asn Leu Pro Met Pro Asp
145 150 155 160

Val Arg Asn Asn Phe Phe His Tyr Asn Gln Gly Ser Asp Ser Arg Leu
165 170 175

Arg Leu Ile Ala Met Leu Tyr Thr Pro Leu Arg Ala Asn Asn Ser Gly
180 185 190

Asp Asp Val Phe Thr Val Ser Cys Arg Val Leu Thr Arg Pro Ser Pro
195 200 205

Asp Phe Ser Phe Asn Phe Leu Val Pro Pro Thr Val Glu Ser Lys Thr
210 215 220

Lys Pro Phe Ser Leu Pro Ile Leu Thr Ile Ser Glu Met Ser Asn Ser
225 230 235 240

Arg Phe Pro Val Pro Ile Asp Ser Leu His Thr Ser Pro Thr Glu Asn
245 250 255

Ile Val Val Gln Cys Gln Asn Gly Arg Val Thr Leu Asp Gly Glu Leu
260 265 270

Met Gly Thr Thr Gln Leu Leu Pro Ser Gln Ile Cys Ala Phe Arg Gly
275 280 285

Thr Leu Thr Arg Ser Thr Ser Arg Ala Ser Asp Gln Ala Asp Thr Ala
290 295 300

Thr Pro Arg Leu Phe Asn Tyr Tyr Trp His Ile Gln Leu Asp Asn Leu
305 310 315 320

Asn Gly Thr Pro Tyr Asp Pro Ala Glu Asp Ile Pro Ala Pro Leu Gly
325 330 335

Thr Pro Asp Phe Arg Gly Lys Val Phe Gly Val Ala Ser Gln Arg Asn
340 345 350

Pro Asp Ala Thr Thr Arg Ala His Glu Ala Lys Ile Asp Thr Thr Ser
355 360 365

Gly Arg Phe Thr Pro Lys Leu Gly Ser Leu Glu Ile Ser Thr Glu Ser
370 375 380

Gly Asp Phe Asp Gln Asn Gln Pro Thr Arg Phe Thr Pro Val Gly Ile
385 390 395 400

Gly Val Asp His Glu Pro Asp Phe Gln Gln Trp Ala Leu Pro Asp Tyr
405 410 415

```
Ala Gly Gln Phe Thr His Asn Met Asn Leu Ala Pro Ala Val Ala Pro
            420                 425                 430

Asn Phe Pro Gly Glu Gln Leu Leu Phe Phe Arg Ser Gln Leu Pro Ser
        435                 440                 445

Ser Gly Gly Arg Ser Asn Gly Ile Leu Asp Cys Leu Val Pro Gln Glu
    450                 455                 460

Trp Val Gln His Phe Tyr Gln Glu Ser Ala Pro Ser Gln Thr Gln Val
465                 470                 475                 480

Ala Leu Val Arg Tyr Val Asn Pro Asp Thr Gly Arg Val Leu Phe Glu
                485                 490                 495

Ala Lys Leu His Lys Leu Arg Phe Met Thr Ile Ala Lys Ser Gly Asp
            500                 505                 510

Ser Pro Ile Thr Val Pro Pro Asn Gly Tyr Phe Arg Phe Glu Ser Trp
        515                 520                 525

Val Asn Pro Phe Tyr Thr Leu Ala Pro Met Gly Thr Gly Asn Gly Arg
    530                 535                 540

Arg Arg Ile Gln
545


<210> SEQ ID NO 68
<211> LENGTH: 540
<212> TYPE: PRT
<213> ORGANISM: Norovirus GII.5/AlbertaEI390/2013/CA

<400> SEQUENCE: 68

Met Lys Met Ala Ser Asn Asp Ala Thr Pro Ser Asn Asp Gly Ala Ala
1               5                   10                  15

Gly Leu Val Pro Glu Ser Asn Asn Glu Ala Met Ala Leu Glu Pro Val
            20                  25                  30

Val Gly Ala Ser Leu Ala Ala Pro Val Thr Gly Gln Thr Asn Ile Ile
        35                  40                  45

Asp Pro Trp Ile Arg Thr Asn Phe Val Gln Ala Pro Asn Gly Glu Phe
    50                  55                  60

Thr Val Ser Pro Arg Asn Ser Pro Gly Glu Ile Leu Val Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Leu Leu Ala Gly Asn
            100                 105                 110

Ala Phe Thr Ala Gly Lys Ile Ile Phe Ala Ala Val Pro Pro Tyr Phe
        115                 120                 125

Pro Val Glu Asn Leu Ser Pro Ser Gln Ile Thr Met Phe Pro His Val
    130                 135                 140

Ile Ile Asp Val Arg Thr Leu Glu Pro Val Leu Leu Pro Met Pro Asp
145                 150                 155                 160

Val Arg Ser Thr Leu Phe His Phe Asn Gln Lys Asp Glu Pro Lys Met
                165                 170                 175

Arg Leu Val Ala Met Leu Tyr Thr Pro Leu Arg Ser Asn Gly Ser Gly
            180                 185                 190

Asp Asp Val Phe Thr Val Ser Cys Arg Ile Leu Thr Arg Pro Ser Pro
        195                 200                 205

Glu Phe Asp Phe Thr Tyr Leu Val Pro Pro Thr Val Glu Ser Lys Thr
    210                 215                 220

Lys Pro Phe Thr Leu Pro Val Leu Thr Leu Gly Glu Leu Ser Asn Ser
```

225 230 235 240

Arg Phe Pro Leu Ser Ile Asp Glu Met Val Thr Ser Pro Asn Glu Ser
245 250 255

Ile Val Val Gln Pro Gln Asn Gly Arg Val Thr Leu Asp Gly Glu Leu
260 265 270

Leu Gly Thr Thr Gln Leu Gln Ala Cys Asn Ile Cys Ser Ile Arg Gly
275 280 285

Lys Val Thr Gly Gln Val Pro Asn Glu Gln His Met Trp Asn Leu Glu
290 295 300

Ile Thr Asn Leu Asn Gly Thr Gln Phe Asp Pro Thr Asp Asp Val Pro
305 310 315 320

Ala Pro Leu Gly Val Pro Asp Phe Ala Gly Glu Val Phe Gly Val Leu
325 330 335

Ser Gln Arg Asn Arg Gly Glu Ser Asn Pro Ala Asn Arg Ala His Asp
340 345 350

Ala Val Val Ala Thr Tyr Ser Asp Lys Tyr Thr Pro Lys Leu Gly Leu
355 360 365

Val Gln Ile Gly Thr Trp Asn Thr Asn Asp Val Glu Asn Gln Pro Thr
370 375 380

Lys Phe Thr Pro Ile Gly Leu Asn Glu Val Ala Asn Gly His Arg Phe
385 390 395 400

Glu Gln Trp Thr Leu Pro Arg Tyr Ser Gly Ala Leu Thr Leu Asn Met
405 410 415

Asn Leu Ala Pro Ala Val Ala Pro Leu Phe Pro Gly Glu Arg Leu Leu
420 425 430

Phe Phe Arg Ser Tyr Val Pro Leu Lys Gly Gly Phe Gly Asn Pro Ala
435 440 445

Ile Asp Cys Leu Val Pro Gln Glu Trp Val Gln His Phe Tyr Gln Glu
450 455 460

Ser Ala Pro Ser Leu Gly Asp Val Ala Leu Val Arg Tyr Val Asn Pro
465 470 475 480

Asp Thr Gly Arg Val Leu Phe Glu Ala Lys Leu His Lys Gly Gly Phe
485 490 495

Leu Thr Val Ser Ser Thr Ser Thr Gly Pro Val Val Val Pro Ala Asn
500 505 510

Gly Tyr Phe Arg Phe Asp Ser Trp Val Asn Gln Phe Tyr Ser Leu Ala
515 520 525

Pro Met Gly Thr Gly Asn Gly Arg Arg Arg Phe Gln
530 535 540

<210> SEQ ID NO 69
<211> LENGTH: 540
<212> TYPE: PRT
<213> ORGANISM: Norovirus GII.7/Musahimurayama/2010/JP

<400> SEQUENCE: 69

Met Lys Met Ala Ser Asn Asp Ala Ala Pro Ser Asn Asp Gly Ala Ala
1 5 10 15

Gly Leu Val Pro Glu Ile Asn Asn Glu Val Met Pro Leu Glu Pro Val
20 25 30

Ala Gly Ala Ser Leu Ala Thr Pro Val Val Gly Gln Gln Asn Ile Ile
35 40 45

Asp Pro Trp Ile Arg Asn Asn Phe Val Gln Ala Pro Ala Gly Glu Phe
50 55 60

-continued

```
Thr Val Ser Pro Arg Asn Ser Pro Gly Glu Ile Leu Leu Asp Leu Glu
65                  70                  75                  80

Leu Gly Pro Glu Leu Asn Pro Tyr Leu Ala His Leu Ala Arg Met Tyr
                85                  90                  95

Asn Gly His Ala Gly Gly Met Glu Val Gln Ile Val Leu Ala Gly Asn
            100                 105                 110

Ala Phe Thr Ala Gly Lys Ile Ile Phe Ala Ala Ile Pro Pro Gly Phe
        115                 120                 125

Pro Tyr Glu Asn Leu Ser Pro Ser Gln Ile Thr Met Cys Pro His Val
    130                 135                 140

Ile Ile Asp Val Arg Gln Leu Glu Pro Val Leu Leu Pro Met Pro Asp
145                 150                 155                 160

Ile Arg Asn Asn Phe Phe His Tyr Asn Gln Gly Asn Asp Pro Lys Leu
                165                 170                 175

Arg Leu Ile Ala Met Leu Tyr Thr Pro Leu Arg Ala Asn Asn Ser Gly
            180                 185                 190

Asp Asp Val Phe Thr Val Ser Cys Arg Val Leu Thr Lys Pro Ser Pro
        195                 200                 205

Asp Phe Glu Phe Thr Phe Leu Val Pro Pro Thr Val Glu Ser Lys Thr
    210                 215                 220

Lys Gln Phe Thr Leu Pro Ile Leu Lys Ile Ser Glu Met Thr Asn Ser
225                 230                 235                 240

Arg Phe Pro Val Pro Val Glu Met Met Tyr Thr Ala Arg Asn Glu Asn
                245                 250                 255

Gln Val Val Gln Pro Gln Asn Gly Arg Val Thr Leu Asp Gly Glu Leu
            260                 265                 270

Leu Gly Thr Thr Pro Leu Leu Ala Val Asn Ile Cys Lys Phe Lys Gly
        275                 280                 285

Glu Val Ile Ala Lys Asn Gly Asp Val Arg Ser Tyr Arg Met Asp Met
    290                 295                 300

Glu Ile Thr Asn Thr Asp Gly Thr Pro Ile Asp Pro Thr Glu Asp Thr
305                 310                 315                 320

Pro Gly Pro Ile Gly Ser Pro Asp Phe Gln Gly Ile Leu Phe Gly Val
                325                 330                 335

Ala Ser Gln Arg Asn Lys Asn Glu Gln Asn Pro Ala Thr Arg Ala His
            340                 345                 350

Glu Ala Asn Ile Asn Thr Gly Gly Asp Gln Tyr Ala Pro Lys Leu Ala
        355                 360                 365

Gln Val Lys Phe Phe Ser Glu Ser Gln Asp Phe Glu Val His Gln Pro
    370                 375                 380

Thr Val Phe Thr Pro Val Gly Val Ala Gly Asp Thr Ser His Pro Phe
385                 390                 395                 400

Arg Gln Trp Val Leu Pro Arg Tyr Gly Gly His Leu Thr Asn Asn Thr
                405                 410                 415

His Leu Ala Pro Ala Val Ala Pro Leu Phe Pro Gly Glu Gln Ile Leu
            420                 425                 430

Phe Phe Arg Ser Gln Ile Pro Ser Ser Gly Gly His Glu Leu Gly Tyr
        435                 440                 445

Met Asp Cys Leu Val Pro Gln Glu Trp Val Gln His Phe Tyr Gln Glu
    450                 455                 460

Ala Ala Thr Ala Gln Ser Glu Val Ala Leu Ile Arg Phe Ile Asn Pro
465                 470                 475                 480

Asp Thr Gly Arg Val Leu Phe Glu Ala Lys Leu His Lys Gln Gly Phe
```

```
                485                 490                 495

Ile Thr Val Ala His Thr Gly Asp Asn Pro Ile Val Met Pro Pro Asn
            500                 505                 510

Gly Tyr Phe Arg Phe Glu Ala Trp Val Asn Gln Phe Tyr Ser Leu Ala
        515                 520                 525

Pro Val Gly Thr Gly Asn Gly Arg Arg Arg Ile Gln
    530                 535                 540


<210> SEQ ID NO 70
<211> LENGTH: 571
<212> TYPE: PRT
<213> ORGANISM: Artificial
<220> FEATURE:
<223> OTHER INFORMATION: Amino acid sequence of VP1 consensus sequence
      from genotypes GI.1, GI.2, GI.3, GII.4, GII.6, GII.13 and GII.17
<220> FEATURE:
<221> NAME/KEY: VARIANT
<222> LOCATION: (2)..(2)
<223> OTHER INFORMATION: Xaa can be Lys or Met
<220> FEATURE:
<221> NAME/KEY: VARIANT
<222> LOCATION: (6)..(6)
<223> OTHER INFORMATION: Xaa can be Asn, Ser or Lys
<220> FEATURE:
<221> NAME/KEY: VARIANT
<222> LOCATION: (9)..(9)
<223> OTHER INFORMATION: Xaa can be Ala, Asn, Pro or Thr
<220> FEATURE:
<221> NAME/KEY: VARIANT
<222> LOCATION: (10)..(10)
<223> OTHER INFORMATION: Xaa can be Pro, Thr, Gln or Ser
<220> FEATURE:
<221> NAME/KEY: VARIANT
<222> LOCATION: (11)..(11)
<223> OTHER INFORMATION: Xaa can be Ser or Asn
<220> FEATURE:
<221> NAME/KEY: VARIANT
<222> LOCATION: (12)..(12)
<223> OTHER INFORMATION: Xaa can be Asn, Asp, Met, Ala or Val
<220> FEATURE:
<221> NAME/KEY: VARIANT
<222> LOCATION: (13)..(13)
<223> OTHER INFORMATION: Xaa can be Asp or Gly
<220> FEATURE:
<221> NAME/KEY: VARIANT
<222> LOCATION: (15)..(15)
<223> OTHER INFORMATION: Xaa can be Ala, Thr or absent
<220> FEATURE:
<221> NAME/KEY: VARIANT
<222> LOCATION: (15)..(315)
<223> OTHER INFORMATION: Xaa can be Arg, Try, Asp or absent
<220> FEATURE:
<221> NAME/KEY: VARIANT
<222> LOCATION: (17)..(17)
<223> OTHER INFORMATION: Xaa can be Gly or absent
<220> FEATURE:
<221> NAME/KEY: VARIANT
<222> LOCATION: (19)..(19)
<223> OTHER INFORMATION: Xaa can be Ala or Gly
<220> FEATURE:
<221> NAME/KEY: VARIANT
<222> LOCATION: (20)..(20)
<223> OTHER INFORMATION: Xaa can be Gly, Ser, Asn or Gln
<220> FEATURE:
<221> NAME/KEY: VARIANT
<222> LOCATION: (25)..(25)
<223> OTHER INFORMATION: Xaa can be Gly, Ala or Val
<220> FEATURE:
<221> NAME/KEY: VARIANT
<222> LOCATION: (26)..(26)
<223> OTHER INFORMATION: Xaa can be Asn, Ile or Ser
<220> FEATURE:
<221> NAME/KEY: VARIANT
<222> LOCATION: (27)..(27)
<223> OTHER INFORMATION: Xaa can be Asn, Thr or Ala
```

<220> FEATURE:
<221> NAME/KEY: VARIANT
<222> LOCATION: (28)..(28)
<223> OTHER INFORMATION: Xaa can be Asn, Ser or absent
<220> FEATURE:
<221> NAME/KEY: VARIANT
<222> LOCATION: (29)..(29)
<223> OTHER INFORMATION: Xaa can be Glu or Asp
<220> FEATURE:
<221> NAME/KEY: VARIANT
<222> LOCATION: (30)..(30)
<223> OTHER INFORMATION: Xaa can be Thr, Val or Pro
<220> FEATURE:
<221> NAME/KEY: VARIANT
<222> LOCATION: (31)..(31)
<223> OTHER INFORMATION: Xaa can be Leu, Met or Ile
<220> FEATURE:
<221> NAME/KEY: VARIANT
<222> LOCATION: (32)..(32)
<223> OTHER INFORMATION: Xaa can be Pro, Ala or Ser
<220> FEATURE:
<221> NAME/KEY: VARIANT
<222> LOCATION: (33)..(33)
<223> OTHER INFORMATION: Xaa can be Leu or Met
<220> FEATURE:
<221> NAME/KEY: VARIANT
<222> LOCATION: (34)..(34)
<223> OTHER INFORMATION: Xaa can be Glu or Asp
<220> FEATURE:
<221> NAME/KEY: VARIANT
<222> LOCATION: (37)..(37)
<223> OTHER INFORMATION: Xaa can be Ala or Val
<220> FEATURE:
<221> NAME/KEY: VARIANT
<222> LOCATION: (39)..(39)
<223> OTHER INFORMATION: Xaa can be Ala, Pro or Ser
<220> FEATURE:
<221> NAME/KEY: VARIANT
<222> LOCATION: (40)..(40)
<223> OTHER INFORMATION: Xaa can be Ala, Ser or Thr
<220> FEATURE:
<221> NAME/KEY: VARIANT
<222> LOCATION: (41)..(41)
<223> OTHER INFORMATION: Xaa can be Ile or Thr
<220> FEATURE:
<221> NAME/KEY: VARIANT
<222> LOCATION: (43)..(43)
<223> OTHER INFORMATION: Xaa can be Ala or Val
<220> FEATURE:
<221> NAME/KEY: VARIANT
<222> LOCATION: (44)..(44)
<223> OTHER INFORMATION: Xaa can be Pro or Ala
<220> FEATURE:
<221> NAME/KEY: VARIANT
<222> LOCATION: (45)..(45)
<223> OTHER INFORMATION: Xaa can be Val or Thr
<220> FEATURE:
<221> NAME/KEY: VARIANT
<222> LOCATION: (46)..(46)
<223> OTHER INFORMATION: Xaa can be Thr, Ala or Val
<220> FEATURE:
<221> NAME/KEY: VARIANT
<222> LOCATION: (49)..(49)
<223> OTHER INFORMATION: Xaa can be Asn, Thr, Gln or Val
<220> FEATURE:
<221> NAME/KEY: VARIANT
<222> LOCATION: (51)..(51)
<223> OTHER INFORMATION: Xaa can be Ile, Val, Met or Pro
<220> FEATURE:
<221> NAME/KEY: VARIANT
<222> LOCATION: (57)..(57)
<223> OTHER INFORMATION: Xaa can be Arg, Met, Val or Ile
<220> FEATURE:
<221> NAME/KEY: VARIANT
<222> LOCATION: (58)..(58)
<223> OTHER INFORMATION: Xaa can be Thr, Glu, Asn or Ser
<220> FEATURE:
<221> NAME/KEY: VARIANT
<222> LOCATION: (60)..(60)

<223> OTHER INFORMATION: Xaa can be Phe or Tyr
<220> FEATURE:
<221> NAME/KEY: VARIANT
<222> LOCATION: (63)..(63)
<223> OTHER INFORMATION: Xaa can be Ala or Ser
<220> FEATURE:
<221> NAME/KEY: VARIANT
<222> LOCATION: (65)..(65)
<223> OTHER INFORMATION: Xaa can be Asn, Gln or Gly
<220> FEATURE:
<221> NAME/KEY: VARIANT
<222> LOCATION: (70)..(70)
<223> OTHER INFORMATION: Xaa can be Val or Ile
<220> FEATURE:
<221> NAME/KEY: VARIANT
<222> LOCATION: (73)..(73)
<223> OTHER INFORMATION: Xaa can be Arg or Asn
<220> FEATURE:
<221> NAME/KEY: VARIANT
<222> LOCATION: (75)..(75)
<223> OTHER INFORMATION: Xaa can be Ser, Ala or Thr
<220> FEATURE:
<221> NAME/KEY: VARIANT
<222> LOCATION: (78)..(78)
<223> OTHER INFORMATION: Xaa can be Glu or Asp
<220> FEATURE:
<221> NAME/KEY: VARIANT
<222> LOCATION: (79)..(79)
<223> OTHER INFORMATION: Xaa can be Ile, Met or Val
<220> FEATURE:
<221> NAME/KEY: VARIANT
<222> LOCATION: (81)..(81)
<223> OTHER INFORMATION: Xaa can be Leu, Trp or Phe
<220> FEATURE:
<221> NAME/KEY: VARIANT
<222> LOCATION: (82)..(82)
<223> OTHER INFORMATION: Xaa can be Asn, Ser or Asp
<220> FEATURE:
<221> NAME/KEY: VARIANT
<222> LOCATION: (83)..(83)
<223> OTHER INFORMATION: Xaa can be Leu or Ala
<220> FEATURE:
<221> NAME/KEY: VARIANT
<222> LOCATION: (84)..(84)
<223> OTHER INFORMATION: Xaa can be Glu, Pro, Gln or Ser
<220> FEATURE:
<221> NAME/KEY: VARIANT
<222> LOCATION: (88)..(88)
<223> OTHER INFORMATION: Xaa can be Asp, Glu or His
<220> FEATURE:
<221> NAME/KEY: VARIANT
<222> LOCATION: (92)..(92)
<223> OTHER INFORMATION: Xaa can be Tyr or Phe
<220> FEATURE:
<221> NAME/KEY: VARIANT
<222> LOCATION: (94)..(94)
<223> OTHER INFORMATION: Xaa can be Ala, Ser or Leu
<220> FEATURE:
<221> NAME/KEY: VARIANT
<222> LOCATION: (97)..(97)
<223> OTHER INFORMATION: Xaa can be Ser or Ala
<220> FEATURE:
<221> NAME/KEY: VARIANT
<222> LOCATION: (98)..(98)
<223> OTHER INFORMATION: Xaa can be Arg or Gln
<220> FEATURE:
<221> NAME/KEY: VARIANT
<222> LOCATION: (103)..(103)
<223> OTHER INFORMATION: Xaa can be Tyr or Trp
<220> FEATURE:
<221> NAME/KEY: VARIANT
<222> LOCATION: (104)..(104)
<223> OTHER INFORMATION: Xaa can be Ala or Val
<220> FEATURE:
<221> NAME/KEY: VARIANT
<222> LOCATION: (106)..(106)
<223> OTHER INFORMATION: Xaa can be Gly or Asn
<220> FEATURE:
<221> NAME/KEY: VARIANT
<222> LOCATION: (107)..(107)
<223> OTHER INFORMATION: Xaa can be Val, Met or Phe
<220> FEATURE:
<221> NAME/KEY: VARIANT
<222> LOCATION: (108)..(108)
<223> OTHER INFORMATION: Xaa can be Glu, Gln, Lys or Arg
<220> FEATURE:
<221> NAME/KEY: VARIANT
<222> LOCATION: (110)..(110)
<223> OTHER INFORMATION: Xaa can be Gln or Arg
<220> FEATURE:
<221> NAME/KEY: VARIANT
<222> LOCATION: (111)..(111)
<223> OTHER INFORMATION: Xaa can be Val or Ile
<220> FEATURE:
<221> NAME/KEY: VARIANT
<222> LOCATION: (112)..(112)
<223> OTHER INFORMATION: Xaa can be Leu, Val, Ile or Met
<220> FEATURE:
<221> NAME/KEY: VARIANT
<222> LOCATION: (119)..(119)
<223> OTHER INFORMATION: Xaa can be Thr or Ser
<220> FEATURE:
<221> NAME/KEY: VARIANT
<222> LOCATION: (123)..(123)
<223> OTHER INFORMATION: Xaa can be Ile or Val
<220> FEATURE:
<221> NAME/KEY: VARIANT
<222> LOCATION: (124)..(124)
<223> OTHER INFORMATION: Xaa can be Leu or Ile
<220> FEATURE:
<221> NAME/KEY: VARIANT
<222> LOCATION: (125)..(125)
<223> OTHER INFORMATION: Xaa can be Phe, Ile or Val
<220> FEATURE:
<221> NAME/KEY: VARIANT
<222> LOCATION: (126)..(126)
<223> OTHER INFORMATION: Xaa can be Ala, Ser or Cys
<220> FEATURE:
<221> NAME/KEY: VARIANT
<222> LOCATION: (127)..(127)
<223> OTHER INFORMATION: Xaa can be Ala or Cys
<220> FEATURE:
<221> NAME/KEY: VARIANT
<222> LOCATION: (128)..(128)
<223> OTHER INFORMATION: Xaa can be Val or Ile
<220> FEATURE:
<221> NAME/KEY: VARIANT
<222> LOCATION: (131)..(131)
<223> OTHER INFORMATION: Xaa can be Asn, His or Gly
<220> FEATURE:
<221> NAME/KEY: VARIANT
<222> LOCATION: (133)..(133)
<223> OTHER INFORMATION: Xaa can be Pro, Ala, Thr or Gly
<220> FEATURE:
<221> NAME/KEY: VARIANT
<222> LOCATION: (134)..(134)
<223> OTHER INFORMATION: Xaa can be Val, Thr, Ala or Ser
<220> FEATURE:
<221> NAME/KEY: VARIANT
<222> LOCATION: (135)..(135)
<223> OTHER INFORMATION: Xaa can be Glu, Asp, Gln, Ser or His
<220> FEATURE:
<221> NAME/KEY: VARIANT
<222> LOCATION: (136)..(136)
<223> OTHER INFORMATION: Xaa can be Phe, Met, Asn, Gly or Ser
<220> FEATURE:
<221> NAME/KEY: VARIANT
<222> LOCATION: (137)..(137)
<223> OTHER INFORMATION: Xaa can be Leu, Ile or Val
<220> FEATURE:
<221> NAME/KEY: VARIANT
<222> LOCATION: (138)..(138)
<223> OTHER INFORMATION: Xaa can be Ser, Asn or Thr
<220> FEATURE:
<221> NAME/KEY: VARIANT
<222> LOCATION: (139)..(139)
<223> OTHER INFORMATION: Xaa can be Pro, Ala or Ile
<220> FEATURE:

<221> NAME/KEY: VARIANT
<222> LOCATION: (140)..(140)
<223> OTHER INFORMATION: Xaa can be Ala or Ser
<220> FEATURE:
<221> NAME/KEY: VARIANT
<222> LOCATION: (142)..(142)
<223> OTHER INFORMATION: Xaa can be Ile, Val or Ala
<220> FEATURE:
<221> NAME/KEY: VARIANT
<222> LOCATION: (144)..(144)
<223> OTHER INFORMATION: Xaa can be Met or Leu
<220> FEATURE:
<221> NAME/KEY: VARIANT
<222> LOCATION: (145)..(145)
<223> OTHER INFORMATION: Xaa can be Leu, Cys or Phe
<220> FEATURE:
<221> NAME/KEY: VARIANT
<222> LOCATION: (148)..(148)
<223> OTHER INFORMATION: Xaa can be Leu, Val or Ile
<220> FEATURE:
<221> NAME/KEY: VARIANT
<222> LOCATION: (149)..(149)
<223> OTHER INFORMATION: Xaa can be Ile or Val
<220> FEATURE:
<221> NAME/KEY: VARIANT
<222> LOCATION: (150)..(150)
<223> OTHER INFORMATION: Xaa can be Val or Ala
<220> FEATURE:
<221> NAME/KEY: VARIANT
<222> LOCATION: (154)..(154)
<223> OTHER INFORMATION: Xaa can be Thr, Gln or Val
<220> FEATURE:
<221> NAME/KEY: VARIANT
<222> LOCATION: (156)..(156)
<223> OTHER INFORMATION: Xaa can be Glu or Asp
<220> FEATURE:
<221> NAME/KEY: VARIANT
<222> LOCATION: (158)..(158)
<223> OTHER INFORMATION: Xaa can be Ile or Val
<220> FEATURE:
<221> NAME/KEY: VARIANT
<222> LOCATION: (159)..(159)
<223> OTHER INFORMATION: Xaa can be Met, Leu or Glu
<220> FEATURE:
<221> NAME/KEY: VARIANT
<222> LOCATION: (160)..(160)
<223> OTHER INFORMATION: Xaa can be Ile, Leu, Val or Met
<220> FEATURE:
<221> NAME/KEY: VARIANT
<222> LOCATION: (163)..(163)
<223> OTHER INFORMATION: Xaa can be Phe or Glu
<220> FEATURE:
<221> NAME/KEY: VARIANT
<222> LOCATION: (165)..(165)
<223> OTHER INFORMATION: Xaa can be Val or Ile
<220> FEATURE:
<221> NAME/KEY: VARIANT
<222> LOCATION: (168)..(168)
<223> OTHER INFORMATION: Xaa can be Thr, Val, Arg or Asn
<220> FEATURE:
<221> NAME/KEY: VARIANT
<222> LOCATION: (169)..(169)
<223> OTHER INFORMATION: Xaa can be Phe or Leu
<220> FEATURE:
<221> NAME/KEY: VARIANT
<222> LOCATION: (170)..(170)
<223> OTHER INFORMATION: Xaa can be Phe, Tyr or Glu
<220> FEATURE:
<221> NAME/KEY: VARIANT
<222> LOCATION: (172)..(172)
<223> OTHER INFORMATION: Xaa can be Tyr, Phe, Asn or Thr
<220> FEATURE:
<221> NAME/KEY: VARIANT
<222> LOCATION: (174)..(174)
<223> OTHER INFORMATION: Xaa can be Asn, Gln or Asp
<220> FEATURE:
<221> NAME/KEY: VARIANT
<222> LOCATION: (175)..(175)
<223> OTHER INFORMATION: Xaa can be Gln, Glu, Ser, Arg or absent
<220> FEATURE:
<221> NAME/KEY: VARIANT
<222> LOCATION: (176)..(176)
<223> OTHER INFORMATION: Xaa can be Pro, Asn or Ser
<220> FEATURE:
<221> NAME/KEY: VARIANT
<222> LOCATION: (177)..(177)
<223> OTHER INFORMATION: Xaa can be Asn, Gln, Thr or Asp
<220> FEATURE:
<221> NAME/KEY: VARIANT
<222> LOCATION: (178)..(178)
<223> OTHER INFORMATION: Xaa can be Ser, Pro or Gln
<220> FEATURE:
<221> NAME/KEY: VARIANT
<222> LOCATION: (179)..(179)
<223> OTHER INFORMATION: Xaa can be Arg or Thr
<220> FEATURE:
<221> NAME/KEY: VARIANT
<222> LOCATION: (180)..(180)
<223> OTHER INFORMATION: Xaa can be Met or Ile
<220> FEATURE:
<221> NAME/KEY: VARIANT
<222> LOCATION: (181)..(181)
<223> OTHER INFORMATION: Xaa can be Arg or Lys
<220> FEATURE:
<221> NAME/KEY: VARIANT
<222> LOCATION: (183)..(183)
<223> OTHER INFORMATION: Xaa can be Val or Ile
<220> FEATURE:
<221> NAME/KEY: VARIANT
<222> LOCATION: (184)..(184)
<223> OTHER INFORMATION: Xaa can be Ala or Cys
<220> FEATURE:
<221> NAME/KEY: VARIANT
<222> LOCATION: (192)..(192)
<223> OTHER INFORMATION: Xaa can be Ser, Ala or Thr
<220> FEATURE:
<221> NAME/KEY: VARIANT
<222> LOCATION: (193)..(193)
<223> OTHER INFORMATION: Xaa can be Asn, Ser or Gln
<220> FEATURE:
<221> NAME/KEY: VARIANT
<222> LOCATION: (194)..(194)
<223> OTHER INFORMATION: Xaa can be Asn, Gln or absent
<220> FEATURE:
<221> NAME/KEY: VARIANT
<222> LOCATION: (195)..(195)
<223> OTHER INFORMATION: Xaa can be Ser, Ala or Gln
<220> FEATURE:
<221> NAME/KEY: VARIANT
<222> LOCATION: (196)..(196)
<223> OTHER INFORMATION: Xaa can be Ser, Thr or absent
<220> FEATURE:
<221> NAME/KEY: VARIANT
<222> LOCATION: (197)..(197)
<223> OTHER INFORMATION: Xaa can be Ser, Gln or absent
<220> FEATURE:
<221> NAME/KEY: VARIANT
<222> LOCATION: (198)..(198)
<223> OTHER INFORMATION: Xaa can be Gln, Asn or absent
<220> FEATURE:
<221> NAME/KEY: VARIANT
<222> LOCATION: (199)..(199)
<223> OTHER INFORMATION: Xaa can be Asp, Glu, Thr, Ser or absent
<220> FEATURE:
<221> NAME/KEY: VARIANT
<222> LOCATION: (201)..(201)
<223> OTHER INFORMATION: Xaa can be Val, Pro or Ser
<220> FEATURE:
<221> NAME/KEY: VARIANT
<222> LOCATION: (203)..(203)
<223> OTHER INFORMATION: Xaa can be Thr or Val
<220> FEATURE:
<221> NAME/KEY: VARIANT
<222> LOCATION: (204)..(204)
<223> OTHER INFORMATION: Xaa can be Val or Ile
<220> FEATURE:
<221> NAME/KEY: VARIANT
<222> LOCATION: (205)..(205)

<223> OTHER INFORMATION: Xaa can be Ser or Ala
<220> FEATURE:
<221> NAME/KEY: VARIANT
<222> LOCATION: (206)..(206)
<223> OTHER INFORMATION: Xaa can be Cys or Gln
<220> FEATURE:
<221> NAME/KEY: VARIANT
<222> LOCATION: (209)..(209)
<223> OTHER INFORMATION: Xaa can be Leu or Met
<220> FEATURE:
<221> NAME/KEY: VARIANT
<222> LOCATION: (211)..(211)
<223> OTHER INFORMATION: Xaa can be Arg, Cys or Ala
<220> FEATURE:
<221> NAME/KEY: VARIANT
<222> LOCATION: (213)..(213)
<223> OTHER INFORMATION: Xaa can be Thr, Ala or Ser
<220> FEATURE:
<221> NAME/KEY: VARIANT
<222> LOCATION: (214)..(214)
<223> OTHER INFORMATION: Xaa can be Pro or Ser
<220> FEATURE:
<221> NAME/KEY: VARIANT
<222> LOCATION: (217)..(217)
<223> OTHER INFORMATION: Xaa can be Glu, Asp, Asn or Ser
<220> FEATURE:
<221> NAME/KEY: VARIANT
<222> LOCATION: (219)..(219)
<223> OTHER INFORMATION: Xaa can be Thr, Ile or Leu
<220> FEATURE:
<221> NAME/KEY: VARIANT
<222> LOCATION: (220)..(220)
<223> OTHER INFORMATION: Xaa can be Tyr or Phe
<220> FEATURE:
<221> NAME/KEY: VARIANT
<222> LOCATION: (225)..(225)
<223> OTHER INFORMATION: Xaa can be Ser, Thr or Asn
<220> FEATURE:
<221> NAME/KEY: VARIANT
<222> LOCATION: (226)..(226)
<223> OTHER INFORMATION: Xaa can be Val or Ile
<220> FEATURE:
<221> NAME/KEY: VARIANT
<222> LOCATION: (228)..(228)
<223> OTHER INFORMATION: Xaa can be Ser or Gln
<220> FEATURE:
<221> NAME/KEY: VARIANT
<222> LOCATION: (229)..(229)
<223> OTHER INFORMATION: Xaa can be Lys or Arg
<220> FEATURE:
<221> NAME/KEY: VARIANT
<222> LOCATION: (231)..(231)
<223> OTHER INFORMATION: Xaa can be Lys or Arg
<220> FEATURE:
<221> NAME/KEY: VARIANT
<222> LOCATION: (232)..(232)
<223> OTHER INFORMATION: Xaa can be Pro or Ala
<220> FEATURE:
<221> NAME/KEY: VARIANT
<222> LOCATION: (234)..(234)
<223> OTHER INFORMATION: Xaa can be Ser or Thr
<220> FEATURE:
<221> NAME/KEY: VARIANT
<222> LOCATION: (235)..(235)
<223> OTHER INFORMATION: Xaa can be Leu or Val
<220> FEATURE:
<221> NAME/KEY: VARIANT
<222> LOCATION: (237)..(237)
<223> OTHER INFORMATION: Xaa can be Ile, Val or Asn
<220> FEATURE:
<221> NAME/KEY: VARIANT
<222> LOCATION: (238)..(238)
<223> OTHER INFORMATION: Xaa can be Leu or Ile
<220> FEATURE:
<221> NAME/KEY: VARIANT
<222> LOCATION: (239)..(239)
<223> OTHER INFORMATION: Xaa can be Thr or Pro
<220> FEATURE:
<221> NAME/KEY: VARIANT
<222> LOCATION: (240)..(240)
<223> OTHER INFORMATION: Xaa can be Leu, Ile or Val
<220> FEATURE:
<221> NAME/KEY: VARIANT
<222> LOCATION: (242)..(242)
<223> OTHER INFORMATION: Xaa can be Glu, Val, Thr or Ser
<220> FEATURE:
<221> NAME/KEY: VARIANT
<222> LOCATION: (243)..(243)
<223> OTHER INFORMATION: Xaa can be Leu or Met
<220> FEATURE:
<221> NAME/KEY: VARIANT
<222> LOCATION: (244)..(244)
<223> OTHER INFORMATION: Xaa can be Thr or Ser
<220> FEATURE:
<221> NAME/KEY: VARIANT
<222> LOCATION: (248)..(248)
<223> OTHER INFORMATION: Xaa can be Phr, Val or Ala
<220> FEATURE:
<221> NAME/KEY: VARIANT
<222> LOCATION: (250)..(250)
<223> OTHER INFORMATION: Xaa can be Val, Ile, Ala, Ser or Leu
<220> FEATURE:
<221> NAME/KEY: VARIANT
<222> LOCATION: (251)..(251)
<223> OTHER INFORMATION: Xaa can be Pro, Ser or Leu
<220> FEATURE:
<221> NAME/KEY: VARIANT
<222> LOCATION: (252)..(252)
<223> OTHER INFORMATION: Xaa can be Ile or Leu
<220> FEATURE:
<221> NAME/KEY: VARIANT
<222> LOCATION: (253)..(253)
<223> OTHER INFORMATION: Xaa can be Asp, Glu, Lys, Gln or Ser
<220> FEATURE:
<221> NAME/KEY: VARIANT
<222> LOCATION: (254)..(254)
<223> OTHER INFORMATION: Xaa can be Ser, Gln, Met, Lys or Gly
<220> FEATURE:
<221> NAME/KEY: VARIANT
<222> LOCATION: (255)..(255)
<223> OTHER INFORMATION: Xaa can be Leu or Met
<220> FEATURE:
<221> NAME/KEY: VARIANT
<222> LOCATION: (256)..(256)
<223> OTHER INFORMATION: Xaa can be Phe, Tyr, Met, Ile or Gly
<220> FEATURE:
<221> NAME/KEY: VARIANT
<222> LOCATION: (257)..(257)
<223> OTHER INFORMATION: Xaa can be Thr, Val, Leu or Ile
<220> FEATURE:
<221> NAME/KEY: VARIANT
<222> LOCATION: (258)..(258)
<223> OTHER INFORMATION: Xaa can be Ala, Asp, Gly or Ser
<220> FEATURE:
<221> NAME/KEY: VARIANT
<222> LOCATION: (259)..(259)
<223> OTHER INFORMATION: Xaa can be Gln or Pro
<220> FEATURE:
<221> NAME/KEY: VARIANT
<222> LOCATION: (260)..(260)
<223> OTHER INFORMATION: Xaa can be Asn, Ser or Asp
<220> FEATURE:
<221> NAME/KEY: VARIANT
<222> LOCATION: (261)..(261)
<223> OTHER INFORMATION: Xaa can be Asn, Glu, Ser, His or Ala
<220> FEATURE:
<221> NAME/KEY: VARIANT
<222> LOCATION: (262)..(262)
<223> OTHER INFORMATION: Xaa can be Val, Asn, Gly, Ala or Ser
<220> FEATURE:
<221> NAME/KEY: VARIANT
<222> LOCATION: (263)..(263)
<223> OTHER INFORMATION: Xaa can be Leu, Asn, Ile, Phe or Gln
<220> FEATURE:
<221> NAME/KEY: VARIANT
<222> LOCATION: (264)..(264)
<223> OTHER INFORMATION: Xaa can be Gln, Val, Met or Ser
<220> FEATURE:

<221> NAME/KEY: VARIANT
<222> LOCATION: (267)..(267)
<223> OTHER INFORMATION: Xaa can be Cys, Pro or Phe
<220> FEATURE:
<221> NAME/KEY: VARIANT
<222> LOCATION: (272)..(272)
<223> OTHER INFORMATION: Xaa can be Cys or Val
<220> FEATURE:
<221> NAME/KEY: VARIANT
<222> LOCATION: (273)..(273)
<223> OTHER INFORMATION: Xaa can be Thr or Leu
<220> FEATURE:
<221> NAME/KEY: VARIANT
<222> LOCATION: (274)..(274)
<223> OTHER INFORMATION: Xaa can be Leu, Thr or Ile
<220> FEATURE:
<221> NAME/KEY: VARIANT
<222> LOCATION: (277)..(277)
<223> OTHER INFORMATION: Xaa can be Glu, Thr, Val, Gln or Arg
<220> FEATURE:
<221> NAME/KEY: VARIANT
<222> LOCATION: (279)..(279)
<223> OTHER INFORMATION: Xaa can be Gln, Leu or Val
<220> FEATURE:
<221> NAME/KEY: VARIANT
<222> LOCATION: (283)..(283)
<223> OTHER INFORMATION: Xaa can be Gln or Pro
<220> FEATURE:
<221> NAME/KEY: VARIANT
<222> LOCATION: (284)..(284)
<223> OTHER INFORMATION: Xaa can be Leu, Thr, Ala or Val
<220> FEATURE:
<221> NAME/KEY: VARIANT
<222> LOCATION: (285)..(285)
<223> OTHER INFORMATION: Xaa can be Leu, Val, Ser or Thr
<220> FEATURE:
<221> NAME/KEY: VARIANT
<222> LOCATION: (286)..(286)
<223> OTHER INFORMATION: Xaa can be Pro, Ser, Ala or Leu
<220> FEATURE:
<221> NAME/KEY: VARIANT
<222> LOCATION: (287)..(287)
<223> OTHER INFORMATION: Xaa can be Ser, Thr, Val or Gly
<220> FEATURE:
<221> NAME/KEY: VARIANT
<222> LOCATION: (288)..(288)
<223> OTHER INFORMATION: Xaa can be Gly, Ala, Gln, Asn or His
<220> FEATURE:
<221> NAME/KEY: VARIANT
<222> LOCATION: (289)..(289)
<223> OTHER INFORMATION: Xaa can be Ile, Val or Leu
<220> FEATURE:
<221> NAME/KEY: VARIANT
<222> LOCATION: (290)..(290)
<223> OTHER INFORMATION: Xaa can be Cye, Phe or Ala
<220> FEATURE:
<221> NAME/KEY: VARIANT
<222> LOCATION: (291)..(291)
<223> OTHER INFORMATION: Xaa can be Ala, Ser, Thr, Lys or Arg
<220> FEATURE:
<221> NAME/KEY: VARIANT
<222> LOCATION: (292)..(292)
<223> OTHER INFORMATION: Xaa can be Phe, Tyr, Ile or Val
<220> FEATURE:
<221> NAME/KEY: VARIANT
<222> LOCATION: (295)..(295)
<223> OTHER INFORMATION: Xaa can be Arg, Thr, Asp or Lys
<220> FEATURE:
<221> NAME/KEY: VARIANT
<222> LOCATION: (296)..(296)
<223> OTHER INFORMATION: Xaa can be Val, Thr, Leu, Ile or Ser
<220> FEATURE:
<221> NAME/KEY: VARIANT
<222> LOCATION: (297)..(297)
<223> OTHER INFORMATION: Xaa can be Thr, Val, Ile, Tyr or Asn
<220> FEATURE:
<221> NAME/KEY: VARIANT
<222> LOCATION: (298)..(298)
<223> OTHER INFORMATION: Xaa can be Ala, Gly, His or absent
<220> FEATURE:
<221> NAME/KEY: VARIANT
<222> LOCATION: (299)..(299)
<223> OTHER INFORMATION: Xaa can be Glu, Asn, Gln, Ile, Ala or absent
<220> FEATURE:
<221> NAME/KEY: VARIANT
<222> LOCATION: (300)..(300)
<223> OTHER INFORMATION: Xaa can be Thr, Ser, Gln or absent
<220> FEATURE:
<221> NAME/KEY: VARIANT
<222> LOCATION: (301)..(301)
<223> OTHER INFORMATION: Xaa can be Asp, Gln, Ser or absent
<220> FEATURE:
<221> NAME/KEY: VARIANT
<222> LOCATION: (313)..(313)
<223> OTHER INFORMATION: Xaa can be Asp, Arg or absent
<220> FEATURE:
<221> NAME/KEY: VARIANT
<222> LOCATION: (314)..(314)
<223> OTHER INFORMATION: Xaa can be Arg or absent
<220> FEATURE:
<221> NAME/KEY: VARIANT
<222> LOCATION: (316)..(316)
<223> OTHER INFORMATION: Xaa can be Asp, His or absent
<220> FEATURE:
<221> NAME/KEY: VARIANT
<222> LOCATION: (317)..(317)
<223> OTHER INFORMATION: Xaa can be Lys, Gln, Pro, Asn or absent
<220> FEATURE:
<221> NAME/KEY: VARIANT
<222> LOCATION: (318)..(318)
<223> OTHER INFORMATION: Xaa can be Trp, Asn, Leu, Tyr or absent
<220> FEATURE:
<221> NAME/KEY: VARIANT
<222> LOCATION: (319)..(319)
<223> OTHER INFORMATION: Xaa can be His, Val, Thr or Gly
<220> FEATURE:
<221> NAME/KEY: VARIANT
<222> LOCATION: (320)..(320)
<223> OTHER INFORMATION: Xaa can be Met, Leu, Val or Ile
<220> FEATURE:
<221> NAME/KEY: VARIANT
<222> LOCATION: (321)..(321)
<223> OTHER INFORMATION: Xaa can be Gln or Asn
<220> FEATURE:
<221> NAME/KEY: VARIANT
<222> LOCATION: (323)..(323)
<223> OTHER INFORMATION: Xaa can be Gln, Thr, Lys or Ala
<220> FEATURE:
<221> NAME/KEY: VARIANT
<222> LOCATION: (324)..(324)
<223> OTHER INFORMATION: Xaa can be Asn, Tyr, Ser or Glu
<220> FEATURE:
<221> NAME/KEY: VARIANT
<222> LOCATION: (325)..(325)
<223> OTHER INFORMATION: Xaa can be Leu, Pro, Gln, Ile or Val
<220> FEATURE:
<221> NAME/KEY: VARIANT
<222> LOCATION: (326)..(326)
<223> OTHER INFORMATION: Xaa can be Asn, Ser or Asp
<220> FEATURE:
<221> NAME/KEY: VARIANT
<222> LOCATION: (327)..(327)
<223> OTHER INFORMATION: Xaa can be Gly or Trp
<220> FEATURE:
<221> NAME/KEY: VARIANT
<222> LOCATION: (328)..(328)
<223> OTHER INFORMATION: Xaa can be Thr, Ala, Asn or Lys
<220> FEATURE:
<221> NAME/KEY: VARIANT
<222> LOCATION: (329)..(329)
<223> OTHER INFORMATION: Xaa can be Thr, Ser, Gln, Asp or Pro
<220> FEATURE:
<221> NAME/KEY: VARIANT
<222> LOCATION: (330)..(330)
<223> OTHER INFORMATION: Xaa can be Tyr or Phe
<220> FEATURE:
<221> NAME/KEY: VARIANT
<222> LOCATION: (331)..(331)

```
<223> OTHER INFORMATION: Xaa can be Asp, His or Met
<220> FEATURE:
<221> NAME/KEY: VARIANT
<222> LOCATION: (332)..(332)
<223> OTHER INFORMATION: Xaa can be Pro or Ala
<220> FEATURE:
<221> NAME/KEY: VARIANT
<222> LOCATION: (333)..(333)
<223> OTHER INFORMATION: Xaa can be Tre or Phe
<220> FEATURE:
<221> NAME/KEY: VARIANT
<222> LOCATION: (334)..(334)
<223> OTHER INFORMATION: Xaa can be Asp, Glu or absent
<220> FEATURE:
<221> NAME/KEY: VARIANT
<222> LOCATION: (335)..(335)
<223> OTHER INFORMATION: Xaa can be Asp or Glu
<220> FEATURE:
<221> NAME/KEY: VARIANT
<222> LOCATION: (336)..(336)
<223> OTHER INFORMATION: Xaa can be Val, Ile, Ser or Gly
<220> FEATURE:
<221> NAME/KEY: VARIANT
<222> LOCATION: (339)..(339)
<223> OTHER INFORMATION: Xaa can be Pro or Val
<220> FEATURE:
<221> NAME/KEY: VARIANT
<222> LOCATION: (340)..(340)
<223> OTHER INFORMATION: Xaa can be Leu, Val or Ile
<220> FEATURE:
<221> NAME/KEY: VARIANT
<222> LOCATION: (342)..(342)
<223> OTHER INFORMATION: Xaa can be Thr, Ala or Phe
<220> FEATURE:
<221> NAME/KEY: VARIANT
<222> LOCATION: (343)..(343)
<223> OTHER INFORMATION: Xaa can be Pro, Gln or Ile
<220> FEATURE:
<221> NAME/KEY: VARIANT
<222> LOCATION: (345)..(345)
<223> OTHER INFORMATION: Xaa can be Phe or Leu
<220> FEATURE:
<221> NAME/KEY: VARIANT
<222> LOCATION: (346)..(346)
<223> OTHER INFORMATION: Xaa can be Lys, Ser, Val or Gly
<220> FEATURE:
<221> NAME/KEY: VARIANT
<222> LOCATION: (347)..(347)
<223> OTHER INFORMATION: Xaa can be Gly, Glu or Lys
<220> FEATURE:
<221> NAME/KEY: VARIANT
<222> LOCATION: (348)..(348)
<223> OTHER INFORMATION: Xaa can be Val, Ile, Thr, Lys or Cys
<220> FEATURE:
<221> NAME/KEY: VARIANT
<222> LOCATION: (349)..(349)
<223> OTHER INFORMATION: Xaa can be Val, Leu, Ile or Asp
<220> FEATURE:
<221> NAME/KEY: VARIANT
<222> LOCATION: (350)..(350)
<223> OTHER INFORMATION: Xaa can be Phe, Tyr, Gln or Trp
<220> FEATURE:
<221> NAME/KEY: VARIANT
<222> LOCATION: (351)..(351)
<223> OTHER INFORMATION: Xaa can be Gly or His
<220> FEATURE:
<221> NAME/KEY: VARIANT
<222> LOCATION: (352)..(352)
<223> OTHER INFORMATION: Xaa can be Val, Ile or Met
<220> FEATURE:
<221> NAME/KEY: VARIANT
<222> LOCATION: (353)..(353)
<223> OTHER INFORMATION: Xaa can be Ala, Leu, Asn or Arg
<220> FEATURE:
<221> NAME/KEY: VARIANT
<222> LOCATION: (354)..(354)
<223> OTHER INFORMATION: Xaa can be Ser, Thr, Ala, Ile or Met
<220> FEATURE:
<221> NAME/KEY: VARIANT
```

<222> LOCATION: (355)..(355)
<223> OTHER INFORMATION: Xaa can be Gln, Ser or Thr
<220> FEATURE:
<221> NAME/KEY: VARIANT
<222> LOCATION: (356)..(356)
<223> OTHER INFORMATION: Xaa can be Arg, Asp, Thr, Pro, Lys or Gln
<220> FEATURE:
<221> NAME/KEY: VARIANT
<222> LOCATION: (357)..(357)
<223> OTHER INFORMATION: Xaa can be Asn, Asp, Thr, Ala or Phe
<220> FEATURE:
<221> NAME/KEY: VARIANT
<222> LOCATION: (358)..(358)
<223> OTHER INFORMATION: Xaa can be Val, Arg, Asn, Pro or Gly
<220> FEATURE:
<221> NAME/KEY: VARIANT
<222> LOCATION: (359)..(359)
<223> OTHER INFORMATION: Xaa can be Gly, Arg, Ser, Ala, Asn, His or absent
<220> FEATURE:
<221> NAME/KEY: VARIANT
<222> LOCATION: (360)..(360)
<223> OTHER INFORMATION: Xaa can be Asn, Gly, Gly, Phe, Ser or Absent
<220> FEATURE:
<221> NAME/KEY: VARIANT
<222> LOCATION: (361)..(361)
<223> OTHER INFORMATION: Xaa can be Asp, Asn, Gln, Thr, Ser or absent
<220> FEATURE:
<221> NAME/KEY: VARIANT
<222> LOCATION: (362)..(362)
<223> OTHER INFORMATION: Xa can be Ala, Thr, Gln, Ser or absent
<220> FEATURE:
<221> NAME/KEY: VARIANT
<222> LOCATION: (363)..(363)
<223> OTHER INFORMATION: Xaa can be Pro, Gln, Val, Asp or absent
<220> FEATURE:
<221> NAME/KEY: VARIANT
<222> LOCATION: (364)..(364)
<223> OTHER INFORMATION: Xaa can be Gly, Glu, Asp, Ser or absent
<220> FEATURE:
<221> NAME/KEY: VARIANT
<222> LOCATION: (365)..(365)
<223> OTHER INFORMATION: Xaa can be Ser, Ala or Gly
<220> FEATURE:
<221> NAME/KEY: VARIANT
<222> LOCATION: (366)..(366)
<223> OTHER INFORMATION: Xaa can be Thr, Lys, Ser, Asp or absent
<220> FEATURE:
<221> NAME/KEY: VARIANT
<222> LOCATION: (367)..(367)
<223> OTHER INFORMATION: Xaa can be Arg, Asn, Ile, Pro or absent
<220> FEATURE:
<221> NAME/KEY: VARIANT
<222> LOCATION: (368)..(368)
<223> OTHER INFORMATION: Xaa can be Ala, Gly, Ile, Met or Gln
<220> FEATURE:
<221> NAME/KEY: VARIANT
<222> LOCATION: (369)..(369)
<223> OTHER INFORMATION: Xaa can be His, Lys, Arg or Thr
<220> FEATURE:
<221> NAME/KEY: VARIANT
<222> LOCATION: (370)..(370)
<223> OTHER INFORMATION: Xaa can be Glu, Gly, Lys, Arg, Ser or Gln
<220> FEATURE:
<221> NAME/KEY: VARIANT
<222> LOCATION: (371)..(371)
<223> OTHER INFORMATION: Xaa can be Ala, Val, Ile or Tyr
<220> FEATURE:
<221> NAME/KEY: VARIANT
<222> LOCATION: (372)..(372)
<223> OTHER INFORMATION: Xaa can be Val, Tyr, His, Thr or Asp
<220> FEATURE:
<221> NAME/KEY: VARIANT
<222> LOCATION: (373)..(373)
<223> OTHER INFORMATION: Xaa can be Ile or Val
<220> FEATURE:
<221> NAME/KEY: VARIANT
<222> LOCATION: (374)..(374)
<223> OTHER INFORMATION: Xaa can be Ser, Asn, Tyr, Ala, Gln or Asp
<220> FEATURE:
<221> NAME/KEY: VARIANT
<222> LOCATION: (375)..(375)
<223> OTHER INFORMATION: Xaa can be Thr or absent
<220> FEATURE:
<221> NAME/KEY: VARIANT
<222> LOCATION: (376)..(376)
<223> OTHER INFORMATION: Xaa can be Tyr, Thr, Gly, Gln or Asp
<220> FEATURE:
<221> NAME/KEY: VARIANT
<222> LOCATION: (377)..(377)
<223> OTHER INFORMATION: Xaa can be Ser, Asp, Val or Pro
<220> FEATURE:
<221> NAME/KEY: VARIANT
<222> LOCATION: (378)..(378)
<223> OTHER INFORMATION: Xaa can be Pro, Gly, Ala, Ser, Gln or Asp
<220> FEATURE:
<221> NAME/KEY: VARIANT
<222> LOCATION: (379)..(379)
<223> OTHER INFORMATION: Xaa can be Gln, Lys, Arg, Asp, Thr or Gly
<220> FEATURE:
<221> NAME/KEY: VARIANT
<222> LOCATION: (380)..(380)
<223> OTHER INFORMATION: Xaa can be Phe or Tyr
<220> FEATURE:
<221> NAME/KEY: VARIANT
<222> LOCATION: (381)..(381)
<223> OTHER INFORMATION: Xaa can be Val, Thr or Ala
<220> FEATURE:
<221> NAME/KEY: VARIANT
<222> LOCATION: (382)..(382)
<223> OTHER INFORMATION: Xaa is Pro
<220> FEATURE:
<221> NAME/KEY: VARIANT
<222> LOCATION: (383)..(383)
<223> OTHER INFORMATION: Xaa can be Lys or His
<220> FEATURE:
<221> NAME/KEY: VARIANT
<222> LOCATION: (384)..(384)
<223> OTHER INFORMATION: Xaa can be Lys or Ile
<220> FEATURE:
<221> NAME/KEY: VARIANT
<222> LOCATION: (386)..(386)
<223> OTHER INFORMATION: Xaa can be Ser, Arg or Thr
<220> FEATURE:
<221> NAME/KEY: VARIANT
<222> LOCATION: (387)..(387)
<223> OTHER INFORMATION: Xaa can be Val or Ile
<220> FEATURE:
<221> NAME/KEY: VARIANT
<222> LOCATION: (388)..(388)
<223> OTHER INFORMATION: Xaa can be Asn, Gly, Leu, Gln or His
<220> FEATURE:
<221> NAME/KEY: VARIANT
<222> LOCATION: (389)..(389)
<223> OTHER INFORMATION: Xaa can be Phe, Leu, Met, Tyr or Ala
<220> FEATURE:
<221> NAME/KEY: VARIANT
<222> LOCATION: (390)..(390)
<223> OTHER INFORMATION: Xaa can be Arg, His, Tyr, Glu, Thr, Asp or Asn
<220> FEATURE:
<221> NAME/KEY: VARIANT
<222> LOCATION: (391)..(391)
<223> OTHER INFORMATION: Xaa can be Ser, Thr, Asn, Glu or Gly
<220> FEATURE:
<221> NAME/KEY: VARIANT
<222> LOCATION: (392)..(392)
<223> OTHER INFORMATION: Xaa can be Asn, Ile, Glu, Asp, Ala or Val
<220> FEATURE:
<221> NAME/KEY: VARIANT
<222> LOCATION: (393)..(393)
<223> OTHER INFORMATION: Xaa can be Thr, Asp, Phe or absent
<220> FEATURE:
<221> NAME/KEY: VARIANT
<222> LOCATION: (394)..(394)
<223> OTHER INFORMATION: Xaa can be Asp, Thr, Ser, Tyr, Asn or absent
<220> FEATURE:
<221> NAME/KEY: VARIANT
<222> LOCATION: (395)..(395)

```
<223> OTHER INFORMATION: Xaa can be Asn, Glu, Asp, Arg, His or absent
<220> FEATURE:
<221> NAME/KEY: VARIANT
<222> LOCATION: (396)..(396)
<223> OTHER INFORMATION: Xaa can be Asp, Ala, Pro or Gly
<220> FEATURE:
<221> NAME/KEY: VARIANT
<222> LOCATION: (397)..(397)
<223> OTHER INFORMATION: Xaa can be Phe, Val, Asn, Thr or Ser
<220> FEATURE:
<221> NAME/KEY: VARIANT
<222> LOCATION: (398)..(398)
<223> OTHER INFORMATION: Xaa can be Gln, Arg, Val, Glu or Gly
<220> FEATURE:
<221> NAME/KEY: VARIANT
<222> LOCATION: (399)..(399)
<223> OTHER INFORMATION: Xaa can be Pro, Thr, Ala or absent
<220> FEATURE:
<221> NAME/KEY: VARIANT
<222> LOCATION: (400)..(400)
<223> OTHER INFORMATION: Xaa can be Leu, Asn, Gly or absent
<220> FEATURE:
<221> NAME/KEY: VARIANT
<222> LOCATION: (401)..(401)
<223> OTHER INFORMATION: Xaa can be Gln or absent
<220> FEATURE:
<221> NAME/KEY: VARIANT
<222> LOCATION: (402)..(402)
<223> OTHER INFORMATION: Xaa can be Pro, Gln, Asn or absent
<220> FEATURE:
<221> NAME/KEY: VARIANT
<222> LOCATION: (403)..(403)
<223> OTHER INFORMATION: Xaa can be Thr, Ser, Val, Gly, Asp or Asn
<220> FEATURE:
<221> NAME/KEY: VARIANT
<222> LOCATION: (404)..(404)
<223> OTHER INFORMATION: Caa can be Lys, Arg, Leu or Tyr
<220> FEATURE:
<221> NAME/KEY: VARIANT
<222> LOCATION: (405)..(405)
<223> OTHER INFORMATION: Xaa can be Phe, Ile or Val
<220> FEATURE:
<221> NAME/KEY: VARIANT
<222> LOCATION: (406)..(406)
<223> OTHER INFORMATION: Xaa can be Thr, Cys or Gly
<220> FEATURE:
<221> NAME/KEY: VARIANT
<222> LOCATION: (407)..(407)
<223> OTHER INFORMATION: Xaa can be Pro, Ser, Thr or Val
<220> FEATURE:
<221> NAME/KEY: VARIANT
<222> LOCATION: (408)..(408)
<223> OTHER INFORMATION: Xaa can be Val, Ile or Leu
<220> FEATURE:
<221> NAME/KEY: VARIANT
<222> LOCATION: (409)..(409)
<223> OTHER INFORMATION: Xaa can be Gly, Glu or Ser
<220> FEATURE:
<221> NAME/KEY: VARIANT
<222> LOCATION: (410)..(410)
<223> OTHER INFORMATION: Xaa can be Ile, Val, Met or Trp
<220> FEATURE:
<221> NAME/KEY: VARIANT
<222> LOCATION: (411)..(411)
<223> OTHER INFORMATION: Xaa can be Asn, Ala, Gly, Ile or Leu
<220> FEATURE:
<221> NAME/KEY: VARIANT
<222> LOCATION: (412)..(412)
<223> OTHER INFORMATION: Xaa can be Asp, Gln or Ser
<220> FEATURE:
<221> NAME/KEY: VARIANT
<222> LOCATION: (413)..(413)
<223> OTHER INFORMATION: Xaa can be Asp, Asn, Pro or Gln
<220> FEATURE:
<221> NAME/KEY: VARIANT
<222> LOCATION: (414)..(414)
<223> OTHER INFORMATION: Xaa can be Gly, Glu, Pro or absent
<220> FEATURE:
<221> NAME/KEY: VARIANT
```

<222> LOCATION: (415)..(415)
<223> OTHER INFORMATION: Xaa can be Asp, Asn, Gly, Ser or absent
<220> FEATURE:
<221> NAME/KEY: misc_feature
<222> LOCATION: (416)..(416)
<223> OTHER INFORMATION: Xaa can be any naturally occurring amino acid
<220> FEATURE:
<221> NAME/KEY: VARIANT
<222> LOCATION: (417)..(417)
<223> OTHER INFORMATION: Xaa can be Thr, Gly, Pro or absent
<220> FEATURE:
<221> NAME/KEY: VARIANT
<222> LOCATION: (418)..(418)
<223> OTHER INFORMATION: Xaa can be His, Pro, Ser or absent
<220> FEATURE:
<221> NAME/KEY: VARIANT
<222> LOCATION: (419)..(419)
<223> OTHER INFORMATION: Xaa can be Arg, Ala Gly or absent
<220> FEATURE:
<221> NAME/KEY: VARIANT
<222> LOCATION: (420)..(420)
<223> OTHER INFORMATION: Xaa can be Asn, Pro, Thr, Ser or absent
<220> FEATURE:
<221> NAME/KEY: VARIANT
<222> LOCATION: (421)..(421)
<223> OTHER INFORMATION: Xaa can be Pro, Asp, Gu, Lys or Gln
<220> FEATURE:
<221> NAME/KEY: VARIANT
<222> LOCATION: (422)..(422)
<223> OTHER INFORMATION: Xaa can be Phe, Trp, Pro, Val or Ile
<220> FEATURE:
<221> NAME/KEY: VARIANT
<222> LOCATION: (423)..(423)
<223> OTHER INFORMATION: Xaa can be Arg, Gln, His, Asn or Asp
<220> FEATURE:
<221> NAME/KEY: VARIANT
<222> LOCATION: (424)..(424)
<223> OTHER INFORMATION: Xaa can be Gln, Pro or Leu
<220> FEATURE:
<221> NAME/KEY: VARIANT
<222> LOCATION: (426)..(426)
<223> OTHER INFORMATION: Xaa can be Glu, Val, Ala or Lys
<220> FEATURE:
<221> NAME/KEY: VARIANT
<222> LOCATION: (427)..(427)
<223> OTHER INFORMATION: Xaa can be Leu or Ile
<220> FEATURE:
<221> NAME/KEY: VARIANT
<222> LOCATION: (429)..(429)
<223> OTHER INFORMATION: Xaa can be Asp, His, Ser, Arg or Asn
<220> FEATURE:
<221> NAME/KEY: VARIANT
<222> LOCATION: (431)..(431)
<223> OTHER INFORMATION: Xaa can be Ser, Ala, Pro or Gly
<220> FEATURE:
<221> NAME/KEY: VARIANT
<222> LOCATION: (432)..(432)
<223> OTHER INFORMATION: Xaa can be Gly or Ser
<220> FEATURE:
<221> NAME/KEY: VARIANT
<222> LOCATION: (433)..(433)
<223> OTHER INFORMATION: Xaa can be Leu, Ala, His, Arg, Thr or Ser
<220> FEATURE:
<221> NAME/KEY: VARIANT
<222> LOCATION: (434)..(434)
<223> OTHER INFORMATION: Xaa can be Leu, Asn or Ile
<220> FEATURE:
<221> NAME/KEY: VARIANT
<222> LOCATION: (435)..(435)
<223> OTHER INFORMATION: Xaa can be Thr, Ala or Ser
<220> FEATURE:
<221> NAME/KEY: VARIANT
<222> LOCATION: (436)..(436)
<223> OTHER INFORMATION: Xaa can be Leu, His, Glu or Gln
<220> FEATURE:
<221> NAME/KEY: VARIANT
<222> LOCATION: (437)..(437)
<223> OTHER INFORMATION: Xaa can be Asn or Ala
<220> FEATURE:

<221> NAME/KEY: VARIANT
<222> LOCATION: (438)..(438)
<223> OTHER INFORMATION: Xaa can be Met, Thr, Val or Ala
<220> FEATURE:
<221> NAME/KEY: VARIANT
<222> LOCATION: (439)..(439)
<223> OTHER INFORMATION: Xaa can be Asn, His or Gln
<220> FEATURE:
<221> NAME/KEY: VARIANT
<222> LOCATION: (443)..(443)
<223> OTHER INFORMATION: Xaa can be Pro, Ala or Ser
<220> FEATURE:
<221> NAME/KEY: VARIANT
<222> LOCATION: (444)..(444)
<223> OTHER INFORMATION: Xaa can be Val or Ile
<220> FEATURE:
<221> NAME/KEY: VARIANT
<222> LOCATION: (445)..(445)
<223> OTHER INFORMATION: Xaa can be Ala, Tyr or Phe
<220> FEATURE:
<221> NAME/KEY: VARIANT
<222> LOCATION: (447)..(447)
<223> OTHER INFORMATION: Xaa can be Asn, Thr, Ala or Pro
<220> FEATURE:
<221> NAME/KEY: VARIANT
<222> LOCATION: (448)..(448)
<223> OTHER INFORMATION: Xaa can be Phe or Gly
<220> FEATURE:
<221> NAME/KEY: VARIANT
<222> LOCATION: (449)..(449)
<223> OTHER INFORMATION: Xaa can be Pro or Phe
<220> FEATURE:
<221> NAME/KEY: VARIANT
<222> LOCATION: (452)..(452)
<223> OTHER INFORMATION: Xaa can be Gln, Arg, Ala or Val
<220> FEATURE:
<221> NAME/KEY: VARIANT
<222> LOCATION: (453)..(453)
<223> OTHER INFORMATION: Xaa can be Leu or Ile
<220> FEATURE:
<221> NAME/KEY: VARIANT
<222> LOCATION: (454)..(454)
<223> OTHER INFORMATION: Xaa can be Leu or Val
<220> FEATURE:
<221> NAME/KEY: VARIANT
<222> LOCATION: (455)..(455)
<223> OTHER INFORMATION: Xaa can be Phe or Tyr
<220> FEATURE:
<221> NAME/KEY: VARIANT
<222> LOCATION: (457)..(457)
<223> OTHER INFORMATION: Xaa can be Arg, Met or Val
<220> FEATURE:
<221> NAME/KEY: misc_feature
<222> LOCATION: (458)..(458)
<223> OTHER INFORMATION: Xaa can be any naturally occurring amino acid
<220> FEATURE:
<221> NAME/KEY: VARIANT
<222> LOCATION: (459)..(459)
<223> OTHER INFORMATION: Xaa can be Phe, Arg, Ile, Thr, Asp, Ala or Lys
<220> FEATURE:
<221> NAME/KEY: VARIANT
<222> LOCATION: (460)..(460)
<223> OTHER INFORMATION: Xaa can be Val, Met, Phe or Met
<220> FEATURE:
<221> NAME/KEY: VARIANT
<222> LOCATION: (462)..(462)
<223> OTHER INFORMATION: Xaa can be Cys, Ser, Gly or Ile
<220> FEATURE:
<221> NAME/KEY: VARIANT
<222> LOCATION: (463)..(463)
<223> OTHER INFORMATION: Xaa can be Ser, Val, Ala, Cys or Pro
<220> FEATURE:
<221> NAME/KEY: VARIANT
<222> LOCATION: (464)..(464)
<223> OTHER INFORMATION: Xaa can be Gly, Gln, Ser or Asn
<220> FEATURE:
<221> NAME/KEY: VARIANT
<222> LOCATION: (465)..(465)
<223> OTHER INFORMATION: Xaa can be Gly, Asn or Ala
<220> FEATURE:
<221> NAME/KEY: VARIANT
<222> LOCATION: (466)..(466)
<223> OTHER INFORMATION: Xaa can be Tyr, Leu, Arg or absent
<220> FEATURE:
<221> NAME/KEY: VARIANT
<222> LOCATION: (467)..(467)
<223> OTHER INFORMATION: Xaa can be Asp, Gln, Gly, Pro, Ser or absent
<220> FEATURE:
<221> NAME/KEY: VARIANT
<222> LOCATION: (468)..(468)
<223> OTHER INFORMATION: Xaa can be Gly or absent
<220> FEATURE:
<221> NAME/KEY: VARIANT
<222> LOCATION: (470)..(470)
<223> OTHER INFORMATION: Xaa can be Gln, Asp, Ser, Asn, Gly, Pro or
absent
<220> FEATURE:
<221> NAME/KEY: misc_feature
<222> LOCATION: (471)..(471)
<223> OTHER INFORMATION: Xaa can be any naturally occurring amino acid
<220> FEATURE:
<221> NAME/KEY: VARIANT
<222> LOCATION: (472)..(472)
<223> OTHER INFORMATION: Xaa can be Ile, Phe, Gln, Asp, Ser or Asn
<220> FEATURE:
<221> NAME/KEY: VARIANT
<222> LOCATION: (473)..(473)
<223> OTHER INFORMATION: Xaa can be Val, Ile or Leu
<220> FEATURE:
<221> NAME/KEY: VARIANT
<222> LOCATION: (474)..(474)
<223> OTHER INFORMATION: Xaa can be Asp or Pro
<220> FEATURE:
<221> NAME/KEY: VARIANT
<222> LOCATION: (476)..(476)
<223> OTHER INFORMATION: Xaa can be Leu or Thr
<220> FEATURE:
<221> NAME/KEY: misc_feature
<222> LOCATION: (477)..(477)
<223> OTHER INFORMATION: Xaa can be any naturally occurring amino acid
<220> FEATURE:
<221> NAME/KEY: VARIANT
<222> LOCATION: (479)..(479)
<223> OTHER INFORMATION: Xaa can be Ile or Leu
<220> FEATURE:
<221> NAME/KEY: VARIANT
<222> LOCATION: (481)..(481)
<223> OTHER INFORMATION: Xaa can be Trp, Phe or Tyr
<220> FEATURE:
<221> NAME/KEY: VARIANT
<222> LOCATION: (482)..(482)
<223> OTHER INFORMATION: Xaa can be Ile or Val
<220> FEATURE:
<221> NAME/KEY: VARIANT
<222> LOCATION: (483)..(483)
<223> OTHER INFORMATION: Xaa can be Gln, Asn, Thr or Ser
<220> FEATURE:
<221> NAME/KEY: VARIANT
<222> LOCATION: (484)..(484)
<223> OTHER INFORMATION: Xaa can be His or Tyr
<220> FEATURE:
<221> NAME/KEY: VARIANT
<222> LOCATION: (485)..(485)
<223> OTHER INFORMATION: Xaa can be Phe or Leu
<220> FEATURE:
<221> NAME/KEY: VARIANT
<222> LOCATION: (486)..(486)
<223> OTHER INFORMATION: Xaa can be Tyr, Val or Ala
<220> FEATURE:
<221> NAME/KEY: VARIANT
<222> LOCATION: (487)..(487)
<223> OTHER INFORMATION: Xaa can be Gln, Asn or Ser
<220> FEATURE:
<221> NAME/KEY: VARIANT
<222> LOCATION: (489)..(489)
<223> OTHER INFORMATION: Xaa can be Ser, Ala or Gln
<220> FEATURE:
<221> NAME/KEY: VARIANT
<222> LOCATION: (492)..(492)
<223> OTHER INFORMATION: Xaa can be Ser, Ala or Thr
<220> FEATURE:
<221> NAME/KEY: VARIANT
<222> LOCATION: (493)..(493)
<223> OTHER INFORMATION: Xaa can be Gln, Arg, Met or Val
<220> FEATURE:
<221> NAME/KEY: VARIANT
<222> LOCATION: (494)..(494)
<223> OTHER INFORMATION: Xaa can be Ser, Ala or Gly
<220> FEATURE:
<221> NAME/KEY: VARIANT
<222> LOCATION: (495)..(495)
<223> OTHER INFORMATION: Xaa can be Asp, Ala or Glu
<220> FEATURE:
<221> NAME/KEY: VARIANT
<222> LOCATION: (496)..(496)
<223> OTHER INFORMATION: Xaa can be Val or Ala
<220> FEATURE:
<221> NAME/KEY: VARIANT
<222> LOCATION: (499)..(499)
<223> OTHER INFORMATION: Xaa can be Leu or Ile
<220> FEATURE:
<221> NAME/KEY: VARIANT
<222> LOCATION: (500)..(500)
<223> OTHER INFORMATION: Xaa can be Arg or His
<220> FEATURE:
<221> NAME/KEY: VARIANT
<222> LOCATION: (501)..(501)
<223> OTHER INFORMATION: Xaa can be Tyr or Phe
<220> FEATURE:
<221> NAME/KEY: VARIANT
<222> LOCATION: (503)..(503)
<223> OTHER INFORMATION: Xaa can be Asn or Asp
<220> FEATURE:
<221> NAME/KEY: VARIANT
<222> LOCATION: (507)..(507)
<223> OTHER INFORMATION: Xaa can be Gly, His or Asn
<220> FEATURE:
<221> NAME/KEY: VARIANT
<222> LOCATION: (509)..(509)
<223> OTHER INFORMATION: Xaa can be Thr, Asn or Val
<220> FEATURE:
<221> NAME/KEY: VARIANT
<222> LOCATION: (510)..(510)
<223> OTHER INFORMATION: Xaa can be Leu or Ile
<220> FEATURE:
<221> NAME/KEY: VARIANT
<222> LOCATION: (511)..(511)
<223> OTHER INFORMATION: Xaa can be Phe or Gly
<220> FEATURE:
<221> NAME/KEY: VARIANT
<222> LOCATION: (513)..(513)
<223> OTHER INFORMATION: Xaa can be Ala, Cys or Phe
<220> FEATURE:
<221> NAME/KEY: VARIANT
<222> LOCATION: (515)..(515)
<223> OTHER INFORMATION: Xaa can be Leu or Ala
<220> FEATURE:
<221> NAME/KEY: VARIANT
<222> LOCATION: (516)..(516)
<223> OTHER INFORMATION: Xaa can be His or Tyr
<220> FEATURE:
<221> NAME/KEY: VARIANT
<222> LOCATION: (517)..(517)
<223> OTHER INFORMATION: Xaa can be Arg, Lys or Pro
<220> FEATURE:
<221> NAME/KEY: VARIANT
<222> LOCATION: (518)..(518)
<223> OTHER INFORMATION: Xaa can be Ser, Glu, Gly or Asp
<220> FEATURE:
<221> NAME/KEY: VARIANT
<222> LOCATION: (520)..(520)
<223> OTHER INFORMATION: Xaa can be Phe or Tyr
<220> FEATURE:
<221> NAME/KEY: VARIANT
<222> LOCATION: (521)..(521)
<223> OTHER INFORMATION: Xaa can be Ile, Val, Met or Leu
<220> FEATURE:

<221> NAME/KEY: VARIANT
<222> LOCATION: (523)..(523)
<223> OTHER INFORMATION: Xaa can be Val or Cys
<220> FEATURE:
<221> NAME/KEY: VARIANT
<222> LOCATION: (524)..(524)
<223> OTHER INFORMATION: Xaa can be Ala, Ser or Val
<220> FEATURE:
<221> NAME/KEY: VARIANT
<222> LOCATION: (525)..(525)
<223> OTHER INFORMATION: Xaa can be His or Pro
<220> FEATURE:
<221> NAME/KEY: VARIANT
<222> LOCATION: (526)..(526)
<223> OTHER INFORMATION: Xaa can be Asn or absent
<220> FEATURE:
<221> NAME/KEY: VARIANT
<222> LOCATION: (527)..(527)
<223> OTHER INFORMATION: Xaa can be Gly, Ser or absent
<220> FEATURE:
<221> NAME/KEY: VARIANT
<222> LOCATION: (528)..(528)
<223> OTHER INFORMATION: Xaa can be Ser, Thr, Val or Ala
<220> FEATURE:
<221> NAME/KEY: VARIANT
<222> LOCATION: (529)..(529)
<223> OTHER INFORMATION: Xaa can be Gly or Ser
<220> FEATURE:
<221> NAME/KEY: VARIANT
<222> LOCATION: (530)..(530)
<223> OTHER INFORMATION: Xaa can be Asp, Ala, Asn, Gln or Ser
<220> FEATURE:
<221> NAME/KEY: VARIANT
<222> LOCATION: (531)..(531)
<223> OTHER INFORMATION: Xaa can be Tyr, Asn, His or Gly
<220> FEATURE:
<221> NAME/KEY: VARIANT
<222> LOCATION: (532)..(532)
<223> OTHER INFORMATION: Xaa can be Pro or Asp
<220> FEATURE:
<221> NAME/KEY: VARIANT
<222> LOCATION: (533)..(533)
<223> OTHER INFORMATION: Xaa can be Leu, Ile or Gln
<220> FEATURE:
<221> NAME/KEY: VARIANT
<222> LOCATION: (534)..(534)
<223> OTHER INFORMATION: Xaa can be Val, Thr or Gln
<220> FEATURE:
<221> NAME/KEY: VARIANT
<222> LOCATION: (535)..(535)
<223> OTHER INFORMATION: Xaa can be Val, Ile or Leu
<220> FEATURE:
<221> NAME/KEY: VARIANT
<222> LOCATION: (537)..(537)
<223> OTHER INFORMATION: Xaa can be Ala, Pro, Ile or Leu
<220> FEATURE:
<221> NAME/KEY: VARIANT
<222> LOCATION: (540)..(540)
<223> OTHER INFORMATION: Xaa can e Tyr, His or Val
<220> FEATURE:
<221> NAME/KEY: VARIANT
<222> LOCATION: (542)..(542)
<223> OTHER INFORMATION: Xaa can be Arg, Thr, Leu or Val
<220> FEATURE:
<221> NAME/KEY: VARIANT
<222> LOCATION: (544)..(544)
<223> OTHER INFORMATION: Xaa can be Asp, Glu, Ile or Val
<220> FEATURE:
<221> NAME/KEY: VARIANT
<222> LOCATION: (545)..(545)
<223> OTHER INFORMATION: Xaa can be Ser or Ala
<220> FEATURE:
<221> NAME/KEY: VARIANT
<222> LOCATION: (548)..(548)
<223> OTHER INFORMATION: Xaa can be Asn or Ser
<220> FEATURE:
<221> NAME/KEY: VARIANT
<222> LOCATION: (549)..(549)
<223> OTHER INFORMATION: Xaa can be Gln or Arg
<220> FEATURE:
<221> NAME/KEY: VARIANT
<222> LOCATION: (552)..(552)
<223> OTHER INFORMATION: Xaa can be Ser, Thr or Gln
<220> FEATURE:
<221> NAME/KEY: VARIANT
<222> LOCATION: (554)..(554)
<223> OTHER INFORMATION: Xaa can be Ala, Thr or Lys
<220> FEATURE:
<221> NAME/KEY: VARIANT
<222> LOCATION: (556)..(556)
<223> OTHER INFORMATION: Xaa can be Met or Val
<220> FEATURE:
<221> NAME/KEY: VARIANT
<222> LOCATION: (558)..(558)
<223> OTHER INFORMATION: Xaa can be Thr or Asn
<220> FEATURE:
<221> NAME/KEY: VARIANT
<222> LOCATION: (559)..(559)
<223> OTHER INFORMATION: Xaa can be Gly, Thr or Ala
<220> FEATURE:
<221> NAME/KEY: VARIANT
<222> LOCATION: (560)..(560)
<223> OTHER INFORMATION: Xaa can be Asn, Gln, Thr, Gly or Ser
<220> FEATURE:
<221> NAME/KEY: VARIANT
<222> LOCATION: (561)..(561)
<223> OTHER INFORMATION: Xaa can be Gly, Pro, Thr or Ser
<220> FEATURE:
<221> NAME/KEY: VARIANT
<222> LOCATION: (562)..(562)
<223> OTHER INFORMATION: Xaa can be Arg, Val or Ala
<220> FEATURE:
<221> NAME/KEY: VARIANT
<222> LOCATION: (564)..(564)
<223> OTHER INFORMATION: Xaa can be Arg, Gly or absent
<220> FEATURE:
<221> NAME/KEY: VARIANT
<222> LOCATION: (565)..(565)
<223> OTHER INFORMATION: Xaa can be Ala, Val, Asp or Arg
<220> FEATURE:
<221> NAME/KEY: VARIANT
<222> LOCATION: (566)..(566)
<223> OTHER INFORMATION: Xaa can be Gln, Val or Leu
<220> FEATURE:
<221> NAME/KEY: VARIANT
<222> LOCATION: (568)..(568)
<223> OTHER INFORMATION: Xaa can be Ile, Val, Leu or absent
<220> FEATURE:
<221> NAME/KEY: VARIANT
<222> LOCATION: (571)..(571)
<223> OTHER INFORMATION: Xaa can be Ser, Ile or absent

<400> SEQUENCE: 70

```
Met Xaa Met Ala Ser Xaa Asp Ala Xaa Xaa Xaa Xaa Xaa Gly Xaa Ser
1               5                   10                  15

Xaa Ala Xaa Xaa Leu Val Pro Glu Xaa Xaa Xaa Xaa Xaa Xaa Xaa Xaa
            20                  25                  30

Xaa Xaa Pro Val Xaa Gly Xaa Xaa Xaa Ala Xaa Xaa Xaa Xaa Gly Gln
        35                  40                  45

Xaa Asn Xaa Ile Asp Pro Trp Ile Xaa Xaa Asn Xaa Val Gln Xaa Pro
    50                  55                  60

Xaa Gly Glu Phe Thr Xaa Ser Pro Xaa Asn Xaa Pro Gly Xaa Xaa Leu
65                  70                  75                  80

Xaa Xaa Xaa Xaa Leu Gly Pro Xaa Leu Asn Pro Xaa Leu Xaa His Leu
                85                  90                  95

Xaa Xaa Met Tyr Asn Gly Xaa Xaa Gly Xaa Xaa Xaa Val Xaa Xaa Xaa
            100                 105                 110

Leu Ala Gly Asn Ala Phe Xaa Ala Gly Lys Xaa Xaa Xaa Xaa Xaa Xaa
        115                 120                 125
```

```
Pro Pro Xaa Phe Xaa Xaa Xaa Xaa Xaa Xaa Xaa Xaa Gln Xaa Thr Xaa
    130                 135                 140

Xaa Pro His Xaa Xaa Xaa Asp Val Arg Xaa Leu Xaa Pro Xaa Xaa Xaa
145                 150                 155                 160

Pro Leu Xaa Asp Xaa Arg Asn Xaa Xaa Xaa His Xaa Asn Xaa Xaa Xaa
                165                 170                 175

Xaa Xaa Xaa Xaa Xaa Leu Xaa Xaa Met Leu Tyr Thr Pro Leu Arg Xaa
            180                 185                 190

Xaa Xaa Xaa Xaa Xaa Xaa Xaa Asp Xaa Phe Xaa Xaa Xaa Xaa Arg Val
        195                 200                 205

Xaa Thr Xaa Pro Xaa Xaa Asp Phe Xaa Phe Xaa Xaa Leu Val Pro Pro
    210                 215                 220

Xaa Xaa Glu Xaa Xaa Thr Xaa Xaa Phe Xaa Xaa Pro Xaa Xaa Xaa Xaa
225                 230                 235                 240

Xaa Xaa Xaa Xaa Asn Ser Arg Xaa Pro Xaa Xaa Xaa Xaa Xaa Xaa Xaa
                245                 250                 255

Xaa Xaa Xaa Xaa Xaa Xaa Xaa Xaa Val Gln Xaa Gln Asn Gly Arg Xaa
            260                 265                 270

Xaa Xaa Asp Gly Xaa Leu Xaa Gly Thr Thr Xaa Xaa Xaa Xaa Xaa Xaa
        275                 280                 285

Xaa Xaa Xaa Xaa Arg Gly Xaa Xaa Xaa Xaa Xaa Xaa Xaa Arg Ser Pro
    290                 295                 300

Asp Ser Thr Asp Ser Ala Pro Arg Xaa Xaa Xaa Xaa Xaa Xaa Xaa Xaa
305                 310                 315                 320

Xaa Leu Xaa Xaa Xaa Xaa Xaa Xaa Xaa Xaa Xaa Xaa Xaa Xaa Xaa Xaa
                325                 330                 335

Pro Ala Xaa Xaa Gly Xaa Xaa Asp Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Gly Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Trp Xaa Xaa Pro Xaa Tyr Xaa Xaa
            420                 425                 430

Xaa Xaa Xaa Xaa Xaa Xaa Xaa Leu Ala Pro Xaa Xaa Xaa Pro Xaa Xaa
        435                 440                 445

Xaa Gly Glu Xaa Xaa Xaa Xaa Phe Xaa Xaa Xaa Xaa Pro Xaa Xaa Xaa
    450                 455                 460

Xaa Xaa Xaa Xaa Gln Xaa Xaa Xaa Xaa Xaa Cys Xaa Xaa Pro Gln Glu
465                 470                 475                 480

Xaa Xaa Xaa Xaa Xaa Xaa Xaa Glu Xaa Ala Pro Xaa Xaa Xaa Xaa Xaa
                485                 490                 495

Ala Leu Xaa Xaa Xaa Val Xaa Pro Asp Thr Xaa Arg Xaa Xaa Xaa Glu
            500                 505                 510

Xaa Lys Xaa Xaa Xaa Xaa Gly Xaa Xaa Thr Xaa Xaa Xaa Xaa Xaa Xaa
        515                 520                 525

Xaa Xaa Xaa Xaa Xaa Xaa Xaa Pro Xaa Asn Gly Xaa Phe Xaa Phe Xaa
    530                 535                 540

Xaa Trp Val Xaa Xaa Phe Tyr Xaa Leu Xaa Pro Xaa Gly Xaa Xaa Xaa
```

```
545                 550                 555                 560

Xaa Xaa Arg Xaa Xaa Xaa Gly Xaa Arg Arg Xaa
                565                 570


<210> SEQ ID NO 71
<211> LENGTH: 539
<212> TYPE: PRT
<213> ORGANISM: Artificial
<220> FEATURE:
<223> OTHER INFORMATION: Amino acid sequence of S(GI.1)+P(GII.12)
      fusion VP1

<400> SEQUENCE: 71

Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220

Glu Ser Lys Thr Lys Pro Phe Thr Leu Pro Ile Leu Thr Ile Gly Glu
225                 230                 235                 240

Leu Thr Asn Ser Arg Phe Pro Val Pro Ile Asp Glu Leu Tyr Thr Ser
                245                 250                 255

Pro Asn Glu Ser Leu Val Val Gln Pro Gln Asn Gly Arg Cys Ala Leu
            260                 265                 270

Asp Gly Glu Leu Gln Gly Thr Thr Gln Leu Leu Pro Thr Ala Ile Cys
        275                 280                 285

Ser Phe Arg Gly Arg Ile Asn Gln Lys Val Ser Gly Glu Asn His Val
    290                 295                 300

Trp Asn Met Gln Val Thr Asn Ile Asp Gly Thr Pro Phe Asp Pro Thr
305                 310                 315                 320

Glu Asp Val Pro Ala Pro Leu Gly Thr Pro Asp Phe Ser Gly Lys Leu
                325                 330                 335
```

```
Phe Gly Val Leu Ser Gln Arg Asp His Asp Asn Ala Cys Arg Ser His
            340                 345                 350

Asp Ala Val Ile Ala Thr Asn Ser Ala Lys Phe Thr Pro Lys Leu Gly
        355                 360                 365

Ala Ile Gln Ile Gly Thr Trp Glu Gln Asp Asp Val His Ile Asn Gln
    370                 375                 380

Pro Thr Lys Phe Thr Pro Val Gly Leu Phe Glu Ser Glu Gly Phe Asn
385                 390                 395                 400

Gln Trp Thr Leu Pro Asn Tyr Ser Gly Ala Leu Thr Leu Asn Met Gly
                405                 410                 415

Leu Ala Pro Pro Val Ala Pro Thr Phe Pro Gly Glu Gln Ile Leu Phe
            420                 425                 430

Phe Arg Ser His Ile Pro Leu Lys Gly Gly Val Ala Asp Pro Val Ile
        435                 440                 445

Asp Cys Leu Leu Pro Gln Glu Trp Ile Gln His Leu Tyr Gln Glu Ser
    450                 455                 460

Ala Pro Ser Gln Thr Asp Val Ala Leu Ile Arg Phe Thr Asn Pro Asp
465                 470                 475                 480

Thr Gly Arg Val Leu Phe Glu Ala Lys Leu His Arg Ser Gly Tyr Ile
                485                 490                 495

Thr Val Ala Asn Thr Gly Ser Arg Pro Ile Val Val Pro Ala Asn Gly
            500                 505                 510

Tyr Phe Arg Phe Asp Ser Trp Val Asn Gln Phe Tyr Ser Leu Ala Pro
        515                 520                 525

Met Gly Thr Gly Asn Gly Arg Arg Arg Val Gln
    530                 535
```

<210> SEQ ID NO 72
<211> LENGTH: 49
<212> TYPE: DNA
<213> ORGANISM: Artificial
<220> FEATURE:
<223> OTHER INFORMATION: IF-NoV(US68)VP1(ORF2).c

<400> SEQUENCE: 72

```
tcgtgcttcg gcaccagtac aatgatgatg gcgtctaagg acgctacat                49
```

<210> SEQ ID NO 73
<211> LENGTH: 59
<212> TYPE: DNA
<213> ORGANISM: Artificial
<220> FEATURE:
<223> OTHER INFORMATION: IF-NoV(US68)VP1(ORF2).r

<400> SEQUENCE: 73

```
actaaagaaa ataggccttt atcggcgcag accaagccta cctcttgccg agctggcag      59
```

<210> SEQ ID NO 74
<211> LENGTH: 4540
<212> TYPE: DNA
<213> ORGANISM: Artificial
<220> FEATURE:
<223> OTHER INFORMATION: Construct 1190

<400> SEQUENCE: 74

```
tggcaggata tattgtggtg taaacaaatt gacgcttaga caacttaata acacattgcg     60

gacgttttta atgtactgaa ttaacgccga atcccgggct ggtatattta tatgttgtca    120

aataactcaa aaaccataaa agtttaagtt agcaagtgtg tacattttta cttgaacaaa    180
```

-continued

```
aatattcacc tactactgtt ataaatcatt attaaacatt agagtaaaga aatatggatg    240
ataagaacaa gagtagtgat attttgacaa caattttgtt gcaacatttg agaaaatttt    300
gttgttctct cttttcattg gtcaaaaaca atagagagag aaaaaggaag agggagaata    360
aaaacataat gtgagtatga gagagaaagt tgtacaaaag ttgtaccaaa atagttgtac    420
aaatatcatt gaggaatttg acaaaagcta cacaaataag ggttaattgc tgtaaataaa    480
taaggatgac gcattagaga gatgtaccat tagagaattt ttggcaagtc attaaaaaga    540
aagaataaat tatttttaaa attaaaagtt gagtcatttg attaaacatg tgattattta    600
atgaattgat gaaagagttg gattaaagtt gtattagtaa ttagaatttg gtgtcaaatt    660
taatttgaca tttgatcttt tcctatatat tgccccatag agtcagttaa ctcattttta    720
tatttcatag atcaaataag agaaataacg gtatattaat ccctccaaaa aaaaaaaacg    780
gtatatttac taaaaaatct aagccacgta ggaggataac aggatccccg taggaggata    840
acatccaatc caaccaatca caacaatcct gatgagataa cccactttaa gcccacgcat    900
ctgtggcaca tctacattat ctaaatcaca cattcttcca cacatctgag ccacacaaaa    960
accaatccac atctttatca cccattctat aaaaaatcac actttgtgag tctacacttt   1020
gattcccttc aaacacatac aaagagaaga gactaattaa ttaattaatc atcttgagag   1080
aaaatggaac gagctataca aggaaacgac gctagggaac aagctaacag tgaacgttgg   1140
gatggaggat caggaggtac cacttctccc ttcaaacttc ctgacgaaag tccgagttgg   1200
actgagtggc ggctacataa cgatgagacg aattcgaatc aagataatcc ccttggtttc   1260
aaggaaagct ggggtttcgg gaaagttgta tttaagagat atctcagata cgacaggacg   1320
gaagcttcac tgcacagagt ccttggatct tggacgggag attcggttaa ctatgcagca   1380
tctcgatttt tcggtttcga ccagatcgga tgtacctata gtattcggtt tcgaggagtt   1440
agtatcaccg tttctggagg gtcgcgaact cttcagcatc tctgtgagat ggcaattcgg   1500
tctaagcaag aactgctaca gcttgcccca atcgaagtgg aaagtaatgt atcaagagga   1560
tgccctgaag gtactcaaac cttcgaaaaa gaaagcgagt aagttaaaat gcttcttcgt   1620
ctcctattta taatatggtt tgttattgtt aattttgttc ttgtagaaga gcttaattaa   1680
tcgttgttgt tatgaaatac tatttgtatg agatgaactg gtgtaatgta attcatttac   1740
ataagtggag tcagaatcag aatgtttcct ccataactaa ctagacatga agacctgccg   1800
cgtacaattg tcttatattt gaacaactaa aattgaacat cttttgccac aactttataa   1860
gtggttaata tagctcaaat atatggtcaa gttcaataga ttaataatgg aaatatcagt   1920
tatcgaaatt cattaacaat caacttaacg ttattaacta ctaattttat atcatcccct   1980
ttgataaatg atagtacacc aattaggaag gagcatgctc gcctaggaga ttgtcgtttc   2040
ccgccttcag tttgcaagct gctctagccg tgtagccaat acgcaaaccg cctctccccg   2100
cgcgttggga attactagcg cgtgtcgaca agcttgcatg ccggtcaaca tggtggagca   2160
cgacacactt gtctactcca aaaatatcaa agatacagtc tcagaagacc aaagggcaat   2220
tgagactttt caacaaaggg taatatccgg aaacctcctc ggattccatt gcccagctat   2280
ctgtcacttt attgtgaaga tagtggaaaa ggaaggtggc tcctacaaat gccatcattg   2340
cgataaagga aaggccatcg ttgaagatgc ctctgccgac agtggtccca aagatggacc   2400
cccacccacg aggagcatcg tggaaaaaga agacgttcca accacgtctt caaagcaagt   2460
ggattgatgt gataacatgg tggagcacga cacacttgtc tactccaaaa atatcaaaga   2520
tacagtctca gaagaccaaa gggcaattga gacttttcaa caaagggtaa tatccggaaa   2580
```

```
cctcctcgga ttccattgcc cagctatctg tcactttatt gtgaagatag tggaaaagga   2640
aggtggctcc tacaaatgcc atcattgcga taaaggaaag gccatcgttg aagatgcctc   2700
tgccgacagt ggtcccaaag atggaccccc acccacgagg agcatcgtgg aaaaagaaga   2760
cgttccaacc acgtcttcaa agcaagtgga ttgatgtgat atctccactg acgtaaggga   2820
tgacgcacaa tcccactatc cttcgcaaga cccttcctct atataaggaa gttcatttca   2880
tttggagagg tattaaaatc ttaataggtt ttgataaaag cgaacgtggg gaaacccgaa   2940
ccaaaccttc ttctaaactc tctctcatct ctcttaaagc aaacttctct cttgtctttc   3000
ttgcgtgagc gatcttcaac gttgtcagat cgtgcttcgg caccgcggat ggcgaaaaac   3060
gttgcgattt tcggcttatt gttttctctt cttgtgttgg ttccttctca gatcttcgcc   3120
tgcaggctcc tcagccaaaa cgacaccccc atctgtctat ccactggccc ctggatctgc   3180
tgcccaaact aactccatgg tgaccctggg atgcctggtc aagggctatt tccctgagcc   3240
agtgacagtg acctggaact ctggatccct gtccagcggt gtgcacacct tcccagctgt   3300
cctgcagtct gacctctaca ctctgagcag ctcagtgact gtcccctcca gcacctggcc   3360
cagcgagacc gtcacctgca acgttgccca cccggccagc agcaccaagg tggacaagaa   3420
aattgtgccc agggattgtg gttgtaagcc ttgcatatgt acagtcccag aagtatcatc   3480
tgtcttcatc ttccccccaa agcccaagga tgtgctcacc attactctga ctcctaaggt   3540
cacgtgtgtt gtggtagaca tcagcaagga tgatcccgag gtccagttca gctggtttgt   3600
agatgatgtg gaggtgcaca cagctcagac gcaaccccgg gaggagcagt tcaacagcac   3660
tttccgctca gtcagtgaac ttcccatcat gcaccaggac tggctcaatg gcaaggagcg   3720
atcgctcacc atcaccatca ccatcaccat caccattaaa ggcctatttt ctttagtttg   3780
aatttactgt tattcggtgt gcatttctat gtttggtgag cggttttctg tgctcagagt   3840
gtgtttattt tatgtaattt aatttctttg tgagctcctg tttagcaggt cgtcccttca   3900
gcaaggacac aaaaagattt taattttatt aaaaaaaaaa aaaaaaaaga ccgggaattc   3960
gatatcaagc ttatcgacct gcagatcgtt caaacatttg gcaataaagt ttcttaagat   4020
tgaatcctgt tgccggtctt gcgatgatta tcatataatt tctgttgaat tacgttaagc   4080
atgtaataat taacatgtaa tgcatgacgt tatttatgag atgggttttt atgattagag   4140
tcccgcaatt atacatttaa tacgcgatag aaaacaaaat atagcgcgca aactaggata   4200
aattatcgcg cgcggtgtca tctatgttac tagatctcta gagtctcaag cttggcgcgc   4260
ccacgtgact agtggcactg gccgtcgttt tacaacgtcg tgactgggaa aaccctggcg   4320
ttacccaact taatcgcctt gcagcacatc ccccttttcgc cagctggcgt aatagcgaag   4380
aggcccgcac cgatcgccct tcccaacagt tgcgcagcct gaatggcgaa tgctagagca   4440
gcttgagctt ggatcagatt gtcgtttccc gccttcagtt taaactatca gtgtttgaca   4500
ggatatattg gcgggtaaac ctaagagaaa agagcgttta                         4540
```

```
<210> SEQ ID NO 75
<211> LENGTH: 2976
<212> TYPE: DNA
<213> ORGANISM: Artificial
<220> FEATURE:
<223> OTHER INFORMATION: Expression cassette number 2720 from 2X35S
      promoter to NOS terminator

<400> SEQUENCE: 75

gtcaacatgg tggagcacga cacacttgtc tactccaaaa atatcaaaga tacagtctca     60
```

```
gaagaccaaa gggcaattga gacttttcaa caaagggtaa tatccggaaa cctcctcgga    120
ttccattgcc cagctatctg tcactttatt gtgaagatag tggaaaagga aggtggctcc    180
tacaaatgcc atcattgcga taaaggaaag gccatcgttg aagatgcctc tgccgacagt    240
ggtcccaaag atggaccccc acccacgagg agcatcgtgg aaaaagaaga cgttccaacc    300
acgtcttcaa agcaagtgga ttgatgtgat aacatggtgg agcacgacac acttgtctac    360
tccaaaaata tcaaagatac agtctcagaa gaccaaaggg caattgagac ttttcaacaa    420
agggtaatat ccggaaacct cctcggattc cattgcccag ctatctgtca ctttattgtg    480
aagatagtgg aaaaggaagg tggctcctac aaatgccatc attgcgataa aggaaaggcc    540
atcgttgaag atgcctctgc cgacagtggt cccaaagatg gacccccacc cacgaggagc    600
atcgtggaaa aagaagacgt tccaaccacg tcttcaaagc aagtggattg atgtgatatc    660
tccactgacg taagggatga cgcacaatcc cactatcctt cgcaagaccc ttcctctata    720
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg atgatggcgt ctaaggacgc tacatcaagc gtggatggcg ctagtggcgc    960
tggtcagttg gtaccggagg ttaatgcttc tgaccctctt gcaatggatc ctgtagcagg   1020
ttcttcgaca gcagtcgcga ctgctggaca agttaatcct attgatccct ggataattaa   1080
taattttgtg caagcccccc aaggtgaatt tactatttcc ccaaataata cccccggtga   1140
tgttttgttt gatttgagtt tgggtcccca tcttaatcct ttcttgctcc atctatcaca   1200
aatgtataat ggttgggttg gtaacatgag agtcaggatt atgctagctg gtaatgcctt   1260
tactgcgggg aagataatag tttcctgcat accccctggt tttggttcac ataatcttac   1320
tatagcacaa gcaactctct ttccacatgt gattgctgat gttaggactc tagaccccat   1380
tgaggtgcct ttggaagatg ttaggaatgt tctctttcat aataatgata gaaatcaaca   1440
aaccatgcgc cttgtgtgca tgctgtacac ccccctccgc actggtggtg gtactggtga   1500
ttcttttgta gttgcagggc gagttatgac ttgccccagt cctgatttta atttcttgtt   1560
tttagtccct cctacggtgg agcagaaaac caggcccttc acactcccaa atctgccatt   1620
gagttctctg tctaactcac gtgcccctct cccaatcagt agtatgggca tttccccaga   1680
caatgtccag agtgtgcagt tccaaaatgg tcggtgtact ctggatggcc gcctggttgg   1740
caccacccca gtttcattgt cacatgttgc caagataaga gggacctcca atggcactgt   1800
aatcaacctt actgaattgg atggcacacc ctttcaccct tttgagggcc ctgcccccat   1860
tgggtttcca gacctcggtg gttgtgattg gcatatcaat atgacacagt ttggccattc   1920
tagccagacc cagtatgatg tagacaccac ccctgacact tttgtccccc atcttggttc   1980
aattcaggca aatggcattg gcagtggtaa ttatgttggt gttcttagct ggatttcccc   2040
cccatcacac ccgtctggct cccaagttga cctttggaag atccccaatt atgggtcaag   2100
tattacggag gcaacacatc tagccccttc tgtatacccc cctggtttcg gagaggtatt   2160
ggtctttttc atgtcaaaaa tgccaggtcc tggtgcttat aatttgccct gtctattacc   2220
acaagagtac atttcacatc ttgctagtga acaagcccct actgtaggtg aggctgccct   2280
gctccactat gttgaccctg ataccggtcg gaatcttggg gaattcaaag cataccctga   2340
tggtttcctc acttgtgtcc ccaatggggc tagctcgggt ccacaacagc tgccgatcaa   2400
```

tggggtcttt gtctttgttt catgggtgtc cagattttat caattaaagc ctgtgggaac 2460
tgccagctcg gcaagaggta ggcttggtct gcgccgataa aggcctattt tctttagttt 2520
gaatttactg ttattcggtg tgcatttcta tgtttggtga gcggttttct gtgctcagag 2580
tgtgtttatt ttatgtaatt taatttcttt gtgagctcct gtttagcagg tcgtcccttc 2640
agcaaggaca caaaaagatt ttaattttat taaaaaaaaa aaaaaaaaag accgggaatt 2700
cgatatcaag cttatcgacc tgcagatcgt tcaaacattt ggcaataaag tttcttaaga 2760
ttgaatcctg ttgccggtct tgcgatgatt atcatataat ttctgttgaa ttacgttaag 2820
catgtaataa ttaacatgta atgcatgacg ttatttatga gatgggtttt tatgattaga 2880
gtcccgcaat tatacattta atacgcgata gaaaacaaaa tatagcgcgc aaactaggat 2940
aaattatcgc gcgcggtgtc atctatgtta ctagat 2976

<210> SEQ ID NO 76
<211> LENGTH: 49
<212> TYPE: DNA
<213> ORGANISM: Artificial
<220> FEATURE:
<223> OTHER INFORMATION: IF-NoV(US68)VP1(ORF2)(hCod).c

<400> SEQUENCE: 76
tcgtgcttcg gcaccagtac aatgatgatg gctagtaaag atgcgacct 49

<210> SEQ ID NO 77
<211> LENGTH: 52
<212> TYPE: DNA
<213> ORGANISM: Artificial
<220> FEATURE:
<223> OTHER INFORMATION: IF-NoV(US68)VP1(ORF2)(hCod).r

<400> SEQUENCE: 77
actaaagaaa ataggccttt atctccgcag accgaggcgt ccgcgggcag aa 52

<210> SEQ ID NO 78
<211> LENGTH: 2976
<212> TYPE: DNA
<213> ORGANISM: Artificial
<220> FEATURE:
<223> OTHER INFORMATION: Expression cassette number 2724 from 2X35S
promoter to NOS terminator

<400> SEQUENCE: 78
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720

```
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg atgatggcta gtaaagatgc gacctcctct gtggatggtg cgtcaggggc    960
aggacaactc gtacccgagg taaacgccag cgacccactt gccatggacc ccgttgccgg   1020
aagttccaca gcagtggcca cagccggtca agtgaatcca attgatccgt ggattatcaa   1080
caatttcgtc caggcacccc agggcgagtt cacaatttca ccaaacaata caccgggcga   1140
tgtgctattc gatctttcct tgggtcctca ccttaaccct tttctactcc atctctcaca   1200
gatgtacaat ggttgggtag gaaacatgag agtccggatc atgctggctg gcaatgcctt   1260
taccgctggc aagatcatcg tcagttgtat tcctcccgga tttggatctc ataatctgac   1320
cattgctcaa gcgactctct ttccccatgt catcgccgac gttaggaccc tggaccccat   1380
cgaggtgccc ctggaggacg tccggaatgt tttgttccac aacaacgaca gaaaccagca   1440
gacgatgaga cttgtctgta tgctctatac cccactgcgg actggaggcg ggactggaga   1500
ctccttcgtt gtggcaggaa gagtgatgac atgcccctcc cccgacttca actttctttt   1560
tctggtccca ccaaccgttg agcagaagac gcggcccttt acactgccca atctcccgct   1620
ttcaagtctg agtaattcac gggccccatt gccgatctcc tcaatgggaa tctcccccga   1680
caacgtccag tctgtccaat tccaaaatgg gagatgcaca ctggacggtc gcctggtggg   1740
aacaactccg gtgtccctct cacatgtcgc caaaatccgc ggcacatcaa atggtaccgt   1800
aatcaatctg acagaacttg atggcacgcc cttccatccc tttgaaggac cagcccctat   1860
tggatttcct gatctgggag gttgcgactg gcacataaac atgacacagt ttggccactc   1920
cagccagaca cagtatgatg tcgatacaac cccagatacc ttcgtgccac acctgggatc   1980
tattcaagct aacggtattg gatccggcaa ctacgtggga gtcttatctt ggatctcacc   2040
accatcccac ccctcaggat cccaggttga cttgtggaag ataccgaatt atggatcctc   2100
gatcactgaa gccacgcacc tcgcaccttc cgtctaccca ccaggttttg gagaagtctt   2160
ggtgtttttc atgagcaaaa tgcccggccc tggagcctac aatctccctt gcctactccc   2220
tcaagagtat attagtcacc tcgcatctga gcaggccccg accgttggcg aggcagccct   2280
gctgcattat gtggatccgg acaccggcag gaacctgggt gagttcaaag cttatcctga   2340
cggttttcta acatgtgtac caaatggcgc ttccagcggc cctcaacagc tcccaatcaa   2400
tggcgtgttc gtttttgtca gctgggtaag ccgcttctac cagctgaagc ccgtggggac   2460
agcttcttct gcccgcggac gcctcggtct gcggagataa aggcctattt tctttagttt   2520
gaatttactg ttattcggtg tgcatttcta tgtttggtga gcggttttct gtgctcagag   2580
tgtgtttatt ttatgtaatt taatttcttt gtgagctcct gtttagcagg tcgtcccttc   2640
agcaaggaca caaaaagatt ttaattttat taaaaaaaaa aaaaaaaaag accgggaatt   2700
cgatatcaag cttatcgacc tgcagatcgt tcaaacattt ggcaataaag tttcttaaga   2760
ttgaatcctg ttgccggtct tgcgatgatt atcatataat ttctgttgaa ttacgttaag   2820
catgtaataa ttaacatgta atgcatgacg ttatttatga gatgggtttt tatgattaga   2880
gtcccgcaat tatacattta atacgcgata gaaaacaaaa tatagcgcgc aaactaggat   2940
aaattatcgc gcgcggtgtc atctatgtta ctagat                             2976
```

<210> SEQ ID NO 79
<211> LENGTH: 47

<212> TYPE: DNA
<213> ORGANISM: Artificial
<220> FEATURE:
<223> OTHER INFORMATION: IF-NoV(US68)VP2(ORF3)(hCod).c

<400> SEQUENCE: 79
tcgtgcttcg gcaccagtac aatggctcag gccattattg gcgccat 47

<210> SEQ ID NO 80
<211> LENGTH: 50
<212> TYPE: DNA
<213> ORGANISM: Artificial
<220> FEATURE:
<223> OTHER INFORMATION: IF-NoV(US68)VP2(ORF3)(hCod).r

<400> SEQUENCE: 80
actaaagaaa ataggccttc agcggcggtt gttagcgaac agaggaagtc 50

<210> SEQ ID NO 81
<211> LENGTH: 2022
<212> TYPE: DNA
<213> ORGANISM: Artificial
<220> FEATURE:
<223> OTHER INFORMATION: Expression cassette number 2725 from 2X35S
promoter to NOS terminator

<400> SEQUENCE: 81
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaatg gctcaggcca ttattggcgc catcgctgca agtacagccg ggagtgcatt 960
gggggccgga atacaggtgg gcggggaagc tgcattgcag agccagcggt accagcaaaa 1020
cctgcagtta caggagaata gctttaaaca cgacagggag atgattggat atcaggtgga 1080
ggccagcaat cagctgctcg ccaaaaactt ggctactcga tactcattac tgcgcgccgg 1140
ggggttgact agcgccgacg ccgcacgatc tgtcgcaggc gcccccgtga ctcggatcgt 1200
agactggaac ggggtacgag tctcggctcc cgagtcgtct gcaaccaccc tgaggtcggg 1260
agggtttatg tccgtgccca tcccattcgc tagcaaacag aaacaggtcc agagctccgg 1320
aatctccaat cccaattact cccctagctc tatctctcgt accacttcct gggtcgagag 1380
tcagaacagc agtagatttg gcaacctgag cccctaccat gctgaagccc tgaacactgt 1440
gtggttgact ccacctggta gcacggcctc ctcaaccctg agttccgtgc ctcgcgggta 1500
cttcaatacc gacagacttc ctctgttcgc taacaaccgc cgctgaaggc ctattttctt 1560
tagtttgaat ttactgttat tcggtgtgca tttctatgtt tggtgagcgg ttttctgtgc 1620
tcagagtgtg tttattttat gtaatttaat ttctttgtga gctcctgttt agcaggtcgt 1680
cccttcagca aggacacaaa aagattttaa ttttattaaa aaaaaaaaaa aaaaagaccg 1740
ggaattcgat atcaagctta tcgacctgca gatcgttcaa acatttggca ataaagtttc 1800
ttaagattga atcctgttgc cggtcttgcg atgattatca tataatttct gttgaattac 1860
gttaagcatg taataattaa catgtaatgc atgacgttat ttatgagatg ggtttttatg 1920
attagagtcc cgcaattata catttaatac gcgatagaaa acaaaatata gcgcgcaaac 1980
taggataaat tatcgcgcgc ggtgtcatct atgttactag at 2022

<210> SEQ ID NO 82
<211> LENGTH: 52
<212> TYPE: DNA
<213> ORGANISM: Artificial
<220> FEATURE:
<223> OTHER INFORMATION: IF-GI2Leu03VP1.c

<400> SEQUENCE: 82
tcgtgcttcg gcaccagtac aatgatgatg gcttcaaagg atgctcccca aa 52

<210> SEQ ID NO 83
<211> LENGTH: 57
<212> TYPE: DNA
<213> ORGANISM: Artificial
<220> FEATURE:
<223> OTHER INFORMATION: IF-GI2Leu03VP1.r

<400> SEQUENCE: 83
actaaagaaa ataggccttc agattcggcg gacccctagc ctgccgcgtg ccgtaga 57

<210> SEQ ID NO 84
<211> LENGTH: 3024
<212> TYPE: DNA
<213> ORGANISM: Artificial
<220> FEATURE:
<223> OTHER INFORMATION: Expression cassette number 3300 from 2X35S promoter to NOS terminator

<400> SEQUENCE: 84
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720

```
taaggaagtt catttcattt ggagaggtat taaaatctta ataggttttg ataaaagcga    780
acgtggggaa acccgaacca aaccttcttc taaactctct ctcatctctc ttaaagcaaa    840
cttctctctt gtctttcttg cgtgagcgat cttcaacgtt gtcagatcgt gcttcggcac    900
cagtacaatg atgatggctt caaaggatgc tccccaaagc gcggacggag ctagcggcgc    960
cggacagttg gttccggaag tcaacactgc cgatccactg cccatggaac ccgtagctgg   1020
tccaacaacc gctgttgcca ccgccggcca ggttaacatg atcgatccat ggattgttaa   1080
taactttgta cagagccccc aggggagtt cacaatttct ccgaacaata cccctgggga    1140
cattctgttc gatctgcaac tgggcccaca cttgaatcct ttcctgagcc atctttcaca   1200
gatgtacaac ggatgggttg ggaacatgcg tgttcggatc ctccttgctg gcaacgcctt   1260
cagtgctggc aagattatcg tgtgctgcgt accaccaggg tttacctcga gttcattaac   1320
cattgctcag gccacccttt tccctcacgt gatcgcagac gtgcgtacct tagaaccaat   1380
cgaaatgccc ctggaagatg tacggaacgt gctgtaccat actaatgata accagccaac   1440
gatgagatta gtgtgcatgc tgtacacccc cctgagaact ggaggaggtt ctggaaattc   1500
cgacagtttt gtggtggctg gcagggtcct gaccgctccc agtagcgact tcagcttttt   1560
gttcctcgtt cctcctacaa tcgaacaaaa aacaagagca ttcacagtgc ccaacattcc   1620
actgcagact ttaagcaatt ccaggtttcc cagcttgatc cagggtatga tcctttctcc   1680
cgacgcctcc caagttgtgc agttccagaa tgggagatgt cttatcgacg gtcagcttct   1740
gggaacaacc cctgccacct ccgggcaact cttccgggtg agaggcaaaa tcaatcaggg   1800
cgccagaaca ctgaatctga cagaagtgga cgggaaaccc tttatggcgt tcgatagccc   1860
cgcgcccgtt ggattccctg acttcggcaa gtgtgattgg cacatgcgca tcagtaagac   1920
tcccaacaac acttcatctg gagaccccat gaggagcgtg gatgtccaga ccgacgtgca   1980
gggcttcgtg ccgcacttgg gatctatcca gttcgatgag gtgttcaatc accctactgg   2040
cgactacata ggcacaattg agtggataag tcaaccatct acacctccag ggaccgacat   2100
aaacctgtgg gaaattcctg attacgggtc atccctgagt caagctgcca atcttgcacc   2160
ccctgtcttt ccccccggct ttggtgaggc tcttgtttac ttcgtctctg catttcctgg   2220
tcctaacaac cgctccgccc ctaacgatgt tccgtgtttg ttaccccagg aatatgtgac   2280
tcatttcgtt tccgaacagg cacccaccat gggggacgct gccctgctac actatgtgga   2340
ccccgacacc aatagaaacc tcggcgagtt caaactctac cccgggggat acctgacctg   2400
tgttccaaat ggagtgggag caggcccaca acagctgccc ctgaatgggg tcttcctgtt   2460
cgtttcttgg gtgtcacgct tttaccagct gaagcccgtt ggcacagctt ctacggcacg   2520
cggcaggcta ggggtccgcc gaatctgaag gcctattttc tttagtttga atttactgtt   2580
attcggtgtg catttctatg tttggtgagc ggttttctgt gctcagagtg tgtttatttt   2640
atgtaattta atttctttgt gagctcctgt ttagcaggtc gtcccttcag caaggacaca   2700
aaaagatttt aattttatta aaaaaaaaaa aaaaaaagac cgggaattcg atatcaagct   2760
tatcgacctg cagatcgttc aaacatttgg caataaagtt tcttaagatt gaatcctgtt   2820
gccggtcttg cgatgattat catataattt ctgttgaatt acgttaagca tgtaataatt   2880
aacatgtaat gcatgacgtt atttatgaga tgggttttta tgattagagt cccgcaatta   2940
tacatttaat acgcgataga aaacaaaata tagcgcgcaa actaggataa attatcgcgc   3000
gcggtgtcat ctatgttact agat                                          3024
```

<210> SEQ ID NO 85
<211> LENGTH: 56
<212> TYPE: DNA
<213> ORGANISM: Artificial
<220> FEATURE:
<223> OTHER INFORMATION: GI2Leu+GI1VP1.r

<400> SEQUENCE: 85
atgctcttgt tttttgctca acggttggtg ggaccagaaa aagaaagttg aagtcg 56

<210> SEQ ID NO 86
<211> LENGTH: 49
<212> TYPE: DNA
<213> ORGANISM: Artificial
<220> FEATURE:
<223> OTHER INFORMATION: GI1VP1+GI2Leu.c

<400> SEQUENCE: 86
tcccaccaac cgttgagcaa aaaacaagag cattcacagt gcccaacat 49

<210> SEQ ID NO 87
<211> LENGTH: 3021
<212> TYPE: DNA
<213> ORGANISM: Artificial
<220> FEATURE:
<223> OTHER INFORMATION: Expression cassette number 3360 from 2X35S
promoter to NOS terminator

<400> SEQUENCE: 87
gtcaacatgg tggagcacga cacacttgtc tactccaaaa atatcaaaga tacagtctca 60
gaagaccaaa gggcaattga gacttttcaa caaagggtaa tatccggaaa cctcctcgga 120
ttccattgcc cagctatctg tcactttatt gtgaagatag tggaaaagga aggtggctcc 180
tacaaatgcc atcattgcga taaaggaaag gccatcgttg aagatgcctc tgccgacagt 240
ggtcccaaag atggaccccc acccacgagg agcatcgtgg aaaaagaaga cgttccaacc 300
acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagaggtat taaaatctta ataggttttg ataaaagcga 780
acgtggggaa acccgaacca aaccttcttc taaactctct ctcatctctc ttaaagcaaa 840
cttctctctt gtctttcttg cgtgagcgat cttcaacgtt gtcagatcgt gcttcggcac 900
cagtacaatg atgatggcta gtaaagatgc gacctcctct gtggatggtg cgtcaggggc 960
aggacaactc gtacccgagg taaacgccag cgacccactt gccatggacc ccgttgccgg 1020
aagttccaca gcagtggcca cagccggtca agtgaatcca attgatccgt ggattatcaa 1080
caatttcgtc caggcacccc agggcgagtt cacaatttca ccaaacaata caccgggcga 1140
tgtgctattc gatctttcct tgggtcctca ccttaaccct tttctactcc atctctcaca 1200
gatgtacaat ggttgggtag gaaacatgag agtccggatc atgctggctg gcaatgcctt 1260
taccgctggc aagatcatcg tcagttgtat tcctcccgga tttggatctc ataatctgac 1320

-continued

```
cattgctcaa gcgactctct ttccccatgt catcgccgac gttaggaccc tggaccccat   1380

cgaggtgccc ctggaggacg tccggaatgt tttgttccac aacaacgaca gaaaccagca   1440

gacgatgaga cttgtctgta tgctctatac cccactgcgg actggaggcg ggactggaga   1500

ctccttcgtt gtggcaggaa gagtgatgac atgcccctcc cccgacttca actttctttt   1560

tctggtccca ccaaccgttg agcaaaaaac aagagcattc acagtgccca acattccact   1620

gcagacttta agcaattcca ggtttcccag cttgatccag ggtatgatcc tttctcccga   1680

cgcctcccaa gttgtgcagt tccagaatgg gagatgtctt atcgacggtc agcttctggg   1740

aacaacccct gccacctccg ggcaactctt ccgggtgaga ggcaaaatca atcagggcgc   1800

cagaacactg aatctgacag aagtggacgg gaaacccttt atggcgttcg atagccccgc   1860

gcccgttgga ttccctgact tcggcaagtg tgattggcac atgcgcatca gtaagactcc   1920

caacaacact tcatctggag accccatgag gagcgtggat gtccagaccg acgtgcaggg   1980

cttcgtgccg cacttgggat ctatccagtt cgatgaggtg ttcaatcacc ctactggcga   2040

ctacataggc acaattgagt ggataagtca accatctaca cctccaggga ccgacataaa   2100

cctgtgggaa attcctgatt acgggtcatc cctgagtcaa gctgccaatc ttgcaccccc   2160

tgtctttccc cccggctttg gtgaggctct tgtttacttc gtctctgcat ttcctggtcc   2220

taacaaccgc tccgccccta acgatgttcc gtgtttgtta ccccaggaat atgtgactca   2280

tttcgtttcc gaacaggcac ccaccatggg ggacgctgcc ctgctacact atgtggaccc   2340

cgacaccaat agaaacctcg gcgagttcaa actctacccc gggggatacc tgacctgtgt   2400

tccaaatgga gtgggagcag gcccacaaca gctgcccctg aatggggtct tcctgttcgt   2460

ttcttgggtg tcacgctttt accagctgaa gcccgttggc acagcttcta cggcacgcgg   2520

caggctaggg gtccgccgaa tctgaaggcc tattttcttt agtttgaatt tactgttatt   2580

cggtgtgcat ttctatgttt ggtgagcggt tttctgtgct cagagtgtgt ttattttatg   2640

taatttaatt tctttgtgag ctcctgttta gcaggtcgtc ccttcagcaa ggacacaaaa   2700

agattttaat tttattaaaa aaaaaaaaaa aaaagaccgg gaattcgata tcaagcttat   2760

cgacctgcag atcgttcaaa catttggcaa taaagtttct taagattgaa tcctgttgcc   2820

ggtcttgcga tgattatcat ataatttctg ttgaattacg ttaagcatgt aataattaac   2880

atgtaatgca tgacgttatt tatgagatgg gtttttatga ttagagtccc gcaattatac   2940

atttaatacg cgatagaaaa caaaatatag cgcgcaaact aggataaatt atcgcgcgcg   3000

gtgtcatcta tgttactaga t                                             3021
```

```
<210> SEQ ID NO 88
<211> LENGTH: 15
<212> TYPE: PRT
<213> ORGANISM: Norovirus GI.1/Norwalk/1968/US

<400> SEQUENCE: 88

Leu Val Pro Pro Thr Val Glu Gln Lys Thr Arg Pro Phe Thr Leu
1               5                   10                  15


<210> SEQ ID NO 89
<211> LENGTH: 15
<212> TYPE: PRT
<213> ORGANISM: Norovirus GI.2/Leuven/2003/Bel

<400> SEQUENCE: 89

Leu Val Pro Pro Thr Ile Glu Gln Lys Thr Arg Ala Phe Thr Val
1               5                   10                  15
```

<210> SEQ ID NO 90
<211> LENGTH: 15
<212> TYPE: PRT
<213> ORGANISM: Norovirus GI.3/S29/2008/Lilla Edet/Sweden

<400> SEQUENCE: 90

Leu Val Pro Pro Asn Val Glu Gln Lys Thr Lys Pro Phe Ser Val
1               5                   10                  15

<210> SEQ ID NO 91
<211> LENGTH: 15
<212> TYPE: PRT
<213> ORGANISM: Norovirus GII.4/Sydney/NSW0514/2012/AU

<400> SEQUENCE: 91

Leu Val Pro Pro Thr Val Glu Ser Arg Thr Lys Pro Phe Ser Val
1               5                   10                  15

<210> SEQ ID NO 92
<211> LENGTH: 15
<212> TYPE: PRT
<213> ORGANISM: Norovirus GII.6/Ohio/490/12

<400> SEQUENCE: 92

Leu Val Pro Pro Thr Val Glu Ser Lys Thr Lys Pro Phe Ser Leu
1               5                   10                  15

<210> SEQ ID NO 93
<211> LENGTH: 15
<212> TYPE: PRT
<213> ORGANISM: Norovirus GII.13/VA173/2010/USA

<400> SEQUENCE: 93

Leu Val Pro Pro Ser Val Glu Ser Lys Thr Lys Pro Phe Thr Leu
1               5                   10                  15

<210> SEQ ID NO 94
<211> LENGTH: 15
<212> TYPE: PRT
<213> ORGANISM: Norovirus GII.17/Kawasaki323/2014/JP

<400> SEQUENCE: 94

Leu Val Pro Pro Ser Val Glu Ser Lys Thr Lys Pro Phe Ser Leu
1               5                   10                  15

<210> SEQ ID NO 95
<211> LENGTH: 15
<212> TYPE: PRT
<213> ORGANISM: Artificial
<220> FEATURE:
<223> OTHER INFORMATION: Consensus
<220> FEATURE:
<221> NAME/KEY: VARIANT
<222> LOCATION: (5)..(5)
<223> OTHER INFORMATION: Xaa can be Ser, Thr or Asn
<220> FEATURE:
<221> NAME/KEY: VARIANT
<222> LOCATION: (6)..(6)
<223> OTHER INFORMATION: Xaa can be Val or Ile
<220> FEATURE:
<221> NAME/KEY: VARIANT
<222> LOCATION: (8)..(8)
<223> OTHER INFORMATION: Xaa can be Ser or Gln
<220> FEATURE:
<221> NAME/KEY: VARIANT
<222> LOCATION: (12)..(12)
<223> OTHER INFORMATION: Xaa can be Pro or Ala
<220> FEATURE:
<221> NAME/KEY: VARIANT
<222> LOCATION: (14)..(14)
<223> OTHER INFORMATION: Xaa can be Ser or Thr

<400> SEQUENCE: 95

Leu Val Pro Pro Xaa Xaa Glu Xaa Lys Thr Lys Xaa Phe Xaa Ile
1 5 10 15

<210> SEQ ID NO 96
<211> LENGTH: 56
<212> TYPE: DNA
<213> ORGANISM: Artificial
<220> FEATURE:
<223> OTHER INFORMATION: GI3Lil+GI1VP1.r

<400> SEQUENCE: 96
gaatggcttt gttttctgct caacggttgg tgggaccaga aaaagaaagt tgaagt 56

<210> SEQ ID NO 97
<211> LENGTH: 48
<212> TYPE: DNA
<213> ORGANISM: Artificial
<220> FEATURE:
<223> OTHER INFORMATION: GI1VP1+GI3Lil.c

<400> SEQUENCE: 97
tcccaccaac cgttgagcag aaaacaaagc cattcagcgt gccaaacc 48

<210> SEQ ID NO 98
<211> LENGTH: 49
<212> TYPE: DNA
<213> ORGANISM: Artificial
<220> FEATURE:
<223> OTHER INFORMATION: IF-GI3Lil08VP1.r

<400> SEQUENCE: 98
actaaagaaa ataggcctct agctccgtct gatcccgagc ctccgaact 49

<210> SEQ ID NO 99
<211> LENGTH: 49
<212> TYPE: DNA
<213> ORGANISM: Artificial
<220> FEATURE:
<223> OTHER INFORMATION: GII4Syd+GI1VP1.r

<400> SEQUENCE: 99
aagggcttgg ttcggctctc aacggttggt gggaccagaa aaagaaagt 49

<210> SEQ ID NO 100
<211> LENGTH: 49
<212> TYPE: DNA
<213> ORGANISM: Artificial
<220> FEATURE:
<223> OTHER INFORMATION: GI1VP1+GII4Syd.c

<400> SEQUENCE: 100
tcccaccaac cgttgagagc cgaaccaagc cctttagtgt ccccgtact 49

<210> SEQ ID NO 101
<211> LENGTH: 48
<212> TYPE: DNA
<213> ORGANISM: Artificial
<220> FEATURE:
<223> OTHER INFORMATION: IF-GII4Syd12VP1.r

<400> SEQUENCE: 101
actaaagaaa ataggccttc agacagccct gcgtctgcca gtcccatt 48

<210> SEQ ID NO 102
<211> LENGTH: 50
<212> TYPE: DNA
<213> ORGANISM: Artificial
<220> FEATURE:
<223> OTHER INFORMATION: GII6Ohi+GI1VP1.r

<400> SEQUENCE: 102
tcccaccaac cgttgagagc aagacaaaac ccttcagcct cccaatctta 50

<210> SEQ ID NO 103
<211> LENGTH: 50
<212> TYPE: DNA
<213> ORGANISM: Artificial
<220> FEATURE:
<223> OTHER INFORMATION: GI1VP1+GII6Ohi.c

<400> SEQUENCE: 103
tcccaccaac cgttgagagc aagacaaaac ccttcagcct cccaatctta 50

<210> SEQ ID NO 104
<211> LENGTH: 54
<212> TYPE: DNA
<213> ORGANISM: Artificial
<220> FEATURE:
<223> OTHER INFORMATION: IF-GII6Ohi12VP1.r

<400> SEQUENCE: 104
actaaagaaa ataggccttc actgatcccg gcgtcgcccc tggcctgtcc ccat 54

<210> SEQ ID NO 105
<211> LENGTH: 49
<212> TYPE: DNA
<213> ORGANISM: Artificial
<220> FEATURE:
<223> OTHER INFORMATION: GII13Va+GI1VP1.r

<400> SEQUENCE: 105
aagggtttag tcttgctctc aacggttggt gggaccagaa aaagaaagt 49

<210> SEQ ID NO 106
<211> LENGTH: 50
<212> TYPE: DNA
<213> ORGANISM: Artificial
<220> FEATURE:
<223> OTHER INFORMATION: GI1VP1+GII13Va.c

<400> SEQUENCE: 106
tcccaccaac cgttgagagc aagactaaac cctttactct tcccattctg 50

<210> SEQ ID NO 107
<211> LENGTH: 53
<212> TYPE: DNA
<213> ORGANISM: Artificial
<220> FEATURE:
<223> OTHER INFORMATION: IF-GII13VA10VP1.r

<400> SEQUENCE: 107
actaaagaaa ataggccttc attgcacccg acggcgacca ttcccggtac cca 53

<210> SEQ ID NO 108
<211> LENGTH: 55
<212> TYPE: DNA

<213> ORGANISM: Artificial
<220> FEATURE:
<223> OTHER INFORMATION: GII17Kaw+GI1VP1.r

<400> SEQUENCE: 108
aacggtttgg tcttagactc aacggttggt gggaccagaa aaagaaagtt gaagt 55

<210> SEQ ID NO 109
<211> LENGTH: 48
<212> TYPE: DNA
<213> ORGANISM: Artificial
<220> FEATURE:
<223> OTHER INFORMATION: GI1VP1+GII17Kaw.c

<400> SEQUENCE: 109
tcccaccaac cgttgagtct aagaccaaac cgttttcact gccaatct 48

<210> SEQ ID NO 110
<211> LENGTH: 56
<212> TYPE: DNA
<213> ORGANISM: Artificial
<220> FEATURE:
<223> OTHER INFORMATION: IF-GII17Kaw14VP1.r

<400> SEQUENCE: 110
actaaagaaa ataggcctct actgagcccg gcgtctgccg ttaccggtgc ccattg 56

<210> SEQ ID NO 111
<211> LENGTH: 49
<212> TYPE: DNA
<213> ORGANISM: Artificial
<220> FEATURE:
<223> OTHER INFORMATION: IF-GI3Lil08VP1.c

<400> SEQUENCE: 111
tcgtgcttcg gcaccagtac aatgatgatg gcttccaagg atgctccca 49

<210> SEQ ID NO 112
<211> LENGTH: 49
<212> TYPE: DNA
<213> ORGANISM: Artificial
<220> FEATURE:
<223> OTHER INFORMATION: IF-GII4Syd12VP1.c

<400> SEQUENCE: 112
tcgtgcttcg gcaccagtac aatgaaaatg gcctcgagtg acgctaacc 49

<210> SEQ ID NO 113
<211> LENGTH: 49
<212> TYPE: DNA
<213> ORGANISM: Artificial
<220> FEATURE:
<223> OTHER INFORMATION: IF-GII6Ohi12VP1.c

<400> SEQUENCE: 113
tcgtgcttcg gcaccagtac aatgaagatg gcaagcaacg acgcagctc 49

<210> SEQ ID NO 114
<211> LENGTH: 59
<212> TYPE: DNA
<213> ORGANISM: Artificial
<220> FEATURE:
<223> OTHER INFORMATION: IF-GII13VA10VP1.c

<400> SEQUENCE: 114
tcgtgcttcg gcaccagtac aatgaaaatg gcttctaatg atgccgcgcc cagcaatga 59

<210> SEQ ID NO 115
<211> LENGTH: 53
<212> TYPE: DNA
<213> ORGANISM: Artificial
<220> FEATURE:
<223> OTHER INFORMATION: IF-GII17Kaw14VP1.c

<400> SEQUENCE: 115
tcgtgcttcg gcaccagtac aatgaaaatg gcatctaacg acgcagcccc ctc 53

<210> SEQ ID NO 116
<211> LENGTH: 48
<212> TYPE: DNA
<213> ORGANISM: Artificial
<220> FEATURE:
<223> OTHER INFORMATION: IF-NoV(US68)VP2(ORF3).c

<400> SEQUENCE: 116
tcgtgcttcg gcaccagtac aatggcccaa gccataattg gtgcaatt 48

<210> SEQ ID NO 117
<211> LENGTH: 54
<212> TYPE: DNA
<213> ORGANISM: Artificial
<220> FEATURE:
<223> OTHER INFORMATION: IF-GII4Syd12VP2.c

<400> SEQUENCE: 117
tcgtgcttcg gcaccagtac aatggctggg gcctttttg caggtttggc tagt 54

<210> SEQ ID NO 118
<211> LENGTH: 48
<212> TYPE: DNA
<213> ORGANISM: Artificial
<220> FEATURE:
<223> OTHER INFORMATION: IF-NoV(US68)VP1/VP2(ORF3)NoV3'UTR.r

<400> SEQUENCE: 118
actaaagaaa ataggcctaa catcaaatta aacctaatta aacctaat 48

<210> SEQ ID NO 119
<211> LENGTH: 54
<212> TYPE: DNA
<213> ORGANISM: Artificial
<220> FEATURE:
<223> OTHER INFORMATION: IF-GII4Syd12VP2.r

<400> SEQUENCE: 119
actaaagaaa ataggccttc atgctcgtga ctcacccctt ttgcgtatat gagc 54

<210> SEQ ID NO 120
<211> LENGTH: 804
<212> TYPE: DNA
<213> ORGANISM: Artificial
<220> FEATURE:
<223> OTHER INFORMATION: Nucleic acid sequence of human codon-optimized
VP2 GII.4/ Sydney/NSW0514/2012/AU

<400> SEQUENCE: 120
atggctgggg cctttttgc aggtttggct agtgacgtcc tcgggtcggg cctcggaagt 60
ctgatcaatg caggagctgg agcgattaat caaaaagtcg agttcgagaa taaccggaaa 120
cttcaacagg caagtttcca attctcaagc aatttgcagc aggcctcatt ccaacacgac 180
aaggaaatgc tccaggccca gattgaggcc accaagaaac tgcaacaaga gatgatgaag 240
gtcaaacagg ccatgctgct ggagggcggc tttttcgaga ccgatgctgc gcgcggagcc 300
atcaacgccc caatgacaaa ggcactcgac tggagtggca cacggtattg ggcacccgat 360
gccagaacga ctacctataa tgccggaagg ttctccacac ctcaaccttc tggtgccctc 420
ccagggcgcg caaatctgag ggacgctgtg cccgctaggg gctcctcatc aaagtcttcc 480
aatagctcca ctgcaacctc ggtttactca aaccagacca cttcaacaag attaggatca 540
accgccgtgt cgggaacatc tgtctcctct ttccttcta cagcacgaac caggtcttgg 600
gtcgaggacc agagcagaaa cctgtctccg tccatgcgcg gtgctcacaa catttccttc 660
gtgacccctc cttcttcccg atcctccagc caagggacag tgtccacagt gcccaaagaa 720
gtgctcgact cttggacagg tgcgttcaat accagacgcc agcctctctt tgctcatata 780
cgcaaaaggg gtgagtcacg agca 804

<210> SEQ ID NO 121
<211> LENGTH: 268
<212> TYPE: PRT
<213> ORGANISM: Norovirus GII.4/ Sydney/NSW0514/2012/AU

<400> SEQUENCE: 121

Met Ala Gly Ala Phe Phe Ala Gly Leu Ala Ser Asp Val Leu Gly Ser
1 5 10 15

Gly Leu Gly Ser Leu Ile Asn Ala Gly Ala Gly Ala Ile Asn Gln Lys
20 25 30

Val Glu Phe Glu Asn Asn Arg Lys Leu Gln Gln Ala Ser Phe Gln Phe
35 40 45

Ser Ser Asn Leu Gln Gln Ala Ser Phe Gln His Asp Lys Glu Met Leu
50 55 60

Gln Ala Gln Ile Glu Ala Thr Lys Lys Leu Gln Gln Glu Met Met Lys
65 70 75 80

Val Lys Gln Ala Met Leu Leu Glu Gly Gly Phe Phe Glu Thr Asp Ala
85 90 95

Ala Arg Gly Ala Ile Asn Ala Pro Met Thr Lys Ala Leu Asp Trp Ser
100 105 110

Gly Thr Arg Tyr Trp Ala Pro Asp Ala Arg Thr Thr Thr Tyr Asn Ala
115 120 125

Gly Arg Phe Ser Thr Pro Gln Pro Ser Gly Ala Leu Pro Gly Arg Ala
130 135 140

Asn Leu Arg Asp Ala Val Pro Ala Arg Gly Ser Ser Ser Lys Ser Ser
145 150 155 160

Asn Ser Ser Thr Ala Thr Ser Val Tyr Ser Asn Gln Thr Thr Ser Thr
165 170 175

Arg Leu Gly Ser Thr Ala Val Ser Gly Thr Ser Val Ser Ser Phe Pro
180 185 190

Ser Thr Ala Arg Thr Arg Ser Trp Val Glu Asp Gln Ser Arg Asn Leu
195 200 205

Ser Pro Ser Met Arg Gly Ala His Asn Ile Ser Phe Val Thr Pro Pro
210 215 220

Ser Ser Arg Ser Ser Ser Gln Gly Thr Val Ser Thr Val Pro Lys Glu
225 230 235 240

Val Leu Asp Ser Trp Thr Gly Ala Phe Asn Thr Arg Arg Gln Pro Leu
245 250 255

Phe Ala His Ile Arg Lys Arg Gly Glu Ser Arg Ala
260 265

-continued

```
<210> SEQ ID NO 122
<211> LENGTH: 48
<212> TYPE: DNA
<213> ORGANISM: Artificial
<220> FEATURE:
<223> OTHER INFORMATION: IF-NoV(US68)VP2(ORF3).r

<400> SEQUENCE: 122

actaaagaaa ataggcctaa catcaaatta aacctaatta aacctaat              48
```